US010358643B2

(12) United States Patent
Albaek et al.

(10) Patent No.: US 10,358,643 B2
(45) Date of Patent: Jul. 23, 2019

(54) POLY OLIGOMER COMPOUND WITH BIOCLEAVABLE CONJUGATES

(71) Applicant: Hoffmann-LA Roche Inc., Little Falls, NJ (US)

(72) Inventors: Nanna Albaek, Birkerød (DK); Henrik Frydenlund Hansen, Ringsted (DK); Susanne Kammler, Holte (DK); Morten Lindow, Copenhagen (DK); Jacob Ravn, Skovlunde (DK); Mark Turner, Hoersholm (DK)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 15/114,274

(22) PCT Filed: Jan. 26, 2015

(86) PCT No.: PCT/EP2015/051442
§ 371 (c)(1),
(2) Date: Jul. 26, 2016

(87) PCT Pub. No.: WO2015/113922
PCT Pub. Date: Aug. 6, 2015

(65) Prior Publication Data
US 2017/0349896 A1    Dec. 7, 2017

(30) Foreign Application Priority Data

Jan. 30, 2014 (EP) ..................................... 14153274
May 14, 2014 (EP) ..................................... 14168277
Nov. 14, 2014 (EP) ..................................... 14193206

(51) Int. Cl.
*C12N 15/113* (2010.01)
(52) U.S. Cl.
CPC ...... *C12N 15/113* (2013.01); *C12N 2310/113* (2013.01); *C12N 2310/315* (2013.01); *C12N 2310/341* (2013.01); *C12N 2310/345* (2013.01); *C12N 2310/351* (2013.01); *C12N 2310/51* (2013.01)
(58) Field of Classification Search
None
See application file for complete search history.

(56) References Cited

U.S. PATENT DOCUMENTS 5,994,517 A * 11/1999 Ts'o .................. A61K 47/48092
530/391.7

FOREIGN PATENT DOCUMENTS

| WO | WO 97/20563 | 6/1997 | |
|---|---|---|---|
| WO | WO 2004/044141 | 5/2004 | |
| WO | WO 2004/087931 | 10/2004 | |
| WO | WO 2005/086775 | 9/2005 | |
| WO | WO 2008/113832 | 9/2008 | |
| WO | WO 2009/025669 | 2/2009 | |
| WO | WO 2009/073809 | 6/2009 | |
| WO | WO 2009/126933 | 10/2009 | |
| WO | WO 2011/126937 | 10/2011 | |
| WO | WO-2012148952 A1 * | 11/2012 | ........... C12N 15/113 |
| WO | WO 2013/040429 | 3/2013 | |
| WO | WO 2014/043544 | 3/2014 | |
| WO | WO 2014/076195 | 5/2014 | |

OTHER PUBLICATIONS

International Search Report and Written Opinion in International Application No. PCT/EP2015/051442, dated Apr. 24, 2015, 9 pages.
Chaltin et al., "Delivery of Antisense Oligonucleotides Using Cholesterol-Modified Sense Dendrimers and Cationic Lipids," Bioconjugate Chem., 2005 16:827-836, Published on web Jun. 23, 2005.
Krützfeldt et al., "Silencing of microRNAs in vivo with 'antagomirs,'" Nature, Dec. 1, 2005, 438:685-689.
Soutscheck et al., "Therapeutic silencing of an endogenous gene by systemic administration of modified siRNAs," Nature, Nov. 11, 2004, 432:173-178.
Balkrishen Bhat et al: "RG-101, a GalNAC-conjugated anti-miR employing a unique mechanism of action by targeting host factor microRNA-122 (miR-122), demonstrates potent activity and reduction of HCV in preclinical studies," Hepatology; 64th Annual Meeting of the American-Association-for-the-Study-of-Liver-Diseases; Washington, DC, USA; Nov. 1, 2005, 2013, Wiley, vol. 58, No. 6, suppl, Dec. 1, 2013, p. 1393A.
Bon et al., "Capacity Limits of Asialoglycoprotein Receptor-Mediated Liver Targeting," mAbs, Sep. 21, 2017, 9(8):1942-0862.
International Preliminary Report on Patentability in International Application No. PCT/EP2015/051442, dated Aug. 2, 2016, 7 pages.
Office Action in European Application No. 15701345.9, dated Oct. 6, 2017, 4 pages.

* cited by examiner

*Primary Examiner* — J. E. Angell

(74) *Attorney, Agent, or Firm* — Fish & Richardson P.C.

(57) ABSTRACT

The invention relates to the field of oligonucleotide therapeutics, and in particular to poly oligo oligonucleotides conjugates where two or more antisense oligonucleotides are covalently linked by physiologically labile linkers, and to a biocleavable functional group such as a conjugate group.

18 Claims, 13 Drawing Sheets
Specification includes a Sequence Listing.

Mono GalNAc=

Toc=

Conj 3 =

Conj 4 =

GalNAc 1-5'-$G^L_sT^L_sT_sG_sA_sC_sA_sC_sT_sG_sT^L_s{}^{Me}C^L_sC_oA_oA^L_sT^L_sT^L_sC_sC_sC_sT_sG_sC_sC_sT_sG^L_sT^L_sG^L$-3'

US 10,358,643 B2

POLY OLIGOMER COMPOUND WITH BIOCLEAVABLE CONJUGATES

FIELD OF INVENTION

The invention relates to the field of oligonucleotide therapeutics, and in particular to poly oligo oligonucleotides and conjugates where two or more antisense oligonucleotides are covalently linked by physiologically labile linkers, and a functional group such as a conjugate group.

BACKGROUND

Oligonucleotide conjugates have been extensively evaluated for use in siRNAs, where they are considered essential in order to obtain sufficient in vivo potency. For example, WO2004/044141 refers to modified oligomeric compounds that modulate gene expression via an RNA interference pathway. The oligomeric compounds include one or more conjugate moieties that can modify or enhance the pharmacokinetic and pharmacodynamic properties of the attached oligomeric compound.

In contrast, single stranded antisense oligonucleotides are typically administered therapeutically without conjugation or formulation. The main target tissues for antisense oligonucleotides are the liver and the kidney, although a wide range of other tissues are also accessible by the antisense modality, including lymph node, spleen, bone marrow.

WO2008/113832 discloses LNA phosphorothioate gapmer oligonucleotides where the flanking regions comprise at least one phosphodiester between or adjacent to a LNA nucleoside. The oligomers were preferentially targeted to the kidney.

WO2004/087931 refers to oligonucleotides comprising an acid cleavable hydrophilic polymer (PEG) conjugate.

WO 2005/086775 refers to targeted delivery of therapeutic agents to specific organs using a therapeutic chemical moiety, a cleavable linker and a labeling domain. The cleavable linker may be, for example, a disulfide group, a peptide or a restriction enzyme cleavable oligonucleotide domain.

WO 2009/126933 refers to specific delivery of siRNA nucleic acids by combining targeting ligands with endosomolytic components.

WO 2011/126937 refers to targeted intracellular delivery of oligonucleotides via conjugation with small molecule ligands.

WO2009/025669 refers to polymeric (polyethylene glycol) linkers containing pyridyl disulphide moieties. See also Zhao et al., Bioconjugate Chem. 2005 16 758-766.

WO2014/043544 and WO2014/076195 refer to multimeric oligonucleotide compounds which are linked via cleavable linkages, including DNA phosphodiester linkages.

WO2014/076195 also refers to oligonucleotide conjugates which utilise biocleavable DNA phosphodiester linkages to link the conjugate to the oligonucleotide.

Chaltin et al., Bioconjugate Chem. 2005 16 827-836 reports on cholesterol modified mono- di- and tetrameric oligonucleotides used to incorporate antisense oligonucleotides into cationic liposomes, to produce a dendrimeric delivery system. Cholesterol is conjugated to the oligonucleotides via a lysine linker.

Other non-cleavable cholesterol conjugates have been used to target siRNAs and antagomirs to the liver—see for example, Soutscheck et al., Nature 2004 vol. 432 173-178 and Krützfeldt et al., Nature 2005 vol 438, 685-689. For the partially phosphorothiolated siRNAs and antagomirs, the use of cholesterol as a liver targeting entity was found to be essential for in vivo activity.

Bhat et al., AASLD Nov. 7-11, 2013 (poster) disclosed data from the use of a GalNac conjugated anti-miR, RG-101 targeting miR-122 for reduction of HCV in preclinical studies. The identity of RG-101 was not disclosed.

The present invention refers to the use of such short regions, e.g. 1-5, of physiologically labile nucleotides, such as DNA phosphodiester, to link multiple single stranded antisense oligonucleotides, which enables a single drug entity to target multiple targets, and the use of a single conjugate moiety to target multiple single stranded oligonucleotides to a target tissue or cell.

The present invention is also based upon the discovery that highly effective targeted delivery of multiple oligonucleotides is achieved by the use of a homing device linked to two or more oligonucleotides by means of a short region of nuclease labile nucleosides, such as phosphodiester linked DNA or RNA nucleosides, linking the oligonucleotides to the conjugate moiety.

RELATED APPLICATIONS

WO2014/076195, hereby incorporated by reference, discloses the use of short regions of physiologically labile nucleotides, such as DNA phosphodiesters, to link an antisense oligonucleotide to a conjugate, enabling efficient targeting of potent oligonucleotides to target cells.

SUMMARY OF INVENTION

Poly Oligomeric Compounds

The invention provides for an oligomeric compound (an oligomer) which comprises a first oligomer region (region A), a second oligomer region (A') and a biocleavable linker region (region B), and a third region (region C), wherein the biocleavable linker region (B) is positioned between the first oligomer region (region A), a second oligomer region (A').

The invention provides for an oligomeric compound (an oligomer) which comprises a first oligomer region (region A), a second oligomer region (A') and a region of 1-10 physiologically labile nucleotides (region B), and a third region (region C), wherein the biocleavable linker region (B) is positioned between the first oligomer region (region A), a second oligomer region (A').

The invention provides for an oligomeric compound (an oligomer) which comprises a first oligomer region (region A), a second oligomer region (A') and a region of 1-10 phosphodiester linked DNA or RNA nucleotides (region B), and optionally a third region (region C), wherein the biocleavable linker region (B) is positioned between the first oligomer region (region A), a second oligomer region (A). Suitably, group C is covalently joined to the oligomeric complex via a further region B'.

The invention provides for an oligomeric compound (an oligomer) which comprises a first oligomer region (region A), a second oligomer region (A') and a region of 1-10 phosphodiester linked DNA nucleotides (region B), and a third region (region C), wherein the biocleavable linker region (B) is positioned between the first oligomer region (region A), a second oligomer region (A'). Suitably, group C is covalently joined to the oligomeric complex via a further region B'.

The oligomer regions A and A', and if present A", may target the same nucleic acid target or different nucleic acid targets. The oligomer regions A and A', and if present A", may comprise the same sequence of nucleobases or different sequence of nucleobases. Region (C), when present, may comprise a conjugate moiety, a targeting moiety, a reactive group, an activation group, or a blocking moiety. For therapeutic use, conjugate groups are preferred, and as such the compound of the invention may comprise a conjugation group. The conjugation group may, for example, be a targeting moiety which enhances delivery and/or uptake of the oligomeric compound of the invention to the intended site of action. In some embodiments, the conjugate group is a liver-targeting group which enhances the delivery and/or uptake of the oligomeric compound of the invention to the liver, such as to hepatocytes. Sterols such as cholesterol and tocopherol, as well as GalNAc conjugates are know liver-targeting conjugates. Suitably, group C is covalently joined to the oligomeric complex via a further region B. The beneficial use of biocleavable or physiological labile linkers to join a functional group C to an oligomer is reported in WO2014/076195, which is hereby incorporated by reference. The use of a region B to link a region C or region C-Y to an oligomer allows for the predictable cleavage of the conjugation group at the intended target tissue/cell, allowing the delivery of active and potent oligomers. The linking of lipophilic conjugates, such as sterols, is particularly beneficial.

The invention provides for an oligomeric compound (an oligomer) which comprises a first oligomer region (region A), a second oligomer region (A') and a region of 1, 2, 3, 4 or 5 phosphodiester linked DNA nucleotides (region B), and a third region (region C), wherein the biocleavable linker region (B) is positioned between the first oligomer region (region A), a second oligomer region (A'). Suitably, group C is covalently joined to the oligomeric complex via a further region B'.

Region C may, for example be covalently linked to region A or region A', or a linking group (Y) which is covalently linked to region A or region A'.

Region C, or C-Y, when present may, for example be covalently linked to region A or region A', or a linking group (Y) which via a further physiologically labile group (B'). Region B' may be as according to region B, or may be a different linkage group.

Region B may, for example be a region of at least one phosphodiester linked DNA or RNA (such as DNA), such as two, three, four or five phosphodiester linked DNA or RNA nucleosides (such as DNA nucleosides). Regions B and B' may, in some embodiments have the same structure, e.g. the same number of DNA/RNA nucleosides and phosphodiester linkages and/or the same nucleobase sequence. In other embodiments Regions B and B' may be different. By way of example such poly oligomeric compounds may have a structure such as: (5'-3' or 3'-5') Conjugate-PO-ON-PO'-ON', wherein conjugate is region C, PO is region B, PO' is region B', and ON 1 is region A, and ON' is region A'. In some embodiments, the functional group (C), such as a conjugate group may be covalently linked to a first oligomer via a non-nucleotide cleavable linker (B') such as a peptide linker, such as a lysine linker such as mono or poly lysine, e.g. a tri-lysine or di-lysine linker. Such polylysine linkers may be used with e.g. carbohydrate conjugates such as GalNAc conjugates, such as trivalent GalNAc conjugates. The functional group, such as a conjugate group (C) and biocleavable linker (B'), e.g. C-B'~ may further be joined to a further linker group (Y) which links region C with the first region.

By way of a non-limiting explanation, the poly oligomeric compounds of the invention are referred to as the oligomeric compound here—they are "poly oligomeric" as although they form a single covalently attached entity, upon delivery to a cell, which may be their intended target site in the body, for a non-limiting example, a hepatocyte, it is considered the linker groups (B) are cleaved, releasing separate oligomers into the target cell.

It should be understood that region A' may, in some embodiments, comprise multiple further oligomeric compounds (such as a further 2 or 3 oligomeric compounds) linked in series via biocleavable linkers, for example: Conjugate-PO-ON-PO-ON'-PO"-ON", or Conjugate-PO-ON-[PO-ON']n, wherein n may, for example be 1, 2 or 3, and each ON' may be the same or different, and if different may have the same or different targets. Alternatively two or more oligomer regions may be joined to a common linking group, each via a independent region B (i.e. the oligomer region's are linked in parallel).

When referring to oligomer regions, a first oligomer region may be designated A, and subsequent oligomer regions A', and if present A". In some non-limiting embodiments, one or more oligomer regions (such as A, A & A', or A & A'& A") comprise at least one sugar modified nucleoside analogue, for example at least one LNA unit. The oligomer region(s) may therefore be LNA oligomers.

Each oligomer region (A, A' or A") is 7-26 nucleosides in length, wherein the nucleosides within the oligomer region(s) are other than phosphodiester. In some embodiments, the nucleoside linkages, or at least 70% of the nucleoside linkages within each oligomer region (A, A' and A") are phosphorothioate linkages.

The present invention provides for an oligonucleotide comprising i) a first region (A) of a contiguous sequence of 7-26 phosphorothioate linked nucleosides; ii) a second region (A') of a contiguous sequence of 7-26 phosphorothioate linked nucleosides; wherein the first and the second regions are covalently linked via iii) at least one region (B) of 1-5 physiologically labile nucleotides, such as 1-5 phosphodiester linked nucleotides, such as DNA [or RNA] nucleosides. The oligonucleotide (compound of the invention) may therefore be described as an oligonucleotide complex or poly-oligomer. In some embodiments, the compound of the invention comprises a single contiguous nucleotide sequence which comprises the first oligomer region (A) a region (B) of 1-5 physiologically labile nucleotides, such as 1-5 phosphodiester linked nucleotides, such as DNA [and/or RNA] nucleosides, and a second oligomer (A') region (A-B-A').

In some embodiments, the compound of the invention comprises a single contiguous nucleotide sequence which comprises the first oligomer region (A) a region (B) of 1-5 physiologically labile nucleotides, such as 1-5 phosphodiester linked nucleotides, such as DNA [and/or RNA] nucleosides, a second oligomer (A') region followed by a further region (B) (which may be denoted B') of 1-5 physiologically labile nucleotides, such as 1-5 phosphodiester linked nucleotides, such as DNA [and/or RNA] nucleosides, followed by a third oligomer region (A"), i.e. A-B-A'-B'-A". Such linear compounds may further comprise a functional e.g. a conjugate group (C), which may, by example, be covalently attached to oligomer A or A', or a or A" (when present). The functional or conjugate group may be attached to the single contiguous nucleotide sequence (e.g. A-B-A' or A-B-A'-B'-A") via a linker (Y). The functional or conjugate group (C) or (C-Y) may further be attached to the single contiguous nucleotide sequence via a further region (B) of 1-5 physiologically labile nucleotides, such as 1-5 phosphodiester linked nucleotides, such as DNA [and/or RNA] nucleosides.

In some embodiments, region A-region B and region A' form a single contiguous nucleotide sequence of 15-50, such as 15-40, 15-35, 15-30, 15-25, 15-24 nucleotides in length.

In some embodiments, the compound of the invention comprises two or more oligomer regions (e.g. A, A' and if present A") wherein each oligomer region is covalently attached to a linking group (F) (e.g. a branching group to which each of the oligomers are attached) via a region (B) of 1-5 physiologically labile nucleotides, such as 1-5 phosphodiester linked nucleotides, such as DNA [and/or RNA] nucleosides. A functional or conjugate group may be attached to either one or more of oligomer regions or to the linking group. By way of a non-liming example a tri-lysine linker may be used to join two, three or four oligomers together, or optionally two or three oligomers and a functional/conjugate group. It will be recognized that such a peptide linking group may in itself be physiologically labile, and as such, a peptide linking group may, in some embodiments be the physiological labile linker (B) which joins the two or more oligomer regions. Alternatively, at least one or each oligomer region may be linked to such a peptide linker group via a region (B) of 1-5 physiologically labile nucleotides, such as 1-5 phosphodiester linked nucleotides, such as DNA [and/or RNA] nucleosides. The advantage of using a nucleotide based region B is that cleavage will result in a predictable oligomer product, and as such full efficacy of the oligomer can be retained and delivered to the desired site of therapeutic activity.

Peptide linkers, such as di and trilysine are used a scaffolds for conjugate delivery of siRNAs, and as such the linking group (F) may form part of or be attached to a conjugate group, for example a carbohydrate conjugate group, such as a galactose group, such as a GalNAc group, such as a GalNAc cluster.

In some embodiments the invention provides for a compound (an oligonucleotide) comprising i) a first region (A) of a contiguous sequence of 7-26 phosphorothioate linked nucleosides; ii) a second region (A') of a contiguous sequence of 7-26 phosphorothioate linked nucleosides; wherein the first and the second regions, and optionally further regions of 7-26 phosphorothioate linked nucleosides (e.g. A"), are covalently linked, via a non-nucleotide or conjugate (C) or linking moiety, wherein each of the first (A) and second (A') and optionally further (A") regions are independently or dependently linked to the conjugate or linking moiety via a region (B) of 1-5 physiologically labile nucleotides, such as 1-5 phosphodiester linked nucleotides, such as DNA [and/or RNA] nucleosides.

Region C~, or C-Y~, may, in some embodiments, be covalently attached to one of the regions A, A' or A" (oligomer region), via a phosphorus containing linkage group (illustrated by the ~. The phosphorus linkage group, may, for example, be a phosphate (phosphodiester), a phosphorothioate, a phosphorodithioate or a boranophosphate group. In some embodiments, this phosphorus containing linkage group is positioned between the oligomer region and a linker region (Y) which is attached to region C. In some embodiments, the phosphate group is a phosphodiester. In some embodiments, region C or C-Y~ may be covalently joined (linked) to region B' via a phosphate nucleoside linkage, such as those described herein, including phosphodiester or phosphorothioate, or via an alternative group, such as a triazol group.

In some embodiments, region C is an activation group, such as an activation group for use in conjugation. In this respect, the invention also provides activated oligomeric compound (the compound of the invention with an activation group), e.g. an intermediate which is suitable for subsequent linking to a conjugation or other functional group, such as suitable for conjugation.

In some embodiments, region C is a reactive group, such as a reactive group for use in conjugation. In this respect, the invention also provides an intermediate comprising the oligomer complex which is suitable for subsequent linking to a conjugation or other functional group, such as suitable for conjugation. The reactive group may, in some embodiments comprise an amine of alcohol group, such as an amine group.

In some embodiments the internucleoside linkages within regions A, A' and A" (i.e. the oligomer regions) each comprises at least 50%, such as at least 75%, such as at least 90% phosphorothioate linkages. In some embodiments, all the internucleoside linkages in the oligomer regions are other than phosphodiester, such as are phosphorothioate linkages.

In a preferred embodiment, region B (B' and B") each comprise 1, 2, 3, 4 or 5 contiguous phosphodiester linked nucleotides, such as DNA nucleosides.

The oligomeric complex of the invention may also be referred to as the oligomeric compound, or oligomeric compound conjugate (when C is present and is a conjugate group). The invention provides for a pharmaceutical composition comprising the oligomeric compound of the invention and a pharmaceutically acceptable diluent, carrier, salt or adjuvant.

The invention provides for the oligomeric compound according to the invention for use in the inhibition of a nucleic acid target in a cell. In some embodiments the use is in vitro. In some embodiments the use is in vivo. The oligomer regions of the compound of the invention may, in some embodiments target the same nucleic acid target, for example a mRNA or viral RNA.

The invention provides for the oligomeric compound according to the invention for use in the inhibition of two or more independent (i.e. different) nucleic acid targets in a cell. In some embodiments the use is in vitro. In some embodiments the use is in vivo. When targeting two or more independent nucleic acid targets, the oligomer regions A, A' and if present A" may comprise non-identical nucleobase sequences. The contiguous nucleobase sequence of each oligomer region may therefore be different.

In some embodiments the compounds of the invention are capable of inhibiting the expression of one or two or three or more targets in a cell which is expressing said target(s). The cell, for example may be a mammalian cell, such as a human cell. In some embodiments at least one of the targets is selected from the mRNA, viral and/or microRNA targets listed herein, including the targets listed in table 2 (microRNA targets).

The invention provides for the oligomeric compound according to the invention for use in the inhibition of a microRNA target in a cell. In some embodiments the use is in vitro. In some embodiments the use is in vivo. In some embodiments the compounds of the invention are capable of inhibiting the expression of a (or more, such as 2 or 3) microRNA target(s) in a cell which is expressing said microRNA target(s). The cell, for example may be a mammalian cell, such as a human cell.

The invention provides for the oligomeric compound according to the invention for use in the inhibition of two or more independent (i.e. different) microRNA targets in a cell. In some embodiments the use is in vitro. In some embodiments the use is in vivo.

The invention provides for the oligomeric compound according to the invention for use in the inhibition of one or more mRNA targets in a cell. In some embodiments the use is in vitro. In some embodiments the use is in vivo. In some embodiments the compounds of the invention are capable of inhibiting the expression of a (or more, such as 2 or 3) mRNA target(s) in a cell which is expressing said mRNA target(s). The cell, for example may be a mammalian cell, such as a human cell.

The invention provides for the oligomeric compound according to the invention for use in the inhibition of a viral RNA target in a cell. In some embodiments the use is in vitro. In some embodiments the use is in vivo.

The invention provides for the oligomeric compound according to the invention for use in the inhibition of two or more (such as three) independent (i.e. different) mRNA targets in a cell. In some embodiments the use is in vitro. In some embodiments the use is in vivo. In some embodiments at least one of the mRNA targets is selected from the mRNA targets listed herein.

The invention provides for the oligomeric compound of the invention for use in medicine, such as for use as a medicament.

The invention provides for the oligomeric compound of the invention for use in the treatment of a medical disease or disorder.

The invention provides for the use of the oligomeric compound of the invention for the preparation of a medicament for the treatment of a disease or disorder, such as a metabolic disease or disorder.

The invention provides for a method of treatment of a disease or disorder in a subject in need of treatment, said method comprising the steps of administering a pharmaceutical composition comprising the oligomeric compound of the invention to said subject in a therapeutically effective amount.

The invention provides for a method of inhibiting the expression of one (or more, such as two or three) target gene(s) in a cell, said method comprising administering the oligomeric compound according to the invention to a cell which is expressing said target gene(s), suitably in an amount effective to reduce the expression of the target gene in said cell. In some embodiments the method is in vitro (i.e. not in an organism, but may be in a (e.g. ex-vivo) cell or tissue). In some embodiments the method is in vivo.

The oligomeric compound of the invention may comprise an LNA oligomer (e.g. as region A, A' and/or A"). In some embodiments, region A and region A' are both LNA oligomers. In some embodiments, region A and region A' and A" are all LNA oligomers.

In some embodiments, such as in a non-limiting aspect when regions A and optionally A' (and if present optionally A") are LNA oligomers, region C may be a conjugate. Such as a targeting moiety, may, for example, be a conjugate which targets the compound of the invention to the liver (a liver-targeting conjugate moiety). The conjugate may, for example be or comprise a sterol, such as cholesterol or tocopherol, or may be or comprise a (non-nucleotide) carbohydrate, such as a GalNac conjugate, such as a GalNac cluster, e.g. triGalNac, or another conjugate as described herein. Such compounds may comprise a linker group Y between the conjugate group and an oligomer region, optionally via a region B.

The compound of the invention may therefore, in some embodiments, comprise at least one LNA antisense oligomer region (which may be referred to as region A herein) covalently linked to an asialoglycoprotein receptor targeting moiety conjugate moiety, such as a GalNAc moiety, which may form part of a further region (referred to as region C). An LNA antisense oligomer comprises at least one LNA unit (nucleoside).

The compound of the invention may therefore comprise an LNA antisense oligomer region covalently joined to (e.g. linked to) a (non-nucleoside) carbohydrate or a sterol moiety, such as a carbohydrate conjugate moiety or a cholesterol moiety. In some embodiments the carbohydrate moiety is not a linear carbohydrate polymer. The carbohydrate moiety may however be multi-valent, such as, for example 2, 3, 4 or 4 identical or non-identical carbohydrate moieties may be covalently joined to the oligomer, optionally via a linker or linkers.

The invention provides for a poly oligomeric complex of comprising a contiguous nucleotide sequence of formula $[LNA_s]_{7-18}$-$[DNA]_{1-5}$-$[LNA_s]_{7-18}$, and a non-nucleobase conjugate, such as a sterol (e.g. cholesterol or tocopherol) or a GalNAc conjugate moeity, for example a trivalent GalNAc conjugate, such as a conjugate moeity selected from the group consisting of any one of Conj1, 2, 3, 4, 1a, 2a, 3a, 4a, or other trivalent GalNAc conjugates, such as those disclosed herein. Subscript s refers to a phosphorothioate linkage. At least one internucleoside linkage within or adjacent to the -$[DNA]_{1-5}$-region are phosphodiester linkages. In some embodiments, all internucleoside linkages within or adjacent to the -$[DNA]_{1-5}$-region are phosphodiester linkages. In some embodiments, the -$[DNA]_{1-5}$-region has 2, 3, 4 or 5 contiguous DNA nucleoside which are joined by phosphodiester linkages. In such an embodiment, the internucleoside linkages between the -$[DNA]_{2-5}$- are phosphodiester linkages, and optionally the internucleoside linkages between region -$[DNA]_{1-5}$ and the LNA regions $[LNA_s]_{7-18}$ are independently phosphorothioate or phosphodiester linkages, such as both phosphodiester or both phosphorothioate, or one phosphodiester and one phosphorothioate. In the embodiment when the DNA region is a single DNA nucleoside, at least one or both the internucleoside linkages adjacent to the DNA region is a phosphodiester, and if only a single phosphodiester, the other may be a phosphorothioate. The region -$[DNA]_{1-5}$ may be as defined as described by region B herein—i.e. may be a physiologically cleavable nucleoside linker region. Each $[LNA_s]_{7-18}$ is a LNA phosphorothioate oligomer, and may for example be independently selected from the group consisting of an LNA gapmer, an LNA mixmer or an LNA totalmer. The GalNAc conjugate may for example be located 5' or 3' to the contiguous nucleotide sequence. In a preferred embodiment, at least one of the LNA oligomers, or both the poly oligomer conjugate is a LNA totalmer of 7-12, such as 8, 9 or 10 nucleotides in length. In some embodiments, the LNA totalmer may comprise only LNA nucleotides, such as beta-D-oxy LNA nucleoside, which are linked by phosphorothioate linkages. For example the poly oligomer conjugate may comprise a contiguous nucleositide sequence $[LNA_s]_{7-10}$-$[DNA]_{1-5}$-$[LNA_s]_{7-10}$, such as $[LNA_s]_{7-10}$-$[DNA]_2$-$[LNA_s]_{7-10}$ or $[LNA_s]_{7-10}$-$[DNA]_3$-$[LNA_s]_{7-10}$ or $[LNA_s]_{7-10}$-$[DNA]_4$-$[LNA_s]_{7-10}$. In one embodiment the contiguous nucleositide sequence comprises $[LNA_s]_8$-$[DNA]_{1-5}$-$[LNA_s]_8$, such as $[LNA_s]_8$-$[DNA]_2$-$[LNA_s]_8$, $[LNA_s]_8$-$[DNA]_3$-$[LNA_s]_8$, or $[LNA_s]_8$-$[DNA]_4$-$[LNA_s]_8$. Such poly oligomeric complexes are particularly useful to target microRNAs, such as mature microRNAs. By utilising a first LNA oligomer region which targets a first target (e.g. a mRNA, a microRNA, or a viral sequence), and a second LNA oligomer region which targets a second target (e.g. a mRNA, a microRNA, or a viral sequence), single compounds can be made which target two distinct targets, for example, the first oligomer region may target ApoB, and the second oligomer region may target another mRNA, such as mtGPAT mRNA, for example:

By utilising a first LNA oligomer regions (e.g. [LNA$_s$]$_{7-10}$) which targets one microRNA, and a second LNA oligomer region which targets a second microRNA, single compounds can be made which target two different microRNA targets, for example miR-21 and miR-221, both of which are indicated in hepatocellular carcinoma. Alternatively the first and the second may target the same microRNA, such as e.g. miR-122, miR-21, miR-155, miR-33, miR-221, which allows two oligomers to be delivered to the target cell for a single conjugate moiety.

This of particular importance for receptor mediate conjugate targeting, such as with asialoglycoprotein receptor conjugates, where the receptor mediated uptake of e.g. GalNAc conjugated oligomers is limited by the availability of free receptors on the surface of the target cell, the use of poly-oligomer conjugates allows for enhanced delivery to the target cell. It is also important to avoid complete saturation of cell-surface receptors which are performing an important biological function, the use of the poly-oligomer strategy therefore allows for effective delivery of sufficient compound to ensure relevant pharmacology, whilst reducing the risk of side effects due to receptor saturation/competition by the conjugate moiety. The use of the poly-oligomer conjugate therefore provides an effective solution for enhancing the therapeutic index—increased oligomer delivery and activity with a reduction of undesirable side-effects.

DESCRIPTION OF THE INVENTION

Figure 1:
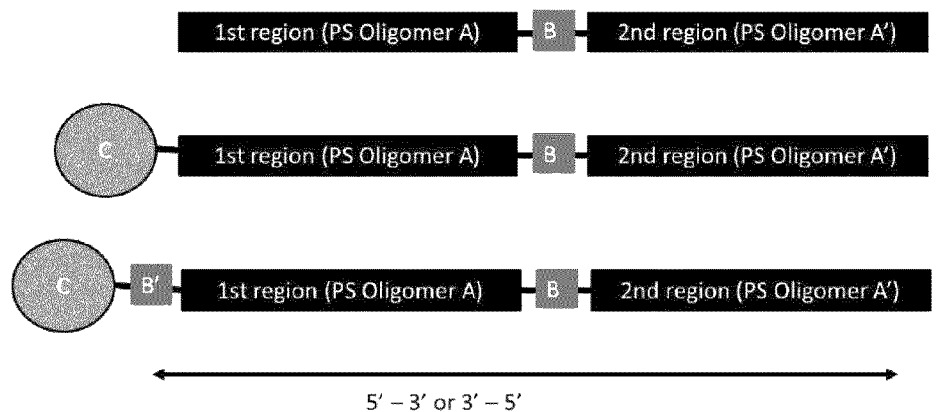
FIG. 1: Examples of poly-oligomers using a bio-cleavable linker (B) between two oligomer regions (A and A'), optionally covalently joined to a functional group (C), which may further be attached to the first (or the second) oligomer via a second bio-cleavable linker (B). A and A' may be LNA oligomers, such as LNA gapmers, mixmers or totalmers. Region C may be a conjugate, such as a targeting conjugate, e.g. (for liver targeting) a sterol or a GalNAc conjugate. Region B and B' may be, for example a region of 1, 2, 3, 4 or 5 phosphodiester linked DNA nucleosides.

In some embodiments, the invention provides for a poly oligomeric compound which may comprise the first region (region A), the second region (region B) and the third region (region C), wherein the first region is covalently linked to at least one further oligomeric compound (region A'), wherein the first region (region A) and region A' are covalently linked via a biocleavable linker (region B'), which may be, by way of example, as according to the second region as disclosed here, for example a region of at least one phosphodiester linked DNA or RNA (such as DNA), such as two, three, four or five phosphodiester linked DNA or RNA nucleosides (such as DNA nucleosides). Regions B and B' may, in some embodiments have the same structure, e.g. the same number of DNA/RNA nucleosides and phosphodiester linkages and/or the same nucleobase sequence. In other embodiments Regions B and B' may be different. By way of example such poly oligomeric compounds may have a structure such as: (5'-3' or 3'-5') Conjugate-PO-ON-PO'-ON', wherein conjugate is region C, PO is region B, PO' is region B', and ON 1 is region A, and ON' is region A'

It should be understood that region A' may, in some embodiments, comprise multiple further oligomeric compounds (such as a further 2 or 3 oligomeric compounds) linked in series (or in parallel) via biocleavable linkers, for example: Conjugate-PO-ON-PO-ON'-PO"-ON", or Conjugate-PO-ON-[PO-ON']n, wherein n may, for example be 1, 2 or 3, and each ON' may be the same or different, and if different may have the same or different targets.

The Oligomer

The term "oligomer" in the context of the present invention, refers to a molecule formed by covalent linkage of two or more nucleotides (i.e. an oligonucleotide). Herein, a single nucleotide (unit) may also be referred to as a monomer or unit. In some embodiments, the terms "nucleoside", "nucleotide", "unit" and "monomer" are used interchangeably. It will be recognized that when referring to a sequence of nucleotides or monomers, what is referred to is the sequence of bases, such as A, T, G, C or U.

In the context of the present invention the term "oligomer", as used herein may refer to the contiguous oligonucleotide sequence of nucleotides or the compound of the invention, or a oligomer region which forms part of the compound of the invention, such as A, A' and A", which may, in some embodiments form part of the contiguous oligonucleotide sequence of nucleotides or the compound of the invention.

The present invention employs poly-oligomeric compounds (also referred herein as oligomer compounds) for use in modulating, such as inhibiting a target nucleic acid in a cell. The oligomer compound comprises at least two oligomer regions, e.g. (A and A') and may comprise further oligomer regions (e.g. A") The oligomer regions may have a length of 7-26 contiguous nucleotides and each oligomer region may be flanked by a bio-cleavable region (region B), which may, for example, be a further region of 1-10 contiguous nucleotides (region B), which comprise at least one phosphodiester linkage. Other physiological labile nucleoside regions may be used.

In some embodiments, the oligomer compounds of the invention are covalently linked to a conjugate group, a targeting group, a reactive group, an activation group, or a blocking group, optionally, via a short region comprising (e.g. 1-10) of phosphodiester linked DNA or RNA nucleoside(s).

In some embodiments, the compound of the invention does not comprise RNA (units). In some embodiments, the compound according to the invention forms a single contiguous sequence), optionally linked to a function group, such as a conjugate group, and is such a linear molecule or is synthesized as a linear molecule. The oligomeric compound may therefore be single stranded molecule. In some embodiments, the oligomer does not comprise short regions of, for example, at least 3, 4 or 5 contiguous nucleotides, which are complementary to equivalent regions within the same oligomeric compound (i.e. duplexes). The oligomer, in some embodiments, may be not (essentially) double stranded. In some embodiments, the oligomer is essentially not double stranded, such as is not a siRNA.

Oligomer regions A, A' and if present A" are phosphorothioate oligomers, i.e. at least 70% of the internucleoside linkages within each oligomer region A, A' and if present A", are phosphorothioate linkages, such as at least 80% or at least 90% or all of the internucleoside linkages present I oligomer regions A, A' and A" (if present), are phosphorothioate.

In some embodiments, oligomer regions A, A' and if present A" may form a single contiguous oligonucleotide sequence. Regions A, A' and A" are interspaced by regions B, for example regions of 1, 2, 3, 4, or 5 phosphodiester linked DNA nucleosides.

When region B comprises only 1 nucleoside, at least one, or both of the internucleoside linkages between the region B nucleoside (e.g. a DNA nucleoside) may be phosphodiester linkages. When region B comprises only 2 or more nucleosides, the internucleoside linkages between the region B nucleoside (e.g. the DNA nucleosides) may be phosphodiester linkages and/or may be another internucleoside linkage, such as phosphorothioate linkages.

The oligomers of the invention, such as A, A' and if present A", do not form part of a siRNA complex.

The oligomers of the invention, such as A, A' and if present A", are non-complementary, e.g. they do not hybridize to one another to form a region of more than 8 or in some embodiments more than 6 contiguous base pairs. In some embodiments, regions A and A" do not hybridize to one another to form a region of more than 4 contiguous base pairs. Exemplary base pairs may be between A-T, G-C or A-U. In the case there are three oligomer regions, A, A' and A", the non-complementarity is between A and A', and A' and A", as well as A and A".

The oligomer regions A, A' and if present A" are not in the form of a duplex with a (substantially) complementary oligonucleotide—e.g. is not an siRNA.

In some embodiments, oligomer regions A, A' and A" share the same contiguous nucleotide sequence. In some embodiments, oligomer regions A and A' share the same contiguous nucleotide sequence. In this respect the invention provides for a single compound which can be used to deliver multiple copies of an oligomer (i.e. with the same contiguous nucleobase sequence and optionally the same chemical modifications) to the target tissue.

Length of Oligomer Regions

Each oligomer region (e.g. A, A' and A"), may be between 7-26 nucleotides, such as 8, 9, 10, 11, 12, 13, 14, 15, 16, 17, 18, 19, 20, 21, 22, 23, 24, 25 or 26. It is recognized that in the embodiment where the oligomer regions, A and A' (and optionally A") form a single contiguous nucleotide sequence (see FIG. 1), the use of shorter oligomer regions is highly preferred, such as between 7 and 18 nucleotides, such as 8, 9, 10, 11, 12, 13, 14, 15, 16 and 17 nucleotides, such as 7-16 nucleotides or 7-14 nucleotides, or 7-12, nucleotides, or in some embodiments, for example when using LNA totalmers, between 7-12 or 7, 8, 9 or 10 contiguous nucleotides. Suitably the combined length of the oligomer regions, and the cleavable region(s) B is less than 40 nucleotides, such as less than 38 nucleotides, such as less than 36 nucleotides, such as less than 34 nucleotides, such as less than 32 nucleotides, such as less than 30 nucleotides, such as less than 28 nucleotides, such as less than 26 nucleotides, such as less than 24 nucleotides, such as less than 22 nucleotides, such as less than 20 nucleotides. The minimum length of the combined length of the oligomer regions, and the cleavable region(s) B is 15 nucleotides, and may be therefore 16 nucleotides, 17 nucleotides or 18 nucleotides.

Figure 2:
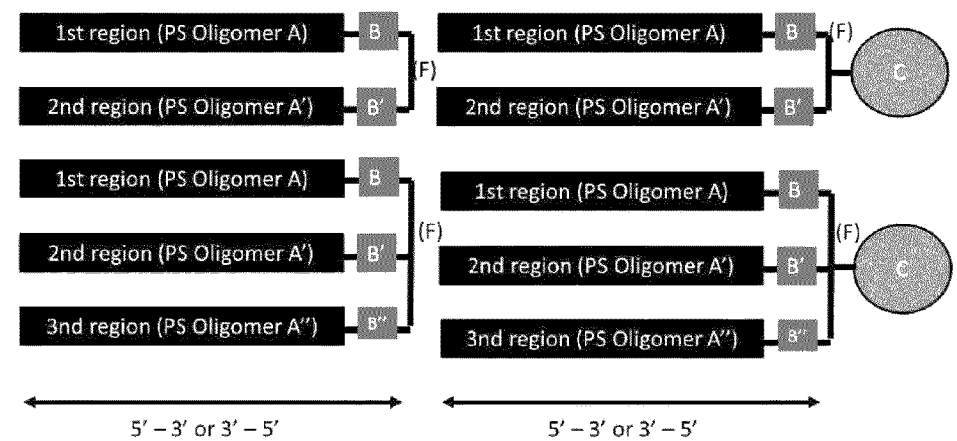
FIG. 2: Examples of branched poly-oligomers, where each oligomer (A, A' and A") is attached to a non-nucleotide linker (F) via a bio-cleavable region (B, B' and B"). The non-nucleotide linker (F) may be attached to a functional group (C), or may be a functional group (C). Region C may be a conjugate, such as a targeting conjugate, e.g. (for liver targeting) a sterol or a GalNAc conjugate. Region B, B' and B" may be, for example a region of 1, 2, 3, 4 or 5 phosphodiester linked DNA nucleosides.

In the embodiment where the oligomer regions do not form a single contiguous nucleotide sequence (e.g. see FIG. 2), such as are joined in parallel, the length of each oligomer region (A, A' or A"), may be between 7 and 26 nucleotides. In some embodiments the length of an (or all) oligomer region may be between 7-20 nucleotides, such as 7-18 nucleotides or 7-18 nucleotides or 7-16 nucleotides. In some embodiments the length of an (or all) oligomer region may be between 8-20 nucleotides, such as 8-18 nucleotides or 8-18 nucleotides or 8-16 nucleotides. In some embodiments the length of an (or all) oligomer region may be between 12-20 nucleotides, such as 12-18 nucleotides or 12-18 nucleotides or 12-16 nucleotides. Such lengths are particularly suited for use with gapmer oligomers, such as LNA gapmer oligomer (regions).

In some embodiments, when the oligomer regions are joined in series (FIG. 1) or in parallel (FIG. 2), the length of an (or all) oligomer regions may be 7-12 nucleotides, such as 7-10 nucleotide, such as 7, 8, 9 or 10 nucleotides. Such lengths are particularly useful when using LNA mixmer or totalmer oligomers, such as oligomers which target a microRNA, such as a microRNA seed region.

In some embodiments, the oligomer regions comprise or consist of a contiguous nucleotide sequence of a total of from 10-22, such as 12-18, such as 13-17 or 12-16, such as 13, 14, 15, 16 contiguous nucleotides in length.

In some embodiments, the oligomer regions comprise or consist of a contiguous nucleotide sequence of a total of 10, 11, 12, 13, or 14 contiguous nucleotides in length.

In some embodiments, the oligomer regions consists of no more than 22 nucleotides, such as no more than 20 nucleotides, such as no more than 18 nucleotides, such as 15, 16 or 17 nucleotides. In some embodiments the regions comprises less than 20 nucleotides. It should be understood that when a range is given for an oligomer, or contiguous nucleotide sequence length it includes the lower an upper lengths provided in the range, for example from (or between) 10-30, includes both 10 and 30.

LNA Oligomer Regions

In some embodiments, at least one of the oligomer regions (A, A' and A" if present), is a LNA oligomer, for example an LNA antisense oligomer. In some embodiments, at least two of the oligomer regions (A and A') are LNA oligomers, such as an LNA antisense oligomer. In some embodiments, at least three of the oligomer regions (A, A' and A") are LNA oligomers, such as an LNA antisense oligomers.

In some embodiments the compound of the invention, such as the LNA oligomer, such as LNA antisense oligomer is conjugated to a carbohydrate moiety, such as a non-linear carbohydrate, such as a GalNac moieties, such as a tri-GalNac cluster. In some embodiments the compound of the invention, such as the LNA oligomer, such as LNA antisense oligomer is conjugated to an asialoglycoprotein receptor targeting moiety conjugate moiety, such as a GalNAc moiety (which may be region C). The carbohydrate moiety may be multi-valent, such as, for example 2, 3, 4 or 4 identical or non-identical carbohydrate moieties may be covalently joined to the oligomer, optionally via a linker or linkers (such as region Y).

In some embodiments, the LNA oligomer region(s), for example an LNA antisense oligomer, (which may be referred to as region A, A' or A" herein) comprising an antisense oligomer, is covalently linked to an asialoglycoprotein receptor targeting moiety conjugate moiety, such as a GalNAc moiety (which may be referred to as region C), optionally via a region B as defined herein. The carbohydrate moiety may be multi-valent, such as, for example 2, 3, 4 or 4 identical or non-identical carbohydrate moieties may be covalently joined to the oligomer ore region B, optionally via a (further) linker or linkers (such as region Y, e.g. a C6 alkyl linker).

Oligomer Regions (e.g. A, A' and if Present A")

In some embodiments, the each oligomer region may comprise a nucleic acid based oligomer, such as an antisense oligonucleotide. In some embodiments, each oligomer region comprises or consists of a phosphorothioate linked oligonucleotide, such as an antisense oligonucleotide, of 7-25 or 26 nucleotides in length. The oligomer region may be referred to as a "first region"—it will be recognized that the invention refers to embodiments where there are multiple first regions which may be the same or different. each oligomer region may comprise at least one modified nucleoside (a nucleoside analogue), such as at least one bicyclic nucleoside (e.g. LNA) or 2' substituted nucleoside. In some embodiments, some or all of the nucleosides each oligomer region may be modified nucleosides, also referred to as nucleoside analogues herein. In some embodiments, the modified nucleosides are sugar-modified (e.g. comprise a sugar or sugar surrogate moiety other than ribose or deoxy-ribose). LNA (also referred to as BNA is a preferred nucleoside modification. In some embodiments, at least one of the oligomer regions, such as all the oligomer regions are antisense oligomers (antisense oligonucleotide), such as a single stranded oligomer which comprises a sequence which is (independently or dependently) complementary to a nucleic acid target.

In some embodiments at least one of the oligomer regions, such as all the oligomer regions is a gapmer. In some embodiments at least one of the oligomer regions, such as all the oligomer regions is a mixmer. In some embodiments at least one of the oligomer regions, such as all the oligomer regions a totalmer.

In some embodiments, each oligomer region (e.g. A, A* and if present A") comprises at least one, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or 25 nucleoside analogues. In some embodiments the nucleoside analogues are (optionally independently selected from the group consisting of bicyclic nucleoside analogues (such as LNA), and/or 2' substituted nucleoside analogues, such as (optionally independently) selected from the group consisting of 2'-O-alkyl-RNA units, 2'-OMe-RNA units, 2'-amino-DNA units, 2'-AP, 2'-FANA, 2'-(3-hydroxy)propyl, and 2'-fluoro-DNA units, and/or other (optionally) sugar modified nucleoside analogues such as morpholine, peptide nucleic acid (PNA), CeNA, unlinked nucleic acid (UNA), hexitol nucleic acid (HNA). bicyclo-HNA (see e.g. WO2009/100320), In some embodiments, the nucleoside analogues increase the affinity of the first region for its target nucleic acid (or a complementary DNA or RNA sequence). Various nucleoside analogues are disclosed in Freier & Altmann; *Nucl. Acid Res.,* 1997, 25, 4429-4443 and Uhlmann; *Curr. Opinion in Drug Development,* 2000, 3(2), 293-213, hereby incorporated by reference.

In some embodiments, at least one or each oligomer region (e.g. A, A* and if present A"), such as the gapmer, mixmer or totalmer comprise at least one bicyclic nucleotide analogue, such as LNA. In some embodiments, at least one or each oligomer region (e.g. A, A* and if present A") comprises of at least one bicyclic nucleoside analogues (e.g. LNA) and/or 2' substituted nucleoside analogues. In some embodiments, the nucleoside analogues present in at least one or each oligomer region (e.g. A, A* and if present A") all comprise the same sugar modification. In some embodiments, at least one nucleoside analogue present at least one or each oligomer region (e.g. A, A* and if present A") is a bicyclic nucleoside analogue, such as at least 2, at least 3, at least 4, at least 5, at least 6, at least 7, at least 8, at least 9, at least 10, at least 11, at least 12, at least 13, at least 14, at least 15, at least 16, for example all nucleoside analogues (or in a totalmer all nucleosides) bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA. In some embodiments, at least one or each oligomer region (e.g. A, A* and if present A"), comprises of DNA and sugar modified nucleoside analogues, such as bicyclic nucleoside analogues and/or 2' substituted nucleoside analogues. In some embodiments, at least one or each oligomer region (e.g. A, A* and if present A"), comprises of DNA and LNA nucleoside analogues. In some embodiments, at least one or each oligomer region (e.g. A, A* and if present A") comprises LNA nucleoside analogues. In some embodiments, at least one or each oligomer region (e.g. A, A* and if present A") comprises only nucleoside analogues, and may include LNA nucleosides. In some embodiments, at least one or each oligomer region (e.g. A, A* and if present A") comprises only LNA nucleosides analogues.

WO05013901, WO07/027775, WO07027894 refers to filly 2' substituted oligomers, such as fully 2'-O-MOE. In some embodiments, the first region of the oligomer may comprise of 2' substituted nucleosides. WO07/027775 also refers to MOE, LNA, DNA mixmers for use in targeting microRNAs.

In some embodiments, at least one or each oligomer region (e.g. A, A* and if present A") do not comprise a region of more than 4 or 5 consecutive DNA units. Such oligomer regions may be (essentially) unable to recruit RNAseH.

The first region is covalently linked to a region B (may also be referred as the second region), such as via a 5' terminal or 3' terminal internucleoside linkage, such as a phosphodiester linkage. A phosphodiester linkage may therefore be positioned between the 5' most nucleoside of region A and the 3' most nucleoside of region B, and/or between the 3' most nucleoside of region A and the 5' most nucleoside of region B. In this respect, in some embodiments, there may be two region B covalently joined to (a) oligomer region A, one at the 5' terminus of a region A and one at the 3' terminus of a region A. The two region Bs may be the same or different. One region B may be joined to a further oligomer region (e.g. region A') see FIG. 1, or a non-nucleotide linker group (see FIG. 2), and the other may be joined to another further oligomer region (A"), or for example a functional group (C) optionally via a linker (Y), for example a sterol or GalNAc conjugate.

In some embodiments, some or all of the nucleosides of an or each oligomer region (e.g. A, A' and/or A") may be modified nucleosides, also referred to as nucleoside analogues herein, such as sugar modified nucleoside analogues, for example bicyclic nucleoside analogues (e.g. LNA) and/or 2' substituted nucleoside analogues. In some embodiments, the nucleoside analogues present in an or each oligomer region (e.g. A, A' and/or A") all comprise the same sugar modification, for example are all bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA.

The internucleoside linkages of an or each oligomer region (e.g. A, A' and/or A") comprise at t least 50%, such as at least 75%, such as at least 90%, such as 100% of the internucleoside linkages in the oligomer region are other than phosphodiester, such as phosphorothioate. In some embodiments, the internucleoside linkages other than phosphodiester are sulphur containing internucleoside linkages, such as phosphorothioate, phosphorodithioate and boranophosphate, such as phosphorothioate.

Region B (Also Referred to as the Second Region, Region B' and Region B", or Nuclease Susceptible Physiological Labile Linkages The oligomer regions (A, A' and if present A") are linked via at least one biocleavable region, referred to as region B herein (and where there is more than one region B, region B' and region B"). In some embodiments, region B comprises 1-10 nucleosides which form a physiologically labile region between oligomer regions, or between an (or each) oligomer region and a linking group (see FIG. 2). Regions of DNA phosphodiester nucleosides may be used, but other nucleotide regions may be used if they are suitably physiologically labile.

In some embodiments, the internucleoside linkage between the oligomer region (A, A' or if present A") and (each) second region B, is a phosphodiester linked to the first (or only) DNA or RNA nucleoside of region B comprises at least one phosphodiester linked DNA or RNA nucleoside.

The region B may, in some embodiments, comprise further DNA or RNA nucleosides which may be phosphodiester linked.

As explained herein, region B may also be used to join a functional group to the oligomeric region(s), optionally via a further linkage group (Y). The use of region B as a cleavable linker to join functional groups to oligomer is described in detail in PCT/EP2013/073858, which is hereby incorporated by reference.

In some embodiments a region B is further covalently linked to a third region which may, for example, be a conjugate, a targeting group a reactive group, and/or a blocking group.

In some aspects, the present invention is based upon the provision of a labile region, the second region, linking the first region, e.g. an antisense oligonucleotide, and a conjugate or functional group, e.g. a targeting or blocking group. The labile region comprises at least one phosphodiester linked nucleoside, such as a DNA or RNA nucleoside, such as 1, 2, 3, 4, 5, 6, 7, 8, 9 or 10 phosphodiester linked nucleosides, such as DNA or RNA. In some embodiments, the oligomeric compound comprises a cleavable (labile) linker. In this respect the cleavable linker is preferably present in region B (or in some embodiments, between region A and B).

In some embodiments, one (or more or all) region B may comprise or consists of at least one DNA or RNA nucleosides linked to the first region via a phosphodiester linkage. In some aspects, the internucleoside linkage between an oligomer region and second region is considered as part of region B.

In some embodiments, a (or more or each) region B comprises or consists of at least between 1 and 10 linked nucleosides, such as 1, 2, 3, 4, 5, 6, 7, 8, 9 or 10 linked DNA or RNA nucleotides. Whilst a region of DNA/RNA phosphodiester is considered important in the provision of a cleavable linker, it is possible that region B also comprises sugar-modified nucleoside analogues, such as those referred to under the first region above. However in some embodiments, the nucleosides of region B are (optionally independently) selected from the group consisting of DNA and RNA. In some embodiments, the nucleosides of region B are (optionally independently) DNA. It will be recognized that the nucleosides of region B may comprise naturally occurring or non-naturally occurring nucleobases. Typically, region B comprises at least one phosphodiester linked DNA or RNA nucleoside (which may, in some embodiments. be the first nucleoside adjacent to an oligomer). If region B comprises other nucleosides, region B may also comprise of other nucleoside linkages other than phosphodiester, such as (optionally independently) phosphorothioate, phosphodithioate, boranophosphate or methyl phosphonate. However, in other exemplified embodiments, all the internucleoside linkages in region B are phosphorothioate. In some embodiments, all the nucleosides of region B comprise (optionally independently) either a 2'-OH ribose sugar (RNA) or a 2'-H sugar—i.e. RNA or DNA. Between 1-5, or 1-4, such as 2, 3, 4 phosphate (phosphodiester) linked DNA nucleosides have been shown to be particularly useful in the compounds of the invention.

In some embodiments, the second region comprises or consists of at least between 1 and 10 (e.g. phosphodiester) linked DNA or RNA nucleosides, such as 1, 2, 3, 4, 5, 6, 7, 8, 9 or 10 (e.g. phosphodiester) linked DNA or RNA nucleotides.

In some embodiments, region B comprises no more than 3 or no more than 4 consecutive DNA or RNA nucleosides (such as DNA nucleosides). As such region B may be so short as it does not recruit RNAseH, an aspect which may be important in embodiments when region B does not form a part of a single contiguous nucleobase sequence which is complementary to the target. Shorter region Bs, e.g. of 1-4 nts in length may also be preferable in some embodiments, as they are unlikely to be the target of sequence specific restriction enzymes. As such it is possible to vary the susceptibility of the region B to endonuclease cleavage, and thereby fine-tune the rate of activation of the active oligomer in vivo, or even intra-cellular. Suitably, if very rapid activation is required, longer region Bs may be employed and/or region Bs which comprise the recognition sites of (e.g. cell or tissue specific or differentially expressed) restriction enzymes.

In some embodiments, a region B may be conjugated to a functional group (C), such as a conjugate, targeting reactive group, an activation group, or blocking group, optionally via a linker group (Y)m such as those provided herein. Functional groups may also be joined to an oligomer region, or the compound of the invention via other means, e.g. via phosphate nucleoside linkage (e.g. phosphodiester, phosphorothioate, phosphodithioate, boranophosphate or methylphosphonate) or a triazol group. In some aspects, the linkage group is the same as the region B between at least two of the oligomer regions, and as such may be a phosphodiester linkage.

In some embodiments the DNA or RNA nucleotides of an (or more or each) region B are independently selected from DNA and RNA nucleotides. In some embodiments the DNA or RNA nucleotides of an (or more or each) region B are DNA nucleotides. In some embodiments the DNA or RNA nucleotides of an (or more or each) region B are RNA nucleotides.

In the context of the second region, the term DNA and RNA nucleoside may comprise a naturally occurring or non-naturally occurring base (also referred to as a base analogue or modified base).

It will be recognized that, in some embodiments, an (or more or each) region B may further comprise other nucleotides or nucleotide analogues. In some embodiments, (or more or each) region B comprises only DNA or RNA nucleosides. In some embodiments, an (or more or each) region B comprises more than one nucleoside, the internucleoside linkages in an or each region B comprise phosphodiester linkages. In some embodiments, when an (or more or each) region B comprises more than one nucleoside, all the internucleoside linkages in the second region comprise phosphodiester linkages.

In some embodiments, at least two consecutive nucleosides of an (or more or each) region B are DNA nucleosides (such as at least 3 or 4 or 5 consecutive DNA nucleotides). In some embodiments the at least two consecutive nucleosides an (or more or each) region B are RNA nucleosides (such as at least 3 or 4 or 5 consecutive RNA nucleotides). In some embodiments the at least two consecutive nucleosides of the an (or more or each) region B are at least one DNA and at least one RNA nucleoside. The internucleoside linkage between a region A and region B may be a phosphodiester linkage. In some embodiments, when region B comprises more than one nucleoside, at least one further internucleoside linkage is phosphodiester—such as the linkage group(s) between the 2 (or 3 or 4 or 5) nucleosides adjacent to a region A.

A region B may be flanked on at least one side (either 5' or 3') by the first region, e.g. an antisense oligonucleotide, and on the other side (either 3' or 5' respectfully, via a further oligomer region (A'), or a conjugate moiety or similar group (e.g. a blocking moiety/group, a targeting moiety/group or therapeutic small molecule moiety), optionally via a linker group (i.e. between the second region and the conjugate/blocking group etc. moiety).

Sequence Selection in Region B:

In some embodiments, region B does not form a complementary sequence when the oligomer region (e.g. A, A' and/or A") and B is aligned to the complementary target sequence.

In some embodiments, region B does form a complementary sequence when the oligomer region (e.g. A, A' and/or A") and B is aligned to the complementary target sequence. In this respect region A and B together may form a single contiguous sequence which is complementary to the target sequence.

In some embodiments, the sequence of bases in region B is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in region B may be selected based upon a preferential cleavage activity in the desired target cell (e.g. liver/hepatocytes) as compared to a non-target cell (e.g. kidney). In this respect, the potency of the compound for target down-regulation may be optimized for the desired tissue/cell.

In some embodiments region B comprises a dinucleotide of sequence AA, AT, AC, AG, TA, TT, TC, TG, CA, CT, CC, CG, GA, GT, GC, or GG, wherein C may be 5-methylcytosine, and/or T may be replaced with U. In some embodiments region B comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-methylcytosine and/or T may be replaced with U. In some embodiments region B comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C and analogues thereof, wherein C may be 5-methylcytosine and/or T may be replaced with U. It will be recognized that when referring to (naturally occurring) nucleobases A, T, U, G, C, these may be substituted with nucleobase analogues which function as the equivalent natural nucleobase (e.g. base pair with the complementary nucleoside).

In some embodiments, the compound of the invention may comprise more than one conjugate group (or more than one functional group X—such as a conjugate, targeting, blocking or activated group or a reactive or activation group), such as 2 or 3 such groups. In some embodiments, region B is covalently linked, optionally via a [e.g. non-nucleotide] linker group), to at least one functional group, such as two or three functional groups. In some embodiments, the first region (A) may be covalently linked (e.g. via internucleoside linkages, such as phosphodiester linkages), to two region Bs, for example, one 5' and one 3' to the first region A, wherein each region B may be (optionally independently) selected from the region B described herein.

Multi Conjugate Oligomeric Compounds

In some embodiments, the compound of the invention comprise more than one conjugate region (region C), which may be the same or different. For example, in some embodiments, one of Conjugate 1 and Conjugate 2 are a carbohydrate or sterol conjugates and the other is a lipophilic conjugate.

The carbohydrate conjugate moiety (represented by Gal-Nac in the preceding formulas (e.g. when used as conj1 or conj2) may for example be selected from the group consisting of galactose, galactosamine, N-formyl-galactosamine, Nacetylgalactosamine, N-propionyl-galactosamine, N-n-butanoyl-galactosamine, and N-isobutanoylgalactose-amine. The lipophilic conjugate (e.g. when used as conj1 or conj2, and represented as palmotoyl in the preceding formulas) may be a hydrophobic group, such as a C16-20 hydrophobic group, a sterol, cholesterol. Other carbohydrate and lipophilic groups which may be used are, for example, disclosed herein.

The Target(s)

The poly oligomeric compounds of the invention may target one or more nucleic acid targets. In some embodiments each oligomer region targets the same nucleic acid target, and each oligomer region may therefore comprise the same nucleobase sequence (i.e. target the exact same nucleobase sequence of the target), or may have a different nucleobase sequence, i.e. when the nucleobase sequence of at least two, such as all, of the oligomer regions targets (i.e. is complementary to) the same nucleic acid target.

In some embodiments each oligomer region targets a different nucleic acid target, and each oligomer region may therefore comprise a different nucleobase sequence, wherein the nucleobase sequence of at least two, such as all, of the oligomer regions targets different nucleic acid targets. It will be recognized that when there are more than 2 oligomeric regions, such as three oligomer regions, two of the oligomer regions may target the same nucleic acid target, and the third oligomer region may target a different nucleic acid target. Oligomer regions may, for a non-limiting example, target a nucleic acid selected from the group consisting of a mRNA, a microRNA, a lncRNA (long non-coding RNA), a snRNA, snoRNA, and a viral RNA.

Exemplary, but not limiting mRNA and microRNA targets include for example:

The genes indicated in cancer, such as Hif1-alpha, survivin, Bcl2, Mcl1, Her2, androgen receptor, beta-catenin, human transforming growth factor TGF-beta2, ras, TNF-alpha, c-RAF, HSPs e.g. Hsp27, eIF-4E (e.g. ISIS-EIF4ER$_x$) STAT3 (e.g. ISIS-STAT3Rx), clusterin (e.g. OGX-011), AurkB, AurkA, PBK, miR-155, miR-21, miR-10b, mir-34 (see WO2011088309), miR-199a, miR-182. Other microRNA targets include miR-221.

The mRNAs of genes involved in inflammation, e.g. ICAM-1 (e.g. Alicoforsen), CD49d, VLA-4 osteopontin, miR-21 (psoriasis), Other medically relevant mRNA targets include CTGF (local fibrosis) and c-Raf-kinase (ocular disease). miR-29 (cardiac fibrosis), Factor XI (clotting), factor VII (clotting) miR15 miR-159 (post-MI modeling (post-MI modeling), miR-138 (bone-loss), mir-21 (see WO12148952) and mir214 (fibrosis)—see WO2012012716.

Metabolic disease or disorders targets, such as Apo-B (high LDL cholesterol, ACS), ApoCIII (high serum TG, diabetes), Apo(a) (cardiovascular disease), FGFR4 (obesity), GCCR (T2 diabetes), GCGR (T2 diabetes), PTP1B (T2 diabetes), DGAT2 (NASH), PCSK9 (hyperlipidaemia and related disorders), MtGPAT (obesity and NAFLD), miR-122 (high cholesterol), miR-33 (metabolic syndrome, atherosclerosis), miR-208 (chronic heart failure), miR-499 (chronic heart failure), miR-378 (cardio metabolic disease), mir-143 (vascular disease), miR-145 (vascular disease), miR-92 (peripheral arterial disease), miR-375 (diabetes), miR-27b (diabetes), miR-34a (diabetes), miR-199a, miR-27a (heart disease, ischemic), miR-338 (diabetes).

Metabolic diseases include, for examples, metabolic syndrome, obesity, hyperlipidemia, HDL/LDL cholesterol imbalance, dyslipidemias, e.g., familial combined hyperlipidemia (FCHL), acquired hyperlipidemia, statin-resistant hypercholesterolemia, coronary artery disease (CAD), and coronary heart disease (CHD), atherosclerosis, heart disease, diabetes (I and/or II), NASH, acute coronary syndrome (ACS), Viral diseases: miR-451(polycythemia), miR-122 (HCV), HBV, HCV, BKV, etc. Severe and rare diseases include SMN2 (spinal muscular atrophy), TTR (TTR amyloidosis), GHr (acromegaly), AAT (AATD associated liver disease), Dystophin (Duchennes muscular dystrophy).

In some embodiments, the oligomer of the invention targets a liver expressed nucleic acid, such as a liver expressed mRNA, such as PCSK9, ApoB, or MtGPAT. In some embodiments, the oligomer of the invention targets PCSK9 mRNA. In some embodiments, the oligomer of the invention targets ApoB mRNA. In some embodiments, the oligomer of the invention targets a liver expressed microRNA, such as miR-122.

Suitable Oligomer regions: In some embodiments, an (or more or all) oligomer region of the invention targets a liver expressed microRNA, such as miR-122 Oligomers targeting miR-122 are disclosed in WO2007/112754, WO2007/112753, WO2009/043353, and may be mixmers, such as SPC3649, also referred to as miravirsen (which has the sequence 5'-CcAttGTcaCaCtCC-3' (SEQ ID NO 1), where capital letters are beta-D-oxy LNA, small letters are DNA, fully phosphorothioate and LNA C are 5-methyl cyctosine), or a tiny LNA, such as those disclosed in WO2009/043353 (e.g. 5'-ACACTCC-3', 5'-CACACTCC-3', 5'-TCACACTCC-3') where capital letters are (optionally beta-D_oxy) LNA, fully phosphorothioate and LNA Cs are, optionally 5-methyl cytosine). In some embodiments, the miR-122 targeting oligomers have a length of 8, 9, 10, 11, 12, 13, 14, 15, 16, 17 or 18 nucleotides in length. In some embodiments, the miR-122 targeting oligomer region comprise a sequence which is fully complementary to miR-122 as measured across the length of the oligomer, and preferably include the sequence 5'-CACACTCC-3'. According to miRBase, the mature microRNA-122 sequence is 5' uggagugugacaauggguguugu 3' (SEQ ID NO 2). In some embodiments, the oligomer region targeting a microRNA such as miR-122, is complementary to a corresponding region of the microRNA across the length of the oligomer and in some embodiments the 3' nucleoside of the oligomer is complementary to (i.e. aligns to) the first, second, third or fourth 5' nucleotides of the microRNA, such as miR-122, such as the second 5' nucleotide of the microRNA, such as miR-122.

In some embodiments, an (or more or all) oligomer of the invention targets a liver expressed microRNA, such as miR-33 (miR-33a and/or miR-33b), which may be used in treating metabolic disorders such as atherosclerosis (see for example WO2010/120508). Oligomer regions targeting miR-33a1b may comprise a nucleobase sequence selected from the group consisting of 5'-TACAATGCA-3', 5'-ACAATGCAC-3', 5'-ACAATGCA-3' & 5'-CAATGCA-3', specific oligomer regions targeting miR-33a/b may be 5'-TACAATGCA-3', 5'-ACAATGCA-3' & 5'-CAATGCA-3', where capital letters are (optionally beta-D-oxy) LNA, fully phosphorothioate and LNA Cs are, optionally, 5-methyl cyctosine). According to miRBase, the mature microRNA-33a sequence is 5'-GUGCAUUGUAGUUG-CAUUGCA-3' (SEQ ID NO 3), and miR-33b is 5' GUG-CAUUGCUGUUGCAUUGC-3' (SEQ ID NO 4).

In some embodiments, the oligomer of the invention targets a liver expressed microRNA, such as miR-21, which may be used in treating diseases such as liver fibrosis or hepatocellular carcinoma. A compound of the invention may comprise (or more or all) oligomer regions targeting miR-21 may comprise a nucleobase sequence selected from the group consisting of 5'-TGATAAGCT-3', 5'-GATAAGCT-3', 5'-ATAAGCT-3', specific oligomer regions targeting miR-21 may be 5'-TGATAAGCT-3', 5'-GATAAGCT-3', 5'-ATAAGCT-3', or 5' TcAGtCTGaTaAgCT 3' (SEQ ID NO 5) where capital letters are (optionally beta-D_oxy) LNA, lower case letters are DNA, fully phosphorothioate and LNA Cs are, optionally, 5-methyl cyctosine). A fully LNA oligomer phosphorothioate (e.g. beta-D-oxy-LNA) with sequence 5'-GATAAGCT-3' (LNA C are 5-methylcytosine) has been extensively used in vivo for inhibiting miR-21 (SEQ ID NO 399). According to miRBase, the mature microRNA-21 sequence is 5'-UAGCUUAUCA-GACUGAUGUUGA-3'. In some embodiments the oligomer of the invention comprises two oligomer regions, one which targets a microRNA-21 sequence and a further oligomer region which targets a microRNA-155 sequence.

In some embodiments, the oligomer of the invention targets a microRNA, such as miR-155, which may be used in treating cancer. A compound of the invention may comprise (or more or all) oligomer regions targeting miR-155 which may comprise a nucleobase sequence selected from the group consisting of 5'-TTAGCATTA-3', 5'-TAGCATTA-3', 5'-AGCATTA-3', specific oligomer regions targeting miR-21 may be 5'-TTAGCATTA-3', 5'-TAGCATTA-3', 5'-AGCATTA-3', or 5° 5'-TcAcgATtaGcAtTA-3' (SEQ ID NO 7) where capital letters are (optionally beta-D-oxy) LNA, lower case letters are DNA, fully phosphorothioate and LNA Cs are, optionally, 5-methyl cytosine). SEQ ID NO 304 is a miR-155 sequence.

In some embodiments, a compound of the invention may comprise (or more or all) oligomer region which targets a liver expressed microRNA, such as miR-221, which may be used in treating, for example, hepatocellular carcinoma. Oligomer regions targeting miR-221 may comprise a nucleobase sequence selected from the group consisting of 5'-CAATGTAGC-3', 5'-AATGTAGC-3', and 5'-ATGTAGC-3' specific oligomer regions targeting miR-221 include 5'-CAATGTAGC-3', 5'-AATGTAGC-3', and 5'-ATGTAGC-3', where capital letters are (optionally beta-D-oxy) LNA, fully phosphorothioate and LNA Cs are, optionally, 5-methyl cytosine). According to miRBase, the mature microRNA-221 sequence is 5' AGCUACAUUGU-CUGCUGGGUUUC 3' (SEQ ID NO 8).

Other suitable oligomer regions for targeting microRNAs are disclosed in table 2.

In some embodiments, the oligomer of the invention is capable of down-regulating (e.g. reducing or removing) expression of the target (e.g. target nucleic acid). In this regards, the oligomer of the invention can affect the inhibition of the target. In some embodiments, the oligomers of the invention bind to the target nucleic acid and affect inhibition of expression of at least 10% or 20% compared to the normal expression level, more preferably at least a 30%, 40%, 50%, 60%, 70%, 80%, 90% or 95% inhibition compared to the normal expression level (such as the expression level in the absence of the oligomer(s) or conjugate(s)). In some embodiments, such modulation is seen when using from 0.04 and 25 nM, such as from 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from 0.04 and 25 nM, such as from 0.8 and 20 nM concentration, is, in some embodiments, typically to a level of from 10-20% the normal levels in the absence of the compound, conjugate or composition of the invention.

The invention therefore provides a method of down-regulating or inhibiting the expression of one or more such as two or three target(s) in a cell which is expressing the target(s), said method comprising administering the oligomer or conjugate according to the invention to said cell to down-regulating or inhibiting the expression of the target(s) in said cell. Suitably the cell is a mammalian cell such as a human cell. The administration may occur, in some embodiments, in vitro. The administration may occur, in some embodiments, in vivo.

Oligomer regions in the compounds of the invention, such as the oligomers and conjugates thereof, may be targeted to different targets, such as mRNA or microRNA or other nucleic acid targets which are expressed in the liver (references to NCBI Genbank/Gene IDs are given as examples of sequences which may be targeted by the compounds of the invention—the Genbank/NCBI sequences are hereby incorporated by reference).

ApoB

In some embodiments, the first region (or first and second region) forms a single contiguous nucleobase sequence which is complementary, to a corresponding region of an ApoB mRNA target (i.e. targets) ApoB-100 (NCBI Genbank ID NM_000384.2 GI:105990531, hereby incorporated by reference).

Compounds of the invention which target ApoB may be used in the treatment of acute coronary syndrome (see WO20100076248). The invention therefore provides for the oligomer according to the invention which targets ApoB100 for use in the treatment of acute coronary syndrome. The invention further provides for a method of treatment of acute coronary syndrome, wherein said method comprises the administration of the oligomer of the invention to a subject in need to said treatment.

Compounds of the invention which target ApoB may be used in the treatment atherosclerosis. The invention therefore provides for the oligomer according to the invention which targets ApoB100 for use in the treatment of atherosclerosis. The invention further provides for a method of treatment of atherosclerosis, wherein said method comprises the administration of the oligomer of the invention to a subject in need to said treatment. Compounds of the invention which target ApoB may be used in the treatment hypercholesterolemia or hyperlipidaemia. The invention therefore provides for the oligomer according to the invention which targets ApoB100 for use in the treatment of hypercholesterolemia or hyperlipidaemia. The invention further provides for a method of treatment of hypercholesterolemia or hyperlipidaemia, wherein said method comprises the administration of the oligomer of the invention to a subject in need to said treatment.

The invention provides for an in vivo or in vitro method for the inhibition of ApoB in a cell which is expressing ApoB, said method comprising administering an oligomer or conjugate or pharmaceutical composition according to the invention to said cell so as to inhibit ApoB in said cell.

Examples of LNA oligomer regions which may be used as the first region in the oligomers/conjugates of the invention include, for example those disclosed in WO2007/031081, WO2008/113830, WO2007131238, and WO2010142805, which are hereby incorporated by reference. Specific preferred oligomer regions include the following:

5'-G$_s$$^m$C$_s$a$_s$t$_s$t$_s$g$_s$g$_s$t$_s$a$_s$t$_s$T$_s$$^m$C$_s$A-3'  (SEQ ID NO 9)

5'-G$_s$T$_s$g$_s$a$_s$c$_s$a$_s$c$_s$t$_s$g$_s$T$_s$$^m$C-3'  (SEQ ID NO 10)

Wherein capital letters are beta-D-oxy LNA units (nucleosides), lower case letters are DNA units, subscript s is a phosphorothioate linkage, and a superscript m before the capital C illustrates that all LNA cytosines are 5-methyl cytosine. Compounds of the invention may therefore comprise a first oligomer region which comprises of SEQ ID NO 9, and a second oligomer region which comprises SEQ ID NO 9 or SEQ ID NO 10. Compounds of the invention may therefore comprise a first oligomer region which comprises of SEQ ID NO 10, and a second oligomer region which comprises SEQ ID NO 9 or SEQ ID NO 10. Compounds of the invention targeting ApoB may be conjugated to a conjugate which targets the oligomer to the liver, as disclosed herein, such as a carbohydrate or lipophilic conjugate, such as a GalNac conjugate or a sterol conjugate (e.g. cholesterol or tocopherol). The conjugate may be, for example, at the 5' end or the 3' end of the oligomer compound (suitably via region B). Other oligomers which target ApoB are disclosed in WO03/011887, WO04/044181, WO20061020676, WO2007/131238, WO2007/031081, and WO2010142805.

PCSK9

In some embodiments, the first region (or first and second region) forms a single contiguous nucleobase sequence which is complementary, to a corresponding region of a PCSK9 mRNA target (i.e. targets), such as the human PCSK9 mRNA: NCBI Genbank ID NM_174936.3 GI:299523249, hereby incorporated by reference.

The invention provides for an oligomer according to the invention which targets PCSK9, for use as a medicament, such as for the treatment of hypercholesterolemia or related disorder, such as a disorder selected from the group consisting of atherosclerosis, hyperlipidaemia, hypercholesterolemia, familiar hypercholesterolemia e.g. gain of function mutations in PCSK9, HDL/LDL cholesterol imbalance, dyslipidemias, e.g., familial hyperlipidaemia (FCHL), acquired hyperlipidaemia, statin-resistant hypercholesterolemia, coronary artery disease (CAD), and coronary heart disease (CHD).

The invention provides for the use of an oligomer of the invention which targets PCSK9, for the manufacture of a medicament for the treatment of hypercholesterolemia or a related disorder, such as a disorder selected from the group consisting of atherosclerosis, hyperlipidaemia, hypercholesterolemia, familiar hypercholesterolemia e.g. gain of function mutations in PCSK9, HDL/LDL cholesterol imbalance, dyslipidemias, e.g., familial hyperlipidaemia (FCHL), acquired hyperlipidaemia, statin-resistant hypercholesterolemia, coronary artery disease (CAD), and coronary heart disease (CHD).

The invention provides for a method of treating hypercholesterolemia or a related disorder, such as a disorder selected from the group consisting atherosclerosis, hyperlipidaemia, hypercholesterolemia, familiar hypercholesterolemia e.g. gain of function mutations in PCSK9, HDL/LDL cholesterol imbalance, dyslipidemias, e.g., familial hyperlipidaemia (FCHL), acquired hyperlipidaemia, statin-resistant hypercholesterolemia, coronary artery disease (CAD), and coronary heart disease (CHD), said method comprising administering an effective amount of an oligomer according to the invention which targets PCSK9, to a patient suffering from, or likely to suffer from hypercholesterolemia or a related disorder.

The invention provides for an in vivo or in vitro method for the inhibition of PCSK9 in a cell which is expressing PCSK9, said method comprising administering an oligomer according to the invention which targets PCSK9 to said cell so as to inhibit PCSK9 in said cell.

The following is an oligomer which targets the human PCSK9 mRNA, and may be used as region A in the compounds of the invention.

(SEQ D NO 11)
5'-T$_s$G$_s$$^m$C$_s$t$_s$a$_s$c$_s$a$_s$a$_s$a$_s$a$_s$c$_s$$^m$C$_s$$^m$C$_s$A-3'

Wherein capital letters are beta-D-oxy LNA units (nucleosides), lower case letters are DNA units, subscript s is a phosphorothioate linkage, and a superscript m before the capital C illustrates that all LNA cytosines are 5-methyl cytosine. Compounds of the invention targeting PCSK9 may be conjugated to a conjugate which targets the oligomer to the liver, as disclosed herein, such as a carbohydrate or lipophilic conjugate, such as a GalNac conjugate or a sterol conjugate (e.g. cholesterol or tocopherol). The conjugate may be, for example, at the 5' end or the 3' end of the oligomer compound (suitably via region B). Other oligomers which target PCSK9 are disclosed in WO20081043753, WO2011/009697, WO08/066776, WO07/090071, WO07/146511, WO07/143315, WO09/148605, WO11/123621, and WO11133871, which are hereby incorporated by reference.

miR-122

In some embodiments, the first region (or first and second region) form a single contiguous nucleobase sequence which is complementary, to a corresponding region of a microRNA-122 such as miR-122a (i.e. targets), such as the has-miR-122 sequences (miRBase release 20: MI0000442), such as:

>hsa-mir-122 MI0000442
(SEQ ID NO 12)
CCUUAGCAGAGCUGUGGAGUGUGACAAUGGUGUUUGUGUCUAAACUAUCA

AACGCCAUUAUCACACUAAAUAGCUACUGCUAGGC

>hsa-miR-122-5p MIMAT0000421
(SEQ ID NO 13)
UGGAGUGUGACAAUGGUGUUUG miR-122 has been indicated in HCV infection, where it is an essential host factor required for maintenance of the infection. Inhibitors of miR-122 may therefore be used in the treatment of hepatitis C infection.

Compounds of the invention which target miR-122 may be used in the treatment of HCV infection. The invention therefore provides for the oligomer according to the invention which targets miR-122 for use in the treatment of HCV infection. The invention further provides for a method of treatment of HCV infection, wherein said method comprises the administration of the oligomer of the invention to a subject in need to said treatment.

The invention provides for the use of an oligomer of the invention which targets miR-122, for the manufacture of a medicament for the treatment of HCV infection.

The invention provides for a method of treating HCV infection, said method comprising administering an effective amount of an oligomer according to the invention which targets miR-122, to a patient suffering from HCV infection.

The invention provides for an in vivo or in vitro method for the inhibition of miR-122 in a cell which is expressing miR-122, such as an HCV infected cell or a HCV replicon expressing cell, said method comprising administering an oligomer or conjugate or pharmaceutical composition according to the invention to said cell so as to inhibit miR-122 in said cell.

miR-122 has also been indicated in cholesterol metabolism, and it has been suggested that inhibition of miR-122 may be used for a treatment to reduce plasma cholesterol levels (Esau, Cell Metab. 2006 February; 3(2):87-98.)

Inhibitors of miR-122 may therefore be used in a treatment to reduce plasma cholesterol levels, or in the treatment of a metabolic disease associated with elevated levels of cholesterol (related disorders), such as indications selected from the group consisting of atherosclerosis, hyperlipidaemia, hypercholesterolemia, familiar hypercholesterolemia, dyslipidemias, coronary artery disease (CAD), and coronary heart disease (CHD)

Compounds of the invention which target miR-122 may be used in the treatment of elevated cholesterol levels or related disorders. The invention therefore provides for the oligomer according to the invention which targets miR-122 for use in the treatment of elevated cholesterol levels or related disorders. The invention further provides for a method of treatment of elevated cholesterol levels or related disorders, wherein said method comprises the administration of the oligomer of the invention to a subject in need to said treatment.

The invention provides for the use of an oligomer of the invention which targets miR-122, for the manufacture of a medicament for the treatment of elevated cholesterol levels or related disorders.

The invention provides for a method of treating elevated cholesterol levels or related disorders, said method comprising administering an effective amount of an oligomer according to the invention which targets miR-122, to a patient suffering from said disorder.

The invention provides for an in vivo or in vitro method for the inhibition of miR-122 in a cell which is expressing miR-122, such as an HCV infected cell or a HCV replicon expressing cell, said method comprising administering an oligomer or conjugate or pharmaceutical composition according to the invention to said cell so as to inhibit miR-122 in said cell.

Oligomer's targeting miR-122 are disclosed in WO2007/112754, WO2007/112753, WO2009/043353, and may be mixmers, such as SPC3649, also referred to as miravirsen see below, or a tiny LNA, such as those disclosed in WO2009/043353 (e.g. 5'-ACACTCC-3', 5'-CACACTCC-3', 5'-TCACACTCC-3', where capital letters are beta-D_oxy LNA, fully phosphorothioate and LNA C are 5-methyl cytosine). In some embodiments, the miR-122 targeting oligomers have a length of 8, 9, 10, 11, 12, 13, 14, 15, 16, 17 or 18 (or 19, 20, 21, 22 or 23 nucleotides) in length. In some embodiments, the miR-122 targeting oligomers a sequence which is fully complementary to miR-122 as measured across the length of the oligomer, and preferably include the sequence 5'-CACACTCC-3'. In some embodiments, the oligomer targeting a microRNA such as miR-122, is complementary to a corresponding region of the microRNA across the length of the oligomer and in some embodiments the 3' nucleoside of the oligomer is complementary to (i.e. aligns to) the first, second, third or fourth 5' nucleotides of the microRNA, such as miR-122, such as the second 5' nucleotide of the microRNA, such as miR-122.

The following is an oligomers which targets the has-miR-122 (human miR-122), and may be used as region A in the compounds of the invention.

Miravirsen:
(SEQ ID NO 1)
5'-$^m$C$_s$c$_s$A$_s$t$_s$t$_s$G$_s$T$_s$c$_s$a$_s$$^m$C$_s$a$_s$$^m$C$_s$t$_s$$^m$C$_s$$^m$C-3'

Other miR-122 targeting compounds which may be used in the context of the present invention (region A) are disclosed in WO2007/027894, WO2007/027775.

MtGPAT:
(NCBI gene ID 57678—Chromosome: 10; NC_000010.10 (113907971 . . . 113975153, complement) Mitochondrial glycerol-3-phosphate acyltransferase 1 (EC 2.3.1.15, also known as GPAT1, mtGPAT1, GPAM, mtG-PAM) plays a major role in hepatic triglyceride formation, where high levels of mtGPAT1 activity results in fatty liver (hepatosteatosis) whereas the absence of mtGPAT1 results in low levels of liver triglycerides and stimulated fatty acid oxidation (see WO2010/000656 which discloses oligomers which target mtGPAT. Compounds of the invention which target MtGPAT may be used to treat conditions such as being overweight, obesity, fatty liver, hepatosteatosis, non alcoholic fatty liver disease (NAFLD), non alcoholic steatohepatitis (NASH), insulin resistance, diabetes such as non insulin dependent diabetes mellitus (NIDDM). The following oligomer targets human mtGPAT and may be used as an oligomer region in the compounds of the invention, for example in conjunction with one of the ApoB targeting compounds listed above (SEQ ID NO 9 or SEQ ID NO 10).

(SEQ ID NO 14)
5'-A$_s$$^o$T$_s$$^o$T$_s$$^o$c$_s$c$_s$c$_s$t$_s$g$_s$c$_s$c$_s$t$_s$G$_s$$^o$T$_s$$^o$G$^o$-3'

Compounds of the invention may therefore comprise a first oligomer region which comprises an mtGPAT targeting oligomer region, and a second oligomer region which targets an ApoB mRNA.

FactorVII
(NCBI Gene ID 2155, NCBI J02933.1 GI:180333, or EU557239.1 GI:182257998). The oligomer or conjugate of the invention may target FactorVII, and thereby inhibit the production of Factor VII, a key component of the tissue factor coagulation pathway. Compounds of the invention which target FactorVII may be used for the treatment or prevention of thrombotic diseases (typically without causing bleeding) and as heart attack, stroke and blood clots, or inflammatory conditions. WO 2013/119979 and WO 2012/

174154, hereby incorporated by reference disclose oligonucleotide compounds which target FVII which may be incorporated into the conjugates of the present invention.

Factor XI (NCBI Genbank BC122863.1 GI:114108211)—Factor XI, a clotting factor that is produced in the liver. High levels of Factor XI are linked to heart attack, stroke and blood clots. WO 2013/070771, hereby incorporated by reference, discloses oligonucleotide compounds which target XI which may be incorporated into the conjugates of the present invention. Compounds of the invention which target FactorXI may be used for the treatment or prevention of thrombotic diseases, and as heart attack, stroke and blood clots, or inflammatory conditions such as arthritis and colitis.

ApoCIII (NCBI Genbank BC027977.1 GI:20379764) a protein that regulates triglyceride metabolism in blood. High levels of apoC-Ill are linked to inflammation, high triglycerides, atherosclerosis and metabolic syndrome. Compounds of the invention which target ApoCIII may be used to reduce serum triglyceride levels or in the treatment of e.g. familial chylomicronemia syndrome and severely high triglycerides either as a single agent or in combination with other triglyceride-lowering agents. WO11085271 hereby incorporated by reference, discloses oligonucleotide compounds which target ApoCIII which may be incorporated into the conjugates of the present invention.

Apo(a)

(NCBI Genbank NM_005577.2 GI:116292749) inhibits the production of apo(a) in the liver and is designed to offer a direct approach to reducing Lp(a), an independent risk factor for cardiovascular disease. High levels of Lp(a) are associated with an increased risk of atherosclerosis, coronary heart disease, heart attack and stroke. Lp(a) promotes premature plaque buildup, or atherosclerosis, in arteries. Compounds of the invention which target Apo(a) may be used in the treatment of e.g. atherosclerosis and coronary heart disease. WO05000201 and WO03014307 hereby incorporated by reference, discloses oligonucleotide compounds which target apolipoprotein (a) which may be incorporated into the conjugates of the present invention.

Hepatitis B (HBV)

(see for example NCBI D23684.1 GI:560092; D23683.1 GI: 560087; D23682.1 GI: 560082; D23681.1 GI: 560077; D23680.1 GI: 560072; D23679.1 GI: 560067; D23678.1 GI: 560062; D23677.1 GI: 560057; all of which are hereby incorporated by reference)

Oligomers which target HBV are well known in the art, for example see, WO96/03152, WO97/03211, WO2011/052911, WO2012/145674, WO2012/145697, WO2013/003520 and WO2013/159109.

Compounds of the invention which target HBV may be used in the treatment HBV infection. The invention therefore provides for the oligomer according to the invention which targets HBV for use in the treatment of HBV. The invention further provides for a method of treatment of HBV infection, wherein said method comprises the administration of the oligomer of the invention to a subject in need to said treatment.

The invention provides for the oligomer or conjugate of the invention which targets hepatitis B (HBV) for use as a medicament, such as for the treatment hepatitis B infection or a related disorder.

The invention provides for the use of an oligomer or conjugate or pharmaceutical composition according to the invention which targets hepatitis B (HBV), for the manufacture of a medicament for the treatment of hepatitis B infection or a related disorder.

The invention provides for a method of treating treatment hepatitis B infection or a related disorder, said method comprising administering an effective amount of an oligomer or conjugate of the invention which targets HBV, to a patient infected with Hepatitis B virus.

The invention provides for an in vivo or in vitro method for the inhibition of HBV replication in a cell infected with HBV, said method comprising administering an oligomer or conjugate of the invention which targets HBV to said cell so as to inhibit HBV replication. An example of an LNA oligomer which target's HBV is (as is disclosed in WO2011/47312) which may be used as the oligomer (region A) of the invention 5'-$G_sA_sG_sG_sc_sa_st_sa_sg_sc_sa_sg_s{}^mC_sA_sG_sG$-3'. Further compounds are disclosed in table 1 of WO2011/47312, and in WO2011/052911, WO2012/145674, WO2012/145697, WO2013/003520 and WO2013/159109, hereby incorporated by reference.

RG-101 is a compound which targets miR-122 and comprises a GalNac conjugate, and is being developed for treatment of HCV by Regulus Therapeutics.

ANGPTL3, (e.g. NCBI BC007059.1 GI: 14712025 or BC058287.1 GI: 34849466) ANGIOPOIETIN-LIKE 3—a protein that regulates lipid, glucose and energy metabolism. Humans with elevated levels of ANGPTL3 have hyperlipidemia associated with an increased risk of premature heart attacks, increased arterial wall thickness as well as multiple metabolic abnormalities, such as insulin resistance. In contrast, humans with lower levels of ANGPTL3 have lower LDL-C and triglyceride levels and a lower risk of cardiovascular disease. Compounds of the invention which target ANGPTL3 may be used in the treatment of e.g. hyperlipidemia and related disorders, metabolic disorder, atherosclerosis, coronary heart disease or insulin resistance. WO11085271 hereby incorporated by reference, discloses oligonucleotide compounds which target ANGPTL3 which may be incorporated into the conjugates of the present invention.

Glucagon Receptor, or GCGR (BC112041.1 GI: 85567507; L20316.1 GI: 405189): Glucagon is a hormone that opposes the action of insulin and stimulates the liver to produce glucose, particularly in type 2 diabetes. In patients with advanced diabetes, uncontrolled glucagon action leads to a significant increase in blood glucose levels. Therefore, attenuating glucagon action may have a significant glucose lowering effect in patients with severe diabetes. In addition, reducing GCGR produces more active glucagon-like peptide, or GLP-1, a hormone that preserves pancreatic function and enhances insulin secretion. Compounds of the invention which target GCGR may be used in the treatment of e.g. or insulin resistance, hyperglycemia, diabetes, such as type 1 or 2 diabetes, preservation of pancreatic function, and to control of blood glucose levels. WO2007/134014 discloses oligonucleotide compounds which target GCGR which may be incorporated into the conjugates of the present invention.

Fibroblast Growth Factor Receptor 4, or FGFR4.

(NCBI Gene 2264—NC_000005.9 (176513906 . . . 176525143) FGFR4 is expressed in the liver and fat tissues, and is indicated in decreasing the body's ability to store fat while simultaneously increasing fat burning and energy expenditure. Many anti-obesity drugs act in the brain to suppress appetite, commonly resulting in CNS side effects. Compounds of the invention which target FGFR4 may be used in the treatment of e.g. or insulin resistance, hyperglycemia, diabetes, such as type 1 or 2 diabetes, preservation of obesity (e.g. when used in combination with an appetite-suppressing drug), reducing body weight, and improvement in insulin sensitivity, diabetes, such as type 1 or 2 diabetes and to control of blood glucose levels. WO09046141 and WO12174476 hereby incorporated by reference disclose oligonucleotide compounds which target FGFR4 which may be incorporated into the conjugates of the present invention.

Diacylglycerol Acyltransferase-2, or DGAT-2

(NCBI GENE ID 84649): A key component in the synthesis of triglycerides. The inhibition of DGAT may reduce liver fat in patients with Nonalcoholic Steatohepatitis (NASH), and may also be used to treat type 2 diabetes and insulin resistance. Compounds of the invention which target DGAT-2 may be used to treat NASH, to reduce liver fat, to treat diabetes, such as type 2 diabetes, and treat insulin resistance. WO05019418 and WO2007136989, hereby incorporated by reference disclose oligonucleotide compounds which target DGAT-2 which may be incorporated into the conjugates of the present invention.

Glucocorticoid Receptor, or GCCR (BC150257.1 GI: 152013043): Glucocorticoid hormones affect a variety of processes throughout the body, and excessive levels of glucocorticoid hormones can have a detrimental effect on many of the tissues and organs in the body. Cushing's Syndrome is an orphan disease caused by prolonged exposure to high levels of glucocorticoids. If untreated, patients with Cushing's Syndrome can develop hypertension, diabetes and impaired immune functions and have an increased risk of early death. Although there are approved treatments for Cushing's Syndrome, current medicines are associated with significant side effects, such as hypertension and diabetes, and there remains a high unmet medical need for new therapies for these patients. Compounds of the invention which target GCCR-2 may be used to treat Cushing's Syndrome and associated conditions (such as those listed above). WO07035759 and WO2007136988, which are hereby incorporated by reference disclose oligonucleotide compounds which target GCCR which may be incorporated into the conjugates of the present invention.

Complement Component C5

(M57729.1 GI: 179982): The complement system plays a central role in immunity as a protective mechanism for host defense, but its dysregulation results in serious, life-threatening complications in a broad range of human diseases including paroxysmal nocturnal hemoglobinuria (PNH), atypical hemolytic-uremic syndrome (aHUS), myasthenia gravis, neuromyelitis optica, amongst others. Compounds of the invention which target complement component C5 may be used to treat one or more of these disorders. C5 is a genetically and clinically validated target; loss of function human mutations are associated with an attenuated immune defense against certain infections and intravenously administered anti-05 monoclonal antibody therapy has demonstrated clinical activity and tolerability in a number of complement-mediated diseases. transmembrane protease, serine 6 (Tmprss6) for the treatment of beta-thalassemia and iron-overload disorders.

Alpha-1 Antitrypsin (AAT):

(M11465.1 GI: 177826) Liver disease associated with— WO13142514 which is hereby incorporated by reference disclose oligonucleotide compounds which target AAT which may be incorporated into the oligomers or conjugates of the present invention. Compounds of the invention which target AAT may be used in methods for decreasing A1AT mRNA and protein expression and treating, ameliorating, preventing, slowing progression, or stopping progression of fibrosis, such as, A1ATD associated liver disease, and pulmonary disease, such as, A1ATD associated pulmonary disease in an individual in need thereof.

Transthyretin—TTR (BC005310.1 GI: 13529049): The oligomers of the invention which target TTR may be used to treat transthyretin amyloidosis, or TTR amyloidosis, a severe and rare genetic disease in which the patient inherits a mutant gene that produces a misfolded form of TTR, which progressively accumulates in tissues. In patients with TTR amyloidosis, both the mutant and normal forms of TTR can build up as fibrils in tissues, including heart, peripheral nerves, and the gastrointestinal tract. The presence of TTR fibrils interferes with the normal functions of these tissues, and as the TTR protein fibrils enlarge more tissue damage occurs and the disease worsens. TTR is a carrier protein that transports a thyroid hormone and retinol in the blood. In patients with TTR amyloidosis, both the mutant and normal forms of TTR can build up as fibrils in tissue. The compounds of the invention may be used to treat TTR amyloidosis. See Benson et al., Amyloid. 2010 June; 17(2):43-9, and Ackermann et al., Amyloid. 2012 June; 19 Suppl Antisense compounds targeting TTR which may be used in the oligomers or conjugates of the invention are disclosed in U.S. Pat. No. 8,101,743, WO11139917 and WO10017509, which are hereby incorporated by reference.

Aminolevulinate Synthase-1 (ALAS-1)

(BC011798.2 GI: 33877783; AK312566.1 GI: 164690365; NM_199166.2 GI: 362999012; NM_000688.5 GI: 362999011). ALAS1 is a validated target for the treatment of porphyria, such as the treatment of hepatic porphyrias including acute intermittent porphyria (AIP). Compounds of the invention which target ALAS-1 may be used in the treatment of these disorders.

Vascular Endothelial Growth Factor, or VEGF (GENE ID 7422, human Sequence: Chromosome: 6; NC_000006.11 (43737946 . . . 43754224)). VEGF is indicated in cancers. Compounds of the invention which target VEGF may be used in the treatment of hyperproliferative disorders, such as cancer, such as liver cancer.

Table 1 provides for a group of liver targets which may be targeted by the compounds of the invention, as well as the medical indication/disorder for which such compounds may be used to treat (such as a person suffering from the associated disorder) (See Sehgal et al., Liver as a target for oligonucleotide therapeutics, J. of Hepatology 2013, In Press).

TABLE 1

| The compound of the invention may target a nucleic acid (e.g. mRNA encoding, or miRNA) selected from the group consisting of | For the treatment of a disease or disorder such as |
|---|---|
| AAT | AAT-LivD |
| ALDH2 | Alcohol dependence |
| HAMP pathway | Anemia or inflammation/CKD |
| miR-33 | Atherosclerosis |
| Apo(a) | Atherosclerosis/high Lp(a) |
| miR-7 | Liver cancer |
| miR-378 | Cardiometabolic diseases |
| miR-21 | Liver cancer |
| Myc | Liver cancer |
| miR-122 | HCV |
| 5'UTR | HCV |
| 5'UTR & NS5B | HCV |
| NS3 | HCV |
| TMPRSS6 | Hemochromatosis |
| Antithrombin III | Hemophilia A, B |
| ApoCIII | Hypertriglyceridemia |

TABLE 1-continued

| The compound of the invention may target a nucleic acid (e.g. mRNA encoding, or miRNA) selected from the group consisting of | For the treatment of a disease or disorder such as |
|---|---|
| ANGPLT3 | Hyperlipidemia |
| MTP | Hyperlipidemia |
| DGAT2 | NASH |
| ALAS1 | Porphyria |
| Antithrombin III | Rare Bleeding disorders |
| Serum amyloid A | SAA-amyloidosis |
| Factor VII | Thrombosis |
| Growth hormone receptor | Acromegaly |
| miR-122 | Hepatitis C virus |
| ApoB-100 | Hypercholesterolemia |
| ApoCIII | Hypertriglyceridemia |
| PCSK9 | Hypercholesterolemia |
| CRP | Inflammatory disorders |
| KSP or VEGF | Liver cancer |
| PLK1 | Liver cancer |
| miR-34 | Liver cancer |
| FGFR4 | Obesity |
| Factor IXa | Thrombosis |
| Factor XI | Thrombosis |
| TTR | TTR amyloidosis |
| GCCR | Type 2 diabetes |
| PTP-1B | Type 2 diabetes |
| GCGR | Cushing's Syndrome |
| Hepatic Glucose 6-Phosphate Transporter-1 | glucose homeostasis, diabetes, type 2 diabetes |

Sequences

In some embodiments, the oligomers, or first region thereof, comprise a contiguous nucleotide sequence which corresponds to the reverse complement of a nucleotide sequence present in the target nucleic acid (i.e. the sequence which the oligomer targets). Table 3 provides a group of mRNA and miRNA targets which are in pre-clinical or clinical development using oligonucleotide compounds for the associated indication, and are therefore suitable for targeting with the compounds of the present invention.

In some embodiments the target is selected from the group consisting of: miR-122, ApoB-100, ApoCIII, PCSK9, CRP, KSP, VEGF, PLK1, miR-34, FGFR4, Factor IXa, Factor XI, TTR, GCCR, PTP-1B, GCGR, AAT, ALDH2, HAMP pathway, miR-33, Apo(a), miR-7, miR-378, miR-21, Myc, miR-122, the HCV genome such as the HCV 5'UTR or HCV NS5B RNA or NS3 RNA, TMPRSS6, Antithrombin III, ApoCIII, ANGPLT3, MTP, DGAT2, ALAS1, Antithrombin III, Serum amyloid A and Factor VII.

In some embodiments, the contiguous nucleotide sequence comprises no more than a single mismatch when hybridizing to the target sequence. Region B may however be non-complementary and may therefore be disregarded when determining the degree of complementarity.

In determining the degree of "complementarity" between oligomers of the invention (or regions thereof) and the target region of the nucleic acid, such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

As used herein, the terms "homologous" and "homology" are interchangeable with the terms "identity" and "identical".

The terms "corresponding to" and "corresponds to" refer to the comparison between the nucleotide sequence of the oligomer (i.e. the nucleobase or base sequence) or contiguous nucleotide sequence (a first region) and the equivalent contiguous nucleotide sequence of a further sequence selected from either i) a sub-sequence of the reverse complement of the nucleic acid target. Nucleotide analogues are compared directly to their equivalent or corresponding nucleotides. A first sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, such as 100% homologous (identical).

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

The terms "reverse complement", "reverse complementary" and "reverse complementarity" as used herein are interchangeable with the terms "complement", "complementary" and "complementarity".

The contiguous nucleobase sequence of the oligomer (first region or first and second region) may therefore be complementary to a target, such as those referred to herein.

In some embodiments, the first region or first and second region form a single contiguous nucleobase sequence which is complementary to a region of a mRNA target, such as those referred to herein, including, for example, ApoB-100 (NM_000384.2 GI:105990531 or PCSK9 (NM_174936.3 GI:299523249).

Nucleosides and Nucleoside Analogues

The term "nucleotide" as used herein, refers to a glycoside comprising a sugar moiety (or analogue thereof), a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

It will be recognized that in the context of the present invention the term nucleoside and nucleotide are used to refer to both naturally occurring nucleotides/sides, such as DNA and RNA, as well as nucleotide/side analogues. Thus, "nucleobase" covers not only the known purine and pyrimidine heterocycles but also heterocyclic analogues and tautomeres thereof. It will be recognised that the DNA or RNA nucleosides of region B may have a naturally occurring and/or non-naturally occurring nucleobase(s), such as DNA nucleobases independently selected from the group A, C, T and G, or the group C, T and G.

In field of biochemistry, the term "nucleoside" is commonly used to refer to a glycoside comprising a sugar moiety and a base moiety, and may therefore be used when referring to the nucleotide units, which are covalently linked by the internucleoside linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

As one of ordinary skill in the art would recognize, the 5' terminal nucleotide of an oligonucleotide does not comprise a 5' internucleoside linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

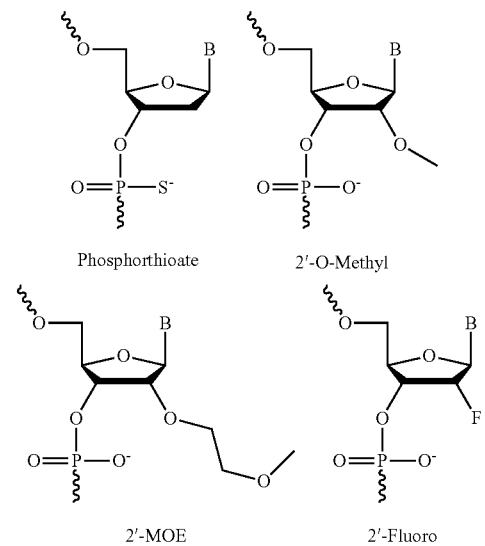

The oligomer may thus comprise or consist of a simple sequence of natural occurring nucleotides—preferably 2'-deoxynucleotides (referred here generally as "DNA"), but also possibly ribonucleotides (referred here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by WO2007/031091 or are referenced therein. Other nucleotide analogues which may be used in the oligomer of the invention include tricyclic nucleic acids, for example please see WO2013154798 and WO2013154798 which are hereby incorporated by reference.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

Oligomeric compounds, such as antisense oligonucleotides, such as the compounds referred to herein, including region A, and in some optional embodiments, region B, may contain one or more nucleosides wherein the sugar group has been modified. Such sugar modified nucleosides (nucleoside analogues) may impart enhanced nuclease stability, increased binding affinity, or some other beneficial biological property to the antisense compounds. In some embodiments, nucleosides comprise a chemically modified ribofiiranose ring moiety.

In some embodiments, the oligomer, or first region thereof, comprises at least one, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or 25 nucleoside analogues, such as sugar modified nucleoside analogues.

Bicyclic nucleoside analogues include nucleoside analogues which comprise a bridge (or biradical) linking the second and forth carbon of the ribose ring, (C4*-C2* bridge or biradical). The presence of the biradical between the $2^{nd}$ and $4^{th}$ carbon locks the ribose into a 3' endo-(north) confirmation, and as such bicyclic nucleoside analogues with a C2*-C4* biradical are often referred to as Locked nucleic acid (LNA). In some embodiments the nucleoside analogues are (optionally independently selected from the group consisting of bicyclic nucleoside analogues (such as LNA), and/or 2° substituted nucleoside analogues, such as (optionally independently) selected from the group consisting of 2'-O-alkyl-RNA units, 2'-OMe-RNA units, 2'-amino-DNA units, 2'-AP, 2-FANA, 2'-(3-hydroxy)propyl, and 2'-fluoro-DNA units, and/or other (optionally) sugar modified nucleoside analogues such as morpholine, peptide nucleic acid (PNA), CeNA, unlinked nucleic acid (UNA), hexitol nucleic acid (HNA). bicyclo-HNA (see e.g. WO2009/100320), In some embodiments, the nucleoside analogues increase the affinity of the first region for its target nucleic acid (or a complementary DNA or RNA sequence).

In some embodiments, the oligomer comprises at least one bicyclic nucleotide analogue, such as LNA. In some embodiments, the first region comprises of at least one bicyclic nucleoside analogues (e.g. LNA) and/or 2' substituted nucleoside analogues. In some embodiments, the nucleoside analogues present in the oligomer all comprise the same sugar modification. In some embodiments, at least one nucleoside analogue present in the first region is a bicyclic nucleoside analogue, such as at least 2, at least 3, at least 4, at least 5, at least 6, at least 7, at least 8, at least 9, at least 10, at least 11, at least 12, at least 13, at least 14, at least 15, at least 16, for example all nucleoside analogues (except the DNA and or RNA nucleosides of region B) are sugar modified nucleoside analogues, such as such as bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA.

Examples of chemically modified ribofiiranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or $C(R_1)(R_2)$ (R=H, $C_1$-$C_2$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5', 2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$, and 2'-O(CH$_2$)2 OCH$_3$ substituent groups. The substituent at the 2' position can also be selected from allyl, amino, azido, thio, O-allyl, O—$C_1$-$C_{10}$ alkyl, OCF$_3$, O(CH$_2$)$_2$SCH$_3$, O(CH$_2$)2-O—N(Rm)(Rn), and O—CH$_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In some embodiments, compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845, issued on Jul. 15, 2008); 4'-C(CH$_3$)(CH$_3$)—O-2', and analogs thereof (see, published PCT International Application WO2009/006478, published Jan. 8, 2009); 4'-CH$_2$—N(OCH$_3$)-2', and analogs thereof (see, published PCT International Application WO2008/150729, published Dec. 11, 2008); 4'-CH$_2$—O—N(CH$_3$)-2' (see, published U.S. Patent Application US2004/0171570, published Sep. 2, 2004); 4'-CH$_2$—N(R)—O-2', wherein R is H, $C_1$-$C_{10}$ alkyl, or a protecting group (see, U.S. Pat. No. 7,427,672, issued on Sep. 23, 2008); 4'-CH$_2$—C(H)(CH$_3$)-2' (see, Chattopadhyaya, et al, J. Org. Chem., 2009, 74, 118-134); and 4'-CH$_2$—C(=CH$_2$)-2', and analogs thereof (see, published PCT International Application WO 2008/154401, published on Dec. 8, 2008). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc, 129(26) 8362-8379 (Jul. 4, 2007); Elayadi et al., Curr. Opinion Invens. Drugs, 2001, 2, 558-561; Braasch et al., Chem. Biol, 2001, 8, 1-7; Oram et al, Curr. Opinion Mol. Ther., 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example a-L-ribofuranose and beta-D-ribofuranose (see PCT international application PCT DK98/00393, published on Mar. 25, 1999 as WO 99/14226).

In some embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from -[CiR$_a$XR$_b$)]-, —C(R$_a$)=C (R$_b$)—, —C(R$_a$)=N—, —C(=NR$_a$)—, —C(=O)—, —C(=S)—, —O—, —Si(R$_a$)$_2$—, —S(=O)$_x$—, and —N(Ra)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$—Ci$_2$ alkenyl, substituted C$_2$-C$_{12}$ alkenyl, C$_2$—Ci$_2$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_6$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C1-C$_{12}$ aminoalkyl, substituted C$_1$-C$_{12}$ aminoalkyl, or a protecting group.

In some embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—. In some embodiments, the bridge is 4'-CH$_2$-2', 4'-(CH$_2$)$_2$-2', 4'-(CH$_2$)$_3$-2', 4'-CH$_2$—O-2', 4*-(CH$_2$)2-O-2', 4'-CH$_2$—O—N(R)-2', and 4'-CH$_2$—N(R)—O-2'-, wherein each R is, independently, H, a protecting group, or C$_1$-C$_{12}$ alkyl.

In some embodiments, bicyclic nucleosides are further defined by isomeric configuration. For example, a nucleoside comprising a 4'-2' methylene-oxy bridge, may be in the a-L configuration or in the beta-D configuration. Previously, a-L-methyleneoxy (4'-CH$_2$—O-2') BNA's have been incorporated into antisense oligonucleotides that showed antisense activity (Frieden et al, Nucleic Acids Research, 2003, 21, 6365-6372).

In some embodiments, bicyclic nucleosides include, but are not limited to, (A) a-L-Methyleneoxy (4'-CH$_2$—O-2') BNA, (B) beta-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

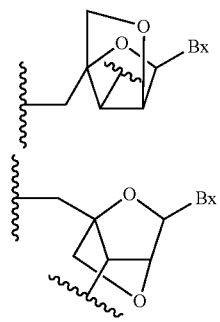

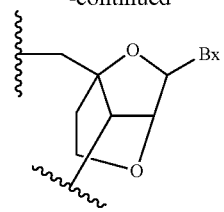

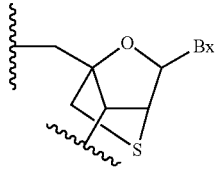

(G)

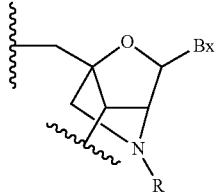

(H)

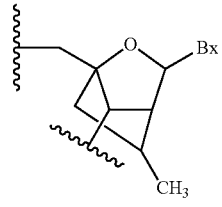

(I)

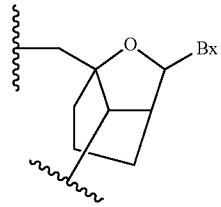

(J)

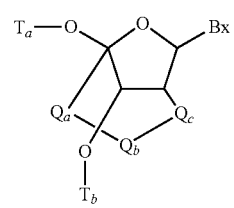

wherein Bx is the base moiety and R is, independently, H, a protecting group or C$_1$-C$_2$ alkyl. odiments, bicyclic nucleoside having Formula I:

$$T_a—O \quad O \quad Bx \\ Q_a \quad Q_c \\ O—Q_b \\ T_b$$

I wherein:
Bx is a heterocyclic base moiety;
-Q$_a$-Q$_b$-Q$_c$- is —CH$_2$—N(Rc)-CH$_2$—, —C(=O)—N(R$_c$)—CH$_2$—, —CH$_2$—O—N(Rc)-, —CH$_2$—N(Rc)-O—, or —N(Rc)-O—CH$_2$;
R$_c$ is C$_1$-C$_{12}$ alkyl or an amino protecting group; and
T$_a$ and T$_b$ are each, independently, H, a hydroxyl protecting group, a conjugate group, a reactive phosphorus group, a phosphorus moiety, or a covalent attachment to a support medium.

In some embodiments, bicyclic nucleoside having Formula II:

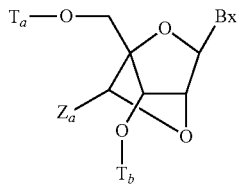

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium; $Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In some embodiments, each of the substituted groups is, independently, mono or poly substituted with substituent groups independently selected from halogen, oxo, hydroxyl, $OJ_c$, $NJ_d$, $SJ_c$, $N_3$, $OC(=X)J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In some embodiments, bicyclic nucleoside having Formula III:

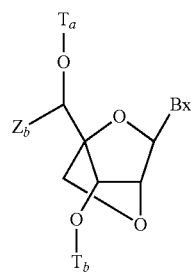

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$R_d$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In some embodiments, bicyclic nucleoside having Formula IV:

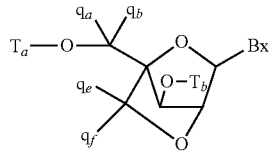

wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl; each $q_b$, $q_c$ and $q_d$ is, independently, H, halogen, $C_1$-$C_6$ alkyl, substituted $C_1$-$C_6$ alkyl, $C_2$—Ce alkenyl, substituted $C_2$-$C_6$ alkenyl, $C_2$-$C_6$ alkynyl, or substituted $C_2$-C6 alkynyl, $C_1$-$C_6$ alkoxyl, substituted Q-$C_6$ alkoxyl, acyl, substituted acyl, $C_1$-$C_6$ aminoalkyl, or substituted $C_1$-$C_6$ aminoalkyl;

In some embodiments, bicyclic nucleoside having Formula V:

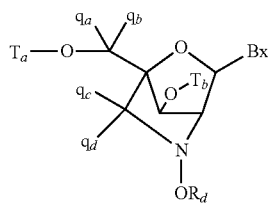

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium; $q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; or $q_e$ and $q_f$ together are $=C(q_g)(q_h)$; $q_g$ and $q_h$ are each, independently, H, halogen, $C_1$-$C_{12}$ alkyl, or substituted $C_1$-$C_{12}$ alkyl.

The synthesis and preparation of the methyleneoxy (4'-CH_2—O-2') BNA monomers adenine, cytosine, guanine, 5-methyl-cytosine, thymine, and uracil, along with their oligomerization, and nucleic acid recognition properties have been described (see, e.g., Koshkin et al., Tetrahedron, 1998, 54, 3607-3630). BNAs and preparation thereof are also described in WO 98/39352 and WO 99/14226.

Analogs of methyleneoxy (4'-CH_2—O-2') BNA, methyleneoxy (4'-CH_2—O-2') BNA, and 2'-thio-BNAs, have also been prepared {see, e.g., Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., J. Org. Chem., 1998, 63, 10035-10039). In addition, 2'-amino- and 2'-methylamino-BNA's have been prepared and the thermal stability of their duplexes with complementary RNA and DNA strands has been previously reported.

In some embodiments, the bicyclic nucleoside has Formula VI:

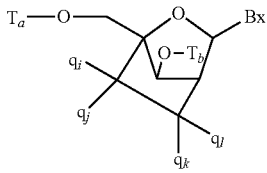

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium; each qj, qj, $q_k$ and ql is, independently, H, halogen, $C_1$-$C_{12}$ alkyl, substituted $C_1$-$C_{12}$ alkyl, $C_2$-C12 alkenyl, substituted $C_2$-$C_{12}$ alkenyl, $C_2$-$C_{12}$alkynyl, substituted $C_2$-$C_{12}$ alkynyl, $C_1$-$C_{12}$alkoxyl, substituted $C_2$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or (H)C(=S)$NJ_jJ_k$; and qi and $q_j$ or ql and $q_k$ together are =C($q_g$)($q_h$), wherein $q_g$ and $q_h$ are each, independently, H, halogen, $C_1$-$C_{12}$ alkyl, or substituted $C_1$-$C_6$ alkyl.

One carbocyclic bicyclic nucleoside having a 4'-(CH$_2$)$_3$-2' bridge and the alkenyl analog, bridge 4'-CH=CH—CH$_2$-2', have been described (see, e.g., Freier et al, Nucleic Acids Research, 1997, 25(22), 4429-4443 and Albaek et al, J. Org. Chem., 2006, 71, 7731-77 '40). The synthesis and preparation of carbocyclic bicyclic nucleosides along with their oligomerization and biochemical studies have also been described (see, e.g., Srivastava et al, J. Am. Chem. Soc. 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocyclic nucleosides" refer to nucleosides comprising modified sugar moieties that are not bicyclic sugar moieties. In some embodiments, the sugar moiety, or sugar moiety analogue, of a nucleoside may be modified or substituted at any position.

As used herein, "2'-modified sugar" means a furanosyl sugar modified at the 2' position. In some embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In some embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$, and O(CH2)$_n$ON[(CH$_2$)$_n$CH$_3$]2, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; SCH$_3$; OCN; Cl; Br; CN; CF$_3$; OCF$_3$; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an R; a cleaving group; a reporter group; an intercalator; a group for improving pharmacokinetic properties; and a group for improving the pharmacodynamic properties of an antisense compound, and other substituents having similar properties. In some embodiments, modified nucleosides comprise a 2'-MOE side chain {see, e.g., Baker et al., J. Biol. Chem., 1997, 272, 1 1944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2-MOE substituent also have been shown to be antisense inhibitors of gene expression with promising features for in vivo use {see, e.g., Martin, P., He/v. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified ?THP nucleosides include, but are not limited to, what is referred to in the art as hexitol nucleic acid (HNA), anitol nucleic acid (ANA), manitol nucleic acid (MNA) {see Leumann, C J. Bioorg. and Med. Chem. (2002) 10:841-854}, fluoro HNA (F-HNA), or those compounds having Formula X:

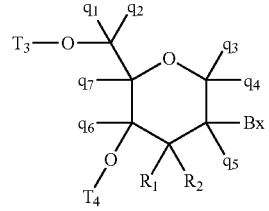

Formula X

X wherein independently for each of said at least one tetrahydropyran nucleoside analog of Formula X:
Bx is a heterocyclic base moiety;
$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and T4 is H, a hydroxyl protecting group, a linked conjugate group, or a 5' or 3'-terminal group; $q_1$ $q_2$ $q_3$ $q_4$ $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, NJ, $J_2$, SJ, $N_3$, OC(=X)$J_1$, OC(=X)$NJ_1J_2$, $NJ_3$C(=X)$NJ_1J_2$, and CN, wherein X is O, S, or $NJ_1$ and each $J_1$, $J_2$, and $J_3$ is, independently, H or $C_1$-$C_6$ alkyl.

In some embodiments, the modified THP nucleosides of Formula X are provided wherein $q_m$, $q_n$, $q_p$, $q_r$, $q_s$, $q_t$, and $q_u$ are each H. In some embodiments, at least one of $q_m$, $q_n$, $q_p$, $q_r$, $q_s$, $q_t$ and $q_u$ is other than H. In some embodiments, at least one of $q_m$, $q_n$, $q_p$, $q_r$, $q_s$, $q_t$ and $q_u$ is methyl. In some embodiments, THP nucleosides of Formula X are provided wherein one of $R_1$ and $R_2$ is F. In some embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to nucleosides with non-bridging 2' substituents, such as allyl, amino, azido, thio, O-allyl, —OCF$_3$, O—(CH$_2$)$_2$—O—CH$_3$, 2'-O(CH$_2$)$_2$SCH$_3$, O—(CH$_2$)$_2$—O—N($R_m$)($R_n$), or O—CH$_2$—C(=O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "oligonucleotide" refers to a compound comprising a plurality of linked nucleosides.

In some embodiments, one or more of the plurality of nucleosides is modified. In some embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds {see, e.g., review article: Leumann, J. C, Bioorganic and Medicinal Chemistry, 2002, 10, 841-854). Such ring systems can undergo various additional substitutions to enhance activity. Methods for the preparations of modified sugars are well known to those skilled in the art. In nucleotides having modified sugar moieties, the nucleobase moieties (natural, modified, or a combination thereof) are maintained for hybridization with an appropriate nucleic acid target.

In some embodiments, antisense compounds comprise one or more nucleotides having modified sugar moieties. In some embodiments, the modified sugar moiety is 2'-MOE. In some embodiments, the 2'-MOE modified nucleotides are arranged in a gapmer motif. In some embodiments, the modified sugar moiety is a cEt. In some embodiments, the cEt modified nucleotides are arranged throughout the wings of a gapmer motif.

In some embodiments, in the BNA (LNA), $R^{4*}$ and $R^{2*}$ together designate the biradical —O—CH(CH$_2$OCH$_3$)— (2'O-methoxyethyl bicyclic nucleic acid—Seth at al., 2010, J. Org. Chem).—in either the R- or S-configuration.

In some embodiments, in the BNA (LNA), $R^{4*}$ and $R^{2*}$ together designate the biradical —O—CH(CH$_2$CH$_3$)— (2'O-ethyl bicyclic nucleic acid—Seth at al., 2010, J. Org. Chem).—in either the R- or S-configuration.

In some embodiments, in the BNA (LNA), $R^{4*}$ and $R^{2*}$ together designate the biradical —O—CH(CH$_3$)—.—in either the R- or S-configuration. In some embodiments, $R^{4*}$ and $R^{2*}$ together designate the biradical —O—CH$_2$—O—CH$_2$— (Seth at al., 2010, J. Org. Chem).

In some embodiments, in the BNA (LNA), $R^{4*}$ and $R^{2*}$ together designate the biradical —O—NR—CH$_3$— (Seth at al., 2010, J. Org. Chem).

In some embodiments, the LNA units have a structure selected from the following group:

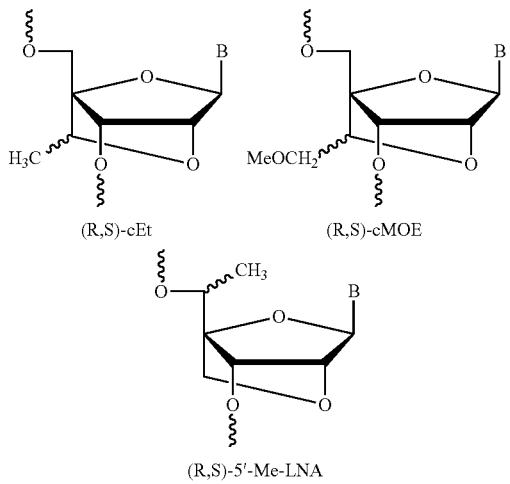

(R,S)-cEt  (R,S)-cMOE (R,S)-5'-Me-LNA

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Incorporation of affinity-enhancing nucleotide analogues in the oligomer, such as BNA, (e.g.) LNA or 2'-substituted sugars, can allow the size of the specifically binding oligomer to be reduced, and may also reduce the upper limit to the size of the oligomer before non-specific or aberrant binding takes place.

In some embodiments, the oligomer comprises at least 1 nucleoside analogue. In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a BNA, such as locked nucleic acid (LNA); for example at least 3 or at least 4, or at least 5, or at least 6, or at least 7, or 8, of the nucleotide analogues may be BNA, such as LNA. In some embodiments all the nucleotides analogues may be BNA, such as LNA.

It will be recognized that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as BNA units or other nucleotide analogues, which raise the duplex stability/$T_m$ of the oligomer/target duplex (i.e. affinity enhancing nucleotide analogues).

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention are independently selected from, for example: 2'-O-alkyl-RNA units, 2'-amino-DNA units, 2'-fluoro-DNA units, BNA units, e.g. LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, such as the first region, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one BNA, e.g. Locked Nucleic Acid (LNA) unit, such as 1, 2, 3, 4, 5, 6, 7, or 8 BNA/LNA units, such as from 3-7 or 4 to 8 BNA/LNA units, or 3, 4, 5, 6 or 7 BNA/LNA units. In some embodiments, all the nucleotide analogues are BNA, such as LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all BNA, such as LNA, cytosine units are 5'methyl-Cytosine. In some embodiments of the invention, the oligomer (such as the first and optionally second regions) may comprise both BNA and LNA and DNA units. In some embodiments, the combined total of LNA and DNA units is 10-25, such as 10-24, preferably 10-20, such as 10-18, such as 12-16. In some embodiments of the invention, the nucleotide sequence of the oligomer, of first region thereof, such as the contiguous nucleotide sequence consists of at least one BNA, e.g. LNA and the remaining nucleotide units are DNA units. In some embodiments the oligomer, or first region thereof, comprises only BNA, e.g. LNA, nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof. It will be recognized that the DNA or RNA nucleosides of region B may have a naturally occurring and/or non-naturally occurring nucleobase(s).

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine. In some embodiments the nucleobases may be independently selected from the group consisting of adenine, guanine, cytosine, thymidine, uracil, 5-methylcytosine. In some embodiments the nucleobases may be independently selected from the group consisting of adenine, guanine, cytosine, thymidine, and 5-methylcytosine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleoside analogue which comprises a C2*-C4* biradical (a bridge), and is known as "Locked Nucleic Acid". It may refer to an LNA monomer, or, when used in the context of an "LNA oligonucleotide", LNA refers to an oligonucleotide containing one or more such bicyclic nucleoside analogues. In some aspects bicyclic nucleoside analogues are LNA nucleotides, and these terms may therefore be used interchangeably, and is such embodiments, both are be characterized by the presence of a linker group (such as a bridge) between C2' and C4' of the ribose sugar ring.

In some embodiments the LNA used in the oligonucleotide compounds of the invention preferably has the structure of the general formula II:

Formula II

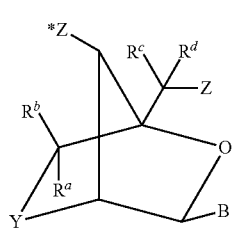

wherein Y is selected from the group consisting of —O—, —CH$_2$O—, —S—, —NH—, N(R$^e$) and/or —CH$_2$—; Z and Z* are independently selected among an internucleotide linkage, R$^H$, a terminal group or a protecting group; B constitutes a natural or non-natural nucleotide base moiety (nucleobase), and R$^H$ is selected from hydrogen and C$_{1-4}$-alkyl; R$^a$, R$^b$ R$^c$, R$^d$ and R$^e$ are, optionally independently, selected from the group consisting of hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkylamino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH$_2$); and R$^H$ is selected from hydrogen and C$_{1-4}$-alkyl. In some embodiments R$^a$, R$^b$ R$^c$, R$^d$ and R$^e$ are, optionally independently, selected from the group consisting of hydrogen and C$_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

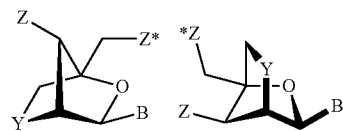

Specific exemplary LNA units are shown below:

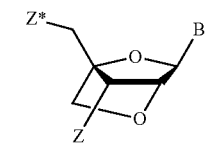

β-D-oxy-LNA

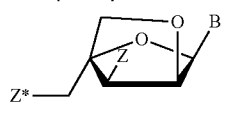

α-L-Oxy-LNA

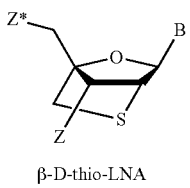

β-D-thio-LNA

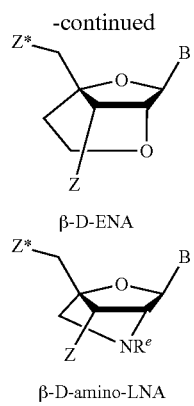

β-D-ENA

β-D-amino-LNA

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

RNAse Recruitment

It is recognized that an oligomeric compound may function via non RNase mediated degradation of target mRNA, such as by steric hindrance of translation, or other methods. In some embodiments, the oligomers of the invention are capable of recruiting an endoribonuclease (RNase), such as RNase H.

It is preferable such oligomers, such as region A, or contiguous nucleotide sequence, comprises of a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region Y' as referred to in the context of a gapmer as described herein. In some embodiments the size of the contiguous sequence which is capable of recruiting RNAse, such as region Y', may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or, more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target. The oligomer of the invention, such as the first region, may comprise a nucleotide sequence which comprises both nucleotides and nucleotide analogues, and may be e.g. in the form of a gapmer, a headmer or a mixmer.

A "headmer" is defined as an oligomer that comprises a region X' and a region Y' that is contiguous thereto, with the 5'-most monomer of region Y' linked to the 3'-most monomer of region X'. Region X' comprises a contiguous stretch of non-RNase recruiting nucleoside analogues and region Y' comprises a contiguous stretch (such as at least 7 contiguous monomers) of DNA monomers or nucleoside analogue monomers recognizable and cleavable by the RNase.

A "tailmer" is defined as an oligomer that comprises a region X' and a region Y' that is contiguous thereto, with the 5'-most monomer of region Y' linked to the 3'-most monomer of the region X'. Region X' comprises a contiguous stretch (such as at least 7 contiguous monomers) of DNA monomers or nucleoside analogue monomers recognizable and cleavable by the RNase, and region X' comprises a contiguous stretch of non-RNase recruiting nucleoside analogues.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNaseH) binding and cleavage. Since a-L-LNA (BNA) monomers recruit RNaseH activity to a certain extent, in some embodiments, gap regions (e.g., region Y' as referred to herein) of oligomers containing α-L-LNA monomers consist of fewer monomers recognizable and cleavable by the RNaseH, and more flexibility in the mixmer construction is introduced.

Gapmer Design

In some embodiments, one ore more, such as 2 or 3 oligomer regions (e.g. A, A and A', or A, A' and A") in the compound of the invention, comprises or is a gapmer. A gapmer oligomer is an oligomer which comprises a contiguous stretch of nucleotides which is capable of recruiting an RNAse, such as RNAseH, such as a region of at least 6 or 7 DNA nucleotides, referred to herein as region Y' (Y'), wherein region Y' is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions X' (X') and Z' (Z') respectively. Examples of gapmers are disclosed in WO2004/046160, WO2008/113832, and WO2007/146511.

In some embodiments, the monomers which are capable of recruiting RNAse are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), X'-Y'-Z', wherein; region X' (X') (5' region) consists or comprises of at least one nucleotide analogue, such as at least one BNA (e.g. LNA) unit, such as from 1-6 nucleotide analogues, such as BNA (e.g. LNA) units, and; region Y' (Y') consists or comprises of at least five consecutive nucleotides which are capable of recruiting RNAse (when formed in a duplex with a complementary RNA molecule, such as the mRNA target), such as DNA nucleotides, and; region Z' (Z') (3' region) consists or comprises of at least one nucleotide analogue, such as at least one BNA (e.g. LNA unit), such as from 1-6 nucleotide analogues, such as BNA (e.g. LNA) units.

In some embodiments, region X' consists of 1, 2, 3, 4, 5 or 6 nucleotide analogues, such as BNA (e.g. LNA) units, such as from 2-5 nucleotide analogues, such as 2-5 LNA units, such as 3 or 4 nucleotide analogues, such as 3 or 4 LNA units; and/or region Z' consists of 1, 2, 3, 4, 5 or 6 nucleotide analogues, such as BNA (e.g. LNA) units, such as from 2-5 nucleotide analogues, such as 2-5 BNA (e.g. LNA units), such as 3 or 4 nucleotide analogues, such as 3 or 4 BNA (e.g. LNA) units.

In some embodiments Y' consists or comprises of 5, 6, 7, 8, 9, 10, 11 or 12 consecutive nucleotides which are capable of recruiting RNAse, or from 6-10, or from 7-9, such as 8 consecutive nucleotides which are capable of recruiting RNAse. In some embodiments region Y' consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units.

In some embodiments region X' consist of 3 or 4 nucleotide analogues, such as BNA (e.g. LNA), region X' consists of 7, 8, 9 or 10 DNA units, and region Z' consists of 3 or 4 nucleotide analogues, such as BNA (e.g. LNA). Such designs include (X'-Y'-Z') 3-10-3, 3-10-4, 4-10-3, 3-9-3, 3-9-4, 4-9-3, 3-8-3, 3-8-4, 4-8-3, 3-7-3, 3-7-4, 4-7-3.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer, e.g. region X', is consisting of a contiguous nucleotide sequence of a total of 10, 11, 12, 13 or 14 nucleotide units, wherein the contiguous nucleotide sequence comprises or is of formula (5'-X'-Y'-Z' wherein; X' consists of 1, 2 or 3 nucleotide analogue units, such as BNA (e.g. LNA) units; Y' consists of 7, 8 or 9 contiguous nucleotide units which are capable of recruiting RNAse when formed in a duplex with a complementary RNA molecule (such as a mRNA target); and Z' consists of 1, 2 or 3 nucleotide analogue units, such as BNA (e.g. LNA) units.

In some embodiments X' consists of 1 BNA (e.g. LNA) unit. In some embodiments X' consists of 2 BNA (e.g. LNA) units. In some embodiments X' consists of 3 BNA (e.g. LNA) units. In some embodiments Z' consists of 1 BNA (e.g. LNA) units. In some embodiments Z' consists of 2 BNA (e.g. LNA) units. In some embodiments Z' consists of 3 BNA (e.g. LNA) units. In some embodiments Y' consists of 7 nucleotide units. In some embodiments Y' consists of 8 nucleotide units. In some embodiments Y' consists of 9 nucleotide units. In certain embodiments, region Y' consists of 10 nucleoside monomers. In certain embodiments, region Y' consists or comprises 1-10 DNA monomers. In some embodiments Y' comprises of from 1-9 DNA units, such as 2, 3, 4, 5, 6, 7, 8 or 9 DNA units. In some embodiments Y' consists of DNA units. In some embodiments Y' comprises of at least one BNA unit which is in the alpha-L configuration, such as 2, 3, 4, 5, 6, 7, 8 or 9 LNA units in the alpha-L-configuration. In some embodiments Y' comprises of at least one alpha-L-oxy BNA/LNA unit or wherein all the LNA units in the alpha-L-configuration are alpha-L-oxy LNA units. In some embodiments the number of nucleotides present in X'-Y'-Z' are selected from the group consisting of (nucleotide analogue units-region Y'-nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in X'-Y-Z' are selected from the group consisting of: 2-7-1, 1-7-2, 2-7-2, 3-7-3, 2-7-3, 3-7-2, 3-7-4, and 4-7-3. In certain embodiments, each of regions X' and Y' consists of three BNA (e.g. LNA) monomers, and region Y' consists of 8 or 9 or 10 nucleoside monomers, preferably DNA monomers. In some embodiments both X' and Z' consists of two BNA (e.g. LNA) units each, and Y' consists of 8 or 9 nucleotide units, preferably DNA units. In various embodiments, other gapmer designs include those where regions X' and/or Z' consists of 3, 4, 5 or 6 nucleoside analogues, such as monomers containing a 2'-O-methoxyethyl-ribose sugar (2'-MOE) or monomers containing a 2'-fluoro-deoxyribose sugar, and region Y' consists of 8, 9, 10, 11 or 12 nucleosides, such as DNA monomers, where regions X'-Y'-Z' have 3-9-3, 3-10-3, 5-10-5 or 4-12-4 monomers. Further gapmer designs are disclosed in WO 2007/146511A2, hereby incorporated by reference.

BNA and LNA Gapmers: The terms BNA and LNA are used interchangeably. A BNA gapmer is a gapmer oligomer (region A) which comprises at least one BNA nucleotide. A LNA gapmer is a gapmer oligomer (region A) which comprises at least one LNA nucleotide.

Splice Switching Oligomers

In some embodiments, an oligomer region is an antisense oligonucleotide which is a splice switching oligomer—i.e. an oligomer which targets the pre-mRNA causing an alternative splicing of the pre-mRNA.

Targets for the splice switching oligomer may include TNF receptor, for example the SSO may be one or more of the TNFR SSOs disclosed in WO2007/058894, WO08051306 A1 and PCT/EP2007/061211, hereby incorporated by reference.

Splice switching oligomers are typically (essentially) not capable of recruiting RNaseH and as such gapmer, tailmer or headmer designs are generally not desirable. However, mixmer and totalmers designs are suitable designs for SSOs.

Spice switching oligomers have also been used to target dystrophin deficiency in Duchenne muscular dystrophy.

Mixmers

Most antisense oligonucleotides are compounds which are designed to recruit RNase enzymes (such as RNaseH) to degrade their intended target. Such compounds include DNA phosphorothioate oligonucleotides and gapmer, headmers and tailmers. These compounds typically comprise a region of at least 5 or 6 DNA nucleotides, and in the case of gapmers are flanked on either side by affinity enhancing nucleotide analogues.

The oligomers of the present invention may operate via an RNase (such as RNaseH) independent mechanism. Examples of oligomers which operate via a non-RNaseH (or non-RNase) mechanism are mixmers and totalmers.

The term 'mixmer' refers to oligomers which comprise both naturally and non-naturally occurring nucleotides, where, as opposed to gapmers, tailmers, and headmers there is no contiguous sequence of more than 5, and in some embodiments no more than 4 consecutive, such as no more than three consecutive, naturally occurring nucleotides, such as DNA units. In some embodiments, the mixmer does not comprise more than 5 consecutive nucleoside analogues, such as BNA (LNA), and in some embodiments no more than 4 consecutive, such as no more than three consecutive, consecutive nucleoside analogues, such as BNA (LNA). In such mixmers the remaining nucleosides may, for example by DNA nucleosides, and/or in non-bicyclic nucleoside analogues, such as those referred to herein, for example, 2' substituted nucleoside analogues, such as 2'-O-MOE and or 2'fluoro.

The oligomer according to the invention may be mixmers—indeed various mixmer designs are highly effective as oligomer or first region thereof, particularly when targeting microRNA (antimiRs), microRNA binding sites on mRNAs (Blockmirs) or as splice switching oligomers (SSOs). See for example WO2007/112754 (LNA-AntimiRs™), WO2008/131807 (LNA splice switching oligos), In some embodiments, the oligomer or mixmer may comprise of BNA and 2' substituted nucleoside analogues, optionally with DNA nucleosides—see for example see WO07027894 and WO2007/112754 which are hereby incorporated by reference. Specific examples include oligomers or first regions which comprise LNA, 2'-O-MOE and DNA, LNA, 2'fluoro and 2'-O-MOE, 2'-O-MOE and 2'fluoro, 2'-O-MOE and 2'fluoro and LNA, or LNA and 2'-O-MOE and LNA and DNA.

In some embodiments, the oligomer or mixmer comprises or consists of a contiguous nucleotide sequence of repeating pattern of nucleotide analogue and naturally occurring nucleotides, or one type of nucleotide analogue and a second type of nucleotide analogues. The repeating pattern, may, for instance be every second or every third nucleotide is a nucleotide analogue, such as BNA (LNA), and the remaining nucleotides are naturally occurring nucleotides, such as DNA, or are a 2' substituted nucleotide analogue such as 2'MOE of 2'fluoro analogues as referred to herein, or, in some embodiments selected form the groups of nucleotide analogues referred to herein. It is recognized that the repeating pattern of nucleotide analogues, such as LNA units, may be combined with nucleotide analogues at fixed positions—e.g. at the 5' or 3' termini.

In some embodiments the first nucleotide of the oligomer or mixmer, counting from the 3' end, is a nucleotide analogue, such as an LNA nucleotide.

In some embodiments, which may be the same or different, the second nucleotide of oligomer or mixmer, counting from the 3' end, is a nucleotide analogue, such as an LNA nucleotide.

In some embodiments, which may be the same or different, the seventh and/or eighth nucleotide of oligomer or mixmer, counting from the 3' end, are nucleotide analogues, such as LNA nucleotides.

In some embodiments, which may be the same or different, the ninth and/or the tenth nucleotides of the first and/or second oligomer, counting from the 3' end, are nucleotide analogues, such as LNA nucleotides.

In some embodiments, which may be the same or different, the 5' terminal of oligomer or mixmer is a nucleotide analogue, such as an LNA nucleotide.

The above design features may, in some embodiments be incorporated into the mixmer design, such as antimiR mixmers.

In some embodiments, the oligomer or mixmer does not comprise a region of more than 4 consecutive DNA nucleotide units or 3 consecutive DNA nucleotide units. In some embodiments, the mixmer does not comprise a region of more than 2 consecutive DNA nucleotide units.

In some embodiments, the oligomer or mixmer comprises at least a region consisting of at least two consecutive nucleotide analogue units, such as at least two consecutive LNA units.

In some embodiments, the oligomer or mixmer comprises at least a region consisting of at least three consecutive nucleotide analogue units, such as at least three consecutive LNA units.

In some embodiments, the oligomer or mixmer of the invention does not comprise a region of more than 7 consecutive nucleotide analogue units, such as LNA units. In some embodiments, the oligomer or mixmer of the invention does not comprise a region of more than 6 consecutive nucleotide analogue units, such as LNA units. In some embodiments, the oligomer or mixmer of the invention does not comprise a region of more than 5 consecutive nucleotide analogue units, such as LNA units. In some embodiments, the oligomer or mixmer of the invention does not comprise a region of more than 4 consecutive nucleotide analogue units, such as LNA units. In some embodiments, the oligomer or mixmer of the invention does not comprise a region of more than 3 consecutive nucleotide analogue units, such as LNA units. In some embodiments, the oligomer or mixmer of the invention does not comprise a region of more than 2 consecutive nucleotide analogue units, such as LNA units. A mixmer is a oligomer which may comprise one or more short regions of DNA of no more than 4 consecutive DNA nucleotides, and typically comprises alternating regions of a nucleotide analogue (such as LNA units) and DNA nucleotides, optionally regions of other nucleotide analogues (e.g. non-LNA nucleotide analogues). Totalmers comprise of no DNA or RNA nucleotides (although may comprise analogues or derivatives of DNA and RNA). In some embodiments, the oligomer (e.g. region A) of the invention may, in some embodiments, comprise of no more than 4 consecutive DNA nucleotides, or no more than 3 consecutive DNA nucleotides.

The following embodiments may apply to mixmers or totalmer oligomers (e.g. as region A):

The oligomer (e.g. region A) of the invention may, in some embodiments, comprise of at least two alternating regions of LNA and non-LNA nucleotides (such as DNA or 2' substituted nucleotide analogues).

The oligomer of the invention may, in some embodiments, comprise a contiguous sequence of formula: 5' ([LNA nucleotides]$_{1-5}$ and [non-LNA nucleotides]$_{1-4}$)$_{2-12}$. 3'.

In some embodiments, the 5' nucleotide of the contiguous nucleotide sequence (or the oligomer) is an LNA nucleotide.

In some embodiments, the 3' nucleotide of the contiguous nucleotide sequence is a nucleotide analogue, such as LNA, or the 2, 3, 4, 5 3' nucleotides are nucleotide analogues, such as LNA nucleotides, or other nucleotide analogues which confer enhanced serum stability to the oligomer.

In some embodiments, the contiguous nucleotide sequence of the oligomer has a formula 5' ([LNA nucleotides]$_{1-5}$-[non-LNA nucleotides]$_{1-4}$)$_{2-11}$-[LNA nucleotides]$_{1-5}$ 3'.

In some embodiments, the contiguous nucleotide sequence of the oligomer has 2, 3 or 4 contiguous regions of LNA and non-LNA nucleotides—e.g. comprises formula 5' ([LNA nucleotides]$_{1-5}$ and [non-LNA nucleotides]$_{1-4}$)$_{2-3}$, optionally with a further 3' LNA region [LNA nucleotides]$_{1-5}$.

In some embodiments, the contiguous nucleotide sequence of the oligomer comprises 5' ([LNA nucleotides]$_{1-3}$ and [non-LNA nucleotides]$_{1-3}$)$_{2-5}$, optionally with a further 3' LNA region [LNA nucleotides]$_{1-3}$.

In some embodiments, the contiguous nucleotide sequence of the oligomer comprises 5' ([LNA nucleotides]$_{1-3}$ and [non-LNA nucleotides]$_{1-3}$)$_3$, optionally with a further 3' LNA region [LNA nucleotides]$_{1-3}$.

In some embodiments the non-LNA nucleotides are all DNA nucleotides.

In some embodiments, the non-LNA nucleotides are independently or dependently selected from the group consisting of DNA units, RNA units, 2'-O-alkyl-RNA units, 2'-OMe-RNA units, 2'-amino-DNA units, and 2'-fluoro-DNA units.

In some embodiments the non-LNA nucleotides are (optionally independently selected from the group consisting of 2' substituted nucleoside analogues, such as (optionally independently) selected from the group consisting of 2'-O-alkyl-RNA units, 2'-OMe-RNA units, 2'-amino-DNA units, 2'-AP, 2'-FANA, 2'-(3-hydroxy)propyl, and 2'-fluoro-DNA units, and/or other (optionally) sugar modified nucleoside analogues such as morpholino, peptide nucleic acid (PNA), CeNA, unlinked nucleic acid (UNA), hexitol nucleic acid (HNA). bicyclo-HNA (see e.g. WO2009/100320), In some embodiments, the nucleoside analogues increase the affinity of the first region for its target nucleic acid (or a complementary DNA or RNA sequence). Various nucleoside analogues are disclosed in Freier & Altmann; *Nucl. Acid Res.*, 1997, 25, 4429-4443 and Uhlmann; *Curr. Opinion in Drug Development*, 2000, 3(2), 293-213, hereby incorporated by reference.

In some embodiments, the non-LNA nucleotides are DNA nucleotides. In some embodiments, the oligomer or contiguous nucleotide sequence comprises of LNA nucleotides and optionally other nucleotide analogues (such as the nucleotide analogues listed under non-LNA nucleotides) which may be affinity enhancing nucleotide analogues and/or nucleotide analogues which enhance serum stability.

In some embodiments, the oligomer or contiguous nucleotide sequence thereof consists of a contiguous nucleotide sequence of said nucleotide analogues.

In some embodiments, the oligomer or contiguous nucleotide sequence thereof consists of a contiguous nucleotide sequence of LNA nucleotides.

In some embodiments, the oligomer or contiguous nucleotide sequence is 8-12, such as 8-10, or 10-20, such as 12-18 or 14-16 nts in length.

In some embodiments, the oligomer or contiguous nucleotide sequence is capable of forming a duplex with a complementary single stranded RNA nucleic acid molecule with phosphodiester internucleoside linkages, wherein the duplex has a $T_m$ of at least about 60° C., such as at least 65° C.

Example of a $T_m$ Assay: The oligonucleotide: Oligonucleotide and RNA target (PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Totalmers

A totalmer is a single stranded oligomer which only comprises non-naturally occurring nucleosides, such as sugar-modified nucleoside analogues.

The first region according to the invention may be totalmers—indeed various totalmer designs are highly effective as oligomers or first region thereof, e.g. particularly when targeting microRNA (antimiRs) or as splice switching oligomers (SSOs). In some embodiments, the totalmer comprises or consists of at least one XYX or YXY sequence motif, such as a repeated sequence XYX or YXY, wherein X is LNA and Y is an alternative (i.e. non LNA) nucleotide analogue, such as a 2'-O-MOE RNA unit and 2'-fluoro DNA unit. The above sequence motif may, in some embodiments, be XXY, XYX, YXY or YYX for example.

In some embodiments, the totalmer may comprise or consist of a contiguous nucleotide sequence of between 7 and 16 nucleotides, such as 9, 10, 11, 12, 13, 14, or 15 nucleotides, such as between 7 and 12 nucleotides.

In some embodiments, the contiguous nucleotide sequence of the totalmer comprises of at least 30%, such as at least 40%, such as at least 50%, such as at least 60%, such as at least 70%, such as at least 80%, such as at least 90%, such as 95%, such as 100% BNA (LNA) units. The remaining units may be selected from the non-LNA nucleotide analogues referred to herein in, such those selected from the group consisting of 2'-O_alkyl-RNA unit, 2'-OMe-RNA unit, 2'-amino-DNA unit, 2'-fluoro-DNA unit, LNA unit, PNA unit, HNA unit, INA unit, and a 2'MOE RNA unit, or the group 2'-OMe RNA unit and 2'-fluoro DNA unit.

In some embodiments the totalmer consist or comprises of a contiguous nucleotide sequence which consists only of LNA units. In some embodiments, the totalmer, such as the LNA totalmer, is between 7-12 nucleoside units in length. In some embodiments, the totalmer (as the oligomer or first region thereof) may be targeted against a microRNA (i.e. be antimiRs)—as referred to WO2009/043353, which are hereby incorporated by reference. In some embodiments, the oligomer or contiguous nucleotide sequence comprises of LNA nucleotides and optionally other nucleotide analogues which may be affinity enhancing nucleotide analogues and/or nucleotide analogues which enhance serum stability.

In some embodiments, the oligomer or contiguous nucleotide sequence thereof consists of a contiguous nucleotide sequence of said nucleotide analogues.

In some embodiments, the oligomer or contiguous nucleotide sequence thereof consists of a contiguous nucleotide sequence of LNA nucleotides.

MicroRNA Modulation Via the Oligomer or First Region Thereof.

In some embodiments, one or more of the oligomer regions (such as A, A and A' and, A and A' and A") are antimiR(s), such as an LNA mixmer or totalmer, which comprises or consists of a contiguous nucleotide sequence which is corresponds to or is fully complementary to a microRNA sequence, such as a mature microRNA sequence or part thereof. The use of the present invention in controlling the in vivo activity of microRNA is considered of primary importance due to the fact that microRNAs typically regulate numerous mRNAs in the subject. The ability to inactivate therapeutic antimiRs is therefore very desirable.

Numerous microRNAs are related to a number of diseases. For example: non-limiting examples of therapeutic indications which may be treated by the pharmaceutical compositions of the invention:

| microRNA | Possible medical indications |
| --- | --- |
| miR-1 | Cardiac arythmia |
| miR-21 | Glioblastoma, breast cancer, hepatocellular carcinoma, colorectal cancer, sensitization of gliomas to cytotoxic drugs, cardiac hypertrophy |
| miR-21, miR-200b and miR-141 | Response to chemotherapy and regulation of cholangiocarcinoma growth |
| miR-122 | hypercholesterolemia, hepatitis C infection, hemochromatosis |
| miR-19b | lymphoma and other tumour types |
| miR-26a | Osteoblast differentiation of human stem cells |
| miR-155 | lymphoma, pancreatic tumor development, breast and lung cancer |
| miR-203 | Psoriasis |
| miR-375 | diabetes, metabolic disorders, glucose-induced insulin secretion from pancreatic endocrine cells |
| miR-181 | myoblast differentiation, auto immune disorders |
| miR-10b | Breast cancer cell invasion and metastasis |
| miR-125b-1 | Breast, lung, ovarian and cervical cancer |
| miR-221 and 222 | Prostate carcinoma, human thyroid papillary car, human hepatocellular carcinoma |
| miRNA-372 and -373 | testicular germ cell tumors. |
| miR-142 | B-cell leukemia |
| miR-17-19b cluster | B-cell lymphomas, lung cancer, hepatocellular carcinoma |

Tumor suppressor gene tropomysin 1 (TPM1) mRNA has been indicated as a target of miR-21. Myotrophin (mtpn) mRNA has been indicated as a target of miR 375.

The oligomer or first region thereof may therefore be an antimir which targets (i.e. comprises or consists of a contiguous nucleotide sequence which is fully complementary to (a corresponding region of) one of the microRNAs listed above or comprises of no more than a single mismatch thereto.

Hence, some aspects of the invention relates to the treatment of a disease associated with the expression of microRNAs selected from the group consisting of infectious diseases such as viral diseases such as hepatitis C virus and HIV, fragile X mental retardation, inflammatory diseases, cancer, such as chronic lymphocytic leukemia, breast cancer, lung cancer and colon cancer.

MicroRNAs (miRNAs) are an abundant class of short endogenous RNAs that act as post-transcriptional regulators of gene expression by base-pairing with their target mRNAs. The mature miRNAs are processed sequentially from longer hairpin transcripts by the RNAse III ribonucleases Drosha. Mature microRNAs (miRs) typically between 20 and 25 contiguous RNA nucleotides. It is now widely established that several microRNAs are associated with medical conditions and disease, and several companies are developing therapeutics based on oligomers which either mimic microRNAs or specifically hybridise to specific microRNAs associated with disease phenotypes—such oligomers are referred to, herein, as microRNA mimics and antimiRs respectfully, and the oligomer or first region thereof, in some embodiments may be such microRNA modulating oligomers.

In some embodiments the oligomer or first region thereof according to the invention, consists or comprises of a contiguous nucleotide sequence which corresponds to or is fully complementary to a microRNA sequence, such as a mature microRNA sequence, such as the human microRNAs published in miRBase (http://microrna.sanger.ac.uk/cgi-bin/sequences/mirna_summary.pl?org=hsa). In some embodiment the microRNA is a viral microRNA. At the time of writing, in miRbase 19, there are 1600 precursors and 2042 mature human miRNA sequences in miRBase which are all hereby incorporated by reference, including the mature microRNA sequence of each human microRNA. Other human microRNAs which may be targeted by the oligomer or first region thereof include those disclosed in WO08040355A, hereby incorporated by reference. In some embodiments the oligomer or first region thereof according to the invention, consists or comprises of a contiguous nucleotide sequence which corresponds to or is fully complementary to a microRNA sequence selected from the group consisting of hsa-miR19b, hsa-miR21, hsa-miR 122, hsa-miR 142 a7b, hsa-miR 155, and hsa-miR 375. In some embodiments the oligomer or first region thereof according to the invention, consists or comprises of a contiguous nucleotide sequence which corresponds to or is fully complementary to a microRNA sequence selected from the group consisting of hsa-miR221 and hsa-miR222.

In some embodiments the oligomer or first region thereof according to the invention, consists or comprises of a contiguous nucleotide sequence which corresponds to or is fully complementary to hsa-miR122 (NR_029667.1 GI:262205241), such as the mature has-miR-122.

In some embodiments when the oligomer or first region thereof targets miR-122, the oligomer is for the use in the treatment of hepatitis C infection.

AntimiR Oligomers

Preferred oligomer or first region thereof 'antimiR' designs and oligomers are disclosed in WO2007/112754, WO2007/112753, PCT/DK2008/000344 and U.S. provisional applications 60/979,217 and 61/028,062, all of which are hereby incorporated by reference. In some embodiments, the oligomer or first region thereof is an antimiR which is a mixmer or a totalmer.

AntimiR oligomers are oligomers which consist or comprise of a contiguous nucleotide sequence which is fully complementary to, or essentially complementary to (i.e. may comprise one or two mismatches), to a microRNA sequence, or a corresponding sub-sequence thereof. In this regards it is considered that the antimiR may be comprise a contiguous nucleotide sequence which is complementary or essentially complementary to the entire mature microRNA, or the antimiR may be comprise a contiguous nucleotide sequence which is complementary or essentially complementary to a sub-sequence of the mature microRNA or pre-microRNA—such a sub-sequence (and therefore the corresponding contiguous nucleotide sequence) is typically at least 8 nucleotides in length, such as between 8 and 25 nucleotides, such as 9, 10, 11, 12, 13, 14, 15, 16, 17, 18, 19, 20, 21, 22, 23, 24 nucleotides in length, such as between 10-17 or 10-16 nucleotides, such as between 12-15 nucleotides.

Numerous designs of AntimiRs have been suggested, and typically antimiRs for therapeutic use, such as the contiguous nucleotide sequence thereof comprise one or more nucleotide analogues units.

In some embodiments the antimiR may have a gapmer structure as herein described. However, as explained in WO2007/112754 and WO2007/112753, other designs may be preferable, such as mixmers, or totalmers.

WO2007/112754 and WO2007/112753, both hereby incorporated by reference, provide antimiR oligomers and antimiR oligomer designs where the oligomers which are complementary to mature microRNA In some embodiments, a subsequence of the antimiR corresponds to the miRNA seed region. In some embodiments, the first or second 3' nucleobase of the oligomer corresponds to the second 5' nucleotide of the microRNA sequence.

In some antimiR embodiments, nucleobase units 1 to 6 (inclusive) of the oligomer as measured from the 3' end the region of the oligomer are complementary to the microRNA seed region sequence.

In some antimiR embodiments, nucleobase units 1 to 7 (inclusive) of the oligomer as measured from the 3' end the region of the oligomer are complementary to the microRNA seed region sequence.

In some e antimiR embodiments, nucleobase units 2 to 7 (inclusive) of the oligomer as measured from the 3' end the region of the oligomer are complementary to the microRNA seed region sequence.

In some embodiments, the antimiR oligomer comprises at least one nucleotide analogue unit, such as at least one LNA unit, in a position which is within the region complementary to the miRNA seed region. The antimiR oligomer may, in some embodiments comprise at between one and 6 or between 1 and 7 nucleotide analogue units, such as between 1 and 6 and 1 and 7 LNA units, in a position which is within the region complementary to the miRNA seed region.

In some embodiments, the antimiR of the invention is 7, 8 or 9 nucleotides long, and comprises a contiguous nucleotide sequence which is complementary to a seed region of a human or viral microRNA, and wherein at least 80%, such as 85%, such as 90%, such as 95%, such as 100% of the nucleotides are LNA.

In some embodiments, the antimiR of the invention is 7, 8 or 9 nucleotides long, and comprises a contiguous nucleotide sequence which is complementary to a seed region of a human or viral microRNA, and wherein at least 80% of the nucleotides are LNA, and wherein at least 80%, such as 85%, such as 90%, such as 95%, such as 100% of the internucleotide bonds are phosphorothioate bonds.

In some embodiments, the antimiR comprises one or two LNA units in positions three to eight, counting from the 3' end. This is considered advantageous for the stability of the A-helix formed by the oligonucleotide:microRNA duplex, a duplex resembling an RNA:RNA duplex in structure.

The table on pages 48 line 15 to page 51, line 9 of WO2007/112754 provides examples of anti microRNA oligomers antimiRs which may be the oligomer or first region thereof) and is hereby specifically incorporated by reference. Some Further Poly AntimiR Oligomer Compounds and Conjugates Thereof In some embodiments two of the oligomer regions target a microRNA nucleic acid, such as region A and region A', and optionally, region A". The oligomer regions may target the same or different microRNA targets. By way of example, the oligomer regions may all target the same microRNA, such as microRNA-122, microRNA-221, microRNA-33 or microRNA-21. Alternatively, one oligomer region may target a first microRNA target, and a further oligomer region may target a second microRNA target. The invention therefore provides for a method for concurrent inhibition of 2 or more different microRNAs, and may therefore be used to target multiple members of a microRNA family, or two microRNAs: An example is poly-oligo compounds which comprise a first oligomer region which is complementary to at least 7 nucleotides present in miR-21, and a further oligomer region which is complementary to at least 7 nucleotides present in miR-221. Both miR-21 and miR-221 are indicated in some forms of cancer, such as hepatocellular carcinoma.

Poly mRNA Targeting Compounds

In some embodiments 2 of the oligomer regions target a mRNA nucleic acid, such as region A and region A', and optionally, region A". The oligomer regions may target the same or different mRNA targets. By way of example, the oligomer regions may all target the same microRNA, such as those provided herein, such as ApoB, for example (SEQ ID NO 15)
(Trivalent GalNAc)- $G_sT_st_sg_sa_sc_sa_sc_st_sg_sT_s$Cca -

$G_s^m C_sa_st_st_sg_sg_st_sa_st_sT_s^m C_sA$ 3'

(SEQ ID NO 16)
(Trivalent GalNAc)- $G_sC_sa_st_st_sg_sg_st_sa_st_sT_sC_sA$ ca -

$G_s^m C_sat_st_sg_sg_st_sa_st_sT_s^m C_sA$ 3'

(SEQ ID NO 17)
(Trivalent GalNAc)- $G_sT_st_sg_sa_sc_sa_sc_st_sg_sT_s$Cca -

$G_sT_st_sg_sa_sc_sa_sc_st_sg_sT_sC$ 3'

(SEQ ID NO 18)
(Trivalent GalNAc)- $G_sC_sa_st_st_sg_sg_st_sa_st_sT_sC_sA$ ca -

$G_sT_st_sg_sa_sc_sa_sc_st_sg_sT_sC$ 3'

Capital letters are LNA such as beta-D-oxy-LNA, lower case letters are DNA, subscript s is phosphorothioate linkage, other internucleoside linkages are phosphodiester. LNA cytosines may be 5-methyl cytosine. The Trivalent GalNAc may for example be Conj 1, 2, 3, 4, 1a, 2a, 3a, or 4a, such as conj2a. The conjugate group may be linked to the oligo via a PD linker, e.g. a region of 1-5 phosphodiester linked DNA nucleosides, e.g. the 5' Conj-ca-3' dinucleotide as used in the examples.

Alternatively, one oligomer region may target a first mRNA target, and a further oligomer region may target a second mRNA target. The invention therefore provides for a method for concurrent inhibition of 2 or more different mRNAs. An example is poly-oligo compounds which comprise a first oligomer region which is complementary to at least 10 nucleotides present in an ApoB mRNA, and a further oligomer region which is complementary to at least 10 nucleotides present in an mtGPAT mRNA. By utilising a first LNA oligomer region which targets a first target (e.g. a mRNA, a microRNA, or a viral sequence), and a second LNA oligomer region which targets a second target (e.g. a mRNA, a microRNA, or a viral sequence), single compounds can be made which target two distinct targets, for example, the first oligomer region may target ApoB, and the second oligomer region may target another mRNA, such as mtGPAT mRNA, for example:

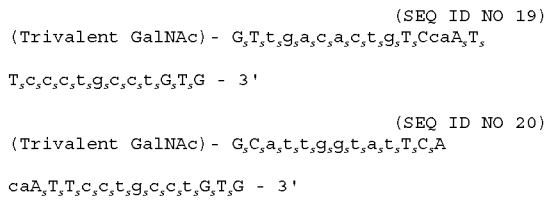

```
                                                (SEQ ID NO 19)
(Trivalent GalNAc)- G_sT_st_sg_sa_sc_sa_sc_st_sg_sT_sCcaA_sT_s T_sc_sc_sc_st_sg_sc_sc_st_sG_sT_sG - 3'

(SEQ ID NO 20)
(Trivalent GalNAc)- G_sC_sa_st_st_sg_sg_st_sa_st_sT_sC_sA caA_sT_sc_sc_st_sg_sc_sc_st_sG_sT_sG - 3'
```

Capital letters are LNA such as beta-D-oxy-LNA, lower case letters are DNA, subscript s is phosphorothioate linkage, other internucleoside linkages are phosphodiester. LNA cytosines may be 5-methyl cytosine. The Trivalent GalNAc may for example be Conj 1, 2, 3, 4, 1a, 2a, 3a, or 4a, such as conj2a. The conjugate group may be linked to the oligo via a PO linker, e.g. a region of 1-5 phosphodiester linked DNA nucleotides, e.g. the 5' Conj-ca-3' dinucleotide as used in the examples.

MicroRNA Mimics

In some embodiments the oligomer or first region thereof is in the form of a miRNA mimic which can be introduced into a cell to repress the expression of one or more mRNA target(s). miRNA mimics are typically fully complementary to the full length miRNA sequence. miRNA mimics are compounds comprising a contiguous nucleotide sequence which are homologous to a corresponding region of one, or more, of the miRNA sequences provided or referenced to herein. The use of miRNA mimics or antimiRs can be used to (optionally) further repress the mRNA targets, or to silence (down-regulate) the miRNA, thereby inhibiting the function of the endogenous miRNA, causing derepression and increased expression of the mRNA target.

Aptamers

In some embodiments the oligomer or first region thereof may be a therapeutic aptamer, a spiegelmer. Please note that aptamers may also be ligands, such as receptor ligands, and may therefore be used as a targeting moiety (i.e. region 3). Aptamers (also referred to as Spiegelmers) in the context of the present invention as nucleic acids of between 20 and 50 nucleotides in length, which have been selected on the basis of their conformational structure rather than the sequence of nucleotides—they elicit their therapeutic effect by binding with a target protein directly in vivo and they do not, therefore, comprise of the reverse complement of their target—indeed their target is not a nucleic acid but a protein. Specific aptamers which may be the oligomer or first region thereof include Macugen (OSI Pharmaceuticals) or ARC1779, (Archemix, Cambridge, Mass.). In some embodiments, the oligomer or first region thereof is not an aptamer. In some embodiments the oligomer or first region thereof is not an aptamer or a spiegelmer.

Internucleotide Linkages

The nucleoside monomers of the oligomers (e.g. first and second regions) described herein are coupled together via [internucleoside] linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" or "internucleotide linkage" are intended to mean a group capable of covalently coupling together two nucleotides. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference).

It is, in some embodiments, other than the phosphodiester linkage(s) or region B, the preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (5) containing internucleotide linkages as provided herein may be preferred, such as phosphorothioate or phosphorodithioate. Phosphorothioate internucleotide linkages are also preferred, particularly for the first region, such as in gapmers, mixmers, antimirs splice switching oligomers, and totalmers.

For gapmers, the internucleotide linkages in the oligomer may, for example be phosphorothioate or boranophosphate so as to allow RNase H cleavage of targeted RNA. Phosphorothioate is preferred, for improved nuclease resistance and other reasons, such as ease of manufacture.

In one aspect, with the exception of the phosphodiester linkage between the first and second region, and optionally within region B, the remaining internucleoside linkages of the oligomer of the invention, the nucleotides and/or nucleotide analogues are linked to each other by means of phosphorothioate groups. In some embodiments, at least 50%, such as at least 70%, such as at least 80%, such as at least 90% such as all the internucleoside linkages between nucleosides in the first region are other than phosphodiester (phosphate), such as are selected from the group consisting of phosphorothioate phosphorodithioate, or boranophosphate. In some embodiments, at least 50%, such as at least 70%, such as at least 80%, such as at least 90% such as all the internucleoside linkages between nucleosides in the first region are phosphorothioate.

WO09124238 refers to oligomeric compounds having at least one bicyclic nucleoside attached to the 3' or 5' termini by a neutral internucleoside linkage. The oligomers of the invention may therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages may be phosphorothioate.

Conjugates, Targeting Moieties and Blocking Groups

The term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

In various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

In some embodiments, the conjugate may be a lipophilic conjugate or a proteins (e.g., antibodies, enzymes, serum proteins); peptides; vitamins (water-soluble or lipid-soluble); polymers (water-soluble or lipid-soluble); small molecules including drugs, toxins, reporter molecules, and receptor ligands; carbohydrate complexes; nucleic acid cleaving complexes; metal chelators (e.g., porphyrins, texaphyrins, crown ethers, etc.); intercalators including hybrid photonuclease/intercalators; crosslinking agents (e.g., photoactive, redox active), and combinations and derivatives thereof. Numerous suitable conjugate moieties, their preparation and linkage to oligomeric compounds are provided, for example, in WO 93/07883 and U.S. Pat. No. 6,395,492, each of which is incorporated herein by reference in its entirety. Oligonucleotide conjugates and their syntheses are also reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety. [0034]

Conjugation (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example from 1-50, such as 2-20 such as 3-10 amino acid residues in length, and/or polyalkylene oxide such as polyethylglycol (PEG) or polypropylene glycol—see WO 2008/034123, hereby incorporated by reference.

The use of a conjugate is often associated with enhanced pharmacokinetic or pharmeodynamic dynamic properties. However, the presence of a conjugate group may interfere with the activity of the oligonucleotide against its intended target, for example via steric hindrance preventing hybridization or nuclease recruitment (e.g. RNAseH or RISC recruitment). The use of a DNA and/or RNA phosphodiester region (region B) between the oligonucleotide (region A) and the conjugate moiety (X), as according to the present invention, allows for the improved properties due to the presence of the conjugate group, whilst ensuring that once at the target tissue, the conjugate group does not prevent effective activity of the oligonucleotide.

The oligomeric compound of the invention is, in some embodiments, covalently attached to one or more conjugate group, optionally through one or more linkers. The resulting conjugate compounds may, for example have modified enhanced properties, such as modified or enhanced pharmacokinetic, pharmeodynamic, and other properties compared with non-conjugated oligomeric compounds. A conjugate moiety that can modify or enhance the pharmacokinetic properties of an oligomeric compound can improve cellular distribution, bioavailability, metabolism, excretion, permeability, and/or cellular uptake of the oligomeric compound. A conjugate moiety that can modify or enhance pharmacodynamic properties of an oligomeric compound can improve activity, resistance to degradation, sequence-specific hybridization, uptake, and the like. In some embodiments, the conjugate group may reduce or prevent in appropriate activity of the oligonucleotide, e.g. off target activity or activity in non-target tissues or organs. This may be achieved by use of a blocking moiety, which may for example be a conjugate, the presence of the blocking group covalently attached to the oligonucleotide (optionally via a linker), may prevent or hinder oligonucleotide hybridization and/or activity. The cleavage of the DNA/RNA phosphodiester region (e.g. at the intended target site), removes the blocking group, allowing delivery of the active oligonucleotide at the intended site.

In some embodiments, the compound of the invention comprises a conjugate group.

It will be recognized that one conjugate group may be used, for example for targeting to a specific tissue, for example a lipophilic group for targeting to the liver, and a second conjugate group may be used to provide a further benefit, for example a blocking group or a further therapeutic entity. Suitable one or both of the conjugates/moieties may be linked to the oligonucleotide via the DNA/RNA phosphodiester region according to the present invention. In some embodiments, the conjugate is covalently bound to the oligonucleotide, optionally via a linker, at the 5' and/or 3' termini of the oligonucleotide. In this respect, if two conjugate/moiety groups are used, one may be linked to the 5' termini and one to the 3' termini.

Carbohydrate Conjugates

In some embodiments, the conjugate group is selected from the group consisting of a carbohydrate, a lipophilic moiety, a polymer, a protein or peptide, a label or dye, a small molecule, such as a small molecule therapeutic moiety, a cell surface receptor ligand.

In some embodiments, the conjugate is or may comprise a carbohydrate or comprises a carbohydrate group. In some embodiments, the carbohydrate is selected from the group consisting of galactose, lactose, n-acetylgalactosamine, mannose, and mannose-6-phosphate. In some embodiments, the conjugate group is or may comprise mannose or mannose-6-phosphate. Carbohydrate conjugates may be used to enhance delivery or activity in a range of tissues, such as liver and/or muscle. See, f or example, EP1495769, WO99/65925, Yang et al., Bioconjug Chem (2009) 20(2): 213-21. Zatsepin & Oretskaya Chem Biodivers. (2004) 1(10): 1401-17.

In some embodiments, the conjugate group is a carbohydrate moiety. In addition, the oligomer may further comprise one or more additional conjugate moieties, of which lipophilic or hydrophobic moieties are particularly interesting. These may for example, act as pharmacokinetic modulators, and may be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a bio cleavable linker. I In some embodiments, the conjugate is or may comprise a carbohydrate or comprises a carbohydrate group. In some embodiments, the carbohydrate is selected from the group consisting of galactose, lactose, n-acetylgalactosamine, mannose, and mannose-6-phosphate. In some embodiments, the conjugate group is or may comprise mannose or mannose-6-phosphate. Carbohydrate conjugates may be used to enhance delivery or activity in a range of tissues, such as liver and/or muscle. See, for example, EP1495769, WO99/65925, Yang et al., Bioconjug Chem (2009) 20(2): 213-21. Zatsepin & Oretskaya Chem Biodivers. (2004) 1(10): 1401-17.

GalNAc Conjugates

The invention also provides oligonucleotides, such as LNA antisense oligomers, which are conjugated to an asialoglycoprotein receptor targeting moiety. In some embodiments, the conjugate moiety (such as the third region or region C) comprises an asialoglycoprotein receptor targeting moiety, such as galactose, galactosamine, N-formyl-galactosamine, Nacetylgalactosamine, N-propionyl-galactosamine, N-n-butanoyl-galactosamine, and N-isobutanoyl-galactos-amine. In some embodiments the conjugate comprises a galactose cluster, such as N-acetylgalactosamine trimer. In some embodiments, the conjugate moiety comprises a GalNAc (N-acetylgalactosamine), such as a mono-valent, di-valent, tri-valent of tetra-valent GalNAc. Trivalent GalNAc conjugates may be used to target the compound to the liver. GalNAc conjugates have been used with methylphosphonate and PNA antisense oligonucleotides (e.g. U.S. Pat. No. 5,994,517 and Hangeland et al., Bioconjug Chem. 1995 November-December; 6(6):695-701) and siRNAs (e.g. WO2009/126933, WO2012/089352 & WO2012/083046). The GalNAc references and the specific conjugates used therein are hereby incorporated by reference. WO2012/083046 discloses siRNAs with GalNAc conjugate moieties which comprise cleavable pharmacokinetic modulators, which are suitable for use in the present invention, the preferred pharmacokinetic modulators are C16 hydrophobic groups such as palmitoyl, hexadec-8-enoyl, oleyl, (9E, 12E)-octadeca-9,12-dienoyl, dioctanoyl, and C16-C20 acyl. The '046 cleavable pharmacokinetic modulators may also be cholesterol.

The 'targeting moieties (conjugate moieties) may be selected from the group consisting of: galactose, galactosamine, N-formyl-galactosamine, N-acetylgalactosamine, Npropionyl-galactosamine, N-n-butanoyl-galactosamine, N-iso-butanoylgalactos-amine, galactose cluster, and N-acetylgalactosamine trimer and may have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNac clusters disclosed in '046 include: (E)-hexadec-8-enoyl (C16), oleyl (C18), (9,E,12E)-octadeca-9,12-dienoyl (018), octanoyl (C8), dodececanoyl (C12), C-20 acyl, C24 acyl, dioctanoyl (2×C8). The targeting moiety-pharmacokinetic modulator targeting moiety may be linked to the polynucleotide via a physiologically labile bond or, e.g. a disulfide bond, or a PEG linker. The invention also relates to the use of phosphodiester linkers, such as DNA phosphodiester linkers, between the oligomer region and the conjugate group (these may be as defined as region B herein, and suitably are positioned between the oligomer region and the carbohydrate conjugate group).

For targeting hepatocytes in liver, a preferred targeting ligand is a galactose cluster.

A galactose cluster comprises a molecule having e.g. comprising two to four terminal galactose derivatives. As used herein, the term galactose derivative includes both galactose and derivatives of galactose having affinity for the asialoglycoprotein receptor equal to or greater than that of galactose. A terminal galactose derivative is attached to a molecule through its C—I carbon. The asialoglycoprotein receptor (ASGPr) is unique to hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, 1. Biol. Chem., 257, 939-945). Multivalency is required to achieve nM affinity. According to WO 2012/083046 the attachment of a single galactose derivative having affinity for the asialoglycoprotein receptor does not enable functional delivery of the RNAi polynucleotide to hepatocytes in vivo when co-administered with the delivery polymer.

A galactose cluster may comprise two or preferably three galactose derivatives each linked to a central branch point. The galactose derivatives are attached to the central branch point through the C—I carbons of the saccharides. The galactose derivative is preferably linked to the branch point via linkers or spacers (which may be region Y). A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a PEG3 spacer. The branch point can be any small molecule which permits attachment of the three galactose derivatives and further permits attachment of the branch point to the oligomer. An exemplary branch point group is a di-lysine. A di-lysine molecule contains three amine groups through which three galactose derivatives may be attached and a carboxyl reactive group through which the di-lysine may be attached to the oligomer. Attachment of the branch point to oligomer may occur through a linker or spacer. A preferred spacer is a flexible hydrophilic spacer. A preferred flexible hydrophilic spacer is a PEG spacer. A preferred PEG spacer is a PEG3 spacer (three ethylene units). The galactose cluster may be attached to the 3' or 5' end of the oligomer using methods known in the art.

A preferred galactose derivative is an N-acetyl-galactosamine (GalNAc). Other saccharides having affinity for the asialoglycoprotein receptor may be selected from the list comprising: galactosamine, N-n-butanoylgalactosamine, and N-iso-butanoylgalactosamine. The affinities of numerous galactose derivatives for the asialoglycoprotein receptor have been studied (see for example: Jobst, S. T. and Drickamer, K. JB. C. 1996, 271, 6686) or are readily determined using methods typical in the art.

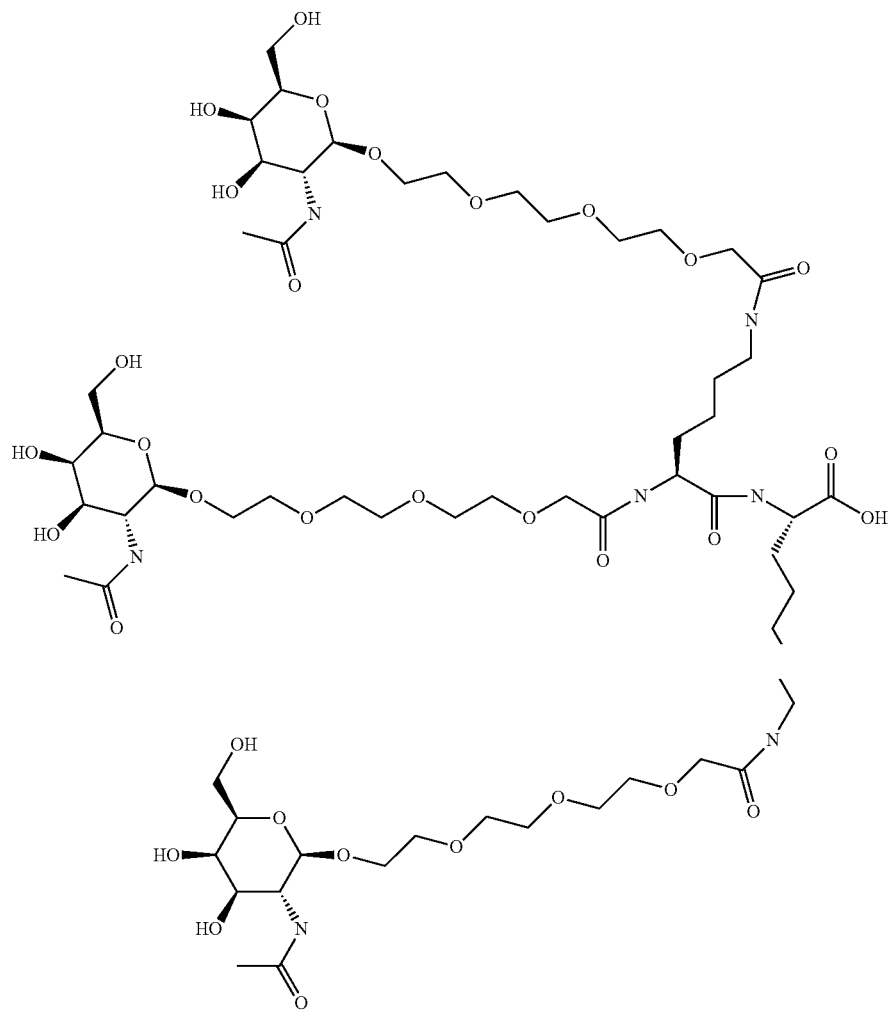

One Embodiment of Galactose Cluster
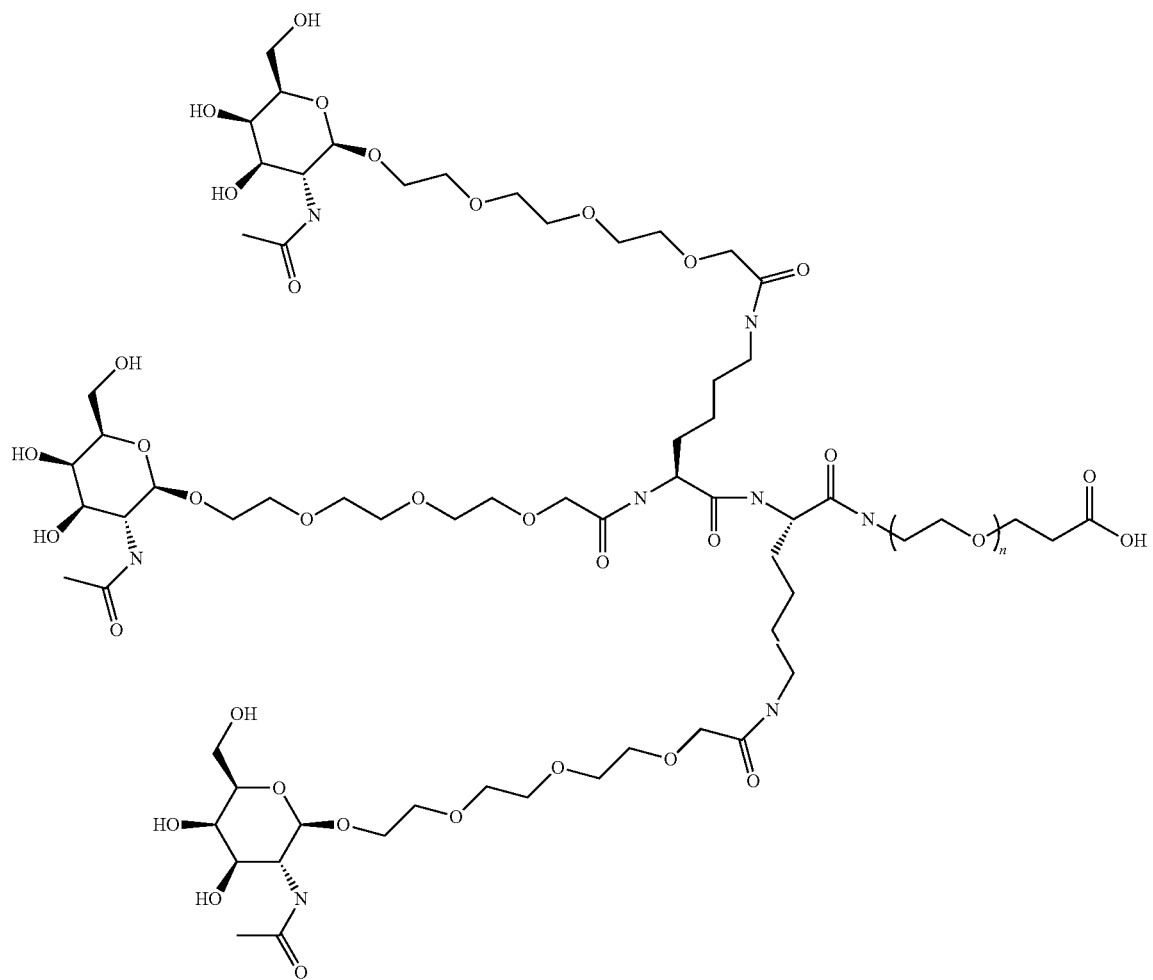
Galactose Cluster with PEG Spacer Between Branch Point and Nucleic Acid
A GalNac conjugate is illustrated in FIG. 1. Further examples of the conjugate of the invention are illustrated below:
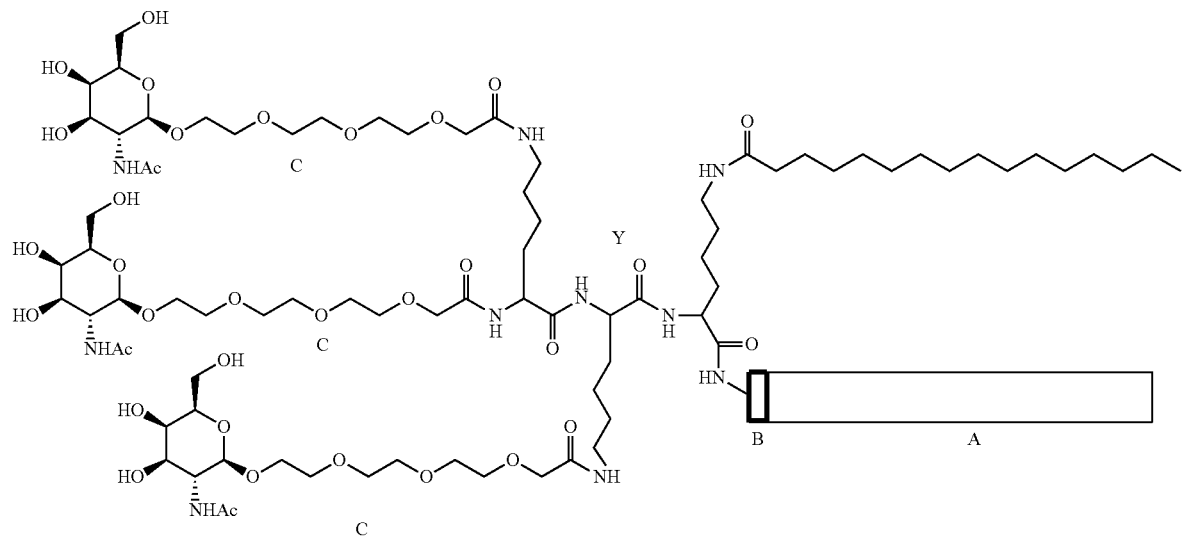

-continued

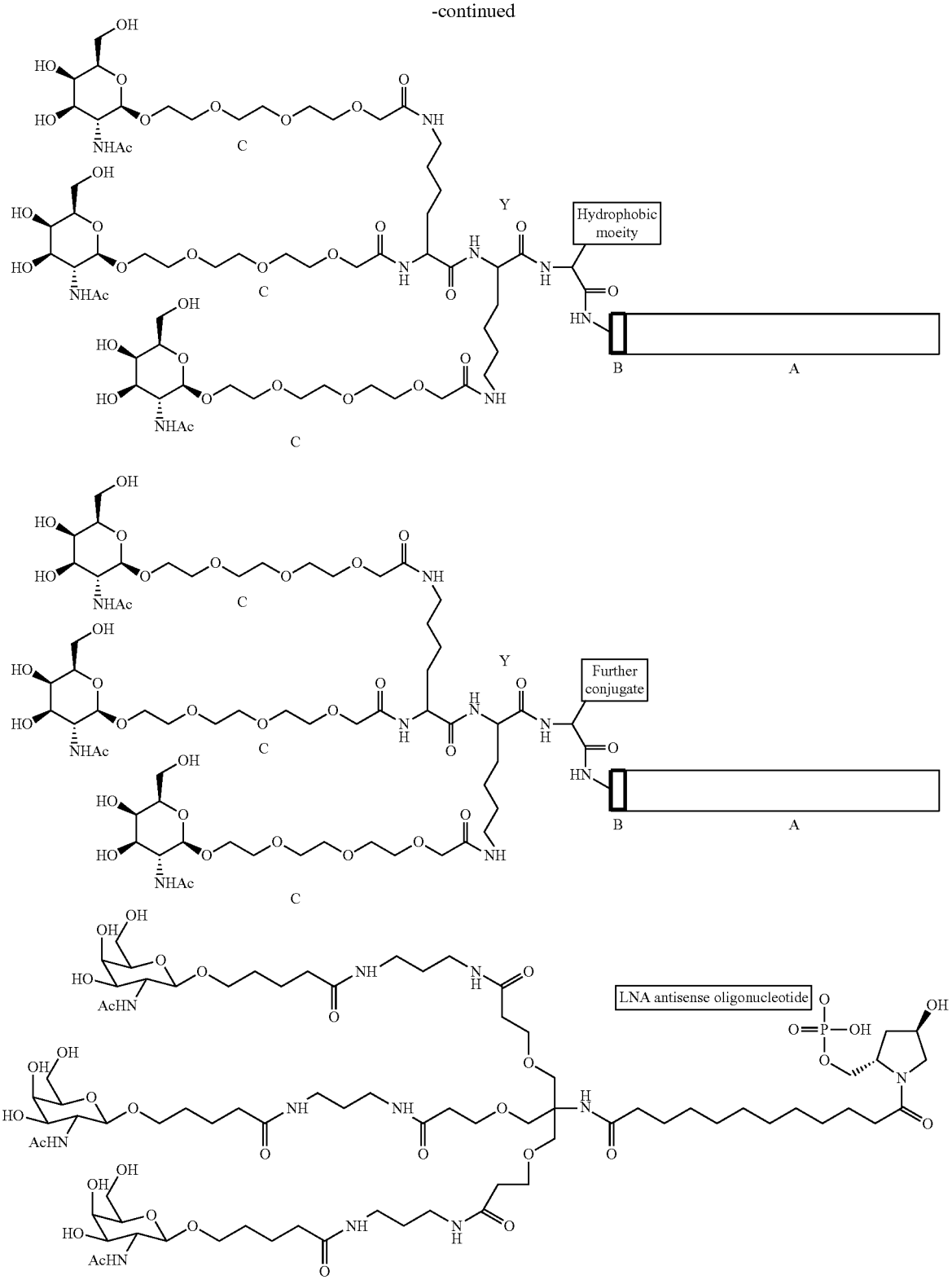

Region A may, for example, be the oligomer region, such as in a non-limiting example an LNA antisense oligonucleotide (shown).

As described herein, a carbohydrate conjugate (e.g. Gal-NAc) may therefore be linked to the oligomer via a bio-cleavable linker, such as region B as defined herein, and optionally region Y, which is illustrated as a di-lysine in the above diagrams.

Where at the hydrophobic or lipophilic (or further conjugate) moiety (i.e. pharmacokinetic modulator) in the above GalNac cluster conjugates is, when using BNA or LNA oligomers, such as LNA antisense oligonucleotides, optional.

See the figures for specific GalNac clusters used in the present study, Conj 1, 2, 3, 4 and Conj1a, 2a, 3a and 4a (which are shown with an optional C6 linker which joins the GalNac cluster to the oligomer—See FIGS. 12 and 17).

Each carbohydrate moiety of a GalNac cluster (e.g. Gal-NAc) may therefore be joined to the oligomer via a spacer, such as (poly)ethylene glycol linker (PEG), such as a di, tri, tetra, penta, hexa-ethylene glycol linker. As is shown above the PEG moiety forms a spacer between the galactose sugar moiety and a peptide (trilysine is shown) linker.

In some embodiments, the GalNac cluster comprises a peptide linker, e.g. a Tyr-Asp(Asp) tripeptide or Asp(Asp) dipeptide, which is attached to the oligomer (or to region Y or region B) via a biradical linker, for example the GalNac cluster may comprise the following biradical linkers:

$R^1$ is a biradical preferably selected from —$C_2H_4$—, —$C_3H_6$—, —$C_4H_8$—, —$C_5H_{10}$—, —$C_6H_{12}$—, 1,4-cyclohexyl (—C6H10-), 1,4-phenyl (—$C_6H_4$—), —$C_2H_4OC_2H_4$—, —$C_2H_4(OC_2H_4)_2$— or —$C_2H_4(OC_2H_4)_3$—, C(O)$CH_2$—, —C(O)$C_2H_4$—, —C(O)$C_3H_6$—, —C(O)$C_4H_8$—, —C(O)$C_6H_{10}$—, —C(O)$C_6H_{12}$—, 1,4-cyclohexyl (—C(O)C6H10-), 1,4-phenyl (—C(O)$C_6H_4$—), —C(O)$C_2H_4OC_2H_4$—, —C(O)$C_2H_4(OC_2H_4)_2$— or —C(O)$C_2H_4(OC_2H_4)_3$—. In some embodiments, $R^1$ is a biradical preferably selected from —$C_2H_4$—, —$C_3H_6$—, —$C_4H_8$—, —$C_5H_{10}$—, —$C_6H_{12}$—, 1,4-cyclohexyl (—C6H10-), 1,4-phenyl (—$C_6H_4$—), —$C_2H_4OC_2H_4$—, —$C_2H_4(OC_2H_4)_2$— or —$C_2H_4(OC_2H_4)_3$—.

In addition, the carbohydrate conjugate (e.g. GalNAc), or carbohydrate-linker moiety (e.g. carbohydrate-PEG moiety) may be covalently joined (linked) to the oligomer (or region B) via a branch point group such as, an amino acid, or peptide, which suitably comprises two or more amino

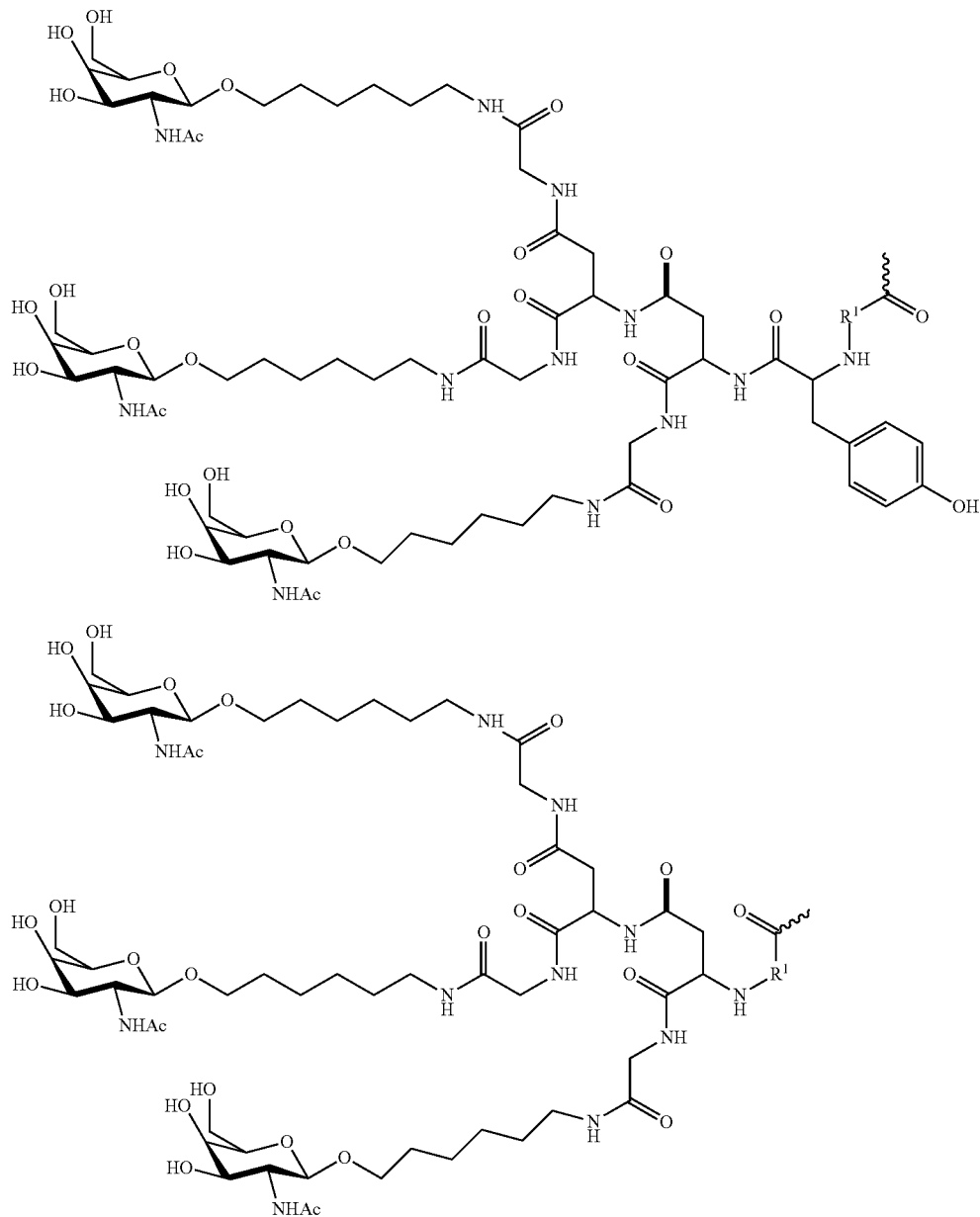

groups (such as 3, 4, or 5), such as lysine, di-lysine or tri-lysine or tetra-lysine. A tri-lysine molecule contains four amine groups through which three carbohydrate conjugate groups, such as galactose & derivatives (e.g. GalNAc) and a further conjugate such as a hydrophobic or lipophilic moiety/group may be attached and a carboxyl reactive group through which the tri-lysine may be attached to the oligomer. The further conjugate, such as lipophilic/hydrophobic moiety may be attached to the lysine residue that is attached to the oligomer. In some embodiments, the conjugate (C) is not a monovalent GalNac. The invention also provides LNA antisense oligonucleotides which are conjugated to an asialoglycoprotein receptor targeting moiety. In some embodiments, the conjugate moiety (such as the third region or region C) comprises an asialoglycoprotein receptor targeting moiety, such as galactose, galactosamine, N-formyl-galactosamine, Nacetylgalactosamine, N-propionyl-galactosamine, N-n-butanoyl-galactosamine, and N-isobutanoyl-galactos-amine. In some embodiments the conjugate comprises a galactose cluster, such as N-acetylgalactosamine trimer. In some embodiments, the conjugate moiety comprises a GalNac (N-acetylgalactosamine), such as a mono-valent, di-valent, tri-valent of tetra-valent GalNac. Trivalent GalNac conjugates may be used to target the compound to the liver. GalNac conjugates have been used with methylphosphonate and PNA antisense oligonucleotides (e.g. U.S. Pat. No. 5,994,517 and Hangeland et al., Bioconjug Chem. 1995 November-December; 6(6):695-701) and siRNAs (e.g. WO2009/126933, WO2012/089352 & WO2012/083046). The GalNac references and the specific conjugates used therein are hereby incorporated by reference. WO2012/083046 discloses GalNac conjugate moieties which comprise cleavable pharmacokinetic modulators, the preferred pharmacokinetic modulators are C16 hydrophobic groups such as palmitoyl, hexadec-8-enoyl, oleyl, (9E,12E)-octadeca-9,12-dienoyl, dioctanoyl, and C16-C20 acyl. The '046 cleavable pharmacokinetic modulators may also be cholesterol. The '046 targeting moieties may be selected from the group consisting of: galactose, galactosamine, N-formyl-galactosamine, N-acetylgalactosamine, Npropionyl-galactosamine, N-n-butanoyl-galactosamine, N-iso-butanoylgalactos-amine, galactose cluster, and N-acetylgalactosamine trimer and may have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNac clusters disclosed in '046 include: (E)-hexadec-8-enoyl (C16), oleyl (C18), (9,E,12E)-octadeca-9,12-dienoyl (C18), octanoyl (C8), dodececanoyl (C12), C-20 acyl, C24 acyl, dioctanoyl (2×C8). According to '046, the targeting moiety-pharmacokinetic modulator targeting moiety may be linked to the polynucleotide via a physiologically labile bond or, e.g. a disulfide bond, or a PEG linker.

Other conjugate moieties can include, for example, oligosaccharides and carbohydrate clusters such as Tyr-Glu-Glu-(aminohexyl GalNAc)3 (YEE(ahGalNAc)3; a glycotripeptide that binds to Gal/GalNAc receptors on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor). Further suitable conjugates can include oligosaccharides that can bind to carbohydrate recognition domains (CRD) found on the asiologlycoprotein-receptor (ASGP-R). Example conjugate moieties containing oligosaccharides and/or carbohydrate complexes are provided in U.S. Pat. No. 6,525,031, which is incorporated herein by reference in its entirety.

Pharmacokinetic Modulators

The compound of the invention may further comprise one or more additional conjugate moieties, of which lipophilic or hydrophobic moieties are particularly interesting, such as when the conjugate group is a carbohydrate moiety. Such lipophilic or hydrophobic moieties may act as pharmacokinetic modulators, and may be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a bio cleavable linker.

The oligomer or conjugate moiety may therefore comprise a pharmacokinetic modulator, such as a lipophilic or hydrophobic moieties. Such moieties are disclosed within the context of siRNA conjugates in WO2012/082046. The hydrophobic moiety may comprise a C8-C36 fatty acid, which may be saturated or un-saturated. In some embodiments, C10, C12, C14, C16, C18, C20, C22, C24, C26, C28, C30, C32 and C34 fatty acids may be used. The hydrophobic group may have 16 or more carbon atoms. Exemplary suitable hydrophobic groups may be selected from the group comprising: sterol, cholesterol, palmitoyl, hexadec-8-enoyl, oleyl, (9E,12E)-octadeca-9,12-dienoyl, dioctanoyl, and C16-C20 acyl. According to WO'346, hydrophobic groups having fewer than 16 carbon atoms are less effective in enhancing polynucleotide targeting, but they may be used in multiple copies (e.g. 2×, such as 2×C8 or C10, C12 or C14) to enhance efficacy. Pharmacokinetic modulators useful as polynucleotide targeting moieties may be selected from the group consisting of: cholesterol, alkyl group, alkenyl group, alkynyl group, aryl group, aralkyl group, aralkenyl group, and aralkynyl group, each of which may be linear, branched, or cyclic. Pharmacokinetic modulators are preferably hydrocarbons, containing only carbon and hydrogen atoms. However, substitutions or heteroatoms which maintain hydrophobicity, for example fluorine, may be permitted.

Surprisingly, the present inventors have found that GalNac conjugates for use with LNA oligomers do not require a pharmacokinetic modulator, and as such, in some embodiments, the GalNac conjugate is not covalently linked to a lipophilic or hydrophobic moiety, such as those described here in, e.g. do not comprise a C8-C36 fatty acid or a sterol. The invention therefore also provides for LNA oligomer GalNac conjugates which do not comprise a lipophilic or hydrophobic pharmacokinetic modulator or conjugate moiety/group. In some embodiments, the conjugate moiety is hydrophilic. In some embodiments, the conjugate group does not comprise a lipophilic substituent group, such as a fatty acid substituent group, such as a C8-C26, such as a palmityl substituent group, or does not comprise a sterol, e.g. a cholesterol substituent group. In this regards, part of the invention is based on the surprising discovery that LNA oligomers GalNAC conjugates have remarkable pharmacokinetic properties even without the use of pharmacokinetic modulators, such as fatty acid substituent groups (e.g. >C8 or >C16 fatty acid groups).

Lipophilic Conjugates

The compounds of the invention may be conjugates comprising of the oligomer (A) and a lipophilic conjugate (C). The biocleavable linker (B) has found to be particularly effective in maintaining or enhancing the activity of such oligomer conjugates. In some embodiments the conjugate group (C) and or linker group (Y) comprises a lipophilic group.

Representative conjugate moieties can include lipophilic molecules (aromatic and non-aromatic) including sterol and steroid molecules. Lipophilic conjugate moieties can be used, for example, to counter the hydrophilic nature of an oligomeric compound and enhance cellular penetration. Lipophilic moieties include, for example, steroids and related compounds such as cholesterol (U.S. Pat. No. 4,958,013 and Letsinger et al., Proc. Natl. Acad. Sci. USA, 1989, 86, 6553), thiocholesterol (Oberhauser et al, Nucl Acids Res., 1992, 20, 533), lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone, 17-hydroxycorticosterone, their derivatives, and the like.

Other lipophilic conjugate moieties include aliphatic groups, such as, for example, straight chain, branched, and cyclic alkyls, alkenyls, and alkynyls. The aliphatic groups can have, for example, 5 to about 50, 6 to about 50, 8 to about 50, or 10 to about 50 carbon atoms. Example aliphatic groups include undecyl, dodecyl, hexadecyl, heptadecyl, octadecyl, nonadecyl, terpenes, bornyl, adamantyl, derivatives thereof and the like. In some embodiments, one or more carbon atoms in the aliphatic group can be replaced by a heteroatom such as O, S, or N (e.g., geranyloxyhexyl). Further suitable lipophilic conjugate moieties include aliphatic derivatives of glycerols such as alkylglycerols, bis(alkyl)glycerols, tris(alkyl)glycerols, monoglycerides, diglycerides, and triglycerides. In some embodiments, the lipophilic conjugate is di-hexyldecyl-rac-glycerol or 1,2-di-O-hexyldecyl-rac-glycerol (Manoharan et al., Tetrahedron Lett., 1995, 36, 3651; Shea, et al., Nuc. Acids Res., 1990, 18, 3777) or phosphonates thereof. Saturated and unsaturated fatty functionalities, such as, for example, fatty acids, fatty alcohols, fatty esters, and fatty amines, can also serve as lipophilic conjugate moieties. In some embodiments, the fatty functionalities can contain from about 6 carbons to about 30 or about 8 to about 22 carbons. Example fatty acids include, capric, caprylic, lauric, palmitic, myristic, stearic, oleic, linoleic, linolenic, arachidonic, eicosenoic acids and the like.

In further embodiments, lipophilic conjugate groups can be polycyclic aromatic groups having from 6 to about 50, 10 to about 50, or 14 to about 40 carbon atoms. Example polycyclic aromatic groups include pyrenes, purines, acridines, xanthenes, fluorenes, phenanthrenes, anthracenes, quinolines, isoquinolines, naphthalenes, derivatives thereof and the like. [0037] Other suitable lipophilic conjugate moieties include menthols, trityls (e.g., dimethoxytrityl (DMT)), phenoxazines, lipoic acid, phospholipids, ethers, thioethers (e.g., hexyl-S-tritylthiol), derivatives thereof and the like. Preparation of lipophilic conjugates of oligomeric compounds are well-described in the art, such as in, for example, Saison-Behmoaras et al, EMBO J., 1991, 10, 1111; Kabanov et al., FEBS Lett., 1990, 259, 327; Svinarchuk et al, Biochimie, 1993, 75, 49; (Mishra et al., Biochim. Biophys. Acta, 1995, 1264, 229, and Manoharan et al., Tetrahedron Lett., 1995, 36, 3651.

Oligomeric compounds containing conjugate moieties with affinity for low density lipoprotein (LDL) can help provide an effective targeted delivery system. High expression levels of receptors for LDL on tumor cells makes LDL an attractive carrier for selective delivery of drugs to these cells (Rump, et al., Bioconjugate Chem., 1998, 9, 341; Firestone, Bioconjugate Chem., 1994, 5, 105; Mishra, et al., Biochim. Biophys. Acta, 1995, 1264, 229). Moieties having affinity for LDL include many lipophilic groups such as steroids (e.g., cholesterol), fatty acids, derivatives thereof and combinations thereof. In some embodiments, conjugate moieties having LDL affinity can be dioleyl esters of cholic acids such as chenodeoxycholic acid and lithocholic acid.

In some embodiments, the conjugate group is or may comprise a lipophilic moiety, such as a sterol (for example, cholesterol, cholesteryl, cholestanol, stigmasterol, cholanic acid and ergosterol). In some embodiments, the conjugate is or may comprise cholesterol. See for example, Soutschek et al., Nature (2004) 432, 173; Krützfeldt Nature 2005, NAR 2007.

In some embodiments, the conjugate is, or may comprise a lipid, a phospholipid or a lipophilic alcohol, such as a cationic lipids, a neutral lipids, sphingolipids, and fatty acids such as stearic, oleic, elaidic, linoleic, linoleaidic, linolenic, and myristic acids. In some embodiments the fatty acid comprises a C4-C30 saturated or unsaturated alkyl chain. The alkyl chain may be linear or branched.

In some embodiments, the lipophilic conjugates may be or may comprise biotin. In some embodiments, the lipophilic conjugate may be or may comprise a glyceride or glyceride ester.

Lipophilic conjugates, such as cholesterol or as disclosed herein, may be used to enhance delivery of the oligonucleotide to, for example, the liver (typically hepatocytes).

The following references refer to the use of lipophilic conjugates: Kobylanska et al., Acta Biochim Pol. (1999); 46(3): 679-91. Felber et al., Biomaterials (2012) 33(25): 599-65); Grijalvo et al., J Org Chem (2010) 75(20): 6806-13. Koufaki et al., Curr Med Chem (2009) 16(35): 4728-42. Godeau et al J. Med. Chem. (2008) 51(15): 4374-6.

Polymer Conjugates

Conjugate moieties can also include polymers. Polymers can provide added bulk and various functional groups to affect permeation, cellular transport, and localization of the conjugated oligomeric compound. For example, increased hydrodynamic radius caused by conjugation of an oligomeric compound with a polymer can help prevent entry into the nucleus and encourage localization in the cytoplasm. In some embodiments, the polymer does not substantially reduce cellular uptake or interfere with hybridization to a complementary strand or other target. In further embodiments, the conjugate polymer moiety has, for example, a molecular weight of less than about 40, less than about 30, or less than about 20 kDa. Additionally, polymer conjugate moieties can be water-soluble and optionally further comprise other conjugate moieties such as peptides, carbohydrates, drugs, reporter groups, or further conjugate moieties.

In some embodiments, polymer conjugates include polyethylene glycol (PEG) and copolymers and derivatives thereof. Conjugation to PEG has been shown to increase nuclease stability of an oligomeric compound. PEG conjugate moieties can be of any molecular weight including for example, about 100, about 500, about 1000, about 2000, about 5000, about 10,000 and higher. In some embodiments, the PEG conjugate moieties contains at least 4, at least 5, at least 6, at least 7, at least 8, at least 9, at least 10, at least 15, at least 20, or at least 25 ethylene glycol residues. In further embodiments, the PEG conjugate moiety contains from about 4 to about 10, about 4 to about 8, about 5 to about 7, or about 6 ethylene glycol residues. The PEG conjugate moiety can also be modified such that a terminal hydroxyl is replaced by alkoxy, carboxy, acyl, amido, or other functionality. Other conjugate moieties, such as reporter groups including, for example, biotin or fluorescein can also be attached to a PEG conjugate moiety. Copolymers of PEG are also suitable as conjugate moieties. [0047] Preparation and biological activity of polyethylene glycol conjugates of oligonucleotides are described, for example, in Bonora, et al., Nucleosides Nucleotides, 1999, 18, 1723; Bonora, et al., Farmaco, 1998, 53, 634; Efimov, Bioorg. Khim. 1993, 19, 800; and Jaschke, et al, Nucleic Acids Res., 1994, 22, 4810. Further example PEG conjugate moieties and preparation of corresponding conjugated oligomeric compounds is described in, for example, U.S. Pat. Nos. 4,904,582 and 5,672,662, each of which is incorporated by reference herein in its entirety. Oligomeric compounds conjugated to one or more PEG moieties are available commercially.

Other polymers suitable as conjugate moieties include polyamines, polypeptides, polymethacrylates (e.g., hydroxylpropyl methacrylate (HPMA)), poly(L-lactide), poly(DL lactide-co-glycolide (PGLA), polyacrylic acids, polyethylenimines (PEI), polyalkylacrylic acids, polyurethanes, polyacrylamides, N-alkylacrylamides, polyspermine (PSP), polyethers, cyclodextrins, derivatives thereof and co-polymers thereof. Many polymers, such as PEG and polyamines have receptors present in certain cells, thereby facilitating cellular uptake. Polyamines and other amine-containing polymers can exist in protonated form at physiological pH, effectively countering an anionic backbone of some oligomeric compounds, effectively enhancing cellular permeation. Some example polyamines include polypeptides (e.g., polylysine, polyornithine, polyhistadine, polyarginine, and copolymers thereof), triethylenetetraamine, spermine, polyspermine, spermidine, synnorspermidine, C-branched spermidine, and derivatives thereof. Preparation and biological activity of polyamine conjugates are described, for example, in Guzaev, et al, Bioorg. Med. Chem. Lett., 1998, 8, 3671; Corey, et al, J Am. Chem. Soc, 1995, 117, 9373; and Prakash, et al, Bioorg. Med. Chem. Lett. 1994, 4, 1733. Example polypeptide conjugates of oligonucleotides are provided in, for example, Wei, et al., Nucleic Acids Res., 1996, 24, 655 and Zhu, et al., Antisense Res. Dev., 1993, 3, 265. Dendrimeric polymers can also be used as conjugate moieties, such as described in U.S. Pat. No. 5,714,166, which is incorporated herein by reference in its entirety. [0049] As discussed above for polyamines and related polymers, other amine-containing moieties can also serve as suitable conjugate moieties due to, for example, the formation of cationic species at physiological conditions. Example amine-containing moieties include 3-aminopropyl, 3-(N,N-dimethylamino)propyl, 2-(2-(N,N-dimethylamino)ethoxy) ethyl, 2-(N-(2-aminoethyl)-N-methylaminooxy)ethyl, 2-(l-imidazolyl)ethyl, and the like. The G-clamp moiety can also serve as an amine-containing conjugate moiety (Lin, et al., J. Am. Chem. Soc, 1998, 120, 8531).

In some embodiments, the conjugate may be, or may comprise a polymer, such as a polymer selected from the group consisting of polyethyleneglycol (PEG), polyamidoamine (PAA), polyethylene oxide and polyethylenimine (PEI). Galactose, lactose, n-acetylgalactosamine, mannose, mannose-6-phosphate n some embodiments, the polymer is a polycationic polymer. In some embodiments, conjugate moieties can be, or based on (include) cationic polymers. Numerous studies have demonstrated that cationic polymers such as cationic albumin can greatly enhance delivery to particular cell types and/or tissues (e.g. brain delivery, see Lu, W. et. al. (2005) J of Control Release 107:428-448). Given the benefits of these molecules, the conjugate moieties can be cationic polymers such as polyethyleneimine, dendrimers, poly(alkylpyridinium) salts, or cationic albumin. In some embodiments is a hydrophilic polymer. In some embodiments, the polymer is Poly(vinylpyrrolidone) (PVP). In some embodiments, the polymer is a polyamine or polyamide (e.g. U.S. Pat. No. 7,816,337 & U.S. Pat. No. 5,525,465. For polymer conjugates see for example, Zhao et al., Bioconjugate Chem 2005, 16, 758-766); Kim et al., J. Control Release (2006) 116; 123. Pettit et al., Ther. Deliv. (2011) 2(7): 907-17. Yang et al., Bioconjug Chem (2009) 20(2): 213-21. Winkler et al (2009) Eur J Med Chem 44(2): 670-7. Zelikin et al, Biomacromolecules (2007) 8(9): 2950-3. See also WO12092373 which refers to enzyme cleavable polynucleotide delivery conjugates.
Protein and Peptide Conjugates Other conjugate moieties can include proteins, subunits, or fragments thereof. Proteins include, for example, enzymes, reporter enzymes, antibodies, receptors, and the like. In some embodiments, protein conjugate moieties can be antibodies or fragments thereof (Kuijpers, et al, Bioconjugate Chem., 1993, 4, 94). Antibodies can be designed to bind to desired targets such as tumor and other disease-related antigens. In further embodiments, protein conjugate moieties can be serum proteins such as HAS or glycoproteins such as asialoglycoprotein (Rajur, et al., Bioconjugate Chem., 1997, 6, 935). In yet further embodiments, oligomeric compounds can be conjugated to RNAi-related proteins, RNAi-related protein complexes, subunits, and fragments thereof. For example, oligomeric compounds can be conjugated to Dicer or RISC. [0067] Intercalators and minor groove binders (MGBs) can also be suitable as conjugate moieties. In some embodiments, the MGB can contain repeating DPI (1,2-dihydro-3H-pyrrolo(2,3-e)indole-7-carboxylate) subunits or derivatives thereof (Lukhtanov, et al., Bioconjugate Chem., 1996, 7, 564 and Afonina, et al., Proc. Natl. Acad. Sci. USA, 1996, 93, 3199). Suitable intercalators include, for example, polycyclic aromatics such as naphthalene, perylene, phenanthridine, benzophenanthridine, phenazine, anthraquinone, acridine, and derivatives thereof. Hybrid intercalator/ligands include the photonuclease/intercalator ligand 6-[[[9-[[6-(4-nitrobenzamido)hexyl]amino] acridin-4-yl]carbonyl]amino]hexan oyl-pentafluorophenyl ester. This compound is both an acridine moiety that is an intercalator and a p-nitro benzamido group that is a photonuclease. [0069] In further embodiments, cleaving agents can serve as conjugate moieties. Cleaving agents can facilitate degradation of target, such as target nucleic acids, by hydrolytic or redox cleavage mechanisms. Cleaving groups that can be suitable as conjugate moieties include, for example, metallocomplexes, peptides, amines, enzymes, and constructs containing constituents of the active sites of nucleases such as imidazole, guanidinium, carboxyl, amino groups, etc.). Example metallocomplexes include, for example, Cu-terpyridyl complexes, Fe-porphyrin complexes, Ru-complexes, and lanthanide complexes such as various Eu(III) complexes (Hall, et al., Chem. Biol, 1994, 1, 185; Huang, et al., J. Biol. Inorg. Chem., 2000, 5, 85; and Baker, et al, Nucleic Acids Res., 1999, 27, 1547). Other metallocomplexes with cleaving properties include metalloporphyrins and derivatives thereof. Example peptides with target cleaving properties include zinc fingers (U.S. Pat. No. 6,365,379; Lima, et al., Proc. Natl. Acad. Sci. USA, 1999, 96, 10010). Example constructs containing nuclease active site constituents include bisimiazole and histamine.

Conjugate moieties can also include peptides. Suitable peptides can have from 2 to about 30, 2 to about 20, 2 to about 15, or 2 to about 10 amino acid residues. Amino acid residues can be naturally or non-naturally occurring, including both D and L isomers. In some embodiments, peptide conjugate moieties are pH sensitive peptides such as fusogenic peptides. Fusogenic peptides can facilitate endosomal release of agents such as oligomeric compounds to the cytoplasm. It is believed that fusogenic peptides change conformation in acidic pH, effectively destabilizing the endosomal membrane thereby enhancing cytoplasmic delivery of endosomal contents. Example fusogenic peptides include peptides derived from polymyxin B, influenza HA2, GALA, KALA, EALA, melittin-derived peptide, a-helical peptide or Alzheimer beta-amyloid peptide, and the like. Preparation and biological activity of oligonucleotides conjugated to fusogenic peptides are described in, for example, Bongartz, et al., Nucleic Acids Res., 1994, 22, 4681 and U.S. Pat. Nos. 6,559,279 and 6,344,436. Other peptides that can serve as conjugate moieties include delivery peptides which have the ability to transport relatively large, polar molecules (including peptides, oligonucleotides, and proteins) across cell membranes. Example delivery peptides include Tat peptide from HIV Tat protein and Ant peptide from *Drosophila* antenna protein. Conjugation of Tat and Ant with oligonucleotides is described in, for example, Astriab-Fisher, et al., Biochem. Pharmacol, 2000, 60, 83. These and other delivery peptides that can be used as conjugate moieties are provided below in Table I:

Conjugated delivery peptides can help control localization of oligomeric compounds to specific regions of a cell, including, for example, the cytoplasm, nucleus, nucleolus, and endoplasmic reticulum (ER). Nuclear localization can be effected by conjugation of a nuclear localization signal (NLS). In contrast, cytoplasmic localization can be facilitated by conjugation of a nuclear export signal (NES). [0054] Peptides suitable for localization of conjugated oligomeric compounds in the nucleus include, for example, N,N-dipalmitylglycyl-apo E peptide or N,N-dipalmitylglycyl-apolipoprotein E peptide (dpGapoE) (Liu, et al, Arterioscler. Thromb. Vasc. Biol, 1999, 19, 2207; Chaloin, et al., Biochem. Biophys. Res. Commun., 1998, 243, 601). Nucleus or nucleolar localization can also be facilitated by peptides having arginine and/or lysine rich motifs, such as in HIV-1 Tat, FXR2P, and angiogenin derived peptides (Lixin, et al, Biochem. Biophys. Res. Commun., 2001, 284, 185). Additionally, the nuclear localization signal (NLS) peptide derived from SV40 antigen T (Branden, et al., Nature Biotech, 1999, 17, 784) can be used to deliver conjugated oligomeric compounds to the nucleus of a cell. Other suitable peptides with nuclear or nucleolar localization properties are described in, for example, Antopolsky, et al., Bioconjugate Chem., 1999, 10, 598; Zanta, et al., Proc. Nati. Acad. Sci. USA, 1999 (simian virus 40 large tumor antigen); Hum. Mol. Genetics, 2000, 9, 1487; and FEBSLett., 2002, 532, 36).

In some embodiments, the delivery peptide for nucleus or nucleolar localization comprises at least three consecutive arginine residues or at least four consecutive arginine residues. Nuclear localization can also be facilitated by peptide conjugates containing RS, RE, or RD repeat motifs (Cazalla, et al., Mol Cell. Biol, 2002, 22, 6871). In some embodiments, the peptide conjugate contains at least two RS, RE, or RD motifs.

Localization of oligomeric compounds to the ER can be effected by, for example, conjugation to the signal peptide KDEL (Arar, et al., Bioconjugate Chem., 1995, 6, 573; Pichon, et al., Mol. Pharmacol. 1997, 57, 431). [0057] Cytoplasmic localization of oligomeric compounds can be facilitated by conjugation to peptides having, for example, a nuclear export signal (NES) (Meunier, et al., Nucleic Acids Res., 1999, 27, 2730). NES peptides include the leucine-rich NES peptides derived from HIV-1 Rev (Henderson, et al., Exp. Cell Res., 2000, 256, 213), transcription factor III A, MAPKK, PKI-alpha, cyclin BI, and actin (Wada, et al., EMBO J., 1998, 17, 1635) and related proteins. Antimicrobial peptides, such as dermaseptin derivatives, can also facilitate cytoplasmic localization (Hariton-Gazal, et al., Biochemistry, 2002, 41, 9208). Peptides containing RG and/or KS repeat motifs can also be suitable for directing oligomeric compounds to the cytoplasm. In some embodiments, the peptide conjugate moieties contain at least two RG motifs, at least two KS motifs, or at least one RG and one KS motif. [0058] As used throughout, "peptide" includes not only the specific molecule or sequence recited herein (if present), but also includes fragments thereof and molecules comprising all or part of the recited sequence, where desired functionality is retained. In some embodiments, peptide fragments contain no fewer than 6 amino acids. Peptides can also contain conservative amino acid substitutions that do not substantially change its functional characteristics. Conservative substitution can be made among the following sets of functionally similar amino acids: neutral-weakly hydrophobic (A, G, P, S, T), hydrophilic-acid amine (N, D, Q, E), hydrophilic-basic (I, M, L, V), and hydrophobic-aromatic (F, W, Y). Peptides also include homologous peptides. Homology can be measured according to percent identify using, for example, the BLAST algorithm (default parameters for short sequences). For example, homologous peptides can have greater than 50, 60, 70, 80, 90, 95, or 99 percent identity. Methods for conjugating peptides to oligomeric compounds such as oligonucleotides is described in, for example, U.S. Pat. No. 6,559,279, which is incorporated herein by reference in its entirety.

In some embodiments, the conjugate moiety is or comprises a protein or peptide. In some embodiments the peptide is a cell penetrating peptides, e.g. Penetratin, transportan, Peptaibol (e.g. trichorovin-XIIa (TV-XIIa)), TAT peptide (HIV). In some embodiments, the peptide is polyarginine (e.g. stearyl-(RxR)(4)). In some embodiments the peptide is N-(2-hydroxypropyl) methacrylamide (HPMA) containing tetrapeptide Gly-Phe-Leu-Gly (GFLG). In some embodiments, the peptide is a beta-amyloid peptide. In some embodiments the protein or peptide in an antibody or antigen binding site containing fragment thereof (epitope binding site). In some embodiments the conjugate is or comprises M6P-HPMA-GFLG (see Yang et al 2009). In some embodiments, the conjugate is or comprises arginine rich peptides (WO2005/115479)—see also WO09005793 RGD peptides. In some embodiments, the conjugate is or comprises a protein carrier (e.g. albumin, albumin-PEG conjugate—RGD-PEG-albumin) (Kang et al) see also WO09045536. In some embodiments, the conjugate is or comprises histidylated oligolysine (e.g. WO0032764). In some embodiments, the conjugate is or comprises Glycoproteins: transferrin-polycation (e.g. U.S. Pat. No. 5,354,844, WO9217210, WO9213570). In some embodiments, the conjugate is or comprises asialoglycoprotein (U.S. Pat. No. 5,346,696). In some embodiments, the conjugate is or comprises a polycationic protein (e.g. U.S. Pat. No. 603,095). In some embodiments, the conjugate is or comprises polypseudo-lysine conjugates (e.g. WO07113531).

Reporter and Dye Conjugate Groups

Reporter groups that are suitable as conjugate moieties include any moiety that can be detected by, for example, spectroscopic means. Example reporter groups include dyes, flurophores, phosphors, radiolabels, and the like. In some embodiments, the reporter group is biotin, flourescein, rhodamine, coumarin, or related compounds. Reporter groups can also be attached to other conjugate moieties. In some embodiments, the conjugate is or comprises a label or dye, such as a fluorophore, such as FAM (Carboxyfluorescein).

Cross-linking agents can also serve as conjugate moieties. Cross-linking agents facilitate the covalent linkage of the conjugated oligomeric compounds with other compounds. In some embodiments, cross-linking agents can covalently link double-stranded nucleic acids, effectively increasing duplex stability and modulating pharmacokinetic properties. In some embodiments, cross-linking agents can be photoactive or redox active. Example cross-linking agents include psoralens which can facilitate interstrand cross-linking of nucleic acids by photoactivation (Lin, et al, Faseb J, 1995, 9, 1371). Other cross-linking agents include, for example, mitomycin C and analogs thereof (Maruenda, et al., Bioconjugate Chem., 1996, 7, 541; Maruenda, et al., Anti-Cancer Drug Des., 1997, 12, 473; and Huh, et al, Bioconjugate Chem., 1996, 7, 659). Cross-linking mediated by mitomycin C can be effected by reductive activation, such as, for example, with biological reductants (e.g., NADPH-cytochrome c reductase/NADPH system). Further photocrosslinking agents include aryl azides such as, for example, N-hydroxysucciniimidyl-4-azidobenzoate (HSAB) and N-succinimidyl-6(-4'-azido-2'-nitrophenyl-amino)hexanoate (SANPAH). Aryl azides conjugated to oligonucleotides effect crosslinking with nucleic acids and proteins upon irradiation. They can also crosslink with earner proteins (such as KLH or BSA).

Various Functional Conjugate Groups

Other suitable conjugate moieties include, for example, polyboranes, carboranes, metallopolyboranes, metallocarborane, derivatives thereof and the like (see, e.g., U.S. Pat. No. 5,272,250, which is incorporated herein by reference in its entirety).

Many drugs, receptor ligands, toxins, reporter molecules, and other small molecules can serve as conjugate moieties. Small molecule conjugate moieties often have specific interactions with certain receptors or other biomolecules, thereby allowing targeting of conjugated oligomeric compounds to specific cells or tissues. Example small molecule conjugate moieties include mycophenolic acid (inhibitor of inosine-5'-monophosphate dihydrogenase; useful for treating psoriasis and other skin disorders), curcumin (has therapeutic applications to psoriasis, cancer, bacterial and viral diseases). In further embodiments, small molecule conjugate moieties can be ligands of serum proteins such as human serum albumin (HSA). Numerous ligands of HSA are known and include, for example, arylpropionic acids, ibuprofen, warfarin, phenylbutazone, suprofen, carprofen, fenfufen, ketoprofen, aspirin, indomethacin, (S)-(+)-pranoprofen, dansylsarcosine, 2,3,5-triiodobenzoic acid, flufenamic acid, folinic acid, benzothiadiazide, chlorothiazide, diazepines, indomethicin, barbituates, cephalosporins, sulfa drugs, antibacterials, antibiotics (e.g., puromycin and pamamycin), and the like. Oligonucleotide-drug conjugates and their preparation are described in, for example, WO 00/76554, which is incorporated herein by reference in its entirety.

In some embodiments, the conjugate may be or comprise a small molecule, such as a small molecule drug or pro-drug. Certain drugs are highly effective at targeting specific target tissue or cells, and as such they may be used to target an oligonucleotide to its intended site of action. Furthermore, the small molecule may in itself have a therapeutic activity, typically once cleaved from the oligonucleotide component of the conjugate. Examples include bisphosphonates (widely used for the treatment of osteoporosis and effective in targeting bone tissues), anti-cancer drugs and chemotherapeutic agents (e.g. doxorubicin or mitomycein C—see U.S. Pat. No. 5,776,907). In some embodiments, the drug may be a nucleoside analogue, such as a nucleoside polymerase inhibitor.

In yet further embodiments, small molecule conjugates can target or bind certain receptors or cells. T-cells are known to have exposed amino groups that can form Schiff base complexes with appropriate molecules. Thus, small molecules containing functional groups such as aldehydes that can interact or react with exposed amino groups can also be suitable conjugate moieties. Tucaresol and related compounds can be conjugated to oligomeric compounds in such a way as to leave the aldehyde free to interact with T-cell targets. Interaction of tucaresol with T-cells in believed to result in therapeutic potentiation of the immune system by Schiff-base formation (Rhodes, et al., Nature, 1995, 377, 6544).

In some embodiments, the conjugate is or comprises a (e.g. cell surface) receptor ligand. In some embodiments the conjugate is or comprises a folate receptor ligand, such as a folic acid group—see for example, EP1572067 or WO2005/069994, WO2010/045584). Other cell surface receptor ligands include antibodies and fragments thereof, prostate-specific membrane antigen, neuron surface antigens (see WO2011/131693)

In some embodiments, the conjugate moieties are ligands for receptors or can associate with molecules that (in turn) associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g. capsids), toxins (e.g. bacterial toxins), and more. Also included in this class are conjugates that are steroidal in nature e.g. cholesterol, cholestanol, cholanic acid, stigmasterols, pregnolones, progesterones, corticosterones, aldosterones, testosterones, estradiols, ergosterols, and more), Preferred conjugate moieties of the disclosure are cholesterol (CHOL), cholestanol (CHLN), cholanic acid (CHLA), stigmasterol (STIG), and ergosterol (ERGO). In certain preferred embodiments, the conjugate moiety is cholesterol.

In some embodiments the conjugate comprises a sterol, such as cholesterol or tocopherol, optionally including a linker, such as a fatty acid linker, e.g. a C6 linker. In some embodiments the conjugates comprise Conj5a or Conj 6a.

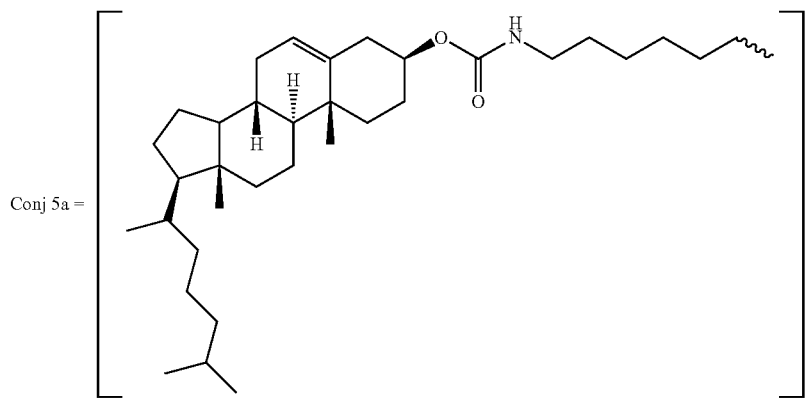

Conj 5a =

-continued

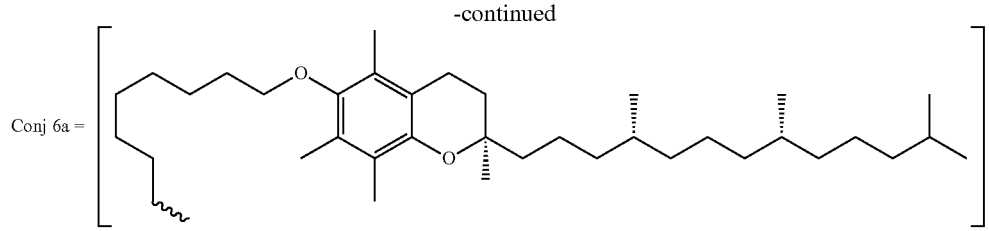

Conj 6a =

Conjugate moieties can also include vitamins. Vitamins are known to be transported into cells by numerous cellular transport systems. Typically, vitamins can be classified as water soluble or lipid soluble. Water soluble vitamins include thiamine, riboflavin, nicotinic acid or niacin, the vitamin B6 pyridoxal group, pantothenic acid, biotin, folic acid, the B]2 cobamide coenzymes, inositol, choline and ascorbic acid. Lipid soluble vitamins include the vitamin A family, vitamin D, the vitamin E tocopherol family and vitamin K (and phytols). Related compounds include retinoid derivatives such as tazarotene and etretinate. [0040] In some embodiments, the conjugate moiety includes folic acid folate) and/or one or more of its various forms, such as dihydrofolic acid, tetrahydrofolic acid, folinic acid, pteropolyglutamic acid, dihydrofolates, tetrahydrofolates, tetrahydropterins, 1-deaza, 3-deaza, 5-deaza, 8-deaza, 10-deaza, 1,5-dideaza, 5,10-dideaza, 8,10-dideaza and 5,8-dideaza folate analogs, and antifolates. Folate is involved in the biosynthesis of nucleic acids and therefore impacts the survival and proliferation of cells. Folate cofactors play a role in the one-carbon transfers that are needed for the biosynthesis of pyrimidine nucleosides. Cells therefore have a system of transporting folates into the cytoplasm. Folate receptors also tend to be overexpressed in many human cancer cells, and folate-mediated targeting of oligonucleotides to ovarian cancer cells has been reported (Li, et al, Pharm. Res. 1998, 15, 1540, which is incorporated herein by reference in its entirety). Preparation of folic acid conjugates of nucleic acids are described in, for example, U.S. Pat. No. 6,528,631, which is incorporated herein by reference in its entirety.

Vitamin conjugate moieties include, for example, vitamin A (retinol) and/or related compounds. The vitamin A family (retinoids), including retinoic acid and retinol, are typically absorbed and transported to target tissues through their interaction with specific proteins such as cytosol retinol-binding protein type II (CRBP-II), retinol-binding protein (RBP), and cellular retinol-binding protein (CRBP). The vitamin A family of compounds can be attached to oligomeric compounds via acid or alcohol functionalities found in the various family members. For example, conjugation of an N-hydroxy succinimide ester of an acid moiety of retinoic acid to an amine function on a linker pendant to an oligonucleotide can result in linkage of vitamin A compound to the oligomeric compound via an amide bond. Also, retinol can be converted to its phosphoramidite, which is useful for 5' conjugation. alpha-Tocopherol (vitamin E) and the other tocopherols (beta through zeta) can be conjugated to oligomeric compounds to enhance uptake because of their lipophilic character. Also, vitamin D, and its ergosterol precursors, can be conjugated to oligomeric compounds through their hydroxyl groups by first activating the hydroxyl groups to, for example, hemisuccinate esters. Conjugation can then be effected directly to the oligomeric compound or to an aminolinker pendant from the oligomeric compound. Other vitamins that can be conjugated to oligomeric compounds in a similar manner on include thiamine, riboflavin, pyridoxine, pyridoxamine, pyridoxal, deoxypyridoxine. Lipid soluble vitamin K's and related quinone-containing compounds can be conjugated via carbonyl groups on the quinone ring. The phytol moiety of vitamin K can also serve to enhance binding of the oligomeric compounds to cells.

Other functional groups which may be used as conjugates in compounds of the invention, include imidazole conjugate—RNase A catalytic center mimics (polyamine-imidazole conjugates)—see Guerniou et al Nucleic Acids Res (2007); 35 (20): 6778-87.

Conjugates are typically non-nucleotide moieties. However, in the context of blocking groups or targeting groups, or nucleotide analog small therapeutics, it is recognized that the oligonucleotide may be covalently linked to a nucleotide moiety via the DNA/RNA phosphodiester region of the invention. Suitably, a nucleic acid group, as used in the context of the invention may, in some embodiments, lack complementarity to the target of the oligonucleotide (region A).

In some embodiments, the blocking or targeting moiety is an aptamer (see e.g. Meng et al., PLoS One (2012) 7(4): e33434, WO2005/111238 & WO12078637).

A blocking group may also be or comprise a oligonucleotide region which is complementary to, e.g. part of, the antisense oligonucleotide. In this regard the blocking oligonucleotide is covalently bound to an antisense oligonucleotide via the DNA/RNA phosphodiester region (region b), and optionally a linker. The blocking oligonucleotide is, in some embodiments, therefore able to form a duplex with the antisense oligonucleotide. Suitably the blocking nucleotide sequence (as third region or region C) is a short oligonucleotide sequence of e.g. 3-10 nucleotides in length which forms a duplex (i.e. is complementary to) with an equivalent length of the first region. In some embodiments a linker is used between the second region and the blocking region.

Like delivery peptides, nucleic acids can also serve as conjugate like moieties that can affect localization of conjugated oligomeric compounds in a cell. For example, nucleic acid conjugate moieties can contain poly A, a motif recognized by poly A binding protein (PABP), which can localize poly A-containing molecules in the cytoplasm (Gorlach, et al., Exp. Cell Res., 1994, 211, 400. In some embodiments, the nucleic acid conjugate moiety contains at least 3, at least 4, at least 5, at least 6, at least 7, at least 8, at least 9, at least 10, at least 15, at least 20, and at least 25 consecutive A bases. The nucleic acid conjugate moiety can also contain one or more AU-rich sequence elements (AREs). AREs are recognized by ELAV family proteins which can facilitate localization to the cytoplasm (Bollig, et al, Biochem. Bioophys. Res. Commun., 2003, 301, 665). Example AREs include UUAUUUAUU and sequences containing multiple repeats of this motif. In other embodiments, the nucleic acid conjugate moiety contains two or more AU or AUU motifs. Similarly, the nucleic acid conjugate moiety can also contain one or more CU-rich sequence elements CREs) (Wein, et al, Eur. J. Biochem., 2003, 270, 350) which can bind to proteins Huff and/or HuR of the ELAV family of proteins. As with AREs, CREs can help localize conjugated oligomeric compounds to the cytoplasm. In some embodiments, the nucleic acid conjugate moiety contains the motif (CUUU)n, wherein, for example, n can be 1 to about 20, 1 to about 15, or 1 to about 11. The (CUUU)n motif can optionally be followed or preceded by one or more U. In some embodiments, n is about 9 to about 12 or about 11. The nucleic acid conjugate moiety can also include substrates of hnRNP proteins (heterogeneous nuclear ribonucleoprotein), some of which are involved in shuttling nucleic acids between the nucleus and cytoplasm, (e.g., nhRNP Al and nhRNP K; see, e.g., Mili, et al, Mol. Cell Biol, 2001, 21, 7307). Some example hnRNP substrates include nucleic acids containing the sequence UAGGA/U or (GG)AC-UAGC(A). Other nucleic acid conjugate moieties can include Y strings or other tracts that can bind to, for example, linRNP I. In some embodiments, the nucleic acid conjugate can contain at least 3, at least 4, at least 5, at least 6, at least 7, at least 8, at least 9, at least 10, at least 15, at least 20, and at least 25 consecutive pyrimidine bases. In other embodiments the nucleic acid conjugate can contain greater than 50, greater than 60, greater than 70, greater than 80, greater than 90, or greater than 95 percent pyrimidine bases.

Other nucleic acid conjugate-like moieties can include pumilio (puf protein) recognition sequences such as described in Wang, et al., Cell, 2002, 110, 501. Example pumilio recognition sequences can include UGUANAUR, where N can be any base and R can be a purine base. Localization to the cytoplasm can be facilitated by nucleic acid conjugate moieties containing AREs and/or CREs. Nucleic acid conjugate-like moieties serving as substrates of hnRNPs can facilitate localization of conjugated oligomeric compounds to the cytoplasm (e.g., hnRNP Al or K) or nucleus (e.g., hnRNP I). Additionally, nucleus localization can be facilitated by nucleic acid conjugate-like moieties containing polypyrimidine tracts.

A Reactive Group

A reactive group is a group which is used in chemical synthesis, which in the context of the present invention may be used "conjugate" the oligonucleotide, or otherwise covalently link the oligonucleotide to the third region (X), such as the conjugate, blocking group or targeting group, or optionally the linker (Y). An example of a reactive group is a phosphoramidite, which is widely used in oligonucleotide synthesis.

An Activation Group

An activation group is a group which may be activated to form a reactive group. In this respect, an activation group may be considered as a protected reactive group, which may be deprotected prior to enable use of the reactive group, for example in the methods of synthesis/manufacture disclosed herein.

Linkage Group

A nucleoside linkage is the linkage group either between nucleosides in the oligonucleotide, or, when present, may also describe the group which attaches the third region (X or C) or the linker (Y) to region B—for example this linker may be a phosphate (containing) linkage group or a triazol group.

Blocker Group (Also Referred to as a Blocking/Blocker Moiety)

In some aspects, the third region is a blocking region. A blocker is typically a conjugate or an oligonucleotide (typically not complementary to the target region), which, for example (but not limited to) either through steric hindrance, or through hybridization to the first region (or first and second regions), prevents or reduces activity of the oligomer. The (blocked) activity may be against its intended target (the target) or in some embodiments unintended targets (off-targets).

The oligomeric compound of the invention may therefore comprise a first region, such as a gapmer or LNA gaper oligonucleotide (such as a gapmer of formula X'Y'Z), a second region which is a biocleavable linker, such as region B as described herein, and a third region, region C, which comprises a region of at least 2 consecutive nucleosides, such as 3, 4, 5, 6, 7, 8, 9, 10, 11, 12, 13, 14, 15, 16 nucleotides which are complementary to a corresponding part of the first region. In some embodiments at least 2 nucleosides of region C, such as 3, 4, 5, 6, 7, 8, 9, or 10 nucleosides are high affinity nucleoside analogues, such as LNA (BNA)—in some embodiments, these may form the distal part of region C. The high affinity nucleoside analogues of region C may form a contiguous sequence of high affinity nucleoside analogues, which may be flanked by other nucleosides, such as DNA nucleosides (also part of region C, referred to as the proximal part of region C). In some embodiments, region C comprises between 2-8 (such as 3, 4, 5, 6, & 7 LNA (BNA) nucleotides, and in the same or in a different embodiment a region of between 2-16 DNA nucleotides (such as 3, 4, 5, 6, 7, 8, 9, 10, 11, 12, 13, 14, 15). In some embodiments, the distal part of region B comprises a contiguous region of high affinity nucleotide analogues, for example a contiguous region of 2, 3, 4, 5, 6, 7, or 8 LNA nucleotides. The proximal region may comprise a contiguous region of non-LNA nucleotides, such as those referred to herein, such as DNA nucleotides, such as a region of 2-16 non-LNA nucleotides. It is however also understood that the proximal region may comprise high affinity nucleotide analogues including LNA, but as contiguous regions of LNA can restrict the conformational flexibility of the proximal region (which is thought to act as a loop) it may, in some embodiments be useful to limit the use of long stretches of LNA in the proximal (or loop forming part), such as no more than 4 consecutive LNAs, such as no more than 3 consecutive LNAs, or no more than 2 consecutive LNAs.

In some embodiments, the region of other nucleotides in region C (such as DNA nucleotides) forms a contiguous sequence with region B, i.e. is proximal to the terminal nucleotide of region B), so that the region of high affinity nucleotides is distal to region B. In such an embodiment, region B and the proximal part of region C (e.g. the region comprising DNA nucleotides) may form a flexible loop, which allows the distal part of region C to hybridize with the first region. The proximal part of region C may or may not be complementary to a corresponding part of region A. In some embodiments, the distal part of region C is complementary to nucleotides which form a region which is capable of recruiting RNaseH, such as the gap region of a gapmer (referred to herein region Y'). In such an embodiment, the blocking region (region C) forms a duplex with the gap region, or part thereof, thereby blocking the availability of the central region of the gapmer to interact with other molecules or the target or off-targets. The invention therefore provides a solution to the inherent toxicity of DNA phosphorothioate oligonucleotides (which are typically used for the gap region of gapmers), as it allows for the controlled activation of gapmer oligomers (region A) within the target tissue or cells. In this respect, the use of a blocking region can act as a pro-drug. It is recognized that the blocking region (region C or distal part thereof), may also be directed towards other regions of an oligomer, including a mixmer or totalmer oligomer, or the flanking regions of a gapmer, or across the wing region and the gap region of a gapmer. In such an embodiment, the hybridization or region C (or distal part thereof) to region A (or part of region A), prevents the hybridization of the corresponding part of region A to biomolecules, and may therefore also be used to prevent unintended interaction with other biomolecules, enhancing specificity, tissue specific activity, and diminishing the risk of toxicity. The internucleoside linkages between the nucleotides of region C may be other than phosphodiester, such as may be phosphorothioate.

Targeting Group (Also Referred to as a Targeting Moiety)

A targeting moiety is a group whose presence on the oligomeric compound causes a differential pattern of biodistribution and/or cellular uptake of the oligomeric compound. Targeting groups may be, for example, receptor ligands, antibodies, hormones or hormone analogues, aptamers etc. The examples show the use of cholesterol as a targeting group—cholesterol is recognized by the LDL receptor in the surface of hepatocytes, resulting in the preferential uptake of cholesterol conjugated oligonucleotides into the liver. The examples also illustrate the use of GalNac, tocopherol, and folic acid as targeting groups.

Oligomer Linked Biocleavable Conjugates

The oligomeric compound comprises at least one region B (second region (region B) which is positioned between at least two of the oligomer regions (referred to as region A and A' and optionally A").

Further region B regions may be positioned, e.g. between regions A' and A", or between an oligomer region and a function group, such as the conjugate (referred to as region C). Region B (or region Bs) may be a linker such as a cleavable linker (also referred to as a physiologically labile linkage).

In some embodiments, the compound of the invention comprises a biocleavable linker (also referred to as the physiologically labile linker, Nuclease Susceptible Physiological Labile Linkages, or nuclease susceptible linker), for example the phosphate nucleotide linker (such as region B) or a peptide linker, which joins the oligomer regions (or contiguous nucleotide sequence or region A), and optionally joins a conjugate moiety (or region C) to one of the oligomers, optionally via a further linker (Y).

Biocleavable linkers according to the present invention refers to linkers which are susceptible to cleavage in a target tissue (i.e. physiologically labile), for example liver and/or kidney. It is preferred that the cleavage rate seen in the target tissue is greater than that found in blood serum. Suitable methods for determining the level (%) of cleavage in tissue (e.g. liver or kidney) and in serum are found in example 6. In some embodiments, the biocleavable linker (also referred to as the physiologically labile linker, or nuclease susceptible linker), such as region B, in a compound of the invention, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved, in the liver or kidney homogenate assay of Example 6. In some embodiments, the cleavage (%) in serum, as used in the assay in Example 6, is less than about 20%, such as less than about 10%, such less than 5%, such as less than about 1%.

Biocleavable linkers according to the present invention refers to linkers which are susceptible to cleavage in a target tissue (i.e. physiologically labile), for example liver and/or kidney. It is preferred that the cleavage rate seen in the target tissue is greater than that found in blood serum. Suitable methods for determining the level (%) of cleavage in tissue (e.g. liver or kidney) and in serum are found in example 6. In some embodiments, the biocleavable linker (also referred to as the physiologically labile linker, or nuclease susceptible linker), such as region B, in a compound of the invention, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved, in the liver or kidney homogenate assay of Example 6. In some embodiments, the cleavage (%) in serum, as used in the assay in Example 6, is less than about 30%, is less than about 20%, such as less than about 10%, such as less than 5%, such as less than about 1%.

In some embodiments, which may be the same of different, the biocleavable linker (also referred to as the physiologically labile linker, or nuclease susceptible linker), such as region B, in a compound of the invention, are susceptible to S1 nuclease cleavage. Susceptibility to S1 cleavage may be evaluated using the S1 nuclease assay shown in Example 6. In some embodiments, the biocleavable linker (also referred to as the physiologically labile linker, or nuclease susceptible linker), such as region B, in a compound of the invention, are at least about 30% cleaved, such as at least about 40% cleaved, such as at least about 50% cleaved, such as at least about 60% cleaved, such as at least about 70% cleaved, such as at least about 80% cleaved, such as at least about 90% cleaved, such as at least 95% cleaved after 120 min incubation with S1 nuclease according to the assay used in Example 6.

Nuclease Susceptible Physiological Labile Linkages: In some embodiments, the oligomer (also referred to as oligomeric compound) of the invention (or conjugate) comprises:
  i) a first region (region A), which comprises 7-18 contiguous nucleotides;
  ii) a second region (region B) which comprises a biocleavable linker
  iii) a further first region (region A'), which comprises 7-18 contiguous nucleotides
  iv) optionally a further region B
  v) a third region (C) which comprises a conjugate moiety, a targeting moiety, an activation moiety, wherein the third region is covalent linked to the second region.

Suitably the first regions are phosphorothioate linked oligomer regions. In some embodiments, region B may be a phosphate nucleotide linker. The third region may be a conjugate, e.g. a lipophilic conjugate, such as a lipid, a fatty acid, sterol, such as cholesterol or tocopherol. Phosphate nucleotide linkers may also be used for other conjugates, for example carbohydrate conjugates, such as GalNac.

Peptide and Other Linkers

In some embodiments, the biocleavable linker (region B) is a peptide, such as a trilysine peptide linker which may be used in a polyGalNac conjugate, such a triGalNac conjugate. Other linkers known in the art which may be used, including disulfide linkers (also referred to as dithio or disulphide herein). Other peptide linkers include, e.g. a Tyr-Asp(Asp) tripeptide or Asp(Asp) dipeptide.

Other Phosphate Nucleotide Linkers as Region B

In some embodiments, region B (a second region) comprises between 1-6 nucleotides, which is covalently linked to the 5' or 3' nucleotide of the first region (an oligomer region), such as via a internucleoside linkage group such as a phosphodiester linkage.

In some embodiments, region B may be physiologically labile internucleoside linkages for example, the internucleoside linkage between the first (A) and second oligomer region (A') and optionally between the second oligomer region (A') and a third oligomer region (A") may be phosphodiester linkage and, optionally the nucleoside of the second oligomer region [such as immediately] adjacent to the first region is either DNA or RNA (See FIG. 1).

In some embodiments, region B may be a physiologically labile internucleoside linkages for example, the internucleoside linkage between the one or more (or each) oligomer region and a linkage group (see FIG. 2) may be phosphodiester linkage and, optionally the nucleoside of the oligomer region [such as immediately] adjacent to linkage group is either DNA or RNA.

In some embodiments, one or more (or each) region A and region B form a single contiguous nucleotide sequence of 8-22, such as 10-20 nucleotides in length.

In some aspects the internucleoside linkage between a region A and a region B may be considered part of region B.

Linkers

A linkage or linker is a connection between two atoms that links one chemical group or segment of interest to another chemical group or segment of interest via one or more covalent bonds. Conjugate moieties (or targeting or blocking moieties) can be attached to the oligomeric compound directly or through a linking moiety (linker or tether)—a linker. Linkers are bifunctional moieties that serve to covalently connect a third region, e.g. a conjugate moiety, to an oligomeric compound (such as to region B). In some embodiments, the linker comprises a chain structure or an oligomer of repeating units such as ethylene glyol or amino acid units. The linker can have at least two functionalities, one for attaching to the oligomeric compound and the other for attaching to the conjugate moiety. Example linker functionalities can be electrophilic for reacting with nucleophilic groups on the oligomer or conjugate moiety, or nucleophilic for reacting with electrophilic groups. In some embodiments, linker functionalities include amino, hydroxyl, carboxylic acid, thiol, phosphoramidate, phosphate, phosphite, unsaturations (e.g., double or triple bonds), and the like. Some example linkers include 8-amino-3,6-dioxaoctanoic acid (ADO), succinimidyl 4-(N-maleimidomethyl)cyclohexane-1-carboxylate (SMCC), 6-aminohexanoic acid (AHEX or AHA), 6-aminohexyloxy, 4-aminobutyric acid, 4-aminocyclohexylcarboxylic acid, succinimidyl 4-(N-maleimidomethyl)cyclohexane-1-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like.

A wide variety of further linker groups are known in the art that can be useful in the attachment of conjugate moieties to oligomeric compounds. A review of many of the useful linker groups can be found in, for example, Antisense Research and Applications, S. T. Crooke and B. Lebleu, Eds., CRC Press, Boca Raton, Fla., 1993, p. 303-350. A disulfide linkage has been used to link the 3' terminus of an oligonucleotide to a peptide (Corey, et al., Science 1987, 238, 1401; Zuckermann, et al, J Am. Chem. Soc. 1988, 110, 1614; and Corey, et al., J Am. Chem. Soc. 1989, 111, 8524). Nelson, et al., Nuc. Acids Res. 1989, 17, 7187 describe a linking reagent for attaching biotin to the 3'-terminus of an oligonucleotide. This reagent, N-Fmoc-O-DMT-3-amino-1, 2-propanediol is commercially available from Clontech Laboratories (Palo Alto, Calif.) under the name 3'-Amine. It is also commercially available under the name 3'-Amino-Modifier reagent from Glen Research Corporation (Sterling, Va.). This reagent was also utilized to link a peptide to an oligonucleotide as reported by Judy, et al., Tetrahedron Letters 1991, 32, 879. A similar commercial reagent for linking to the 5'-terminus of an oligonucleotide is 5'-Amino-Modifier C6. These reagents are available from Glen Research Corporation (Sterling, Va.). These compounds or similar ones were utilized by Krieg, et al, Antisense Research and Development 1991, 1, 161 to link fluorescein to the 5'-terminus of an oligonucleotide. Other compounds such as acridine have been attached to the 3'-terminal phosphate group of an oligonucleotide via a polymethylene linkage (Asseline, et al., Proc. Natl. Acad. Sci. USA 1984, 81, 3297). [0074] Any of the above groups can be used as a single linker or in combination with one or more further linkers.

Linkers and their use in preparation of conjugates of oligomeric compounds are provided throughout the art such as in WO 96/11205 and WO 98/52614 and U.S. Pat. Nos. 4,948,882; 5,525,465; 5,541,313; 5,545,730; 5,552,538; 5,580,731; 5,486,603; 5,608,046; 4,587,044; 4,667,025; 5,254,469; 5,245,022; 5,112,963; 5,391,723; 5,510475; 5,512,667; 5,574,142; 5,684,142; 5,770,716; 6,096,875; 6,335,432; and 6,335,437, each of which is incorporated by reference in its entirety.

As used herein, a physiologically labile bond is a labile bond that is cleavable under conditions normally encountered or analogous to those encountered within a mammalian body (also referred to as a cleavable linker). Physiologically labile linkage groups are selected such that they undergo a chemical transformation (e.g., cleavage) when present in certain physiological conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. In some embodiments, the cleavable linker is susceptible to nuclease(s) which may for example, be expressed in the target cell—and as such, as detailed herein, the linker may be a short region (e.g. 1-10) phosphodiester linked nucleosides, such as DNA nucleosides, Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond. As used herein, a pH-labile bond is a labile bond that is selectively broken under acidic conditions (pH<7). Such bonds may also be termed endosomally labile bonds, since cell endosomes and lysosomes have a pH less than 7.

Activated Oligomers

In some embodiments, the invention provides an activated oligomer—i.e. an intermediate used in the synthesis of the oligomer of the invention—e.g. the conjugated oligomer. In this respect, the oligomer of the invention may, in some embodiments comprise region A and region B as described herein, and region B in covalently linked to an activation (or reactive) group, suitable for use in conjugation of the oligomer.

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group ($-O-C(O)-(CH_2)_w NH$).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alky- lamino group can be straight chain or branched chain, and wherein the functional group attached to the oligomer via an ester group ($-O-C(O)-(CH_2)_w SH$)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Methods of Synthesis and Manufacture

The invention also provides methods of synthesis or manufacture of the oligomer of the invention. The oligomer may be made using standard oligonucleotide synthesis, which is typically performed on a solid support, such as a universal support. The oligomer of the invention may be synthesized, for example, by the sequential synthesis of a oligomer region A', region B (B), and a second oligomer region (A'), optionally followed by the addition (e.g. conjugation) of the third region (C) optionally via a linker (Y). In some embodiments, the oligomer of the invention may be synthesized, for example, by the sequential synthesis of a oligomer region A', region B (B), and a second oligomer region (A'), a second region B (B') optionally followed by the addition (e.g. conjugation) of the third region (C) optionally via a linker (Y). In some embodiments, the oligomer of the invention may be synthesized, for example, by the sequential synthesis of a oligomer region A', region B (B), and a second oligomer region (A'), a second region B (B') and a third oligomer region (A") optionally followed by the addition (e.g. conjugation) of the third region (C) optionally via a linker (Y). In some embodiments, the oligomer of the invention may be synthesized, for example, by the sequential synthesis of a oligomer region A', region B (B), and a second oligomer region (A'), a second region B (B') and a third oligomer region (A") followed by a third region B (B"), followed by the addition (e.g. conjugation) of the third region (C) optionally via a linker (Y).

Region Y, when present may be joined to the region B, and region C subsequently added to region Y, or region Y and C may be added to region B in a single reaction step.

Alternatively, the oligomer synthesis my occur via the initial coupling of region C, or region C and Y to the oligonucleotide support column, followed by sequential oligonucleotide synthesis of the oligonucleotide part of the compound of the invention.

Alternatively, the use of a cleavable bidirectional group attached to the oligonucleotide synthesis support (in an initial or pre-step), allows for a method where the oligonucleotide regions of the oligonucleotide are synthesized on one reactive group of the bifunctional group, and region C or region C and Y are synthesized on a second reactive group of the bifunctional group, wherein the oligonucleotide synthesis or addition of C (or C and Y) to the support may occur in any order or even together. The cleavage of the bifunctional group from the support then produces the oligomer of the invention. The bifunctional group may for example be a nucleoside, where one entity (e.g. region B or C or C-Y-) is attached to a phosphate containing group on the nucleoside (e.g. a 5' or 3' group), and the other (e.g. region B or C or C-Y-), is attached, for example to an reactive group present on the nucleobase.

Alternatively region C or C—Y may be joined to the oligomer (region B) after oligonucleotide synthesis, such as after the cleavage step. The invention therefore also relates to the intermediate oligomer, which comprises the oligonucleotide part of the compound of the invention, and a reactive or activation group attached to region B, which is subsequently used to join region C or regions C and Y to region B.

Region Y or region C may be linked to a region B or an oligomer as a phosphoramidite, for example—allowing for the formation of the oligomer in a single oligonucleotide synthesis, followed by cleavage of the oligomer from the oligonucleotide synthesis support (US). In this regard, in some embodiments, the linkage group between an oligomer region or a region B and region C or Y may be a phosphate containing group, such as a nucleoside linkage, such as phosphodiester, phosphorothioate, phosphorodithioate, boranophosphate, methylphosphonate or others, such as those referred to herein. Alternatively other chemical linkages may be used such as a triazol group.

In some embodiments, the third region (C) or C-Y- may be linked to a region B or an oligomer region via a group other than a 5' or 3' phosphate, for example via a reactive group at another position, for example a reactive group, such as an amine on the base of a nucleoside in region B.

Oligonucleotide synthesis may occur in the 5'-3' direction, or, as is typical of most oligonucleotide synthesis, in the 3'-5' direction.

In some non-limiting examples, the oligonucleotide-conjugate construct can be assembled in different ways, e.g.

A) The B-A part of the construct can be made on an oligonucleotide synthesis machine capable of synthesizing both phosphorothioate and phosphorodiester linkages. B-A can then optionally be elongated by standard phosphoramidite chemistry using a building block C-A-P (e.g. conjugate moiety with linker attached) to create C-A-B-A or with building block C-P (conjugate moiety with no linker) to create C-B-A

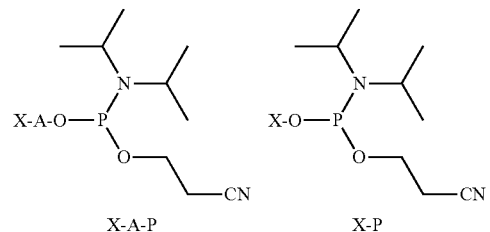

B) The B-A part of the construct can be made on an oligonucleotide synthesis machine capable of synthesizing both phosphorthioate and phosphordiester linkages. B-A can then optionally be sequentially elongated by standard phosphoramidite chemistry using a building block DMTrO-A-P followed by building block C-P to create C-A-B-A with a PO or PS linkage between the C and A part.

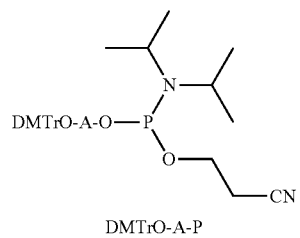

The B-A part of the construct can be made on an oligonucleotide synthesis machine capable of synthesizing both phosphorthioate and phosphordiester linkages. B-A can then optionally be sequentially elongated by standard phosphoramidite chemistry using a building block PGN-A-P to create $H_2N$-A-B-A. After cleavage and deprotection of the oligonucleotide the free amine of the oligonucleotide can be conjugated with moiety C in which a functional group of C has been activated in order to react with the terminal primary amine of the oligonucleotide.

Compositions

The oligomer of the invention may be used in pharmaceutical formulations and compositions. Suitably, such compositions comprise a pharmaceutically acceptable diluent, carrier, salt or adjuvant. WO2007/031091 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in WO2007/031091—which are also hereby incorporated by reference.

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound. In this regard the prodrug may comprise region B and a conjugate, targeting or blocking moiety as according to the present invention. In some embodiments, the oligomer of the invention is a pro-drug.

The use of lipophilic conjugates according to the invention allows for the incorporation of the oligomer of the invention into lipidoids or liposomes, e.g. cationic liposomes (e.g. cationic liposome SNALPs (stable nucleic acid lipid particle), which are particularly useful for delivery of oligomers e.g. to the liver, e.g. siRNAs.

Applications

The oligomers of the invention may be utilized as research reagents for, for example, diagnostics, therapeutics and prophylaxis.

In research, in some embodiments, such oligomers may be used to specifically inhibit the synthesis of protein (typically by degrading or inhibiting the mRNA and thereby prevent protein formation) in cells and experimental animals thereby facilitating functional analysis of the target or an appraisal of its usefulness as a target for therapeutic intervention.

For therapeutics, an animal or a human, suspected of having a disease or disorder, which can be treated by modulating the expression of the target is treated by administering oligomeric compounds in accordance with this invention. Further provided are methods of treating a mammal, such as treating a human, suspected of having or being prone to a disease or condition, associated with expression of the target by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

In some embodiments, the disease is cancer. In some embodiments, the disease is an inflammatory disease. In some embodiments, the disease is a cardiovascular disease, such as In some embodiments the disease or disorder is myocardial infarction (MI).

In some embodiments, the disease or disorder is, or results in or is associated with fibrosis, such as liver-fibrosis, cardiac fibrosis or local fibrosis.

In some embodiments, the disease or disorder is blood clotting disorder.

In some embodiments the disease or disorder is or comprises (results in or is associated with) bone-lose.

In some embodiments, the disease or disorder is a liver disease or disorder.

In some embodiments the disease or disorder is a metabolic disorder, which may for example be a liver disease or disorder, and/or in some aspects a cardiovascular disease or disorder).

Cardiovascular/Metabolic diseases include, for examples, metabolic syndrome, obesity, hyperlipidemia, HDL/LDL cholesterol imbalance, dyslipidemias, e.g., familial combined hyperlipidemia (FCHL), acquired hyperlipidemia, statin-resistant, hypercholesterolemia, coronary artery disease (CAD), and coronary heart disease (CHD), atherosclerosis, heart disease, diabetes (I and/or II), NASH, acute coronary syndrome (ACS), NASH, chronic heart failure, cardiovascular disease, cardio metabolic disease, hyperlipidaemia and related disorders, metabolic syndrome, atherosclerosis, chronic heart failure, vascular disease, peripheral arterial disease, heart disease, ischemia, type 2 diabetes, type 1 diabetes, In some embodiments, the disease or disorder is selected from the group consisting of metabolic syndrome, obesity, hyperlipidemia, atherosclerosis, HDL/LDL cholesterol imbalance, dyslipidemias, e.g., familial combined hyperlipidemia (FCHL), acquired hyperlipidemia, statin-resistant, hypercholesterolemia, coronary artery disease (CAD), and coronary heart disease (CHD).

In some embodiments, the disease or disorder is selected from the group consisting of chronic heart failure, cardiovascular disease, cardio metabolic disease, chronic heart failure, vascular disease, peripheral arterial disease, heart disease, ischemia, acute coronary syndrome (ACS).

In some embodiments, the disease or disorder is type 2 diabetes, type 1 diabetes, In some embodiments, the disease or disorder is a viral disease, such as polycythemia, hepatitis C, hepatitis B, BKV, HIV.

In some embodiments, the disease or disorder is a severe and rare diseases (or genetic disorder).

The invention further provides use of a compound of the invention in the manufacture of a medicament for the treatment of a disease, disorder or condition, such as those as referred to herein.

Generally stated, some aspects of the invention is directed to a method of treating a mammal suffering from or susceptible to conditions associated with abnormal levels of the target, comprising administering to the mammal and therapeutically effective amount of an oligomer targeted to the target that comprises one or more LNA units. The oligomer, a conjugate or a pharmaceutical composition according to the invention is typically administered in an effective amount.

An interesting aspect of the invention is directed to the use of the compound as defined herein for the preparation of a medicament for the treatment of a disease, disorder or condition as referred to herein.

Moreover, the invention relates to a method of treating a subject suffering from a disease or condition such as those referred to herein.

A patient who is in need of treatment is a patient suffering from or likely to suffer from the disease or disorder.

In some embodiments, the term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

TABLE 2

| | | miR | | Comp | | | | | |
|---|---|---|---|---|---|---|---|---|---|
| microRNA | MicroRNA target Sequence | miR ID NO | 9-mer | Comp ID NO | 8-mer | C ID NO | 7-mer | C ID NO | |
| ebv-miR-BART1-3p | UAGCACCGCUAUCCACUAUGUC | 40 | AGCGGTGCT | 977 | GCGGTGCT | 1914 | CGGTGCT | 2851 | |
| ebv-miR-BART1-5p | UCUUAGUGGAAGUGACGUGCUGUG | 41 | TCCACTAAG | 978 | CCACTAAG | 1915 | CACTAAG | 2852 | |
| ebv-miR-BART10 | UACAUAACCAUGGAGUUGGCUGU | 42 | TGGTTATGT | 979 | GGTTATGT | 1916 | GTTATGT | 2853 | |
| ebv-miR-BART10* | GCCACCUCUUUGGUUCUGUACA | 43 | AAGAGGTGG | 980 | AGAGGTGG | 1917 | GAGGTGG | 2854 | |
| ebv-miR-BART11-3p | ACGCACACCAGGCUGACUGCC | 44 | TGGTGTGCG | 981 | GGTGTGCG | 1918 | GTGTGCG | 2855 | |
| ebv-miR-BART11-5p | UCAGACAGUUUGGUGCGCUAGUUG | 45 | AACTGTCTG | 982 | ACTGTCTG | 1919 | CTGTCTG | 2856 | |
| ebv-miR-BART12 | UCCUGUGGUGUUUGGUGUGGUU | 46 | CACCACAGG | 983 | ACCACAGG | 1920 | CCACAGG | 2857 | |
| ebv-miR-BART13 | UGUAACUUGCCAGGGACGGCUGA | 47 | GCAAGTTAC | 984 | CAAGTTAC | 1921 | AAGTTAC | 2858 | |
| ebv-miR-BART13* | AACCGGCUCGUGGCUCGUACAG | 48 | CGAGCCGGT | 985 | GAGCCGGT | 1922 | AGCCGGT | 2859 | |
| ebv-miR-BART14 | UAAAUGCUGCAGUAGUAGGGAU | 49 | GCAGCATTT | 986 | CAGCATTT | 1923 | AGCATTT | 2860 | |
| ebv-miR-BART14* | UACCCUACGCUGCCGAUUUACA | 50 | GCGTAGGGT | 987 | CGTAGGGT | 1924 | GTAGGGT | 2861 | |
| ebv-miR-BART15 | GUCAGUGGUUUUGUUUCCUUGA | 51 | AACCACTGA | 988 | ACCACTGA | 1925 | CCACTGA | 2862 | |
| ebv-miR-BART16 | UUAGAUAGAGUGGGUGUGUGCUCU | 52 | CTCTATCTA | 989 | TCTATCTA | 1926 | CTATCTA | 2863 | |
| ebv-miR-BART17-3p | UGUAUGCCUGGUGUCCCCUUAGU | 53 | CAGGCATAC | 990 | AGGCATAC | 1927 | GGCATAC | 2864 | |
| ebv-miR-BART17-5p | UAAGAGGACGCAGGCAUACAAG | 54 | CGTCCTCTT | 991 | GTCCTCTT | 1928 | TCCTCTT | 2865 | |
| ebv-miR-BART18-3p | UAUCGGAAGUUUGGGCUUCGUC | 55 | ACTTCCGAT | 992 | CTTCCGAT | 1929 | TTCCGAT | 2866 | |
| ebv-miR-BART18-5p | UCAAGUUCGCACUUCCUAUACA | 56 | GCGAACTTG | 993 | CGAACTTG | 1930 | GAACTTG | 2867 | |
| ebv-miR-9ART19-3p | UUUUGUUUGCUUGGGAAUGCU | 57 | GCAAACAAA | 994 | CAAACAAA | 1931 | AAACAAA | 2868 | |
| ebv-miR-BART19-5p | ACAUUCCCCGCAAACAUGACAUG | 58 | CGGGGAATG | 995 | GGGGAATG | 1932 | GGGAATG | 2869 | |
| ebv-miR-BART2-3p | AAGGAGCGAUUUGGAGAAAAUAAA | 59 | ATCGCTCCT | 996 | TCGCTCCT | 1933 | CGCTCCT | 2870 | |
| ebv-miR-BART2-5p | UAUUUUCUGCAUUCGCCCUUGC | 60 | GCAGAAAAT | 997 | CAGAAAAT | 1934 | AGAAAAT | 2871 | |
| ebv-miR-BART20-3p | CAUGAAGGCACAGCCUGUUACC | 61 | TGCCTTCAT | 998 | GCCTTCAT | 1935 | CCTTCAT | 2872 | |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| ebv-miR-BART20-5p | UAGCAGGCAUGUCUUCAUUCC | 62 | ATGCCTGCT | 999 | TGCCTGCT | 1936 | GCCTGCT | 2873 |
| ebv-miR-BART3 | CGCACCACUAGUCACCAGGUGU | 63 | TAGTGGTGC | 1000 | AGTGGTGC | 1937 | GTGGTGC | 2874 |
| ebv-miR-BART3* | ACCUAGUGUUAGUGUUGUGCU | 64 | AACACTAGG | 1001 | ACACTAGG | 1938 | CACTAGG | 2875 |
| ebv-miR-BART4 | GACCUGAUGCUGCUGGUGUGCU | 65 | GCATCAGGT | 1002 | CATCAGGT | 1939 | ATCAGGT | 2876 |
| ebv-miR-BART5 | CAAGGUGAAUAUAGCUGCCCAUCG | 66 | ATTCACCTT | 1003 | TTCACCTT | 1940 | TCACCTT | 2877 |
| ebv-miR-BART6-3p | CGGGGAUCGGACUAGCCUUAGA | 67 | CCGATCCCC | 1004 | CGATCCCC | 1941 | GATCCCC | 2878 |
| ebv-miR-BART6-5p | UAAGGUUGGUCCAAUCCAUAGG | 68 | ACCAACCTT | 1005 | CCAACCTT | 1942 | CAACCTT | 2879 |
| ebv-miR-BART7 | CAUCAUAGUCCAGUGUCCAGGG | 69 | GACTATGAT | 1006 | ACTATGAT | 1943 | CTATGAT | 2880 |
| ebv-miR-BART7* | CCUGGACCUUGACUAUGAAACA | 70 | AAGGTCCAG | 1007 | AGGTCCAG | 1944 | GGTCCAG | 2881 |
| ebv-miR-BART8 | UACGGUUUCCUAGAUUGUACAG | 71 | GGAAACCGT | 1008 | GAAACCGT | 1945 | AAACCGT | 2882 |
| ebv-miR-BART8* | GUCACAAUCUAUGGGGUCGUAGA | 72 | AGATTGTGA | 1009 | GATTGTGA | 1946 | ATTGTGA | 2883 |
| ebv-miR-BART9 | UAACACUUCAUGGGUCCCGUAGU | 73 | TGAAGTGTT | 1010 | GAAGTGTT | 1947 | AAGTGTT | 2884 |
| ebv-miR-BART9* | UACUGGACCCUGAAUUGGAAAC | 74 | GGGTCCAGT | 1011 | GGTCCAGT | 1948 | GTCCAGT | 2885 |
| ebv-miR-BHRF1-1 | UAACCUGAUCAGCCCCGGAGUU | 75 | GATCAGGTT | 1012 | ATCAGGTT | 1949 | TCAGGTT | 2886 |
| ebv-miR-BHRF1-2 | UAUCUUUUGCGGCAGAAAUUGA | 76 | GCAAAAGAT | 1013 | CAAAAGAT | 1950 | AAAAGAT | 2887 |
| ebv-miR-BHRF1-2* | AAAUUCUGUUGCAGCAGAUAGC | 77 | AACAGAATT | 1014 | ACAGAATT | 1951 | CAGAATT | 2888 |
| ebv-miR-BHRF1-3 | UAACGGGAAGUGUGUAAGCACA | 78 | CTTCCCGTT | 1015 | TTCCCGTT | 1952 | TCCCGTT | 2889 |
| hcmv-miR-UL112 | AAGUGACGGUGAGAUCCAGGCU | 79 | ACCGTCACT | 1016 | CCGTCACT | 1953 | CGTCACT | 2890 |
| hcmv-miR-UL148D | UCGUCCUCCCCUUCUUCACCG | 80 | GGGAGGACG | 1017 | GGAGGACG | 1954 | GAGGACG | 2891 |
| hcmv-miR-UL22A | UAACUAGCCUUCCCGUGAGA | 81 | AGGCTAGTT | 1018 | GGCTAGTT | 1955 | GCTAGTT | 2892 |
| hcmv-miR-UL22A* | UCACCAGAAUGCUAGUUUGUAG | 82 | ATTCTGGTG | 1019 | TTCTGGTG | 1956 | TCTGGTG | 2893 |
| hcmv-miR-UL36 | UCGUUGAAGACACCUGGAAAGA | 83 | TCTTCAACG | 1020 | CTTCAACG | 1957 | TTCAACG | 2894 |
| hcmv-miR-UL36* | UUUCCAGGUGUUUUCAACGUGC | 84 | CACCTGGAA | 1021 | ACCTGGAA | 1958 | CCTGGAA | 2895 |
| hcmv-miR-UL70-3p | GGGGAUGGGCUGGCGCGCGG | 85 | GCCCATCCC | 1022 | CCCATCCC | 1959 | CCATCCC | 2896 |
| hcmv-miR-UL70-5p | UGCGUCUCGGCCUCGUCCAGA | 86 | CCGAGACGC | 1023 | CGAGACGC | 1960 | GAGACGC | 2897 |
| hcmv-miR-US25-1 | AACCGCUCAGUGGCUCGGACC | 87 | CTGAGCGGT | 1024 | TGAGCGGT | 1961 | GAGCGGT | 2898 |
| hcmv-miR-US25-1* | UCCGAACGCUAGGUCGGUUCUC | 88 | AGCGTTCGG | 1025 | GCGTTCGG | 1962 | CGTTCGG | 2899 |
| hcmv-miR-US25-2-3p | AUCCACUUGGAGAGCUCCCGCGG | 89 | CCAAGTGGA | 1026 | CAAGTGGA | 1963 | AAGTGGA | 2900 |
| hcmv-miR-US25-2-5p | AGCGGUCUGUUCAGGUGGAUGA | 90 | ACAGACCGC | 1027 | CAGACCGC | 1964 | AGACCGC | 2901 |
| hcmv-miR-US33-3p | UCACGGUCCGAGCACAUCCA | 91 | CGGACCGTG | 1028 | GGACCGTG | 1965 | GACCGTG | 2902 |
| hcmv-miR-US33-5p | GAUUGUGCCCGGACCGUGGGCG | 92 | GGGCACAAT | 1029 | GGCACAAT | 1966 | GCACAAT | 2903 |
| hcmv-miR-US4 | CGACAUGGACGUGCAGGGGAU | 93 | GTCCATGTC | 1030 | TCCATGTC | 1967 | CCATGTC | 2904 |
| hcmv-miR-US5-1 | UGACAAGCCUGACGAGAGCGU | 94 | AGGCTTGTC | 1031 | GGCTTGTC | 1968 | GCTTGTC | 2905 |
| hcmv-miR-US5-2 | UUAUGAUAGGUGUGACGAUGUC | 95 | CCTATCATA | 1032 | CTATCATA | 1969 | TATCATA | 2906 |
| hsa-let-7a | UGAGGUAGUAGGUUGUAUAGUU | 96 | TACTACCTC | 1033 | ACTACCTC | 1970 | CTACCTC | 2907 |
| hsa-let-7a* | CUAUACAAUCUACUGUCUUUC | 97 | GATTGTATA | 1034 | ATTGTATA | 1971 | TTGTATA | 2908 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-let-7b | UGAGGUAGUAGGUUGUGUGGUU | 98 | TACTACCTC | 1035 | ACTACCTC | 1972 | CTACCTC | 2909 |
| hsa-let-7b* | CUAUACAACCUACUGCCUUCCC | 99 | GGTTGTATA | 1036 | GTTGTATA | 1973 | TTGTATA | 2910 |
| hsa-let-7c | UGAGGUAGUAGGUUGUAUGGUU | 100 | TACTACCTC | 1037 | ACTACCTC | 1974 | CTACCTC | 2911 |
| hsa-let-7c* | UAGAGUUACACCCUGGGAGUUA | 101 | TGTAACTCT | 1038 | GTAACTCT | 1975 | TAACTCT | 2912 |
| hsa-let-7d | AGAGGUAGUAGGUUGCAUAGUU | 102 | TACTACCTC | 1039 | ACTACCTC | 1976 | CTACCTC | 2913 |
| hsa-let-7d* | CUAUACGACCUGCUGCCUUUCU | 103 | GGTCGTATA | 1040 | GTCGTATA | 1977 | TCGTATA | 2914 |
| hsa-let-7e | UGAGGUAGGAGGUUGUAUAGUU | 104 | TCCTACCTC | 1041 | CCTACCTC | 1978 | CTACCTC | 2915 |
| hsa-let-7e* | CUAUACGGCCUCCUAGCUUUCC | 105 | GGCCGTATA | 1042 | GCCGTATA | 1979 | CCGTATA | 2916 |
| hsa-let-7f | UGAGGUAGUAGAUUGUAUAGUU | 106 | TACTACCTC | 1043 | ACTACCTC | 1980 | CTACCTC | 2917 |
| hsa-let-7f-1* | CUAUACAAUCUAUUGCCUUCCC | 107 | GATTGTATA | 1044 | ATTGTATA | 1981 | TTGTATA | 2918 |
| hsa-let-7f-2* | CUAUACAGUCUACUGUCUUUCC | 108 | GACTGTATA | 1045 | ACTGTATA | 1982 | CTGTATA | 2919 |
| hsa-let-7g | UGAGGUAGUAGUUUGUACAGUU | 109 | TACTACCTC | 1046 | ACTACCTC | 1983 | CTACCTC | 2920 |
| hsa-let-7g* | CUGUACAGGCCACUGCCUUGC | 110 | GCCTGTACA | 1047 | CCTGTACA | 1984 | CTGTACA | 2921 |
| hsa-let-7i | UGAGGUAGUAGUUUGUGCUGUU | 111 | TACTACCTC | 1048 | ACTACCTC | 1985 | CTACCTC | 2922 |
| hsa-let-7i* | CUGCGCAAGCUACUGCCUUGCU | 112 | GCTTGCGCA | 1049 | CTTGCGCA | 1986 | TTGCGCA | 2923 |
| hsa-miR-1 | UGGAAUGUAAAGAAGUAUGUAU | 113 | TTACATTCC | 1050 | TACATTCC | 1987 | ACATTCC | 2924 |
| hsa-miR-100 | AACCCGUAGAUCCGAACUUGUG | 114 | TCTACGGGT | 1051 | CTACGGGT | 1988 | TACGGGT | 2925 |
| hsa-miR-100* | CAAGCUUGUAUCUAUAGGUAUG | 115 | TACAAGCTT | 1052 | ACAAGCTT | 1989 | CAAGCTT | 2926 |
| hsa-miR-101 | UACAGUACUGUGAUAACUGAA | 116 | CAGTACTGT | 1053 | AGTACTGT | 1990 | GTACTGT | 2927 |
| hsa-miR-101* | CAGUUAUCACAGUGCUGAUGCU | 117 | GTGATAACT | 1054 | TGATAACT | 1991 | GATAACT | 2928 |
| hsa-miR-103 | AGCAGCAUUGUACAGGGCUAUGA | 118 | CAATGCTGC | 1055 | AATGCTGC | 1992 | ATGCTGC | 2929 |
| hsa-miR-103-as | UCAUAGCCCUGUACAAUGCUGCU | 119 | AGGGCTATG | 1056 | GGGCTATG | 1993 | GGCTATG | 2930 |
| hsa-miR-105 | UCAAAUGCUCAGACUCCUGUGGU | 120 | GAGCATTTG | 1057 | AGCATTTG | 1994 | GCATTTG | 2931 |
| hsa-miR-105* | ACGGAUGUUUGAGCAUGUGCUA | 121 | AAACATCCG | 1058 | AACATCCG | 1995 | ACATCCG | 2932 |
| hsa-miR-106a | AAAAGUGCUUACAGUGCAGGUAG | 122 | AAGCACTTT | 1059 | AGCACTTT | 1996 | GCACTTT | 2933 |
| hsa-miR-106a* | CUGCAAUGUAAGCACUUCUUAC | 123 | TACATTGCA | 1060 | ACATTGCA | 1997 | CATTGCA | 2934 |
| hsa-miR-106b | UAAAGUGCUGACAGUGCAGAU | 124 | CAGCACTTT | 1061 | AGCACTTT | 1998 | GCACTTT | 2935 |
| hsa-miR-106b* | CCGCACUGUGGGUACUUGCUGC | 125 | CACAGTGCG | 1062 | ACAGTGCG | 1999 | CAGTGCG | 2936 |
| hsa-miR-107 | AGCAGCAUUGUACAGGGCUAUCA | 126 | CAATGCTGC | 1063 | AATGCTGC | 2000 | ATGCTGC | 2937 |
| hsa-miR-10a | UACCCUGUAGAUCCGAAUUUGUG | 127 | CTACAGGGT | 1064 | TACAGGGT | 2001 | ACAGGGT | 2938 |
| hsa-miR-10a* | CAAAUUCGUAUCUAGGGGAAUA | 128 | TACGAATTT | 1065 | ACGAATTT | 2002 | CGAATTT | 2939 |
| hsa-miR-10b | UACCCUGUAGAACCGAAUUUGUG | 129 | CTACAGGGT | 1066 | TACAGGGT | 2003 | ACAGGGT | 2940 |
| hsa-miR-10b* | ACAGAUUCGAUUCUAGGGGAAU | 130 | TCGAATCTG | 1067 | CGAATCTG | 2004 | GAATCTG | 2941 |
| hsa-miR-1178 | UUGCUCACUGUUCUUCCCUAG | 131 | CAGTGAGCA | 1068 | AGTGAGCA | 2005 | GTGAGCA | 2942 |
| hsa-miR-1179 | AAGCAUUCUUUCAUUGGUUGG | 132 | AAGAATGCT | 1069 | AGAATGCT | 2006 | GAATGCT | 2943 |
| hsa-miR-1180 | UUUCCGGCUCGCGUGGGUGUGU | 133 | GAGCCGGAA | 1070 | AGCCGGAA | 2007 | GCCGGAA | 2944 |
| hsa-miR-1181 | CCGUCGCCGCCACCCGAGCCG | 134 | GCGGCGACG | 1071 | CGGCGACG | 2008 | GGCGACG | 2945 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-1182 | GAGGGUCUUGGGAGGGAUGUGAC | 135 | CAAGACCCT | 1072 | AAGACCCT | 2009 | AGACCCT | 2946 |
| hsa-miR-1183 | CACUGUAGGUGAUGGUGAGAGUGGGCA | 136 | ACCTACAGT | 1073 | CCTACAGT | 2010 | CTACAGT | 2947 |
| hsa-miR-1184 | CCUGCAGCGACUUGAUGGCUUCC | 137 | TCGCTGCAG | 1074 | CGCTGCAG | 2011 | GCTGCAG | 2948 |
| hsa-miR-1185 | AGAGGAUACCCUUUGUAUGUU | 138 | GGTATCCTC | 1075 | GTATCCTC | 2012 | TATCCTC | 2949 |
| hsa-miR-1197 | UAGGACACAUGGUCUACUUCU | 139 | ATGTGTCCT | 1076 | TGTGTCCT | 2013 | GTGTCCT | 2950 |
| hsa-miR-1200 | CUCCUGAGCCAUUCUGAGCCUC | 140 | GGCTCAGGA | 1077 | GCTCAGGA | 2014 | CTCAGGA | 2951 |
| hsa-miR-1201 | AGCCUGAUUAAACACAUGCUCUGA | 141 | TAATCAGGC | 1078 | AATCAGGC | 2015 | ATCAGGC | 2952 |
| hsa-miR-1202 | GUGCCAGCUGCAGUGGGGAG | 142 | CAGCTGGCA | 1079 | AGCTGGCA | 2016 | GCTGGCA | 2953 |
| hsa-miR-1203 | CCCGGAGCCAGGAUGCAGCUC | 143 | TGGCTCCGG | 1080 | GGCTCCGG | 2017 | GCTCCGG | 2954 |
| hsa-miR-1204 | UCGUGGCCUGGUCUCCAUUAU | 144 | CAGGCCACG | 1081 | AGGCCACG | 2018 | GGCCACG | 2955 |
| hsa-miR-1205 | UCUGCAGGGUUUGCUUUGAG | 145 | ACCCTGCAG | 1082 | CCCTGCAG | 2019 | CCTGCAG | 2956 |
| hsa-miR-1206 | UGUUCAUGUAGAUGUUUAAGC | 146 | TACATGAAC | 1083 | ACATGAAC | 2020 | CATGAAC | 2957 |
| hsa-miR-1207-3p | UCAGCUGGCCCUCAUUUC | 147 | GGCCAGCTG | 1084 | GCCAGCTG | 2021 | CCAGCTG | 2958 |
| hsa-miR-1207-5p | UGGCAGGGAGGCUGGGAGGGG | 148 | CTCCCTGCC | 1085 | TCCCTGCC | 2022 | CCCTGCC | 2959 |
| hsa-miR-1208 | UCACUGUUCAGACAGGCGGA | 149 | TGAACAGTG | 1086 | GAACAGTG | 2023 | AACAGTG | 2960 |
| hsa-miR-122 | UGGAGUGUGACAAUGGUGUUUG | 150 | TCACACTCC | 1087 | CACACTCC | 2024 | ACACTCC | 2961 |
| hsa-miR-122* | AACGCCAUUAUCACACUAAAUA | 151 | TAATGGCGT | 1088 | AATGGCGT | 2025 | ATGGCGT | 2962 |
| hsa-miR-1224-3p | CCCCACCUCCUCUCUCCUCAG | 152 | GGAGGTGGG | 1089 | GAGGTGGG | 2026 | AGGTGGG | 2963 |
| hsa-miR-1224-5p | GUGAGGACUCGGGAGGUGG | 153 | GAGTCCTCA | 1090 | AGTCCTCA | 2027 | GTCCTCA | 2964 |
| hsa-miR-1225-3p | UGAGCCCCUGUGCCGCCCCAG | 154 | CAGGGGCTC | 1091 | AGGGGCTC | 2028 | GGGGCTC | 2965 |
| hsa-miR-1225-5p | GUGGGUACGGCCCAGUGGGGGG | 155 | CCGTACCCA | 1092 | CGTACCCA | 2029 | GTACCCA | 2966 |
| hsa-miR-1226 | UCACCAGCCCUGUGUUCCCUAG | 156 | GGGCTGGTG | 1093 | GGCTGGTG | 2030 | GCTGGTG | 2967 |
| hsa-miR-1226* | GUGAGGGCAUGCAGGCCUGGAUGGGG | 157 | ATGCCCTCA | 1094 | TGCCCTCA | 2031 | GCCCTCA | 2968 |
| hsa-miR-1227 | CGUGCCACCCUUUUCCCCAG | 158 | GGGTGGCAC | 1095 | GGTGGCAC | 2032 | GTGGCAC | 2969 |
| hsa-miR-1228 | UCACACCUGCCUCGCCCCCC | 159 | GCAGGTGTG | 1096 | CAGGTGTG | 2033 | AGGTGTG | 2970 |
| hsa-miR-1228* | GUGGGCGGGGCAGGUGUGUG | 160 | CCCCGCCCA | 1097 | CCCGCCCA | 2034 | CCGCCCA | 2971 |
| hsa-miR-1229 | CUCUCACCACUGCCCUCCCACAG | 161 | GTGGTGAGA | 1098 | TGGTGAGA | 2035 | GGTGAGA | 2972 |
| hsa-miR-1231 | GUGUCUGGGCGGACAGCUGC | 162 | GCCCAGACA | 1099 | CCCAGACA | 2036 | CCAGACA | 2973 |
| hsa-miR-1233 | UGAGCCCUGUCCUCCCGCAG | 163 | ACAGGGCTC | 1100 | CAGGGCTC | 2037 | AGGGCTC | 2974 |
| hsa-miR-1234 | UCGGCCUGACCACCCACCCCAC | 164 | GTCAGGCCG | 1101 | TCAGGCCG | 2038 | CAGGCCG | 2975 |
| hsa-miR-1236 | CCUCUUCCCCUUGUCUCUCCAG | 165 | GGGGAAGAG | 1102 | GGGAAGAG | 2039 | GGAAGAG | 2976 |
| hsa-miR-1237 | UCCUUCUGCUCCGUCCCCAG | 166 | AGCAGAAGG | 1103 | GCAGAAGG | 2040 | CAGAAGG | 2977 |
| hsa-miR-1238 | CUUCCUCGUCUGUCUGCCCC | 167 | GACGAGGAA | 1104 | ACGAGGAA | 2041 | CGAGGAA | 2978 |
| hsa-miR-124 | UAAGGCACGCGGUGAAUGCC | 168 | GCGTGCCTT | 1105 | CGTGCCTT | 2042 | GTGCCTT | 2979 |
| hsa-miR-124* | CGUGUUCACAGCGGACCUUGAU | 169 | TGTGAACAC | 1106 | GTGAACAC | 2043 | TGAACAC | 2980 |
| hsa-miR-1243 | AACUGGAUCAAUUAUAGGAGUG | 170 | TGATCCAGT | 1107 | GATCCAGT | 2044 | ATCCAGT | 2981 |
| hsa-miR-1244 | AAGUAGUUGGUUUGUAUGAGAUGGUU | 171 | CCAACTACT | 1108 | CAACTACT | 2045 | AACTACT | 2982 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-1245 | AAGUGAUCUAAAGGCCUACAU | 172 | TAGATCACT | 1109 | AGATCACT | 2046 | GATCACT | 2983 |
| hsa-miR-1246 | AAUGGAUUUUUGGAGCAGG | 173 | AAAATCCAT | 1110 | AAATCCAT | 2047 | AATCCAT | 2984 |
| hsa-miR-1247 | ACCCGUCCCGUUCGUCCCCGGA | 174 | CGGGACGGG | 1111 | GGGACGGG | 2048 | GGACGGG | 2985 |
| hsa-miR-1248 | ACCUUCUUGUAUAAGCACUGUGCUAAA | 175 | ACAAGAAGG | 1112 | CAAGAAGG | 2049 | AAGAAGG | 2986 |
| hsa-miR-1249 | ACGCCCUUCCCCCCCUUCUUCA | 176 | GGAAGGGCG | 1113 | GAAGGGCG | 2050 | AAGGGCG | 2987 |
| hsa-miR-1250 | ACGGUGCUGGAUGUGGCCUUU | 177 | CCAGCACCG | 1114 | CAGCACCG | 2051 | AGCACCG | 2988 |
| hsa-miR-1251 | ACUCUAGCUGCCAAAGGCGCU | 178 | CAGCTAGAG | 1115 | AGCTAGAG | 2052 | GCTAGAG | 2989 |
| hsa-miR-1252 | AGAAGGAAAUUGAAUUCAUUUA | 179 | ATTTCCTTC | 1116 | TTTCCTTC | 2053 | TTCCTTC | 2990 |
| hsa-miR-1253 | AGAGAAGAAGAUCAGCCUGCA | 180 | CTTCTTCTC | 1117 | TTCTTCTC | 2054 | TCTTCTC | 2991 |
| hsa-miR-1254 | AGCCUGGAAGCUGGAGCCUGCAGU | 181 | CTTCCAGGC | 1118 | TTCCAGGC | 2055 | TCCAGGC | 2992 |
| hsa-miR-1255a | AGGAUGAGCAAAGAAAGUAGAUU | 182 | TGCTCATCT | 1119 | GCTCATCC | 2056 | CTCATCC | 2993 |
| hsa-miR-1255b | CGGAUGAGCAAAGAAAGUGGUU | 183 | TGCTCATCC | 1120 | GCTCATCC | 2057 | CTCATCC | 2994 |
| hsa-miR-1256 | AGGCAUUGACUUCUCACUAGCU | 184 | GTCAATGCC | 1121 | TCAATGCC | 2058 | CAATGCC | 2995 |
| hsa-miR-1257 | AGUGAAUGAUGGGUUCUGACC | 185 | ATCATTCAC | 1122 | TCATTCAC | 2059 | CATTCAC | 2996 |
| hsa-miR-1258 | AGUUAGGAUUAGGUCGUGGAA | 186 | AATCCTAAC | 1123 | ATCCTAAC | 2060 | TCCTAAC | 2997 |
| hsa-miR-1259 | AUAUAUGAUGACUUAGCUUUU | 187 | CATCATATA | 1124 | ATCATATA | 2061 | TCATATA | 2998 |
| hsa-miR-125a-3p | ACAGGUGAGGUUCUUGGGAGCC | 188 | CCTCACCTG | 1125 | CTCACCTG | 2062 | TCACCTG | 2999 |
| hsa-miR-125a-5p | UCCCUGAGACCCUUUAACCUGUGA | 189 | GTCTCAGGG | 1126 | TCTCAGGG | 2063 | CTCAGGG | 3000 |
| hsa-miR-125b | UCCCUGAGACCCUAACUUGUGA | 190 | GTCTCAGGG | 1127 | TCTCAGGG | 2064 | CTCAGGG | 3001 |
| hsa-miR-125b-1* | ACGGGUUAGGCUCUUGGGAGCU | 191 | CCTAACCCG | 1128 | CTAACCCG | 2065 | TAACCCG | 3002 |
| hsa-miR-125b-2* | UCACAAGUCAGGCUCUUGGGAC | 192 | TGACTTGTG | 1129 | GACTTGTG | 2066 | ACTTGTG | 3003 |
| hsa-miR-126 | UCGUACCGUGAGUAAUAAUGCG | 193 | CACGGTACG | 1130 | ACGGTACG | 2067 | CGGTACG | 3004 |
| hsa-miR-126* | CAUUAUUACUUUUGGUACGCG | 194 | AGTAATAAT | 1131 | GTAATAAT | 2068 | TAATAAT | 3005 |
| hsa-miR-1260 | AUCCCACCUCUGCCACCA | 195 | GAGGTGGGA | 1132 | AGGTGGGA | 2069 | GGTGGGA | 3006 |
| hsa-miR-1261 | AUGGAUAAGGCUUUGGCUU | 196 | CCTTATCCA | 1133 | CTTATCCA | 2070 | TTATCCA | 3007 |
| hsa-miR-1262 | AUGGGUGAAUUUGUAGAAGGAU | 197 | ATTCACCCA | 1134 | TTCACCCA | 2071 | TCACCCA | 3008 |
| hsa-miR-1263 | AUGGUACCCUGGCAUACUGAGU | 198 | AGGGTACCA | 1135 | GGGTACCA | 2072 | GGTACCA | 3009 |
| hsa-miR-1264 | CAAGUCUAUUUGAGCACCUGUU | 199 | ATAAGACTT | 1136 | TAAGACTT | 2073 | AAGACTT | 3010 |
| hsa-miR-1265 | CAGGAUGUGGUCAAGUGUUGUU | 200 | CCACATCCT | 1137 | CACATCCT | 2074 | ACATCCT | 3011 |
| hsa-miR-1266 | CCUCAGGGCUGUAGAACAGGGCU | 201 | AGCCCTGAG | 1138 | GCCCTGAG | 2075 | CCCTGAG | 3012 |
| hsa-miR-1267 | CCUGUUGAAGUGUAAUCCCCA | 202 | CTTCAACAG | 1139 | TTCAACAG | 2076 | TCAACAG | 3013 |
| hsa-miR-1268 | CGGGCGUGGUGGUGGGGG | 203 | ACCACGCCC | 1140 | CCACGCCC | 2077 | CACGCCC | 3014 |
| hsa-miR-1269 | CUGGACUGAGCCGUGCUACUGG | 204 | CTCAGTCCA | 1141 | TCAGTCCA | 2078 | CAGTCCA | 3015 |
| hsa-miR-127-3p | UCGGAUCCGUCUGAGCUUGGCU | 205 | ACGGATCCG | 1142 | CGGATCCG | 2079 | GGATCCG | 3016 |
| hsa-miR-127-5p | CUGAAGCUCAGAGGGCUCUGAU | 206 | TGAGCTTCA | 1143 | GAGCTTCA | 2080 | AGCTTCA | 3017 |
| hsa-miR-1270 | CUGGAGAUAUGGAAGAGCUGUGU | 207 | ATATCTCCA | 1144 | TATCTCCA | 2081 | ATCTCCA | 3018 |
| hsa-miR-1271 | CUUGGCACCUAGCAAGCACUCA | 208 | AGGTGCCAA | 1145 | GGTGCCAA | 2082 | GTGCCAA | 3019 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-1272 | GAUGAUGAUGGCAGCAAAUUCUGAAA | 209 | CATCATCAT | 1146 | ATCATCAT | 2083 | TCATCAT | 3020 |
| hsa-miR-1273 | GGGCGACAAAGCAAGACUCUUUCUU | 210 | TTTGTCGCC | 1147 | TTGTCGCC | 2084 | TGTCGCC | 3021 |
| hsa-miR-1274a | GUCCCUGUUCAGGCGCCA | 211 | GAACAGGGA | 1148 | AACAGGGA | 2085 | ACAGGGA | 3022 |
| hsa-miR-1274b | UCCCUGUUCGGGCGCCA | 212 | CGAACAGGG | 1149 | GAACAGGG | 2086 | AACAGGG | 3023 |
| hsa-miR-1275 | GUGGGGGAGAGGCUGUC | 213 | TCTCCCCCA | 1150 | CTCCCCCA | 2087 | TCCCCCA | 3024 |
| hsa-miR-1276 | UAAAGAGCCCUGUGGAGACA | 214 | GGGCTCTTT | 1151 | GGCTCTTT | 2088 | GCTCTTT | 3025 |
| hsa-miR-1277 | UACGUAGAUAUAUAUGUAUUUU | 215 | TATCTACGT | 1152 | ATCTACGT | 2089 | TCTACGT | 3026 |
| hsa-miR-1278 | UAGUACUGUGCAUAUCAUCUAU | 216 | CACAGTACT | 1153 | ACAGTACT | 2090 | CAGTACT | 3027 |
| hsa-miR-1279 | UCAUAUUGCUUCUUUCU | 217 | AGCAATATG | 1154 | GCAATATG | 2091 | CAATATG | 3028 |
| hsa-miR-128 | UCACAGUGAACCGGUCUCUUU | 218 | TTCACTGTG | 1155 | TCACTGTG | 2092 | CACTGTG | 3029 |
| hsa-miR-1280 | UCCCACCGCUGCCACCC | 219 | AGCGGTGGG | 1156 | GCGGTGGG | 2093 | CGGTGGG | 3030 |
| hsa-miR-1281 | UCGCCUCCUCCUCUCCC | 220 | GAGGAGGCG | 1157 | AGGAGGCG | 2094 | GGAGGCG | 3031 |
| hsa-miR-1282 | UCGUUUGCCUUUUCUGCUU | 221 | AGGCAAACG | 1158 | GGCAAACG | 2095 | GCAAACG | 3032 |
| hsa-miR-1283 | UCUACAAAGGAAAGCGCUUUCU | 222 | CCTTTGTAG | 1159 | CTTTGTAG | 2096 | TTTGTAG | 3033 |
| hsa-miR-1284 | UCUAUACAGACCCUGGCUUUUC | 223 | TCTGTATAG | 1160 | CTGTATAG | 2097 | TGTATAG | 3034 |
| hsa-miR-1285 | UCUGGGCAACAAAGUGAGACCU | 224 | GTTGCCCAG | 1161 | TTGCCCAG | 2098 | TGCCCAG | 3035 |
| hsa-miR-1286 | UGCAGGACCAAGAUGACCCCU | 225 | TGGTCCTGC | 1162 | GGTCCTGC | 2099 | GTCCTGC | 3036 |
| hsa-miR-1287 | UGCUGGAUCAGUGGUUCGAGUC | 226 | TGATCCAGC | 1163 | GATCCAGC | 2100 | ATCCAGC | 3037 |
| hsa-miR-1288 | UGGACUGCCCUGAUCUGGAGA | 227 | GGGCAGTCC | 1164 | GGCAGTCC | 2101 | GCAGTCC | 3038 |
| hsa-miR-1289 | UGGAGUCCAGGAAUCUGCAUUUU | 228 | CTGGACTCC | 1165 | TGGACTCC | 2102 | GGACTCC | 3039 |
| hsa-miR-129* | AAGCCCUUACCCCAAAAAGUAU | 229 | GTAAGGGCT | 1166 | TAAGGGCT | 2103 | AAGGGCT | 3040 |
| hsa-miR-129-3p | AAGCCCUUACCCCAAAAAGCAU | 230 | GTAAGGGCT | 1167 | TAAGGGCT | 2104 | AAGGGCT | 3041 |
| hsa-miR-129-5p | CUUUUUGCGGUCUGGGCUUGC | 231 | CCGCAAAAA | 1168 | CGCAAAAA | 2105 | GCAAAAA | 3042 |
| hsa-miR-1290 | UGGAUUUUUGGAUCAGGGA | 232 | CAAAAATCC | 1169 | AAAAATCC | 2106 | AAAATCC | 3043 |
| hsa-miR-1291 | UGGCCCUGACUGAAGACCAGCAGU | 233 | GTCAGGGCC | 1170 | TCAGGGCC | 2107 | CAGGGCC | 3044 |
| hsa-miR-1292 | UGGGAACGGGUUCCGGCAGACGCUG | 234 | CCCGTTCCC | 1171 | CCGTTCCC | 2108 | CGTTCCC | 3045 |
| hsa-miR-1293 | UGGGUGGUCUGGAGAUUUGUGC | 235 | AGACCACCC | 1172 | GACCACCC | 2109 | ACCACCC | 3046 |
| hsa-miR-1294 | UGUGAGGUUGGCAUUGUUGUCU | 236 | CAACCTCAC | 1173 | AACCTCAC | 2110 | ACCTCAC | 3047 |
| hsa-miR-1295 | UUAGGCCGCAGAUCUGGGUGA | 237 | TGCGGCCTA | 1174 | GCGGCCTA | 2111 | CGGCCTA | 3048 |
| hsa-miR-1296 | UUAGGGCCCUGGCUCCAUCUCC | 238 | AGGGCCCTA | 1175 | GGGCCCTA | 2112 | GGCCCTA | 3049 |
| hsa-miR-1297 | UUCAAGUAAUUCAGGUG | 239 | ATTACTTGA | 1176 | TTACTTGA | 2113 | TACTTGA | 3050 |
| hsa-miR-1298 | UUCAUUCGGCUGUCCAGAUGUA | 240 | GCCGAATGA | 1177 | CCGAATGA | 2114 | CGAATGA | 3051 |
| hsa-miR-1299 | UUCUGGAAUUCUGUGUGAGGGA | 241 | AATTCCAGA | 1178 | ATTCCAGA | 2115 | TTCCAGA | 3052 |
| hsa-miR-1300 | UUGAGAAGGAGGCUGCUG | 242 | TCCTTCTCA | 1179 | CCTTCTCA | 2116 | CTTCTCA | 3053 |
| hsa-miR-1301 | UUGCAGCUGCCUGGGAGUGACUUC | 243 | GCAGCTGCA | 1180 | CAGCTGCA | 2117 | AGCTGCA | 3054 |
| hsa-miR-1302 | UUGGGACAUACUUAUGCUAAA | 244 | TATGTCCCA | 1181 | ATGTCCCA | 2118 | TGTCCCA | 3055 |
| hsa-miR-1303 | UUUAGAGACGGGGUCUUGCUCU | 245 | CGTCTCTAA | 1182 | GTCTCTAA | 2119 | TCTCTAA | 3056 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-1304 | UUUGAGGCUACAGUGAGAUGUG | 246 | TAGCCTCAA | 1183 | AGCCTCAA | 2120 | GCCTCAA | 3057 |
| hsa-miR-1305 | UUUUCAACUCUAAUGGGAGAGA | 247 | GAGTTGAAA | 1184 | AGTTGAAA | 2121 | GTTGAAA | 3058 |
| hsa-miR-1306 | ACGUUGCCUCUGGUGGUG | 248 | GAGCCAACG | 1185 | AGCCAACG | 2122 | GCCAACG | 3059 |
| hsa-miR-1307 | ACUCGGCGUGGCGUCGGUCGUG | 249 | CACGCCGAG | 1186 | ACGCCGAG | 2123 | CGCCGAG | 3060 |
| hsa-miR-1308 | GCAUGGGUGGUUCAGUGG | 250 | CCACCCATG | 1187 | CACCCATG | 2124 | ACCCATG | 3061 |
| hsa-miR-130a | CAGUGCAAUGUUAAAGGGCAU | 251 | CATTGCACT | 1188 | ATTGCACT | 2125 | TTGCACT | 3062 |
| hsa-miR-130a* | UUCACAUUGUGCUACUGUCUGC | 252 | ACAATGTGA | 1189 | CAATGTGA | 2126 | AATGTGA | 3063 |
| hsa-miR-130b | CAGUGCAAUGAUGAAAGGGCAU | 253 | CATTGCACT | 1190 | ATTGCACT | 2127 | TTGCACT | 3064 |
| hsa-miR-130b* | ACUCUUUCCCUGUUGCACUAC | 254 | GGGAAAGAG | 1191 | GGAAAGAG | 2128 | GAAAGAG | 3065 |
| hsa-miR-132 | UAACAGUCUACAGCCAUGGUCG | 255 | TAGACTGTT | 1192 | AGACTGTT | 2129 | GACTGTT | 3066 |
| hsa-miR-132* | ACCGUGGCUUUCGAUUGUUACU | 256 | AAGCCACGG | 1193 | AGCCACGG | 2130 | GCCACGG | 3067 |
| hsa-miR-1321 | CAGGGAGGUGAAUGUGAU | 257 | CACCTCCCT | 1194 | ACCTCCCT | 2131 | CCTCCCT | 3068 |
| hsa-miR-1322 | GAUGAUGCUGCUGAUGCUG | 258 | CAGCATCAT | 1195 | AGCATCAT | 2132 | GCATCAT | 3069 |
| hsa-miR-1323 | UCAAAACUGAGGGGCAUUUUCU | 259 | TCAGTTTTG | 1196 | CAGTTTTG | 2133 | AGTTTTG | 3070 |
| hsa-miR-1324 | CCAGACAGAAUUCUAUGCACUUUC | 260 | TTCTGTCTG | 1197 | TCTGTCTG | 2134 | CTGTCTG | 3071 |
| hsa-miR-133a | UUUGGUCCCCUUCAACCAGCUG | 261 | GGGGACCAA | 1198 | GGGACCAA | 2135 | GGACCAA | 3072 |
| hsa-miR-133b | UUUGGUCCCCUUCAACCAGCUA | 262 | GGGGACCAA | 1199 | GGGACCAA | 2136 | GGACCAA | 3073 |
| hsa-miR-134 | UGUGACUGGUUGACCAGAGGGG | 263 | ACCAGTCAC | 1200 | CCAGTCAC | 2137 | CAGTCAC | 3074 |
| hsa-miR-135a | UAUGGCUUUUUAUUCCUAUGUGA | 264 | AAAAGCCAT | 1201 | AAAGCCAT | 2138 | AAGCCAT | 3075 |
| hsa-miR-135a* | UAUAGGGAUUGGAGCCGUGGCG | 265 | AATCCCTAT | 1202 | ATCCCTAT | 2139 | TCCCTAT | 3076 |
| hsa-miR-135b | UAUGGCUUUUCAUUCCUAUGUGA | 266 | AAAAGCCAT | 1203 | AAAGCCAT | 2140 | AAGCCAT | 3077 |
| hsa-miR-135b* | AUGUAGGGCUAAAAGCCAUGGG | 267 | AGCCCTACA | 1204 | GCCCTACA | 2141 | CCCTACA | 3078 |
| hsa-miR-136 | ACUCCAUUUGUUUUGAUGAUGGA | 268 | CAAATGGAG | 1205 | AAATGGAG | 2142 | AATGGAG | 3079 |
| hsa-miR-136* | CAUCAUCGUCUCAAAUGAGUCU | 269 | GACGATGAT | 1206 | ACGATGAT | 2143 | CGATGAT | 3080 |
| hsa-miR-137 | UUAUUGCUUAAGAAUACGCGUAG | 270 | TAAGCAATA | 1207 | AAGCAATA | 2144 | AGCAATA | 3081 |
| hsa-miR-138 | AGCUGGUGUUGUGAAUCAGGCCG | 271 | AACACCAGC | 1208 | ACACCAGC | 2145 | CACCAGC | 3082 |
| hsa-miR-138-1* | GCUACUUCACAACACCAGGGCC | 272 | GTGAAGTAG | 1209 | TGAAGTAG | 2146 | GAAGTAG | 3083 |
| hsa-miR-138-2* | GCUAUUUCACGACACCAGGGUU | 273 | GTGAAATAG | 1210 | TGAAATAG | 2147 | GAAATAG | 3084 |
| hsa-miR-139-3p | GGAGACGCGGCCCUGUUGGAGU | 274 | CCGCGTCTC | 1211 | CGCGTCTC | 2148 | GCGTCTC | 3085 |
| hsa-miR-139-5p | UCUACAGUGCACGUGUCUCCAG | 275 | GCACTGTAG | 1212 | CACTGTAG | 2149 | ACTGTAG | 3086 |
| hsa-miR-140-3p | UACCACAGGGUAGAACCACGG | 276 | CCCTGTGGT | 1213 | CCTGTGGT | 2150 | CTGTGGT | 3087 |
| hsa-miR-140-5p | CAGUGGUUUUACCCUAUGGUAG | 277 | AAAACCACT | 1214 | AAACCACT | 2151 | AACCACT | 3088 |
| hsa-miR-141 | UAACACUGUCUGGUAAAGAUGG | 278 | GACAGTGTT | 1215 | ACAGTGTT | 2152 | CAGTGTT | 3089 |
| hsa-miR-141* | CAUCUUCCAGUACAGUGUUGGA | 279 | CTGGAAGAT | 1216 | TGGAAGAT | 2153 | GGAAGAT | 3090 |
| hsa-miR-142-3p | UGUAGUGUUUCCUACUUUAUGGA | 280 | AAACACTAC | 1217 | AACACTAC | 2154 | ACACTAC | 3091 |
| hsa-miR-142-5p | CAUAAAGUAGAAAGCACUACU | 281 | CTACTTTAT | 1218 | TACTTTAT | 2155 | ACTTTAT | 3092 |
| hsa-miR-143 | UGAGAUGAAGCACUGUAGCUC | 282 | CTTCATCTC | 1219 | TTCATCTC | 2156 | TCATCTC | 3093 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-143* | GGUGCAGUGCUGCAUCUCUGGU | 283 | GCACTGCAC | 1220 | CACTGCAC | 2157 | ACTGCAC | 3094 |
| hsa-miR-144 | UACAGUAUAGAUGAUGUACU | 284 | CTATACTGT | 1221 | TATACTGT | 2158 | ATACTGT | 3095 |
| hsa-miR-144* | GGAUAUCAUCAUAUACUGUAAG | 285 | GATGATATC | 1222 | ATGATATC | 2159 | TGATATC | 3096 |
| hsa-miR-145 | GUCCAGUUUUCCCAGGAAUCCCU | 286 | AAAACTGGA | 1223 | AAACTGGA | 2160 | AACTGGA | 3097 |
| hsa-miR-145* | GGAUUCCUGGAAAUACUGUUCU | 287 | CCAGGAATC | 1224 | CAGGAATC | 2161 | AGGAATC | 3098 |
| hsa-miR-1468 | CUCCGUUUGCCUGUUUCGCUG | 288 | GCAAACGGA | 1225 | CAAACGGA | 2162 | AAACGGA | 3099 |
| hsa-miR-1469 | CUCGGCGCGGGGCGCGGGCUCC | 289 | CCGCGCCGA | 1226 | CGCGCCGA | 2163 | GCGCCGA | 3100 |
| hsa-miR-146a | UGAGAACUGAAUUCCAUGGGUU | 290 | TCAGTTCTC | 1227 | CAGTTCTC | 2164 | AGTTCTC | 3101 |
| hsa-miR-146a* | CCUCUGAAAUUCAGUUCUUCAG | 291 | ATTTCAGAG | 1228 | TTTCAGAG | 2165 | TTCAGAG | 3102 |
| hsa-miR-146b-3p | UGCCCUGUGGACUCAGUUCUGG | 292 | CCACAGGGC | 1229 | CACAGGGC | 2166 | ACAGGGC | 3103 |
| hsa-miR-146b-5p | UGAGAACUGAAUUCCAUAGGCU | 293 | TCAGTTCTC | 1230 | CAGTTCTC | 2167 | AGTTCTC | 3104 |
| hsa-miR-147 | GUGUGUGGAAAUGCUUCUGC | 294 | TTCCACACA | 1231 | TCCACACA | 2168 | CCACACA | 3105 |
| hsa-miR-1470 | GCCCUCCGCCCGUGCACCCCG | 295 | GGCGGAGGG | 1232 | GCGGAGGG | 2169 | CGGAGGG | 3106 |
| hsa-miR-1471 | GCCCGCGUGUGGAGCCAGGUGU | 296 | ACACGCGGG | 1233 | CACGCGGG | 2170 | ACGCGGG | 3107 |
| hsa-miR-147b | GUGUGCGGAAAUGCUUCUGCUA | 297 | TTCCGCACA | 1234 | TCCGCACA | 2171 | CCGCACA | 3108 |
| hsa-miR-148a | UCAGUGCACUACAGAACUUUGU | 298 | AGTGCACTG | 1235 | GTGCACTG | 2172 | TGCACTG | 3109 |
| hsa-miR-148a* | AAAGUUCUGAGACACUCCGACU | 299 | TCAGAACTT | 1236 | CAGAACTT | 2173 | AGAACTT | 3110 |
| hsa-miR-148b | UCAGUGCAUCACAGAACUUUGU | 300 | GATGCACTG | 1237 | ATGCACTG | 2174 | TGCACTG | 3111 |
| hsa-miR-148b* | AAGUUCUGUUAUACACUCAGGC | 301 | AACAGAACT | 1238 | ACAGAACT | 2175 | CAGAACT | 3112 |
| hsa-miR-149 | UCUGGCUCCGUGUCUUCACUCCC | 302 | CGGAGCCAG | 1239 | GGAGCCAG | 2176 | GAGCCAG | 3113 |
| hsa-miR-149* | AGGGAGGGACGGGGGCUGUGC | 303 | GTCCCTCCC | 1240 | TCCCTCCC | 2177 | CCCTCCC | 3114 |
| hsa-miR-150 | UCUCCCAACCCUUGUACCAGUG | 304 | GGTTGGGAG | 1241 | GTTGGGAG | 2178 | TTGGGAG | 3115 |
| hsa-miR-150* | CUGGUACAGGCCUGGGGGACAG | 305 | CCTGTACCA | 1242 | CTGTACCA | 2179 | TGTACCA | 3116 |
| hsa-miR-151-3p | CUAGACUGAAGCUCCUUGAGG | 306 | TTCAGTCTA | 1243 | TCAGTCTA | 2180 | CAGTCTA | 3117 |
| hsa-miR-151-5p | UCGAGGAGCUCACAGUCUAGU | 307 | AGCTCCTCG | 1244 | GCTCCTCG | 2181 | CTCCTCG | 3118 |
| hsa-miR-152 | UCAGUGCAUGACAGAACUUGG | 308 | CATGCACTG | 1245 | ATGCACTG | 2182 | TGCACTG | 3119 |
| hsa-miR-153 | UUGCAUAGUCACAAAAGUGAUC | 309 | GACTATGCA | 1246 | ACTATGCA | 2183 | CTATGCA | 3120 |
| hsa-miR-1537 | AAAACCGUCUAGUUACAGUUGU | 310 | AGACGGTTT | 1247 | GACGGTTT | 2184 | ACGGTTT | 3121 |
| hsa-miR-1538 | CGGCCCGGGCUGCUGCUGUUCCU | 311 | GCCCGGGCC | 1248 | CCCGGGCC | 2185 | CCGGGCC | 3122 |
| hsa-miR-1539 | UCCUGCGCGUCCCAGAUGCCC | 312 | ACGCGCAGG | 1249 | CGCGCAGG | 2186 | GCGCAGG | 3123 |
| hsa-miR-154 | UAGGUUAUCCGUGUUGCCUUCG | 313 | GGATAACCT | 1250 | GATAACCT | 2187 | ATAACCT | 3124 |
| hsa-miR-154* | AAUCAUACACGGUUGACCUAUU | 314 | GTGTATGAT | 1251 | TGTATGAT | 2188 | GTATGAT | 3125 |
| hsa-miR-155 | UUAAUGCUAAUCGUGAUAGGGGU | 315 | TTAGCATTA | 1252 | TAGCATTA | 2189 | AGCATTA | 3126 |
| hsa-miR-155* | CUCCUACAUAUUAGCAUUAACA | 316 | TATGTAGGA | 1253 | ATGTAGGA | 2190 | TGTAGGA | 3127 |
| hsa-miR-15a | UAGCAGCACAUAAUGGUUUGUG | 317 | TGTGCTGCT | 1254 | GTGCTGCT | 2191 | TGCTGCT | 3128 |
| hsa-miR-15a* | CAGGCCAUAUUGUGCUGCCUCA | 318 | ATATGGCCT | 1255 | TATGGCCT | 2192 | ATGGCCT | 3129 |
| hsa-miR-15b | UAGCAGCACAUCAUGGUUUACA | 319 | TGTGCTGCT | 1256 | GTGCTGCT | 2193 | TGCTGCT | 3130 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-15b* | CGAAUCAUUAUUUGCUGCUCUA | 320 | TAATGATTC | 1257 | AATGATTC | 2194 | ATGATTC | 3131 |
| hsa-miR-16 | UAGCAGCACGUAAAUAUUGGCG | 321 | CGTGCTGCT | 1258 | GTGCTGCT | 2195 | TGCTGCT | 3132 |
| hsa-miR-16-1* | CCAGUAUUAACUGUGCUGCUGA | 322 | TTAATACTG | 1259 | TAATACTG | 2196 | AATACTG | 3133 |
| hsa-miR-16-2* | CCAAUAUUACUGUGCUGCUUUA | 323 | GTAATATTC | 1260 | TAATATTG | 2197 | AATATTG | 3134 |
| hsa-miR-17 | CAAAGUGCUUACAGUGCAGGUAG | 324 | AAGCACTTT | 1261 | AGCACTTT | 2198 | GCACTTT | 3135 |
| hsa-miR-17* | ACUGCAGUGAAGGCACUUGUAG | 325 | TCACTGCAG | 1262 | CACTGCAG | 2199 | ACTGCAG | 3136 |
| hsa-miR-181a | AACAUUCAACGCUGUCGGUGAGU | 326 | GTTGAATGT | 1263 | TTGAATGT | 2200 | TGAATGT | 3137 |
| hsa-miR-181a* | ACCAUCGACCGUUGAUUGUACC | 327 | GGTCGATGG | 1264 | GTCGATGG | 2201 | TCGATGG | 3138 |
| hsa-miR-181a-2* | ACCACUGACCGUUGACUGUACC | 328 | GGTCAGTGG | 1265 | GTCAGTGG | 2202 | TCAGTGG | 3139 |
| hsa-miR-181b | AACAUUCAUUGCUGUCGGUGGGU | 329 | AATGAATGT | 1266 | ATGAATGT | 2203 | TGAATGT | 3140 |
| hsa-miR-181c | AACAUUCAACCUGUCGGUGAGU | 330 | GTTGAATGT | 1267 | TTGAATGT | 2204 | TGAATGT | 3141 |
| hsa-miR-181c* | AACCAUCGACCGUUGAGUGGAC | 331 | GTCGATGGT | 1268 | TCGATGGT | 2205 | CGATGGT | 3142 |
| hsa-miR-181d | AACAUUCAUUGUUGUCGGUGGGU | 332 | AATGAATGT | 1269 | ATGAATGT | 2206 | TGAATGT | 3143 |
| hsa-miR-182 | UUUGGCAAUGGUAGAACUCACACU | 333 | CATTGCCAA | 1270 | ATTGCCAA | 2207 | TTGCCAA | 3144 |
| hsa-miR-182* | UGGUUCUAGACUUGCCAACUA | 334 | TCTAGAACC | 1271 | CTAGAACC | 2208 | TAGAACC | 3145 |
| hsa-miR-1825 | UCCAGUGCCCUCCUCUCC | 335 | GGGCACTGG | 1272 | GGCACTGG | 2209 | GCACTGG | 3146 |
| hsa-miR-1826 | AUUGAUCAUCGACACUUCGAACGCAAU | 336 | GATGATCAA | 1273 | ATGATCAA | 2210 | TGATCAA | 3147 |
| hsa-miR-1827 | UGAGGCAGUAGAUUGAAU | 337 | TACTGCCTC | 1274 | ACTGCCTC | 2211 | CTGCCTC | 3148 |
| hsa-miR-183 | UAUGGCACUGGUAGAAUUCACU | 338 | CAGTGCCAT | 1275 | AGTGCCAT | 2212 | GTGCCAT | 3149 |
| hsa-miR-183* | GUGAAUUACCGAAGGGCCAUAA | 339 | GGTAATTCA | 1276 | GTAATTCA | 2213 | TAATTCA | 3150 |
| hsa-miR-184 | UGGACGGAGAACUGAUAAGGGU | 340 | TCTCCGTCC | 1277 | CTCCGTCC | 2214 | TCCGTCC | 3191 |
| hsa-miR-185 | UGGAGAGAAAGGCAGUUCCUGA | 341 | TTTCTCTCC | 1278 | TTCTCTCC | 2215 | TCTCTCC | 3152 |
| hsa-miR-185* | AGGGGCUGGCUUUCCUCUGGUC | 342 | GCCAGCCCC | 1279 | CCAGCCCC | 2216 | CAGCCCC | 3153 |
| hsa-miR-186 | CAAAGAAUUCUCCUUUUGGGCU | 343 | GAATTCTTT | 1280 | AATTCTTT | 2217 | ATTCTTT | 3154 |
| hsa-miR-186* | GCCCAAAGGUGAAUUUUUGGG | 344 | ACCTTTGGG | 1281 | CCTTTGGG | 2218 | CTTTGGG | 3155 |
| hsa-miR-187 | UCGUGUCUUGUGUUGCAGCCGG | 345 | CAAGACACG | 1282 | AAGACACG | 2219 | AGACACG | 3156 |
| hsa-miR-187* | GGCUACAACACAGGACCCGGGC | 346 | TGTTGTAGC | 1283 | GTTGTAGC | 2220 | TTGTAGC | 3157 |
| hsa-miR-188-3p | CUCCCACAUGCAGGGUUUGCA | 347 | CATGTGGGA | 1284 | ATGTGGGA | 2221 | TGTGGGA | 3158 |
| hsa-miR-188-5p | CAUCCCUUGCAUGGUGGAGGG | 348 | GCAAGGGAT | 1285 | CAAGGGAT | 2222 | AAGGGAT | 3159 |
| hsa-miR-18a | UAAGGUGCAUCUAGUGCAGAUAG | 349 | ATGCACCTT | 1286 | TGCACCTT | 2223 | GCACCTT | 3160 |
| hsa-miR-18a* | ACUGCCCUAAGUGCUCCUUCUGG | 350 | TTAGGGCAG | 1287 | TAGGGCAG | 2224 | AGGGCAG | 3161 |
| hsa-miR-18b | UAAGGUGCAUCUAGUGCAGUUAG | 351 | ATGCACCTT | 1288 | TGCACCTT | 2225 | GCACCTT | 3162 |
| hsa-miR-18b* | UGCCCUAAAUGCCCCUUCUGGC | 352 | ATTTAGGGC | 1289 | TTTAGGGC | 2226 | TTAGGGC | 3163 |
| hsa-miR-190 | UGAUAUGUUUGAUAUAUUAGGU | 353 | AAACATATC | 1290 | AACATATC | 2227 | ACATATC | 3164 |
| hsa-miR-1908 | CGGCGGGGACGGCGAUUGGUC | 354 | GTCCCCGCC | 1291 | TCCCCGCC | 2228 | CCCCGCC | 3165 |
| hsa-miR-1909 | CGCAGGGGCCGGGUGCUCACCG | 355 | GGCCCCTGC | 1292 | GCCCCTGC | 2229 | CCCCTGC | 3166 |
| hsa-miR-1909* | UGAGUGCCGGUGCCUGCCCUG | 356 | CCGGCACTC | 1293 | CGGCACTC | 2230 | GGCACTC | 3167 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-190b | UGAUAUGUUUGAUAUUGGGUU | 357 | AAACATATC | 1294 | AACATATC | 2231 | ACATATC | 3168 |
| hsa-miR-191 | CAACGGAAUCCCAAAAGCAGCUG | 358 | GATTCCGTT | 1295 | ATTCCGTT | 2232 | TTCCGTT | 3169 |
| hsa-miR-191* | GCUGCGCUUGGAUUUCGUCCCC | 359 | CAAGCGCAG | 1296 | AAGCGCAG | 2233 | AGCGCAG | 3170 |
| hsa-miR-1910 | CCAGUCCUGUGCCUGCCGCCU | 360 | ACAGGACTG | 1297 | CAGGACTG | 2234 | AGGACTG | 3171 |
| hsa-miR-1911 | UGAGUACCGCCAUGUCUGUUGGG | 361 | GCGGTACTC | 1298 | CGGTACTC | 2235 | GGTACTC | 3172 |
| hsa-miR-1911* | CACCAGGCAUUGUGGUCUCC | 362 | ATGCCTGGT | 1299 | TGCCTGGT | 2236 | GCCTGGT | 3173 |
| hsa-miR-1912 | UACCCAGAGCAUGCAGUGUGAA | 363 | GCTCTGGGT | 1300 | CTCTGGGT | 2237 | TCTGGGT | 3174 |
| hsa-miR-1913 | UCUGCCCCUCCGCUGCUGCCA | 364 | AGGGGGCAG | 1301 | GGGGGCAG | 2238 | GGGGCAG | 3175 |
| hsa-miR-1914 | CCCUGUGCCCGGCCCACUUCUG | 365 | GGGCACAGG | 1302 | GGCACAGG | 2239 | GCACAGG | 3176 |
| hsa-miR-1914* | GGAGGGGUCCCGCACUGGGAGG | 366 | GGACCCCTC | 1303 | GACCCCTC | 2240 | ACCCCTC | 3177 |
| hsa-miR-1915 | CCCCAGGGCGACGCGGCGGG | 367 | CGCCCTGGG | 1304 | GCCCTGGG | 2241 | CCCTGGG | 3178 |
| hsa-miR-1915* | ACCUUGCCUUGCUGCCCGGGCC | 368 | AAGGCAAGG | 1305 | AGGCAAGG | 2242 | GGCAAGG | 3179 |
| hsa-miR-192 | CUGACCUAUGAAUUGACAGCC | 369 | CATAGGTCA | 1306 | ATAGGTCA | 2243 | TAGGTCA | 3180 |
| hsa-miR-192* | CUGCCAAUUCCAUAGGUCACAG | 370 | GAATTGGCA | 1307 | AATTGGCA | 2244 | ATTGGCA | 3181 |
| hsa-miR-193a-3p | AACUGGCCUACAAAGUCCCAGU | 371 | TAGGCCAGT | 1308 | AGGCCAGT | 2245 | GGCCAGT | 3182 |
| hsa-miR-193a-5p | UGGGUCUUUGCGGGCGAGAUGA | 372 | CAAAGACCC | 1309 | AAAGACCC | 2246 | AAGACCC | 3183 |
| hsa-miR-193b | AACUGGCCCUCAAAGUCCCGCU | 373 | AGGGCCAGT | 1310 | GGGCCAGT | 2247 | GGCCAGT | 3184 |
| hsa-miR-193b* | CGGGGUUUUGAGGGCGAGAUGA | 374 | CAAAACCCC | 1311 | AAAACCCC | 2248 | AAACCCC | 3185 |
| hsa-miR-194 | UGUAACAGCAACUCCAUGUGGA | 375 | TGCTGTTAC | 1312 | GCTGTTAC | 2249 | CTGTTAC | 3186 |
| hsa-miR-194* | CCAGUGGGGCUGCUGUUAUCUG | 376 | GCCCCACTG | 1313 | CCCCACTG | 2250 | CCCACTG | 3187 |
| hsa-miR-195 | UAGCAGCACAGAAAUAUUGGC | 377 | TGTGCTGCT | 1314 | GTGCTGCT | 2251 | TGCTGCT | 3188 |
| hsa-miR-195* | CCAAUAUUGGCUGUGCUGCUCC | 378 | CCAATATTG | 1315 | CAATATTG | 2252 | AATATTG | 3189 |
| hsa-miR-196a | UAGGUAGUUUCAUGUUGUUGGG | 379 | AAACTACCT | 1316 | AACTACCT | 2253 | ACTACCT | 3190 |
| hsa-miR-196a* | CGGCAACAAGAAACUGCCUGAG | 380 | CTTGTTGCC | 1317 | TTGTTGCC | 2254 | TGTTGCC | 3191 |
| hsa-miR-196b | UAGGUAGUUUCCUGUUGUUGGG | 381 | AAACTACCT | 1318 | AACTACCT | 2255 | ACTACCT | 3192 |
| hsa-miR-197 | UUCACCACCUUCUCCACCCAGC | 382 | AGGTGGTGA | 1319 | GGTGGTGA | 2256 | GTGGTGA | 3193 |
| hsa-miR-198 | GGUCCAGAGGGGAGAUAGGUUC | 383 | CCTCTGGAC | 1320 | CTCTGGAC | 2257 | TCTGGAC | 3194 |
| hsa-miR-199a-5p | CCCAGUGUUCAGACUACCUGUUC | 384 | GAACACTGG | 1321 | AACACTGG | 2258 | ACACTGG | 3195 |
| hsa-miR-199b-3p | ACAGUAGUCUGCACAUUGGUUA | 385 | AGACTACTG | 1322 | GACTACTG | 2259 | ACTACTG | 3196 |
| hsa-miR-199b-5p | CCCAGUGUUUAGACUAUCUGUUC | 386 | AAACACTGG | 1323 | AACACTGG | 2260 | ACACTGG | 3197 |
| hsa-miR-19a | UGUGCAAAUCUAUGCAAAACUGA | 387 | GATTTGCAC | 1324 | ATTTGCAC | 2261 | TTTGCAC | 3198 |
| hsa-miR-19a* | AGUUUUGCAUAGUUGCACUACA | 388 | ATGCAAAAC | 1325 | TGCAAAAC | 2262 | GCAAAAC | 3199 |
| hsa-miR-19b | UGUGCAAAUCCAUGCAAAACUGA | 389 | GATTTGCAC | 1326 | ATTTGCAC | 2263 | TTTGCAC | 3200 |
| hsa-miR-19b-1* | AGUUUUGCAGGUUUGCAUCCAGC | 390 | CTGCAAAAC | 1327 | TGCAAAAC | 2264 | GCAAAAC | 3201 |
| hsa-miR-19b-2* | AGUUUUGCAGGUUUGCAUUUCA | 391 | CTGCAAAAC | 1328 | TGCAAAAC | 2265 | GCAAAAC | 3202 |
| hsa-miR-200a | UAACACUGUCUGGUAACGAUGU | 392 | GACAGTGTT | 1329 | ACAGTGTT | 2266 | CAGTGTT | 3203 |
| hsa-miR-200a* | CAUCUUACCGGACAGUGCUGGA | 393 | CGGTAAGAT | 1330 | GGTAAGAT | 2267 | GTAAGAT | 3204 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-200b | UAAUACUGCCUGGUAAUGAUGA | 394 | GGCAGTATT | 1331 | GCAGTATT | 2268 | CAGTATT | 3205 |
| hsa-miR-200b* | CAUCUUACUGGGCAGCAUUGGA | 395 | CAGTAAGAT | 1332 | AGTAAGAT | 2269 | GTAAGAT | 3206 |
| hsa-miR-200c | UAAUACUGCCGGGUAAUGAUGGA | 396 | GGCAGTATT | 1333 | GCAGTATT | 2270 | CAGTATT | 3207 |
| hsa-miR-200c* | CGUCUUACCCAGCAGUGUUUGG | 397 | GGGTAAGAC | 1334 | GGTAAGAC | 2271 | GTAAGAC | 3208 |
| hsa-miR-202 | AGAGGUAUAGGGCAUGGGAA | 398 | CTATACCTC | 1335 | TATACCTC | 2272 | ATACCTC | 3209 |
| hsa-miR-202* | UUCCUAUGCAUAUACUUCUUUG | 399 | TGCATAGGA | 1336 | GCATAGGA | 2273 | CATAGGA | 3210 |
| hsa-miR-203 | GUGAAAUGUUUAGGACCACUAG | 400 | AACATTTCA | 1337 | ACATTTCA | 2274 | CATTTCA | 3211 |
| hsa-miR-204 | UUCCCUUUGUCAUCCUAUGCCU | 401 | ACAAAGGGA | 1338 | CAAAGGGA | 2275 | AAAGGGA | 3212 |
| hsa-miR-205 | UCCUUCAUUCCACCGGAGUCUG | 402 | GAATGAAGG | 1339 | AATGAAGG | 2276 | ATGAAGG | 3213 |
| hsa-miR-206 | UGGAAUGUAAGGAAGUGUGUGG | 403 | TTACATTCC | 1340 | TACATTCC | 2277 | ACATTCC | 3214 |
| hsa-miR-208a | AUAAGACGAGCAAAAAGCUUGU | 404 | CTCGTCTTA | 1341 | TCGTCTTA | 2278 | CGTCTTA | 3215 |
| hsa-miR-208b | AUAAGACGAACAAAAGGUUUGU | 405 | TTCGTCTTA | 1342 | TCGTCTTA | 2279 | CGTCTTA | 3216 |
| hsa-miR-20a | UAAAGUGCUUAUAGUGCAGGUAG | 406 | AAGCACTTT | 1343 | AGCACTTT | 2280 | GCACTTT | 3217 |
| hsa-miR-20a* | ACUGCAUUAUGAGCACUUAAAG | 407 | ATAATGCAG | 1344 | TAATGCAG | 2281 | AATGCAG | 3218 |
| hsa-miR-20b | CAAAGUGCUCAUAGUGCAGGUAG | 408 | GAGCACTTT | 1345 | AaCACTTT | 2282 | GCACTTT | 3219 |
| hsa-miR-20b* | ACUGUAGUAUGGGCACUUCCAG | 409 | ATACTACAG | 1346 | TACTACAG | 2283 | ACTACAG | 3220 |
| hsa-miR-21 | UAGCUUAUCAGACUGAUGUUGA | 410 | TGATAAGCT | 1347 | GATAAGCT | 2284 | ATAAGCT | 3221 |
| hsa-miR-21* | CAACACCAGUCGAUGGGCUGU | 411 | ACTGGTGTT | 1348 | CTGGTGTT | 2285 | TGGTGTT | 3222 |
| hsa-miR-210 | CUGUGCGUGUGACAGCGGCUGA | 412 | ACACGCACA | 1349 | CACGCACA | 2286 | ACGCACA | 3223 |
| hsa-miR-211 | UUCCCUUUGUCAUCCUUCGCCU | 413 | ACAAAGGGA | 1350 | CAAAGGGA | 2287 | AAAGGGA | 3224 |
| hsa-miR-212 | UAACAGUCUCCAGUCACGGCC | 414 | GAGACTGTT | 1351 | AGACTGTT | 2288 | GACTGTT | 3225 |
| hsa-miR-214 | ACAGCAGGCACAGACAGGCAGU | 415 | TGCCTGCTG | 1352 | GCCTGCTG | 2289 | CCTGCTG | 3226 |
| hsa-miR-214* | UGCCUGUCUACACUUGCUGUGC | 416 | TAGACAGGC | 1353 | AGACAGGC | 2290 | GACAGGC | 3227 |
| hsa-miR-215 | AUGACCUAUGAAUUGACAGAC | 417 | CATAGGTCA | 1354 | ATAGGTCA | 2291 | TAGGTCA | 3228 |
| hsa-miR-216a | UAAUCUCAGCUGGCAACUGUGA | 418 | GCTGAGATT | 1355 | CTGAGATT | 2292 | TGAGATT | 3229 |
| hsa-miR-216b | AAAUCUCUGCAGGCAAAUGUGA | 419 | GCAGAGATT | 1356 | CAGAGATT | 2293 | AGAGATT | 3230 |
| hsa-miR-217 | UACUGCAUCAGGAACUGAUUGGA | 420 | TGATGCAGT | 1357 | GATGCAGT | 2294 | ATGCAGT | 3231 |
| hsa-miR-218 | UUGUGCUUGAUCUAACCAUCU | 421 | TCAAGCACA | 1358 | CAAGCACA | 2295 | AAGCACA | 3232 |
| hsa-miR-218-1* | AUGGUUCCGUCAAGCACCAUGG | 422 | ACGGAACCA | 1359 | CGGAACCA | 2296 | GGAACCA | 3233 |
| hsa-miR-218-2* | CAUGGUUCUGUCAAGCACCGCG | 423 | CAGAACCAT | 1360 | AGAACCAT | 2297 | GAACCAT | 3234 |
| hsa-miR-219-1-3p | AGAGUUGAGUCUGGACGUCCCG | 424 | ACTCAACTC | 1361 | CTCAACTC | 2298 | TCAACTC | 3235 |
| hsa-miR-219-2-3p | AGAAUUGUGGCUGGACAUCUGU | 425 | CCACAATTC | 1362 | CACAATTC | 2299 | ACAATTC | 3236 |
| hsa-miR-219-5p | UGAUUGUCCAAACGCAAUUCU | 426 | TGGACAATC | 1363 | GGACAATC | 2300 | GACAATC | 3237 |
| hsa-miR-22 | AAGCUGCCAGUUGAAGAACUGU | 427 | CTGGCAGCT | 1364 | TGGCAGCT | 2301 | GGCAGCT | 3238 |
| hsa-miR-22* | AGUUCUUCAGUGGCAAGCUUUA | 428 | CTGAAGAAC | 1365 | TGAAGAAC | 2302 | GAAGAAC | 3239 |
| hsa-miR-220a | CCACACCGUAUCUGACACUUU | 429 | TACGGTGTG | 1366 | ACGGTGTG | 2303 | CGGTGTG | 3240 |
| hsa-miR-220b | CCACCACCGUGUCUGACACUU | 430 | ACGGTGCTG | 1367 | CGGTGGTG | 2304 | GGTGGTG | 3241 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-220c | ACACAGGGCUGUUGUGAAGACU | 431 | AGCCCTGTG | 1368 | GCCCTGTG | 2305 | CCCTGTG | 3242 |
| hsa-miR-221 | ACCUACAUUGUCUCCUGGGUUUC | 432 | CAATGTAGC | 1369 | AATGTAGC | 2306 | ATGTAGC | 3243 |
| hsa-miR-221* | ACCUGGCAUACAAUGUAGAUUU | 433 | TATGCCAGG | 1370 | ATGCCAGG | 2307 | TGCCAGG | 3244 |
| hsa-miR-222 | AGCUACAUCUGGCUACUGCGU | 434 | AGATGTAGC | 1371 | GATGTAGC | 2308 | ATGTAGC | 3245 |
| hsa-miR-222* | CUCAGUAGCCAGUGUAGAUCCU | 435 | GGCTACTGA | 1372 | GCTACTGA | 2309 | CTACTGA | 3246 |
| hsa-miR-223 | UGUCAGUUUGUCAAAUACCCCA | 436 | CAAACTGAC | 1373 | AAACTGAC | 2310 | AACTGAC | 3247 |
| hsa-miR-223* | CGUGUAUUUGACAAGCUGAGUU | 437 | CAAATACAC | 1374 | AAATACAC | 2311 | AATACAC | 3248 |
| hsa-miR-224 | CAAGUCACUAGUGGUUCCGUU | 438 | TAGTGACTT | 1375 | AGTGACTT | 2312 | GTGACTT | 3249 |
| hsa-miR-23a | AUCACAUUGCCAGGGAUUUCC | 439 | GCAATGTGA | 1376 | CAATGTGA | 2313 | AATGTGA | 3250 |
| hsa-miR-23a* | GGGGUUCCUCGGGAUGGGAUUU | 440 | CAGGAACCC | 1377 | AGGAACCC | 2314 | GGAACCC | 3251 |
| hsa-miR-23b | AUCACAUUGCCAGGGAUUACC | 441 | GCAATGTGA | 1378 | CAATGTGA | 2315 | AATGTGA | 3252 |
| hsa-miR-23b* | UGGGUUCCUGGCAUGCUGAUUU | 442 | CAGGAACCC | 1379 | AGGAACCC | 2316 | GGAACCC | 3253 |
| hsa-miR-24 | UGGCUCAGUUCAGCAGGAACAG | 443 | AACTGAGCC | 1380 | ACTGAGCC | 2317 | CTGAGCC | 3254 |
| hsa-miR-24-1* | UGCCUACUGAGCUGAUAUCAGU | 444 | TCAGTAGGC | 1381 | CAGTAGGC | 2318 | AGTAGGC | 3255 |
| hsa-miR-24-2* | UGCCUACUGAGCUGAAACACAG | 445 | TCAGTAGGC | 1382 | CACTAGGC | 2319 | AGTAGGC | 3256 |
| hsa-miR-25 | CAUUGCACUUGUCUCGGUCUGA | 446 | AAGTGCAAT | 1383 | AGTGCAAT | 2320 | GTGCAAT | 3257 |
| hsa-miR-25* | AGGCGGAGACUUGGGCAAUUG | 447 | GTCTCCGCC | 1384 | TCTCCGCC | 2321 | CTCCGCC | 3258 |
| hsa-miR-26a | UUCAAGUAAUCCAGGAUAGGCU | 448 | ATTACTTGA | 1385 | TTACTTGA | 2322 | TACTTGA | 3259 |
| hsa-miR-26a-1* | CCUAUUCUUGGUUACUUGCACC | 449 | CAAGAATAG | 1386 | AAGAATAG | 2323 | AGAATAG | 3260 |
| hsa-miR-26a-2* | CCUAUUCUUGAUUACUUCUUUC | 450 | CAAGAATAG | 1387 | AAGAATAG | 2324 | AGAATAG | 3261 |
| hsa-miR-26b | UUCAAGUAAUUCAGGAUAGGU | 451 | ATTACTTGA | 1388 | TTACTTGA | 2325 | TACTTGA | 3262 |
| hsa-miR-26b* | CCUGUUCUCCAUUACUUGGCUC | 452 | GGAGAACAG | 1389 | GAGAACAG | 2326 | AGAACAG | 3263 |
| hsa-miR-27a | UUCACAGUGGCUAAGUUCCGC | 453 | CCACTGTGA | 1390 | CACTGTGA | 2327 | ACTGTGA | 3264 |
| hsa-miR-27a* | AGGGCUUAGCUGCUUGUGAGCA | 454 | GCTAAGCCC | 1391 | CTAAGCCC | 2328 | TAAGCCC | 3265 |
| hsa-miR-27b | UUCACAGUGGCUAAGUUCUGC | 455 | CCACTGTGA | 1392 | CACTGTGA | 2329 | ACTGTGA | 3266 |
| hsa-miR-27b* | AGAGCUUAGCUGAUUGGUGAAC | 456 | GCTAAGCTC | 1393 | CTAAGCTC | 2330 | TAAGCTC | 3267 |
| hsa-miR-28-3p | CACUAGAUUGUGAGCUCCUGGA | 457 | CAATCTAGT | 1394 | AATCTAGT | 2331 | ATCTAGT | 3268 |
| hsa-miR-28-5p | AAGGAGCUCACAGUCUAUUGAG | 458 | TGAGCTCCT | 1395 | GAGCTCCT | 2332 | AGCTCCT | 3269 |
| hsa-miR-296-3p | GAGCGUUGGGUGGAGGCUCUCC | 459 | CCCAACCCT | 1396 | CCAACCCT | 2333 | CAACCCT | 3270 |
| hsa-miR-296-5p | AGGGCCCCCCUCAAUCCUGU | 460 | GGGGGGCCC | 1397 | GGGGGCCC | 2334 | GGGGCCC | 3271 |
| hsa-miR-297 | AUGUAUGUGUGCAUGUGCAUG | 461 | ACACATACA | 1398 | CACATACA | 2335 | ACATACA | 3272 |
| hsa-miR-298 | AGCAGAAGCAGGGAGGUUCUCCCA | 462 | TGCTTCTGC | 1399 | GCTTCTGC | 2336 | CTTCTGC | 3273 |
| hsa-miR-299-3p | UAUGUGGGAUGGUAAACCGCUU | 463 | ATCCCACAT | 1400 | TCCCACAT | 2337 | CCCACAT | 3274 |
| hsa-miR-299-5p | UGGUUUACCGUCCCACAUACAU | 464 | CGGTAAACC | 1401 | GGTAAACC | 2338 | GTAAACC | 3275 |
| hsa-miR-29a | UAGCACCAUCUGAAAUCGGUUA | 465 | GATGCTGCT | 1402 | ATGGTGCT | 2339 | TGGTGCT | 3276 |
| hsa-miR-29a* | ACUGAUUUCUUUUGGUGUUCAG | 466 | AGAAATCAG | 1403 | GAAATCAG | 2340 | AAATCAG | 3277 |
| hsa-miR-29b | UAGCACCAUUUGAAAUCAGUGUU | 467 | AATGGTGCT | 1404 | ATGGTGCT | 2341 | TGGTGCT | 3278 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-29b-1* | GCUGGUUUCAUAUGGUGGUUUAGA | 468 | TGAAACCAG | 1405 | GAAACCAG | 2342 | AAACCAG | 3279 |
| hsa-miR-29b-2* | CUGGUUUCACAUGGUGGCUUAG | 469 | GTGAAACCA | 1406 | TGAAACCA | 2343 | GAAACCA | 3280 |
| hsa-miR-29c | UAGCACCAUUUGAAAUCGGUUA | 470 | AATGGTGCT | 1407 | ATGGTGCT | 2344 | TGGTGCT | 3281 |
| hsa-miR-29c* | UGACCGAUUUCUCCUGGUGUUC | 471 | AAATCGGTC | 1408 | AATCGGTC | 2345 | ATCGGTC | 3282 |
| hsa-miR-300 | UAUACAACGGCAGACUCUCUCU | 472 | CCCTTGTAT | 1409 | CCTTGTAT | 2346 | CTTGTAT | 3283 |
| hsa-miR-301a | CAGUGCAAUAGUAUUGUCAAAGC | 473 | TATTGCACT | 1410 | ATTGCACT | 2347 | TTGCACT | 3284 |
| hsa-miR-301b | CAGUGCAAUGAUAUUGUCAAAGC | 474 | CATTGCACT | 1411 | ATTGCACT | 2348 | TTGCACT | 3285 |
| hsa-miR-302a | UAAGUGCUUCCAUGUUUUGGUGA | 475 | GAAGCACTT | 1412 | AAGCACTT | 2349 | AGCACTT | 3286 |
| hsa-miR-302a* | ACUUAAACGUGGAUGUACUUGCU | 476 | ACGTTTAAG | 1413 | CGTTTAAG | 2350 | GTTTAAG | 3287 |
| hsa-miR-302b | UAAGUGCUUCCAUGUUUUAGUAG | 477 | GAAGCACTT | 1414 | AAGCACTT | 2351 | AGCACTT | 3288 |
| hsa-miR-302b* | ACUUUAACAUGGAAGUGCUUUC | 478 | ATGTTAAAG | 1415 | TGTTAAAG | 2352 | GTTAAAG | 3289 |
| hsa-miR-302c | UAAGUGCUUCCAUGUUUCAGUGG | 479 | GAAGCACTT | 1416 | AAGCACTT | 2353 | AGCACTT | 3290 |
| hsa-miR-302c* | UUUAACAUGGGGGUACCUGCUG | 480 | CCATGTTAA | 1417 | CATGTTAA | 2354 | ATGTTAA | 3291 |
| hsa-miR-302d | UAAGUGCUUCCAUGUUUGAGUGU | 481 | GAAGCACTT | 1418 | AAGCACTT | 2355 | AGCACTT | 3292 |
| hsa-miR-302d* | ACUUUAACAUGGAGCCACUUGC | 482 | ATGTTAAAG | 1419 | TGTTAAAG | 2356 | GTTAAAG | 3293 |
| hsa-miR-302e | UAAGUGCUUCCAUGCUU | 483 | GAAGCACTT | 1420 | AAGCACTT | 2357 | AGCACTT | 3294 |
| hsa-miR-302f | UAAUUCCUUCCAUGUUU | 484 | GAAGCAATT | 1421 | AAGCAATT | 2358 | AGCAATT | 3295 |
| hsa-miR-30a | UGUAAACAUCCUCGACUGGAAG | 485 | GATGTTTAC | 1422 | ATGTTTAC | 2359 | TGTTTAC | 3296 |
| hsa-miR-30a* | CUUUCAGUCGGAUGUUUGCAGC | 486 | CGACTGAAA | 1423 | GACTGAAA | 2360 | ACTGAAA | 3297 |
| hsa-miR-30b | UGUAAACAUCCUACACUCAGCU | 487 | GATGTTTAC | 1424 | ATGTTTAC | 2361 | TGTTTAC | 3298 |
| hsa-miR-30b* | CUGGGAGGUGGAUGUUUACUUC | 488 | CACCTCCCA | 1425 | ACCTCCCA | 2362 | CCTCCCA | 3299 |
| hsa-miR-30c | UGUAAACAUCCUACACUCUCAGC | 489 | GATGTTTAC | 1426 | ATGTTTAC | 2363 | TGTTTAC | 3300 |
| hsa-miR-30c-1* | CUGGGAGAGGGUUGUUUACUCC | 490 | CCTCTCCCA | 1427 | CTCTCCCA | 2364 | TCTCCCA | 3301 |
| hsa-miR-30c-2* | CUGGGAGAAGGCUGUUUACUCU | 491 | CTTCTCCCA | 1428 | TTCTCCCA | 2365 | TCTCCCA | 3302 |
| hsa-miR-30d | UGUAAACAUCCCCGACUGGAAG | 492 | GATGTTTAC | 1429 | ATGTTTAC | 2366 | TGTTTAC | 3303 |
| hsa-miR-30d* | CUUUCAGUCAGAUGUUUGCUGC | 493 | TGACTGAAA | 1430 | GACTGAAA | 2367 | ACTGAAA | 3304 |
| hsa-miR-30e | UGUAAACAUCCUUGACUGGAAG | 494 | GATGTTTAC | 1431 | ATGTTTAC | 2368 | TGTTTAC | 3305 |
| hsa-miR-30e* | CUUUCAGUCGGAUGUUUACAGC | 495 | CGACTGAAA | 1432 | GACTGAAA | 2369 | ACTGAAA | 3306 |
| hsa-miR-31 | AGGCAAGAUGCUGGCAUAGCU | 496 | CATCTTGCC | 1433 | ATCTTGCC | 2370 | TCTTGCC | 3307 |
| hsa-miR-31* | UGCUAUGCCAACAUAUUGCCAU | 497 | TGGCATAGC | 1434 | GGCATAGC | 2371 | GCATAGC | 3308 |
| hsa-miR-32 | UAUUGCACAUUACUAAGUUGCA | 498 | ATGTGCAAT | 1435 | TGTGCAAT | 2372 | GTGCAAT | 3309 |
| hsa-miR-32* | CAAUUUAGUGUGUGUGAUAUUU | 499 | CACTAAATT | 1436 | ACTAAATT | 2373 | CTAAATT | 3310 |
| hsa-miR-320a | AAAAGCUGGGUUGAGAGGGCGA | 500 | CCCAGCTTT | 1437 | CCAGCTTT | 2374 | CAGCTTT | 3311 |
| hsa-miR-320b | AAAAGCUGGGUUGAGAGGGCAA | 501 | CCCAGCTTT | 1438 | CCAGCTTT | 2375 | CAGCTTT | 3312 |
| hsa-miR-320c | AAAAGCUGGGUUGAGAGGGU | 502 | CCCAGCTTT | 1439 | CCAGCTTT | 2376 | CAGCTTT | 3313 |
| hsa-miR-320d | AAAAGCUGGGUUGAGAGGA | 503 | CCCAGCTTT | 1440 | CCAGCTTT | 2377 | CAGCTTT | 3314 |
| hsa-miR-323-3p | CACAUUACACGGUCGACCUCU | 504 | GTGTAATGT | 1441 | TGTAATGT | 2378 | GTAATGT | 3315 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-323-5p | AGGUGGUCCGUGGCGCGUUCGC | 505 | CGGACCACC | 1442 | GGACCACC | 2379 | GACCACC | 3316 |
| hsa-miR-324-3p | ACUGCCCCAGGUGCUGCUGG | 506 | CTGGGGCAG | 1443 | TGGGGCAG | 2380 | GGGGCAG | 3317 |
| hsa-miR-324-5p | CGCAUCCCCUAGGGCAUUGGUGU | 507 | AGGGGATGC | 1444 | GGGGATGC | 2381 | GGGATGC | 3318 |
| hsa-miR-325 | CCUAGUAGGUGUCCAGUAAGUGU | 508 | ACCTACTAG | 1445 | CCTACTAG | 2382 | CTACTAG | 3319 |
| hsa-miR-326 | CCUCUGGGCCCUUCCUCCAG | 509 | GGCCCAGAG | 1446 | GCCCAGAG | 2383 | CCCAGAG | 3320 |
| hsa-miR-328 | CUGGCCCUCUCUGCCCUUCCGU | 510 | AGAGGGCCA | 1447 | GAGGGCCA | 2384 | AGGGCCA | 3321 |
| hsa-miR-329 | AACACACCUGGUUAACCUCUUU | 511 | CAGGTGTGT | 1448 | AGGTGTGT | 2385 | GGTGTGT | 3322 |
| hsa-miR-330-3p | GCAAAGCACACGGCCUGCAGAGA | 512 | TGTGCTTTG | 1449 | GTGCTTTG | 2386 | TGCTTTG | 3323 |
| hsa-miR-330-5p | UCUCUGGGCCUGUGUCUUAGGC | 513 | GGCCCAGAG | 1450 | GCCCAGAG | 2387 | CCCAGAG | 3324 |
| hsa-miR-331-3p | GCCCCUGGGCCUAUCCUAGAA | 514 | GCCCAGGGG | 1451 | CCCAGGGG | 2388 | CCAGGGG | 3325 |
| hsa-miR-331-5p | CUAGGUAUGGUCCCAGGGAUCC | 515 | CCATACCTA | 1452 | CATACCTA | 2389 | ATACCTA | 3326 |
| hsa-miR-335 | UCAAGAGCAAUAACGAAAAAUGU | 516 | TTGCTCTTG | 1453 | TGCTCTTG | 2390 | GCTCTTG | 3327 |
| hsa-miR-335* | UUUUUCAUUAUUGCUCCUGACC | 517 | TAATGAAAA | 1454 | AATGAAAA | 2391 | ATGAAAA | 3328 |
| hsa-miR-337-3p | CUCCUAUAUGAUGCCUUUCUUC | 518 | CATATAGGA | 1455 | ATATAGGA | 2392 | TATAGGA | 3329 |
| hsa-miR-337-5p | GAACGGCUUCAUACAGGAGUU | 519 | GAAGCCGTT | 1456 | AAGCCGTT | 2393 | AGCCGTT | 3330 |
| hsa-miR-338-3p | UCCAGCAUCAGUGAUUUUGUUG | 520 | TGATGCTGG | 1457 | GATGCTGG | 2394 | ATGCTGG | 3331 |
| hsa-miR-338-5p | AACAAUAUCCUGGUGCUGAGUG | 521 | GGATATTGT | 1458 | GATATTGT | 2395 | ATATTGT | 3332 |
| hsa-miR-339-3p | UGAGCGCCUCGACGACAGAGCCG | 522 | GAGGCGCTC | 1459 | AGGCGCTC | 2396 | GGCGCTC | 3333 |
| hsa-miR-339-5p | UCCCUGUCCUCCAGGAGCUCACG | 523 | AGGACAGGG | 1460 | GGACAGGG | 2397 | GACAGGG | 3334 |
| hsa-miR-33a | GUGCAUUGUAGUUGCAUUGCA | 524 | TACAATGCA | 1461 | ACAATGCA | 2398 | CAATGCA | 3335 |
| hsa-miR-33a* | CAAUGUUUCCACAGUGCAUCAC | 525 | GGAAACATT | 1462 | GAAACATT | 2399 | AAACATT | 3336 |
| hsa-miR-33b | GUGCAUUGCUGUUGCAUUGC | 526 | AGCAATGCA | 1463 | GCAATGCA | 2400 | CAATGCA | 3337 |
| hsa-miR-33b* | CAGUGCCUCGGCAGUGCAGCCC | 527 | CGAGGCACT | 1464 | GAGGCACT | 2401 | AGGCACT | 3338 |
| hsa-miR-340 | UUAUAAAGCAAUGAGACUGAUU | 528 | TGCTTTATA | 1465 | GCTTTATA | 2402 | CTTTATA | 3339 |
| hsa-miR-340* | UCCGUCUCAGUUACUUUAUAGC | 529 | CTGAGACGG | 1466 | TGAGACGG | 2403 | GAGACGG | 3340 |
| hsa-miR-342-3p | UCUCACACAGAAAUCGCACCCGU | 530 | CTGTGTGAG | 1467 | TGTGTGAG | 2404 | GTGTGAG | 3341 |
| hsa-miR-342-5p | AGGGGUGCUAUCUGUGAUUGA | 531 | TAGCACCCC | 1468 | AGCACCCC | 2405 | GCACCCC | 3342 |
| hsa-miR-345 | GCUGACUCCUAGUCCAGGGCUC | 532 | AGGAGTCAG | 1469 | GGAGTCAG | 2406 | GAGTCAG | 3343 |
| hsa-miR-346 | UGUCUGCCCGCAUGCCUGCCUCU | 533 | CGGGCAGAC | 1470 | GGGCAGAC | 2407 | GGCAGAC | 3344 |
| hsa-miR-34a | UGGCAGUGUCUUAGCUGGUUGU | 534 | GACACTGCC | 1471 | ACACTGCC | 2408 | CACTGCC | 3345 |
| hsa-miR-34a* | CAAUCAGCAAGUAUACUGCCCU | 535 | TTGCTGATT | 1472 | TGCTGATT | 2409 | GCTGATT | 3346 |
| hsa-miR-34b | CAAUCACUAACUCCACUGCCAU | 536 | TTAGTGATT | 1473 | TAGTGATT | 2410 | AGTGATT | 3347 |
| hsa-miR-34b* | UAGGCAGUGUCAUUAGCUGAUUG | 537 | ACACTGCCT | 1474 | CACTGCCT | 2411 | ACTGCCT | 3348 |
| hsa-miR-34c-3p | AAUCACUAACCACACGGCCAGG | 538 | GTTAGTGAT | 1475 | TTAGTGAT | 2412 | TAGTGAT | 3349 |
| hsa-miR-34c-5p | AGGCAGUGUAGUUAGCUGAUUGC | 539 | TACACTGCC | 1476 | ACACTGCC | 2413 | CACTGCC | 3350 |
| hsa-miR-361-3p | UCCCCCAGGUGUGAUUCUGAUUU | 540 | ACCTGGGGG | 1477 | CCTGGGGG | 2414 | CTGGGGG | 3351 |
| hsa-miR-361-5p | UUAUCAGAAUCUCCAGGGGUAC | 541 | ATTCTGATA | 1478 | TTCTGATA | 2415 | TCTGATA | 3352 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-362-3p | AACACACCUAUUCAAGGAUUCA | 542 | TAGGTGTGT | 1479 | AGGTGTGT | 2416 | GGTGTGT | 3353 |
| hsa-miR-362-5p | AAUCCUUGGAACCUAGGUGUGAGU | 543 | TCCAAGGAT | 1480 | CCAAGGAT | 2417 | CAAGGAT | 3354 |
| hsa-miR-363 | AAUUGCACGGUAUCCAUCUGUA | 544 | CCGTGCAAT | 1481 | CGTGCAAT | 2418 | GTGCAAT | 3355 |
| hsa-miR-363* | CGGGUGGAUCACGAUGCAAUUU | 545 | GATCCACCC | 1482 | ATCCACCC | 2419 | TCCACCC | 3356 |
| hsa-miR-365 | UAAUGCCCCUAAAAAUCCUUAU | 546 | AGGGGCATT | 1483 | GGGGCATT | 2420 | GGGCATT | 3357 |
| hsa-miR-367 | AAUUGCACUUUAGCAAUGGUGA | 547 | AAGTGCAAT | 1484 | AGTGCAAT | 2421 | GTGCAAT | 3358 |
| hsa-miR-367* | ACUGUUGCUAAUAUGCAACUCU | 548 | TAGCAACAG | 1485 | AGCAACAG | 2422 | GCAACAG | 3359 |
| hsa-miR-369-3p | AAUAAUACAUGGUUGAUCUUU | 549 | ATGTATTAT | 1486 | TGTATTAT | 2423 | GTATTAT | 3360 |
| hsa-miR-369-5p | AGAUCGACCGUGUUAUAUUCGC | 550 | CGGTCGATC | 1487 | GGTCGATC | 2424 | GTCGATC | 3361 |
| hsa-miR-370 | GCCUGCUGGGGUGGAACCUGGU | 551 | CCCAGCAGG | 1488 | CCAGCAGG | 2425 | CAGCAGG | 3362 |
| hsa-miR-371-3p | AAGUGCCGCCAUCUUUUGAGUGU | 552 | GGCGGCACT | 1489 | GCGGCACT | 2426 | CGGCACT | 3363 |
| hsa-miR-371-5p | ACUCAAACUGUGGGGGCACU | 553 | CAGTTTGAG | 1490 | AGTTTGAG | 2427 | GTTTGAG | 3364 |
| hsa-miR-372 | AAAGUGCUGCGACAUUUGAGCGU | 554 | GCAGCACTT | 1491 | CAGCACTT | 2428 | AGCACTT | 3365 |
| hsa-miR-373 | GAAGUGCUUCGAUUUUGGGGUGU | 555 | GAAGCACTT | 1492 | AAGCACTT | 2429 | AGCACTT | 3366 |
| hsa-miR-373* | ACUCAAAAUGGGGGCGCUUUCC | 556 | CATTTTGAG | 1493 | ATTTTGAG | 2430 | TTTTGAG | 3367 |
| hsa-miR-374a | UUAUAAUACAACCUGAUAAGUG | 557 | TGTATTATA | 1494 | GTATTATA | 2431 | TATTATA | 3368 |
| hsa-miR-374a* | CUUAUCAGAUUGUAUUGUAAUU | 558 | ATCTGATAA | 1495 | TCTGATAA | 2432 | CTGATAA | 3369 |
| hsa-miR-374b | AUAUAAUACAACCUGCUAAGUG | 559 | TGTATTATA | 1496 | GTATTATA | 2433 | TATTATA | 3370 |
| hsa-miR-374b* | CUUAGCAGGUUGUAUUAUCAUU | 560 | ACCTGCTAA | 1497 | CCTGCTAA | 2434 | CTGCTAA | 3371 |
| hsa-miR-375 | UUUGUUCGUUCGGCUCGCGUGA | 561 | AACGAACAA | 1498 | ACGAACAA | 2435 | CGAACAA | 3372 |
| hsa-miR-376a | AUCAUAGAGGAAAAUCCACGU | 562 | CCTCTATGA | 1499 | CTCTATGA | 2436 | TCTATGA | 3373 |
| hsa-miR-376a* | GUAGAUUCUCCUUCUAUGAGUA | 563 | GAGAATCTA | 1500 | AGAATCTA | 2437 | GAATCTA | 3374 |
| hsa-miR-376b | AUCAUAGAGGAAAAUCCAUGUU | 564 | CCTCTATGA | 1501 | CTCTATGA | 2438 | TCTATGA | 3375 |
| hsa-miR-376c | AACAUAGAGGAAAUUCCACGU | 565 | CCTCTATGT | 1502 | CTCTATGT | 2439 | TCTATGT | 3376 |
| hsa-miR-377 | AUCACACAAAGGCAACUUUUGU | 566 | TTTGTGTGA | 1503 | TTGTGTGA | 2440 | TGTGTGA | 3377 |
| hsa-miR-377* | AGAGGUUGCCCUUGGUGAAUUC | 567 | GGCAACCTC | 1504 | GCAACCTC | 2441 | CAACCTC | 3378 |
| hsa-miR-378 | ACUGGACUUGGAGUCAGAAGG | 568 | CAAGTCCAG | 1505 | AAGTCCAG | 2442 | AGTCCAG | 3379 |
| hsa-miR-378* | CUCCUGACUCCAGGUCCUGUGU | 569 | GAGTCAGGA | 1506 | AGTCAGGA | 2443 | GTCAGGA | 3380 |
| hsa-miR-379 | UGGUAGACUAUGGAACGUAGG | 570 | TAGTCTACC | 1507 | AGTCTACC | 2444 | GTCTACC | 3381 |
| hsa-miR-379* | UAUGUAACAUGGUCCACUAACU | 571 | ATGTTACAT | 1508 | TGTTACAT | 2445 | GTTACAT | 3382 |
| hsa-miR-380 | UAUGUAAUAUGCUCCACAUCUU | 572 | ATATTACAT | 1509 | TATTACAT | 2446 | ATTACAT | 3383 |
| hsa-miR-380* | UGGUUGACCAUAGAACAUGCGC | 573 | TGGTCAACC | 1510 | GGTCAACC | 2447 | GTCAACC | 3384 |
| hsa-miR-381 | UAUACAAGGGCAAGCUCUCUGU | 574 | CCCTTGTAT | 1511 | CCTTGTAT | 2448 | CTTGTAT | 3385 |
| hsa-miR-382 | GAAGUUGUUCGUGGUGGAUUCG | 575 | GAACAACTT | 1512 | AACAACTT | 2449 | ACAACTT | 3386 |
| hsa-miR-383 | AGAUCAGAAGGUGAUUGUGGCU | 576 | CTTCTGATC | 1513 | TTCTGATC | 2450 | TCTGATC | 3387 |
| hsa-miR-384 | AUUCCUAGAAAUUGUUCAUA | 577 | TTCTAGGAA | 1514 | TCTAGGAA | 2451 | CTAGGAA | 3388 |
| hsa-miR-409-3p | GAAUGUUGCUCGGUGAACCCCU | 578 | AGCAACATT | 1515 | GCAACATT | 2452 | CAACATT | 3389 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-409-5p | AGGUUACCCGAGCAACUUUGCAU | 579 | CGGGTAACC | 1516 | GGGTAACC | 2453 | GGTAACC | 3390 |
| hsa-miR-410 | AAUAUAACACAGAUGGCCUCU | 580 | GTGTTATAT | 1517 | TGTTATAT | 2454 | GTTATAT | 3391 |
| hsa-miR-411 | UAGUAGACCGUAUAGCGUACG | 581 | CGGTCTACT | 1518 | GGTCTACT | 2455 | GTCTACT | 3392 |
| hsa-miR-411* | UAUGUAACACGGUCCACUAACC | 582 | GTGTTACAT | 1519 | TGTTACAT | 2456 | GTTACAT | 3393 |
| hsa-miR-412 | ACUUCACCUGGUCCACUAGCCGU | 583 | CAGGTGAAG | 1520 | AGGTGAAG | 2457 | GGTGAAG | 3394 |
| hsa-miR-421 | AUCAACAGACAUUAAUUGGGCGC | 584 | GTCTGTTGA | 1521 | TCTGTTGA | 2458 | CTGTTGA | 3395 |
| hsa-miR-422a | ACUGGACUUAGGGUCAGAAGGC | 585 | TAAGTCCAG | 1522 | AAGTCCAG | 2459 | AGTCCAG | 3396 |
| hsa-miR-423-3p | AGCUCGGUCUGAGGCCCCUCAGU | 586 | AGACCGAGC | 1523 | GACCGAGC | 2460 | ACCGAGC | 3397 |
| hsa-miR-423-5p | UGAGGGGCAGAGAGCGAGACUUU | 587 | CTGCCCCTC | 1524 | TGCCCCTC | 2461 | GCCCCTC | 3398 |
| hsa-miR-424 | CAGCAGCAAUUCAUGUUUUGAA | 588 | ATTGCTGCT | 1525 | TTGCTGCT | 2462 | TGCTGCT | 3399 |
| hsa-miR-424* | CAAAACGUGAGGCGCUGCUAU | 589 | TCACGTTTT | 1526 | CACGTTTT | 2463 | ACGTTTT | 3400 |
| hsa-miR-425 | AAUGACACGAUCACUCCCGUUGA | 590 | TCGTGTCAT | 1527 | CGTGTCAT | 2464 | GTGTCAT | 3401 |
| hsa-miR-425* | AUCGGGAAUGUCGUGUCCGCCC | 591 | CATTCCCGA | 1528 | ATTCCCGA | 2465 | TTCCCGA | 3402 |
| hsa-miR-429 | UAAUACUGUCUGGUAAAACCGU | 592 | GACAGTATT | 1529 | ACAGTATT | 2466 | CAGTATT | 3403 |
| hsa-miR-431 | UGUCUUGCAGGCCGUCAUGCA | 593 | CTGCAAGAC | 1530 | TGCAAGAC | 2467 | GCAAGAC | 3404 |
| hsa-miR-431* | CAGGUCGUCUUGCAGGGCUUCU | 594 | AGACGACCT | 1531 | GACGACCT | 2468 | ACGACCT | 3405 |
| hsa-miR-432 | UCUUGGAGUAGGUCAUUGGGUGG | 595 | TACTCCAAG | 1532 | ACTCCAAG | 2469 | CTCCAAG | 3406 |
| hsa-miR-432* | CUGGAUGGCUCCUCCAUGUCU | 596 | AGCCATCCA | 1533 | GCCATCCA | 2470 | CCATCCA | 3407 |
| hsa-miR-433 | AUCAUGAUGGGCUCCUCGGUGU | 597 | CCATCATGA | 1534 | CATCATGA | 2471 | ATCATGA | 3408 |
| hsa-miR-448 | UUGCAUAUGUAGGAUGUCCCAU | 598 | ACATATGCA | 1535 | CATATGCA | 2472 | ATATGCA | 3409 |
| hsa-miR-449a | UGGCAGUGUAUUGUUAGCUGGU | 599 | TACACTGCC | 1536 | ACACTGCC | 2473 | CACTGCC | 3410 |
| hsa-miR-449b | AGGCAGUGUAUUGUUAGCUGGC | 600 | TACACTGCC | 1537 | ACACTGCC | 2474 | CACTGCC | 3411 |
| hsa-miR-450a | UUUUGCGAUGUGUUCCUAAUAU | 601 | CATCGCAAA | 1538 | ATCGCAAA | 2475 | TCGCAAA | 3412 |
| hsa-miR-450b-3p | UUGGGAUCAUUUUGCAUCCAUA | 602 | ATGATCCCA | 1539 | TGATCCCA | 2476 | GATCCCA | 3413 |
| hsa-miR-450b-5p | UUUUGCAAUAUGUUCCUGAAUA | 603 | TATTGCAAA | 1540 | ATTGCAAA | 2477 | TTGCAAA | 3414 |
| hsa-miR-451 | AAACCGUUACCAUUACUGAGUU | 604 | GTAACGGTT | 1541 | TAACGGTT | 2478 | AACGGTT | 3415 |
| hsa-miR-452 | AACUGUUUGCAGAGGAAACUGA | 605 | GCAAACAGT | 1542 | CAAACAGT | 2479 | AAACAGT | 3416 |
| hsa-miR-452* | CUCAUCUGCAAAGAAGUAAGUG | 606 | TGCAGATGA | 1543 | GCAGATGA | 2480 | CAGATGA | 3417 |
| hsa-miR-453 | AGGUUGUCCGUGGUGAGUUCGCA | 607 | CGGACAACC | 1544 | GGACAACC | 2481 | GACAACC | 3418 |
| hsa-miR-454 | UAGUGCAAUAUUGCUUAUAGGGU | 608 | TATTGCACT | 1545 | ATTGCACT | 2482 | TTGCACT | 3419 |
| hsa-miR-454* | ACCCUAUCAAUAUUGUCUCUGC | 609 | TTGATAGGG | 1546 | TGATAGGG | 2483 | GATAGGG | 3420 |
| hsa-miR-455-3p | GCAGUCCAUGGGCAUAUACAC | 610 | CATGGACTG | 1547 | ATGGACTG | 2484 | TGGACTG | 3421 |
| hsa-miR-455-5p | UAUGUGCCUUUGGACUACAUCG | 611 | AAGGCACAT | 1548 | AGGCACAT | 2485 | GGCACAT | 3422 |
| hsa-miR-483-3p | UCACUCCUCUCCUCCCGUCUU | 612 | AGAGGAGTG | 1549 | GAGGAGTG | 2486 | AGGAGTG | 3423 |
| hsa-miR-483-5p | AAGACGGGAGGAAAGAAGGGAG | 613 | CTCCCGTCT | 1550 | TCCCGTCT | 2487 | CCCGTCT | 3424 |
| hsa-miR-484 | UCAGGCUCAGUCCCCUCCCGAU | 614 | CTGAGCCTG | 1551 | TGAGCCTG | 2488 | GAGCCTG | 3425 |
| hsa-miR-485-3p | GUCAUACACGGCUCUCCUCUCU | 615 | CGTGTATGA | 1552 | GTGTATGA | 2489 | TGTATGA | 3426 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-485-5p | AGAGGCUGGCCGUGAUGAAUUC | 616 | GCCAGCCTC | 1553 | CCAGCCTC | 2490 | CAGCCTC | 3427 |
| hsa-miR-486-3p | CGGGGCAGCUCAGUACAGGAU | 617 | AGCTGCCCC | 1554 | GCTGCCCC | 2491 | CTGCCCC | 3428 |
| hsa-miR-486-5p | UCCUGUACUGAGCUGCCCCGAG | 618 | CAGTACAGG | 1555 | AGTACAGG | 2492 | GTACAGG | 3429 |
| hsa-miR-487a | AAUCAUACAGGGACAUCCAGUU | 619 | CTGTATGAT | 1556 | TGTATGAT | 2493 | GTATGAT | 3430 |
| hsa-miR-487b | AAUCGUACAGGGUCAUCCACUU | 620 | CTGTACGAT | 1557 | TGTACGAT | 2494 | GTACGAT | 3431 |
| hsa-miR-488 | UUGAAAGGCUAUUUCUUGGUC | 621 | AGCCTTTCA | 1558 | GCCTTTCA | 2495 | CCTTTCA | 3432 |
| hsa-miR-488* | CCCAGAUAAUGGCACUCUCAA | 622 | ATTATCTGG | 1559 | TTATCTGG | 2496 | TATCTGG | 3433 |
| hsa-miR-489 | GUGACAUCACAUAUACGGCAGC | 623 | GTGATGTCA | 1560 | TGATGTCA | 2497 | GATGTCA | 3434 |
| hsa-miR-490-3p | CAACCUGGAGGACUCCAUGCUG | 624 | CTCCAGGTT | 1561 | TCCAGGTT | 2498 | CCAGGTT | 3435 |
| hsa-miR-490-5p | CCAUGGAUCUCCAGGUGGGU | 625 | AGATCCATG | 1962 | GATCCATG | 2499 | ATCCATG | 3436 |
| hsa-miR-491-3p | CUUAUGCAAGAUUCCCUUCUAC | 626 | CTTGCATAA | 1563 | TTGCATAA | 2500 | TGCATAA | 3437 |
| hsa-miR-491-5p | AGUGGGGAACCCUUCCAUGAGG | 627 | GTTCCCCAC | 1564 | TTCCCCAC | 2501 | TCCCCAC | 3438 |
| hsa-miR-492 | AGGACCUGCGGGACAAGAUUCUU | 628 | CGCAGGTCC | 1565 | GCAGGTCC | 2502 | CAGGTCC | 3439 |
| hsa-miR-493 | UGAAGGUCUACUGUGUGCCAGG | 629 | TAGACCTTC | 1566 | AGACCTTC | 2503 | GACCTTC | 3440 |
| hsa-miR-493* | UUGUACAUGGUAGGCUUUCAUU | 630 | CCATGTACA | 1567 | CATGTACA | 2504 | ATGTACA | 3441 |
| hsa-miR-494 | UGAAACAUACACGGGAAACCUC | 631 | GTATGTTTC | 1568 | TATGTTTC | 2505 | ATGTTTC | 3442 |
| hsa-miR-495 | AAACAAACAUGGUGCACUUCUU | 632 | ATGTTTGTT | 1569 | TGTTTGTT | 2506 | GTTTGTT | 3443 |
| hsa-miR-496 | UGAGUAUUACAUGGCCAAUCUC | 633 | GTAATACTC | 1570 | TAATACTC | 2507 | AATACTC | 3444 |
| hsa-miR-497 | CAGCAGCACACUGUGGUUUGU | 634 | TGTGCTGCT | 1571 | GTGCTGCT | 2508 | TGCTGCT | 3445 |
| hsa-miR-497* | CAAACCACACUGUGGUGUUAGA | 635 | GTGTGGTTT | 1572 | TGTGGTTT | 2509 | GTGGTTT | 3446 |
| hsa-miR-498 | UUUCAAGCCAGGGGCGUUUUUC | 636 | TGGCTTGAA | 1573 | GGCTTGAA | 2510 | GCTTGAA | 3447 |
| hsa-miR-499-3p | AACAUCACAGCAAGUCUGUGCU | 637 | CTGTGATGT | 1574 | TGTGATGT | 2511 | GTGATGT | 3448 |
| hsa-miR-499-5p | UUAAGACUUGCAGUGAUGUUU | 638 | CAAGTCTTA | 1575 | AAGTCTTA | 2512 | AGTCTTA | 3449 |
| hsa-miR-500 | UAAUCCUUCCUACCUGGGUGAGA | 639 | GCAAGGATT | 1576 | CAAGGATT | 2513 | AAGGATT | 3450 |
| hsa-miR-500* | AUGCACCUGGGCAAGGAUUCUG | 640 | CCAGGTGCA | 1577 | CAGGTGCA | 2514 | AGGTGCA | 3451 |
| hsa-miR-501-3p | AAUGCACCCGGGCAAGGAUUCU | 641 | CGGGTGCAT | 1578 | GGGTGCAT | 2515 | GGTGCAT | 3452 |
| hsa-miR-501-5p | AAUCCUUUGUCCCUGGGUGAGA | 642 | ACAAAGGAT | 1579 | CAAAGGAT | 2516 | AAAGGAT | 3453 |
| hsa-miR-502-3p | AAUGCACCUGGGCAAGGAUUCA | 643 | CAGGTGCAT | 1580 | AGGTGCAT | 2517 | GGTGCAT | 3454 |
| hsa-miR-502-5p | AUCCUUGCUAUCUGGGUGCUA | 644 | TAGCAAGGA | 1581 | AGCAAGGA | 2518 | GCAAGGA | 3455 |
| hsa-miR-503 | UAGCAGCGGGAACAGUUCUGCAG | 645 | CCCGCTGCT | 1582 | CCGCTGCT | 2519 | CGCTGCT | 3456 |
| hsa-miR-504 | AGACCCUGGUCUGCACUCUAUC | 646 | ACCAGGGTC | 1583 | CCAGGGTC | 2520 | CAGGGTC | 3457 |
| hsa-miR-505 | CGUCAACACUUGCUGGUUUCCU | 647 | AGTGTTGAC | 1584 | GTGTTGAC | 2521 | TGTTGAC | 3458 |
| hsa-miR-505* | GGGAGCCAGGAAGUAUUGAUGU | 648 | CCTGGCTCC | 1585 | CTGGCTCC | 2522 | TGGCTCC | 3459 |
| hsa-miR-506 | UAAGGCACCCUUCUGAGUAGA | 649 | GGGTGCCTT | 1586 | GGTGCCTT | 2523 | GTGCCTT | 3460 |
| hsa-miR-507 | UUUUGCACCUUUUGGAGUGAA | 650 | AGGTGCAAA | 1587 | GGTGCAAA | 2524 | GTGCAAA | 3461 |
| hsa-miR-508-3p | UGAUUGUAGCCUUUUGGAGUAGA | 651 | GCTACAATC | 1588 | CTACAATC | 2525 | TACAATC | 3462 |
| hsa-miR-508-5p | UACUCCAGAGGGCGUCACUCAUG | 652 | CTCTGGAGT | 1589 | TCTGGAGT | 2526 | CTGGAGT | 3463 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-509-3-5p | UACUGCAGACGUGGCAAUCAUG | 653 | GTCTGCAGT | 1590 | TCTGCAGT | 2527 | CTGCAGT | 3464 |
| hsa-miR-509-3p | UGAUUGGUACGUCUGUGGGUAG | 654 | GTACCAATC | 1591 | TACCAATC | 2528 | ACCAATC | 3465 |
| hsa-miR-509-5p | UACUGCAGACAGUGGCAAUCA | 655 | GTCTGCAGT | 1592 | TCTGCAGT | 2529 | CTGCAGT | 3466 |
| hsa-miR-510 | UACUCAGGAGAGUGGCAAUCAC | 656 | CTCCTGAGT | 1593 | TCCTGAGT | 2530 | CCTGAGT | 3467 |
| hsa-miR-511 | GUGUCUUUUGCUCUGCAGUCA | 657 | CAAAAGACA | 1594 | AAAAGACA | 2531 | AAAGACA | 3468 |
| hsa-miR-512-3p | AAGUGCUGUCAUAGCUGAGGUC | 658 | GACAGCACT | 1595 | ACAGCACT | 2532 | CAGCACT | 3469 |
| hsa-miR-512-5p | CACUCAGCCUUGAGGGCACUUUC | 659 | AGGCTGAGT | 1596 | GGCTGAGT | 2533 | GCTGAGT | 3470 |
| hsa-miR-513a-3p | UAAAUUUCACCUUUCUGAGAAGG | 660 | GTGAAATTT | 1597 | TGAAATTT | 2534 | GAAATTT | 3471 |
| hsa-miR-513a-5p | UUCACAGGGAGGUGUCAU | 661 | TCCCTGTGA | 1598 | CCCTGTGA | 2535 | CCTGTGA | 3472 |
| hsa-miR-513b | UUCACAAGGAGGUGUCAUUUAU | 662 | TCCTTGTGA | 1599 | CCTTGTGA | 2536 | CTTGTGA | 3473 |
| hsa-miR-513c | UUCUCAAGGAGGUGUCGUUUAU | 663 | TCCTTGAGA | 1600 | CCTTGAGA | 2537 | CTTGAGA | 3474 |
| hsa-miR-514 | AUUGACACUUCUGUGAGUAGA | 664 | AAGTGTCAA | 1601 | AGTGTCAA | 2538 | GTGTCAA | 3475 |
| hsa-miR-515-3p | GAGUGCCUUCUUUUGGAGCGUU | 665 | GAAGGCACT | 1602 | AAGGCACT | 2539 | AGGCACT | 3476 |
| hsa-miR-515-5p | UUCUCCAAAAGAAAGCACUUUCUG | 666 | TTTTGGAGA | 1603 | TTTGGAGA | 2540 | TTGGAGA | 3477 |
| hsa-miR-516a-3p | UGCUUCCUUUCAGAGGGU | 667 | AAAGGAAGC | 1604 | AAGGAAGC | 2541 | AGGAAGC | 3478 |
| hsa-miR-516a-5p | UUCUCGAGGAAAGAAGCACUUUC | 668 | TCCTCGAGA | 1605 | CCTCGAGA | 2542 | CTCGAGA | 3479 |
| hsa-miR-516b | AUCUGGAGGUAAGAAGCACUUU | 669 | ACCTCCAGA | 1606 | CCTCCAGA | 2543 | CTCCAGA | 3480 |
| hsa-miR-517* | CCUCUAGAUGGAAGCACUGUCU | 670 | CATCTAGAG | 1607 | ATCTAGAG | 2544 | TCTAGAG | 3481 |
| hsa-miR-517a | AUCGUGCAUCCCUUUAGAGUGU | 671 | GATGCACGA | 1608 | ATGCACGA | 2545 | TGCACGA | 3482 |
| hsa-miR-517b | UCGUGCAUCCCUUUAGAGUGUU | 672 | GGATGCACG | 1609 | GATGCACG | 2546 | ATGCACG | 3483 |
| hsa-miR-517c | AUCGUGCAUCCUUUUAGAGUGU | 673 | GATGCACGA | 1610 | ATGCACGA | 2547 | TGCACGA | 3484 |
| hsa-miR-518a-3p | GAAAGCGCUUCCCUUUGCUGGA | 674 | AAGCGCTTT | 1611 | AGCGCTTT | 2548 | GCGCTTT | 3485 |
| hsa-miR-518b | CAAAGCGCUCCCCUUUAGAGGU | 675 | GAGCGCTTT | 1612 | AGCGCTTT | 2549 | GCGCTTT | 3486 |
| hsa-miR-518c | CAAAGCGCUUCUCUUUAGAGUGU | 676 | AAGCGCTTT | 1613 | AGCGCTTT | 2550 | GCGCTTT | 3487 |
| hsa-miR-518c* | UCUCUGGAGGGAAGCACUUUCUG | 677 | CCTCCAGAG | 1614 | CTCCAGAG | 2551 | TCCAGAG | 3488 |
| hsa-miR-518d-3p | CAAAGCGCUUCCCUUUGGAGC | 678 | AAGCGCTTT | 1615 | AGCGCTTT | 2552 | GCGCTTT | 3489 |
| hsa-miR-518d-5p | CUCUAGAGGGAAGCACUUUCUG | 679 | CCCTCTAGA | 1616 | CCTCTAGA | 2553 | CTCTAGA | 3490 |
| hsa-miR-518e | AAAGCGCUUCCCUUCAGAGUG | 680 | GAAGCGCTT | 1617 | AAGCGCTT | 2554 | AGCGCTT | 3491 |
| hsa-miR-518f | GAAAGCGCUUCUCUUUAGAGG | 681 | AAGCGCTTT | 1618 | AGCGCTTT | 2555 | GCGCTTT | 3492 |
| hsa-miR-518f* | CUCUAGAGGGAAGCACUUUCUC | 682 | CCCTCTAGA | 1619 | CCTCTAGA | 2556 | CTCTAGA | 3493 |
| hsa-miR-519a | AAAGUGCAUCCUUUUAGAGUGU | 683 | GATGCACTT | 1620 | ATGCACTT | 2557 | TGCACTT | 3494 |
| ha-miR-519a* | CUCUAGAGGGAAGCGCUUUCUG | 684 | CCCTCTAGA | 1621 | CCTCTAGA | 2558 | CTCTAGA | 3495 |
| hsa-miR-519b-3p | AAAGUGCAUCCUUUUAGAGGUU | 685 | GATGCACTT | 1622 | ATGCACTT | 2559 | TGCACTT | 3496 |
| hsa-miR-519c-3p | AAAGUGCAUCUUUUUAGAGGAU | 686 | GATGCACTT | 1623 | ATGCACTT | 2560 | TGCACTT | 3497 |
| hsa-miR-519d | CAAAGUGCCUCCCUUUAGAGUG | 687 | AGGCACTTT | 1624 | GGCACTTT | 2561 | GCACTTT | 3498 |
| hsa-miR-519e | AAGUGCCUCCUUUUAGAGUGUU | 688 | GGAGGCACT | 1625 | GAGGCACT | 2562 | AGGCACT | 3499 |
| hsa-miR-519e* | UUCUCCAAAAGGGAGCACUUUC | 689 | TTTTGGAGA | 1626 | TTTGGAGA | 2563 | TTGGAGA | 3500 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-520a-3p | AAAGUGCUUCCCUUUGGACUGU | 690 | GAAGCACTT | 1627 | AAGCACTT | 2564 | AGCACTT | 3501 |
| hsa-miR-520a-5p | CUCCAGAGGGAAGUACUUUCU | 691 | CCCTCTGGA | 1628 | CCTCTGGA | 2565 | CTCTGGA | 3502 |
| hsa-miR-520b | AAAGUGCUUCCUUUUAGAGGG | 692 | GAAGCACTT | 1629 | AAGCACTT | 2566 | AGCACTT | 3503 |
| hsa-miR-520c-3p | AAAGUGCUUCCUUUUAGAGGGU | 693 | GAAGCACTT | 1630 | AAGCACTT | 2567 | AGCACTT | 3504 |
| hsa-miR-520d-3p | AAAGUGCUUCUCUUUGGUGGGU | 694 | GAAGCACTT | 1631 | AAGCACTT | 2568 | AGCACTT | 3505 |
| hsa-miR-520d-5p | CUACAAAGGGAAGCCCUUUC | 695 | CCCTTTGTA | 1632 | CCTTTGTA | 2569 | CTTTGTA | 3506 |
| hsa-miR-520e | AAAGUGCUUCCUUUUUGAGGG | 696 | GAAGCACTT | 1633 | AAGCACTT | 2570 | AGCACTT | 3507 |
| hsa-miR-520f | AAGUGCUUCCUUUUAGAGGGUU | 697 | GGAAGCACT | 1634 | GAAGCACT | 2571 | AAGCACT | 3508 |
| hsa-miR-520g | ACAAAGUGCUUCCCUUUAGAGUGU | 698 | AGCACTTTG | 1635 | GCACTTTG | 2572 | CACTTTG | 3509 |
| hsa-miR-520h | ACAAAGUGCUUCCCUUUAGAGU | 699 | AGCACTTTG | 1636 | GCACTTTG | 2573 | CACTTTG | 3510 |
| hsa-miR-521 | AACGCACUUCCCUUUAGAGUGU | 700 | GAAGTGCGT | 1637 | AAGTGCGT | 2574 | AGTGCGT | 3511 |
| hsa-miR-522 | AAAAUGGUUCCCUUUAGAGUGU | 701 | GAACCATTT | 1638 | AACCATTT | 2575 | ACCATTT | 3512 |
| hsa-miR-523 | GAACGCGCUUCCCUAUAGAGGGU | 702 | AAGCGCGTT | 1639 | AGCGCGTT | 2576 | GCGCGTT | 3513 |
| hsa-miR-524-3p | GAAGGCGCUUCCCUUUGGAGU | 703 | AAGCGCCTT | 1640 | AGCGCCTT | 2577 | GCGCCTT | 3514 |
| hsa-miR-524-5p | CUACAAAGGGAAGCACUUUCUC | 704 | CCCTTTGTA | 1641 | CCTTTGTA | 2578 | CTTTGTA | 3515 |
| hsa-miR-525-3p | GAAGGCGCUUCCCUUUAGAGCG | 705 | AAGCGCCTT | 1642 | AGCGCCTT | 2579 | GCGCCTT | 3516 |
| hsa-miR-525-5p | CUCCAGAGGGAUGCACUUUCU | 706 | CCCTCTGGA | 1643 | CCTCTGGA | 2580 | CTCTGGA | 3517 |
| hsa-miR-526b | CUCUUGAGGGAAGCACUUUCUGU | 707 | CCCTCAAGA | 1644 | CCTCAAGA | 2581 | CTCAAGA | 3518 |
| hsa-miR-526b* | GAAACUCCUUCCUUUUAGAGGC | 708 | AAGCACTTT | 1645 | AGCACTTT | 2582 | GCACTTT | 3519 |
| hsa-miR-527 | CUGCAAAGGCAAGCCCUUUC | 709 | CCCTTTGCA | 1646 | CCTTTGCA | 2583 | CTTTGCA | 3520 |
| hsa-miR-532-3p | CCUCCCACACCCAAGGCUUGCA | 710 | GTGTGGGAG | 1647 | TGTGGGAG | 2584 | GTGGGAG | 3521 |
| hsa-miR-532-5p | CAUGCCUUGAGUGUAGGACCGU | 711 | TCAAGGCAT | 1648 | CAAGGCAT | 2585 | AAGGCAT | 3522 |
| hsa-miR-539 | GGAGAAAUUAUCCUUGGUGUGU | 712 | TAATTTCTC | 1649 | AATTTCTC | 2586 | ATTTCTC | 3523 |
| hsa-miR-541 | UGGUGGGCACAGAAUCUGGACU | 713 | GTGCCCACC | 1650 | TGCCCACC | 2587 | GCCCACC | 3924 |
| hsa-miR-541* | AAAGGAUUCUGCUGUCGGUCCCACU | 714 | AGAATCCTT | 1651 | GAATCCTT | 2588 | AATCCTT | 3525 |
| hsa-miR-542-3p | UGUGACAGAUUGAUAACUGAAA | 715 | ATCTGTCAC | 1652 | TCTGTCAC | 2589 | CTGTCAC | 3526 |
| hsa-miR-542-5p | UCGGGGAUCAUCAUGUCACGAGA | 716 | TGATCCCCG | 1653 | GATCCCCG | 2590 | ATCCCCG | 3527 |
| hsa-miR-543 | AAACAUUCGCGGUGCACUUCUU | 717 | GCGAATGTT | 1654 | CCAATGTT | 2591 | GAATGTT | 3528 |
| hsa-miR-544 | AUUCUGCAUUUUUAGCAAGUUC | 718 | AATGCAGAA | 1655 | ATGCAGAA | 2592 | TGCACAA | 3529 |
| hsa-miR-545 | UCAGCAAACAUUUAUUGUGUGC | 719 | TGTTTGCTG | 1656 | GTTTGCTG | 2593 | TTTGCTG | 3530 |
| hsa-miR-545* | UCAGUAAAUGUUUAUUAGAUGA | 720 | CATTTACTG | 1657 | ATTTACTG | 2594 | TTTACTG | 3531 |
| hsa-miR-548a-3p | CAAAACUGGCAAUUACUUUUGC | 721 | GCCAGTTTT | 1658 | CCAGTTTT | 2595 | CAGTTTT | 3532 |
| hsa-miR-548a-5p | AAAAGUAAUUGCGAGUUUUACC | 722 | AATTACTTT | 1659 | ATTACTTT | 2596 | TTACTTT | 3533 |
| hsa-miR-548b-3p | CAAGAACCUCAGUUGCUUUUGU | 723 | GAGGTTCTT | 1660 | AGGTTCTT | 2597 | GGTTCTT | 3534 |
| hsa-miR-548b-5p | AAAAGUAAUUGUGGUUUUGGCC | 724 | AATTACTTT | 1661 | ATTACTTT | 2598 | TTACTTT | 3535 |
| hsa-miR-548c-3p | CAAAAAUCUCAAUUACUUUUGC | 725 | GAGATTTTT | 1662 | AGATTTTT | 2599 | GATTTTT | 3536 |
| hsa-miR-548c-5p | AAAAGUAAUUGCGGUUUUUGCC | 726 | AATTACTTT | 1663 | ATTACTTT | 2600 | TTACTTT | 3537 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-548d-3p | CAAAAACCACAGUUUCUUUUGC | 727 | GTCGTTTTT | 1664 | TGGTTTTT | 2601 | GGTTTTT | 3538 |
| hsa-miR-548d-5p | AAAAGUAAUUGUGGUUUUUGCC | 728 | AATTACTTT | 1665 | ATTACTTT | 2602 | TTACTTT | 3539 |
| hsa-miR-548e | AAAAACUGAGACUACUUUUGCA | 729 | CTCAGTTTT | 1666 | TCAGTTTT | 2603 | CAGTTTT | 3540 |
| hsa-miR-548f | AAAAACUGUAAUUACUUUU | 730 | TACACTTTT | 1667 | ACAGTTTT | 2604 | CAGTTTT | 3541 |
| hsa-miR-548g | AAAACUGUAAUUACUUUUGUAC | 731 | TTACAGTTT | 1668 | TACAGTTT | 2605 | ACAGTTT | 3542 |
| hsa-miR-548h | AAAAGUAAUCGCGGUUUUUGUC | 732 | GATTACTTT | 1669 | ATTACTTT | 2606 | TTACTTT | 3543 |
| hsa-miR-548i | AAAAGUAAUUGCGCAUUUUGCC | 733 | AATTACTTT | 1670 | ATTACTTT | 2607 | TTACTTT | 3544 |
| hsa-miR-548j | AAAAGUAAUUGCGGUCUUUGGU | 734 | AATTACTTT | 1671 | ATTACTTT | 2608 | TTACTTT | 3545 |
| hsa-miR-548k | AAAAGUACUUGCGGAUUUUGCU | 735 | AAGTACTTT | 1672 | AGTACTTT | 2609 | GTACTTT | 3546 |
| hsa-miR-548l | AAAAGUAUUUGCGGGUUUUGUC | 736 | AAATACTTT | 1673 | AATACTTT | 2610 | ATACTTT | 3547 |
| hsa-miR-548m | CAAAGGUAUUGUGGUUUUUG | 737 | AATACCTTT | 1674 | ATACCTTT | 2611 | TACCTTT | 3948 |
| hsa-miR-548n | CAAAAGUAAUUGUGGAUUUUGU | 738 | ATTACTTTT | 1675 | TTACTTTT | 2612 | TACTTTT | 3549 |
| hsa-miR-548o | CCAAAACUGCAGUUACUUUUGC | 739 | GCAGTTTTG | 1676 | CAGTTTTG | 2613 | AGTTTTG | 3550 |
| hsa-miR-548p | UAGCAAAAACUGCAGUUACUUU | 740 | GTTTTTGCT | 1677 | TTTTTGCT | 2614 | TTTTCCT | 3551 |
| hsa-miR-549 | UGACAACUAUGGAUGAGCUCU | 741 | ATAGTTGTC | 1678 | TAGTTGTC | 2615 | AGTTGTC | 3552 |
| hsa-miR-550 | AGUGCCUGAGGGAGUAAGAGCCC | 742 | CTCAGGCAC | 1679 | TCAGGCAC | 2616 | CAGGCAC | 3553 |
| hsa-miR-550* | UGUCUUACUCCCUCAGGCACAU | 743 | GAGTAAGAC | 1680 | ACTAAGAC | 2617 | GTAAGAC | 3554 |
| hsa-miR-551a | GCGACCCACUCUUGGUUUCCA | 744 | AGTGGGTCG | 1681 | GTGGGTCG | 2618 | TGGGTCG | 3555 |
| hsa-miR-551b | GCGACCCAUACUUGGUUUCAG | 745 | TATGGGTCG | 1682 | ATGGGTCG | 2619 | TGGGTCG | 3556 |
| hsa-miR-551b* | GAAAUCAAGCGUGGGUGAGACC | 746 | GCTTGATTT | 1683 | CTTGATTT | 2620 | TTGATTT | 3557 |
| hsa-miR-552 | AACAGGUGACUGGUUAGACAA | 747 | GTCACCTGT | 1684 | TCACCTGT | 2621 | CACCTGT | 3558 |
| hsa-miR-553 | AAAACGGUGAGAUUUUGUUUU | 748 | TCACCGTTT | 1685 | CACCGTTT | 2622 | ACCGTTT | 3559 |
| hsa-miR-554 | GCUAGUCCUCACUCAGCCAGU | 749 | CAGGACTAG | 1686 | AGGACTAG | 2623 | GGACTAG | 3560 |
| hsa-miR-555 | AGGGUAAGCUGAACCUCUGAU | 750 | AGCTTACCC | 1687 | GCTTACCC | 2624 | CTTACCC | 3561 |
| hsa-miR-556-3p | AUAUUACCAUUAGCUCAUCUUU | 751 | ATGGTAATA | 1688 | TGGTAATA | 2625 | GGTAATA | 3562 |
| hsa-miR-556-5p | GAUGAGCUCAUUGUAAUAUGAG | 752 | TGAGCTCAT | 1689 | GAGCTCAT | 2626 | AGCTCAT | 3563 |
| hsa-miR-557 | CUUUGCACGGGUGGGCCUUGUCU | 753 | CCGTGCAAA | 1690 | CGTGCAAA | 2627 | GTGCAAA | 3564 |
| hsa-miR-558 | UGAGCUGCUGUACCAAAAU | 754 | CAGCAGCTC | 1691 | ACCAGCTC | 2628 | GCAGCTC | 3565 |
| hsa-miR-559 | UAAAGUAAAUAUGCACCAAAA | 755 | ATTTACTTT | 1692 | TTTACTTT | 2629 | TTACTTT | 3566 |
| hsa-miR-561 | CAAAGUUUAAGAUCCUUGAAGU | 756 | TTAAACTTT | 1693 | TAAACTTT | 2630 | AAACTTT | 3567 |
| hsa-miR-562 | AAAGUAGCUGUACCAUUUGC | 757 | CAGCTACTT | 1694 | AGCTACTT | 2631 | GCTACTT | 3568 |
| hsa-miR-563 | AGGUUGACAUACGUUUCCC | 758 | ATGTCAACC | 1695 | TGTCAACC | 2632 | GTCAACC | 3569 |
| hsa-miR-564 | AGGCACGGUGUCAGCAGGC | 759 | CACCGTGCC | 1696 | ACCGTGCC | 2633 | CCGTGCC | 3570 |
| hsa-miR-566 | GGGCGCCUGUGAUCCCAAC | 760 | ACAGGCGCC | 1697 | CAGGCGCC | 2634 | AGGCGCC | 3571 |
| hsa-miR-567 | AGUAUGUUCUUCCACGACAGAAC | 761 | AGAACATAC | 1698 | GAACATAC | 2635 | AACATAC | 3572 |
| hsa-miR-568 | AUGUAUAAAUGUAUACACAC | 762 | ATTTATACA | 1699 | TTTATACA | 2636 | TTATACA | 3573 |
| hsa-miR-569 | AGUUAAUGAAUCCUGGAAAGU | 763 | TTCATTAAC | 1700 | TCATTAAC | 2637 | CATTAAC | 3574 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-570 | CGAAAACAGCAAUUACCUUUGC | 764 | GCTGTTTTC | 1701 | CTGTTTTC | 2638 | TGTTTTC | 3575 |
| hsa-miR-571 | UGAGUUGGCCAUCUGAGUGAG | 765 | GGCCAACTC | 1702 | GCCAACTC | 2639 | CCAACTC | 3576 |
| hsa-miR-572 | GUCCGCUCGGCGGUGGCCCA | 766 | CCGAGCGGA | 1703 | CGAGCGGA | 2640 | GAGCGGA | 3577 |
| hsa-miR-573 | CUGAAGUGAUGUGUAACUGAUCAG | 767 | ATCACTTCA | 1704 | TCACTTCA | 2641 | CACTTCA | 3578 |
| hsa-miR-574-3p | CACGCUCAUGCACACACCCACA | 768 | CATGAGCGT | 1705 | ATGAGCGT | 2642 | TGAGCGT | 3579 |
| hsa-miR-574-5p | UGAGUGUGUGUGUGUGAGUGUGU | 769 | CACACACTC | 1706 | ACACACTC | 2643 | CACACTC | 3580 |
| hsa-miR-575 | GAGCCAGUUGGACAGGAGC | 770 | CAACTGGCT | 1707 | AACTGGCT | 2644 | ACTGGCT | 3581 |
| hsa-miR-576-3p | AAGAUGUGGAAAAAUUGGAAUC | 771 | TCCACATCT | 1708 | CCACATCT | 2645 | CACATCT | 3582 |
| hsa-miR-576-5p | AUUCUAAUUUCUCCACGUCUUU | 772 | AAATTAGAA | 1709 | AATTAGAA | 2646 | ATTAGAA | 3583 |
| hsa-miR-577 | UAGAUAAAAUAUUGGUACCUG | 773 | ATTTTATCT | 1710 | TTTTATCT | 2647 | TTTATCT | 3584 |
| hsa-miR-578 | CUUCUUGUGCUCUAGGAUUGU | 774 | GCACAAGAA | 1711 | CACAAGAA | 2648 | ACAAGAA | 3585 |
| hsa-miR-579 | UUCAUUUGGUAUAAACCGCGAUU | 775 | ACCAAATGA | 1712 | CCAAATGA | 2649 | CAAATGA | 3586 |
| hsa-miR-580 | UUGAGAAUGAUGAAUCAUUAGG | 776 | TCATTCTCA | 1713 | CATTCTCA | 2650 | ATTCTCA | 3587 |
| hsa-miR-581 | UCUUGUGUUCUCUAGAUCAGU | 777 | GAACACAAG | 1714 | AACACAAG | 2651 | ACACAAG | 3588 |
| hsa-miR-582-3p | UAACUGGUUGAACAACUGAACC | 778 | CAACCAGTT | 1715 | AACCAGTT | 2652 | ACCAGTT | 3589 |
| hsa-miR-582-5p | UUACAGUUGUUCAACCAGUUACU | 779 | ACAACTGTA | 1716 | CAACTGTA | 2653 | AACTGTA | 3590 |
| hsa-miR-583 | CAAAGAGGAAGGUCCCAUUAC | 780 | TTCCTCTTT | 1717 | TCCTCTTT | 2654 | CCTCTTT | 3591 |
| hsa-miR-584 | UUAUGGUUUGCCUGGGACUGAG | 781 | CAAACCATA | 1718 | AAACCATA | 2655 | AACCATA | 3592 |
| hsa-miR-585 | UGGGCGUAUCUGUAUGCUA | 782 | GATACGCCC | 1719 | ATACGCCC | 2656 | TACGCCC | 3593 |
| hsa-miR-586 | UAUGCAUUGUAUUUUUAGGUCC | 783 | ACAATGCAT | 1720 | CAATGCAT | 2657 | AATGCAT | 3594 |
| hsa-miR-587 | UUUCCAUAGGUGAUGAGUCAC | 784 | CCTATGGAA | 1721 | CTATGGAA | 2658 | TATGGAA | 3595 |
| hsa-miR-588 | UUGGCCACAAUGGGUUAGAAC | 785 | TTGTGGCCA | 1722 | TGTGGCCA | 2659 | GTGGCCA | 3596 |
| hsa-miR-589 | UGAGAACCACCUCUCCUCUGAG | 786 | GTGGTTCTC | 1723 | TGGTTCTC | 2660 | GGTTCTC | 3597 |
| hsa-miR-589* | UCAGAACAAAUGCCGGUUCCCAGA | 787 | TTTGTTCTG | 1724 | TTGTTCTG | 2661 | TGTTCTG | 3598 |
| hsa-miR-590-3p | UAAUUUUAUGUAUAAGCUAGU | 788 | CATAAAATT | 1725 | ATAAAATT | 2662 | TAAAATT | 3599 |
| hsa-miR-590-5p | GAGCUUAUUCAUAAAAGUGCAG | 789 | GAATAAGCT | 1726 | AATAAGCT | 2663 | ATAAGCT | 3600 |
| hsa-miR-591 | AGACCAUGGGUUCUCAUUGU | 790 | CCCATGGTC | 1727 | CCATGGTC | 2664 | CATGGTC | 3601 |
| hsa-miR-592 | UUGUGUCAAUAUGCGAUGAUGU | 791 | ATTGACACA | 1728 | TTGACACA | 2665 | TGACACA | 3602 |
| hsa-miR-593 | UGUCUCUGCUGGGGUUUCU | 792 | AGCAGAGAC | 1729 | GCAGAGAC | 2666 | CAGAGAC | 3603 |
| hsa-miR-593* | AGGCACCAGCCAGGCAUUGCUCAGC | 793 | GCTGGTGCC | 1730 | CTGGTGCC | 2667 | TGGTGCC | 3604 |
| hsa-miR-595 | GAAGUGUGCCGUGGUGUGUCU | 794 | GGCACACTT | 1731 | GCACACTT | 2668 | CACACTT | 3605 |
| hsa-miR-596 | AAGCCUGCCCGGCUCCUCGGG | 795 | GGGCAGGCT | 1732 | GGCAGGCT | 2669 | GCAGGCT | 3606 |
| hsa-miR-597 | UGUGUCACUCGAUGACCACUGU | 796 | GAGTGACAC | 1733 | AGTGACAC | 2670 | GTGACAC | 3607 |
| hsa-miR-598 | UACGUCAUCGUUGUCAUCGUCA | 797 | CGATGACGT | 1734 | GATGACGT | 2671 | ATGACGT | 3608 |
| hsa-miR-599 | GUUGUGUCAGUUUAUCAAAC | 798 | CTGACACAA | 1735 | TGACACAA | 2672 | GACACAA | 3609 |
| hsa-miR-600 | ACUUACAGACAAGAGCCUUGCUC | 799 | GTCTGTAAG | 1736 | TCTGTAAG | 2673 | CTGTAAG | 3610 |
| hsa-miR-601 | UGGUCUAGGAUUGUUGGAGGAG | 800 | TCCTAGACC | 1737 | CCTAGACC | 2674 | CTAGACC | 3611 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-602 | GACACGGGCGACAGCUGCGGCCC | 801 | CGCCCGTGT | 1738 | GCCCGTGT | 2675 | CCCGTGT | 3612 |
| hsa-miR-603 | CACACACUGCAAUUACUUUUGC | 802 | GCAGTGTGT | 1739 | CAGTGTGT | 2676 | AGTGTGT | 3613 |
| hsa-miR-604 | AGGCUGCGGAAUUCAGGAC | 803 | TCCGCAGCC | 1740 | CCGCAGCC | 2677 | CGCAGCC | 3614 |
| hsa-miR-605 | UAAAUCCCAUGGUGCCUUCUCCU | 804 | ATGGGATTT | 1741 | TGGGATTT | 2678 | GGGATTT | 3615 |
| hsa-miR-606 | AAACUACUGAAAAUCAAAGAU | 805 | TCAGTAGTT | 1742 | CAGTAGTT | 2679 | AGTAGTT | 3616 |
| hsa-miR-607 | GUUCAAAUCCAGAUCUAUAAC | 806 | GGATTTGAA | 1743 | GATTTGAA | 2680 | ATTTGAA | 3617 |
| hsa-miR-608 | AGGGGUGGUGUUGGGACAGCUCCGU | 807 | CACCACCCC | 1744 | ACCACCCC | 2681 | CCACCCC | 3618 |
| hsa-miR-609 | AGGGUGUUUCUCUCAUCUCU | 808 | GAAACACCC | 1745 | AAACACCC | 2682 | AACACCC | 3619 |
| hsa-miR-610 | UGAGCUAAAUGUGUGCUGGGA | 809 | ATTTAGCTC | 1746 | TTTAGCTC | 2683 | TTAGCTC | 3620 |
| hsa-miR-611 | GCGAGGACCCCUCCGGGUCUGAC | 810 | GGGTCCTCG | 1747 | GGTCCTCG | 2684 | GTCCTCG | 3621 |
| hsa-miR-612 | GCUGGGCAGGGCUUCUGAGCUCCUU | 811 | CCTGCCCAG | 1748 | CTGCCCAG | 2685 | TGCCCAG | 3622 |
| hsa-miR-613 | AGGAAUGUUCCUUCUUUGCC | 812 | GAACATTCC | 1749 | AACATTCC | 2686 | ACATTCC | 3623 |
| hsa-miR-614 | GAACGCCUGUUCUUGCCAGGUGG | 813 | ACAGGCGTT | 1750 | CAGGCGTT | 2687 | AGGCGTT | 3624 |
| hsa-miR-615-3p | UCCGAGCCUGGGUCUCCCUCUU | 814 | CAGGCTCGG | 1751 | AGGCTCGG | 2688 | GGCTCGG | 3625 |
| hsa-miR-615-5p | GGGGGUCCCCGGUGCUCGGAUC | 815 | GGGGACCCC | 1752 | GGGACCCC | 2689 | GGACCCC | 3626 |
| hsa-miR-616 | AGUCAUUGGAGGGUUUGAGCAG | 816 | TCCAATGAC | 1753 | CCAATGAC | 2690 | CAATGAC | 3627 |
| hsa-miR-616* | ACUCAAAACCCUUCAGUGACUU | 817 | GGTTTTGAG | 1754 | GTTTTGAG | 2691 | TTTTGAG | 3628 |
| hsa-miR-617 | AGACUUCCCAUUUGAAGGUGGC | 818 | TGGGAAGTC | 1795 | GGGAAGTC | 2692 | GGAAGTC | 3629 |
| hsa-miR-618 | AAACUCUACUUGUCCUUCUGAGU | 819 | AGTAGAGTT | 1756 | GTAGAGTT | 2693 | TAGAGTT | 3630 |
| hsa-miR-619 | GACCUGGACAUGUUUGUGCCCAGU | 820 | TGTCCAGGT | 1757 | GTCCAGGT | 2694 | TCCAGGT | 3631 |
| hsa-miR-620 | AUGGAGAUAGAUAUAGAAAU | 821 | CTATCTCCA | 1758 | TATCTCCA | 2695 | ATCTCCA | 3632 |
| hsa-miR-621 | GGCUAGCAACAGCGCUUACCU | 822 | GTTGCTAGC | 1759 | TTGCTAGC | 2696 | TGCTAGC | 3633 |
| hsa-miR-622 | ACAGUCUGCUGAGGUUGGAGC | 823 | AGCAGACTG | 1760 | GCAGACTG | 2697 | CAGACTG | 3634 |
| hsa-miR-623 | AUCCCUUGCAGGGGCUGUUGGGU | 824 | TGCAAGGGA | 1761 | GCAAGGGA | 2698 | CAAGGGA | 3635 |
| hsa-miR-624 | CACAAGGUAUUGGUAUUACCU | 825 | ATACCTTGT | 1762 | TACCTTGT | 2699 | ACCTTGT | 3636 |
| hsa-miR-624* | UAGUACCAGUACCUUGUGUUCA | 826 | ACTGGTACT | 1763 | CTGGTACT | 2700 | TGGTACT | 3637 |
| hsa-miR-625 | AGGGGGAAAGUUCUAUAGUCC | 827 | CTTTCCCCC | 1764 | TTTCCCCC | 2701 | TTCCCCC | 3638 |
| hsa-miR-625* | GACAUAGAACUUUCCCCCUCA | 828 | TTCTATAGT | 1765 | TCTATAGT | 2702 | CTATAGT | 3639 |
| hsa-miR-626 | AGCUGUCUGAAAAUGUCUU | 829 | TCAGACAGC | 1766 | CAGACAGC | 2703 | AGACAGC | 3640 |
| hsa-miR-627 | GUGAGUCUCUAAGAAAAGAGGA | 830 | AGAGACTCA | 1767 | GAGACTCA | 2704 | AGACTCA | 3641 |
| hsa-miR-628-3p | UCUAGUAAGAGUGGCAGUCGA | 831 | TCTTACTAG | 1768 | CTTACTAG | 2705 | TTACTAG | 3642 |
| hsa-miR-628-5p | AUGCUGACAUAUUUACUAGAGG | 832 | ATGTCAGCA | 1769 | TGTCAGCA | 2706 | GTCAGCA | 3643 |
| hsa-miR-629 | UGGGUUUACGUUGGGAGAACU | 833 | CGTAAACCC | 1770 | GTAAACCC | 2707 | TAAACCC | 3644 |
| hsa-miR-629* | GUUCUCCCAACGUAAGCCCAGC | 834 | TTGGGAGAA | 1771 | TGGGAGAA | 2708 | GGGAGAA | 3645 |
| hsa-miR-630 | AGUAUUCUGUACCAGGGAAGGU | 835 | ACAGAATAC | 1772 | CAGAATAC | 2709 | AGAATAC | 3646 |
| hsa-miR-631 | AGACCUGGCCCAGACCUCAGC | 836 | GGCCAGGTC | 1773 | GCCAGGTC | 2710 | CCAGGTC | 3647 |
| hsa-miR-632 | GUGUCUGCUUCCUGUGGGA | 837 | AAGCAGACA | 1774 | AGCAGACA | 2711 | GCAGACA | 3648 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-633 | CUAAUAGUAUCUACCACAAUAAA | 838 | ATACTATTA | 1775 | TACTATTA | 2712 | ACTATTA | 3649 |
| hsa-miR-634 | AACCAGCACCCCAACUUUGGAC | 839 | GGTGCTGGT | 1776 | GTGCTGGT | 2713 | TGCTGGT | 3650 |
| hsa-miR-635 | ACUUGGGCACUGAAACAAUGUCC | 840 | GTGCCCAAG | 1777 | TGCCCAAG | 2714 | GCCCAAG | 3651 |
| hsa-miR-636 | UGUGCUUGCUCGUCCCGCCCGCA | 841 | AGCAAGCAC | 1778 | GCAAGCAC | 2715 | CAAGCAC | 3652 |
| hsa-miR-637 | ACUGGGGGCUUUCGGGCUCUGCGU | 842 | AGCCCCAG | 1779 | GCCCCCAG | 2716 | CCCCCAG | 3653 |
| hsa-miR-638 | AGGGAUCGCGGGCGGGUGGCGGCCU | 843 | CGCGATCCC | 1780 | GCGATCCC | 2717 | CGATCCC | 3654 |
| hsa-miR-639 | AUCGCUGCGGUUGCGAGCGCUGU | 844 | CCGCAGCGA | 1781 | CGCAGCGA | 2718 | GCAGCGA | 3655 |
| hsa-miR-640 | AUGAUCCAGGAACCUGCCUCU | 845 | CCTGGATCA | 1782 | CTGGATCA | 2719 | TGGATCA | 3656 |
| hsa-miR-641 | AAAGACAUAGGAUAGAGUCACCUC | 846 | CTATGTCTT | 1783 | TATGTCTT | 2720 | ATGTCTT | 3657 |
| hsa-miR-642 | GUCCCUCUCCAAAUGUGUCUUG | 847 | GGAGAGGGA | 1784 | GAGAGGGA | 2721 | AGAGGGA | 3658 |
| hsa-miR-643 | ACUUGUAUGCUAGCUCAGGUAG | 848 | GCATACAAG | 1785 | CATACAAG | 2722 | ATACAAG | 3659 |
| hsa-miR-644 | AGUGUGGCUUUCUUAGAGC | 849 | AAGCCACAC | 1786 | AGCCACAC | 2723 | GCCACAC | 3660 |
| hsa-miR-645 | UCUAGGCUGGUACUGCUGA | 850 | CCAGCCTAG | 1787 | CAGCCTAG | 2724 | AGCCTAG | 3661 |
| hsa-miR-646 | AAGCAGCUGCCUCUGAGGC | 851 | GCAGCTGCT | 1788 | CAGCTGCT | 2725 | AGCTGCT | 3662 |
| hsa-miR-647 | GUGGCUGCACUCACUUCCUUC | 852 | GTGCAGCCA | 1789 | TGCAGCCA | 2726 | GCAGCCA | 3663 |
| hsa-miR-648 | AAGUGUGCAGGGCACUGGU | 853 | CTGCACACT | 1790 | TGCACACT | 2727 | GCACACT | 3664 |
| hsa-miR-649 | AAACCUGUGUUGUUCAAGAGUC | 854 | ACACAGGTT | 1791 | CACAGGTT | 2728 | ACAGGTT | 3665 |
| hsa-miR-650 | AGGAGGCAGCGCUCUCAGGAC | 855 | GCTGCCTCC | 1792 | CTGCCTCC | 2729 | TGCCTCC | 3666 |
| hsa-miR-651 | UUUAGGAUAAGCUUGACUUUUG | 856 | TTATCCTAA | 1793 | TATCCTAA | 2730 | ATCCTAA | 3667 |
| hsa-miR-652 | AAUGGCGCCACUAGGGUUGUG | 857 | TGGCGCCAT | 1794 | GGCGCCAT | 2731 | GCGCCAT | 3668 |
| hsa-miR-653 | GUGUUGAAACAAUCUCUACUG | 858 | GTTTCAACA | 1795 | TTTCAACA | 2732 | TTCAACA | 3669 |
| hsa-miR-654-3p | UAUGUCUGCUGACCAUCACCUU | 859 | AGCAGACAT | 1796 | GCAGACAT | 2733 | CAGACAT | 3670 |
| hsa-miR-654-5p | UGGUGGGCCGCAGAACAUGUGC | 860 | CGGCCCACC | 1797 | GGCCCACC | 2734 | GCCCACC | 3671 |
| hsa-miR-655 | AUAAUACAUGGUUAACCUCUUU | 861 | CATGTATTA | 1798 | ATGTATTA | 2735 | TGTATTA | 3672 |
| hsa-miR-656 | AAUAUUAUACAGUCAACCUCU | 862 | GTATAATAT | 1799 | TATAATAT | 2736 | ATAATAT | 3673 |
| hsa-miR-657 | GGCAGGUUCUCACCCUCUCUAGG | 863 | AGAACCTGC | 1800 | GAACCTGC | 2737 | AACCTGC | 3674 |
| hsa-miR-658 | GGCGGAGGGAAGUAGGUCCGUUGGU | 864 | TCCCTCCGC | 1801 | CCCTCCGC | 2738 | CCTCCGC | 3675 |
| hsa-miR-659 | CUUGGUUCAGGGAGGGUCCCCA | 865 | CTGAACCAA | 1802 | TGAACCAA | 2739 | GAACCAA | 3676 |
| hsa-miR-660 | UACCCAUUGCAUAUCGGAGUUG | 866 | GCAATGGGT | 1803 | CAATGGGT | 2740 | AATGGGT | 3677 |
| hsa-miR-661 | UGCCUGGGUCUCUGGCCUGCGCGU | 867 | GACCCAGGC | 1804 | ACCCAGGC | 2741 | CCCAGGC | 3678 |
| hsa-miR-662 | UCCCACGUUGUGGCCCAGCAG | 868 | CAACGTGGG | 1805 | AACGTGGG | 2742 | ACGTGGG | 3679 |
| hsa-miR-663 | AGGCGGGGCGCCGCGGGACCGC | 869 | CGCCCCGCC | 1806 | GCCCCGCC | 2743 | CCCCGCC | 3680 |
| hsa-miR-663b | GGUGGCCCGGCCGUGCCUGAGG | 870 | CCGGGCCAC | 1807 | CGGGCCAC | 2744 | GGGCCAC | 3681 |
| hsa-miR-664 | UAUUCAUUUAUCCCCAGCCUACA | 871 | TAAATGAAT | 1808 | AAATGAAT | 2745 | AATGAAT | 3682 |
| hsa-miR-664* | ACUGGCUAGGGAAAAUGAUUGGAU | 872 | CCTAGCCAG | 1809 | CTAGCCAG | 2746 | TAGCCAG | 3683 |
| hsa-miR-665 | ACCAGGAGGCUGAGGCCCCU | 873 | GCCTCCTGG | 1810 | CCTCCTGG | 2747 | CTCCTGG | 3684 |
| hsa-miR-668 | UGUCACUCGGCUCGGCCCACUAC | 874 | CCGAGTGAC | 1811 | CGAGTGAC | 2748 | GAGTGAC | 3685 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-671-3p | UCCGGUUCUCAGGGCUCCACC | 875 | GAGAACCGG | 1812 | AGAACCGG | 2749 | GAACCGG | 3686 |
| hsa-miR-671-5p | AGGAAGCCCUGGAGGGGCUGGAG | 876 | AGGGCTTCC | 1813 | GGGCTTCC | 2750 | GGCTTCC | 3687 |
| hsa-miR-675 | UGGUGCGGAGAGGGCCCACAGUG | 877 | CTCCGCACC | 1814 | TCCGCACC | 2751 | CCGCACC | 3688 |
| hsa-miR-675b | CUGUAUGCCCUCACCGCUCA | 878 | GGGCATACA | 1815 | GGCATACA | 2752 | GCATACA | 3689 |
| hsa-miR-7 | UGGAAGACUAGUGAUUUUGUUGU | 879 | TAGTCTTCC | 1816 | AGTCTTCC | 2753 | GTCTTCC | 3690 |
| hsa-miR-7-1* | CAACAAAUCACAGUCUGCCAUA | 880 | TGATTTGTT | 1817 | GATTTGTT | 2754 | ATTTGTT | 3691 |
| hsa-miR-7-2* | CAACAAAUCCCAGUCUACCUAA | 881 | GGATTTGTT | 1818 | GATTTGTT | 2755 | ATTTGTT | 3692 |
| hsa-miR-708 | AAGGAGCUUACAAUCUAGCUGGG | 882 | TAAGCTCCT | 1819 | AAGCTCCT | 2756 | AGCTCCT | 3693 |
| hsa-miR-708* | CAACUAGACUGUGAGCUUCUAG | 883 | AGTCTAGTT | 1820 | GTCTAGTT | 2757 | TCTAGTT | 3694 |
| hsa-miR-720 | UCUCGCUGGGGCCUCCA | 884 | CCCAGCGAG | 1821 | CCAGCGAG | 2758 | CAGCGAG | 3695 |
| hsa-miR-744 | UGCGGGGCUAGGGCUAACAGCA | 885 | TAGCCCCGC | 1822 | AGCCCCGC | 2759 | GCCCCGC | 3696 |
| hsa-miR-744* | CUGUUGCCACUAACCUCAACCU | 886 | GTGGCAACA | 1823 | TGGCAACA | 2760 | GGCAACA | 3697 |
| hsa-miR-758 | UUUGUGACCUGGUCCACUAACC | 887 | AGGTCACAA | 1824 | GGTCACAA | 2761 | GTCACAA | 3698 |
| hsa-miR-760 | CGGCUCUGGGUCUGUGGGGA | 888 | CCCAGAGCC | 1825 | CCAGAGCC | 2762 | CAGAGCC | 3699 |
| hsa-miR-765 | UGGAGGAGAAGGAAGGUGAUG | 889 | TTCTCCTCC | 1826 | TCTCCTCC | 2763 | CTCCTCC | 3700 |
| hsa-miR-766 | ACUCCAGCCCCACAGCCUCAGC | 890 | GGGCTGGAG | 1827 | GGCTGGAG | 2764 | GCTGGAG | 3701 |
| hsa-miR-767-3p | UCUGCUCAUACCCCAUGGUUUCU | 891 | TATGAGCAG | 1828 | ATGAGCAG | 2765 | TGAGCAG | 3702 |
| hsa-miR-767-5p | UGCACCAUGGUUGUCUGAGCAUG | 892 | CCATGGTGC | 1829 | CATGGTGC | 2766 | ATGGTGC | 3703 |
| hsa-miR-769-3p | CUGGGAUCUCCGGGGUCUUGGUU | 893 | GAGATCCCA | 1830 | AGATCCCA | 2767 | GATCCCA | 3704 |
| hsa-miR-769-5p | UGAGACCUCUGGGUUCUGAGCU | 894 | AGAGGTCTC | 1831 | GAGGTCTC | 2768 | AGGTCTC | 3705 |
| hsa-miR-770-5p | UCCAGUACCACGUGUCAGGGCCA | 895 | TGGTACTGG | 1832 | GGTACTGG | 2769 | GTACTGG | 3706 |
| hsa-miR-802 | CAGUAACAAAGAUUCAUCCUUGU | 896 | TTTGTTACT | 1833 | TTGTTACT | 2770 | TGTTACT | 3707 |
| hsa-miR-873 | GCAGGAACUUGUGAGUCUCCU | 897 | AAGTTCCTG | 1834 | AGTTCCTG | 2771 | GTTCCTG | 3708 |
| hsa-miR-874 | CUGCCCUGGCCCGAGGGACCGA | 898 | GCCAGGGCA | 1835 | CCAGGGCA | 2772 | CAGGGCA | 3709 |
| hsa-miR-875-3p | CCUGGAAACACUGAGGUUGUG | 899 | TGTTTCCAG | 1836 | GTTTCCAG | 2773 | TTTCCAG | 3710 |
| hsa-miR-875-5p | UAUACCUCAGUUUUAUCAGGUG | 900 | CTGAGGTAT | 1837 | TGAGGTAT | 2774 | GAGGTAT | 3711 |
| hsa-miR-876-3p | UGGUGGUUUACAAAGUAAUUCA | 901 | TAAACCACC | 1838 | AAACCACC | 2775 | AACCACC | 3712 |
| hsa-miR-876-5p | UGGAUUUCUUUGUGAAUCACCA | 902 | AAGAAATCC | 1839 | AGAAATCC | 2776 | GAAATCC | 3713 |
| hsa-miR-877 | GUAGAGGAGAUGGCGCAGGG | 903 | TCTCCTCTA | 1840 | CTCCTCTA | 2777 | TCCTCTA | 3714 |
| hsa-miR-877* | UCCUCUUCUCCCUCCUCCCAG | 904 | GAGAAGAGG | 1841 | AGAAGAGG | 2778 | GAAGAGG | 3715 |
| hsa-miR-885-3p | AGGCAGCGGGGUGUAGUGGAUA | 905 | CCCGCTGCC | 1842 | CCGCTGCC | 2779 | CGCTGCC | 3716 |
| hsa-miR-885-5p | UCCAUUACACUACCCUGCCUCU | 906 | GTGTAATGG | 1843 | TGTAATGG | 2780 | GTAATGG | 3717 |
| hsa-miR-886-3p | CGCGGGUGCUUACUGACCCUU | 907 | AGCACCCGC | 1844 | GCACCCGC | 2781 | CACCCGC | 3718 |
| hsa-miR-886-5p | CGGGUCGGAGUUAGCUCAAGCGG | 908 | CTCCGACCC | 1845 | TCCGACCC | 2782 | CCGACCC | 3719 |
| hsa-miR-887 | GUGAACGGGCGCCAUCCCGAGG | 909 | GCCCGTTCA | 1846 | CCCGTTCA | 2783 | CCGTTCA | 3720 |
| hsa-miR-888 | UACUCAAAAAGCUGUCAGUCA | 910 | TTTTTGAGT | 1847 | TTTTGAGT | 2784 | TTTGAGT | 3721 |
| hsa-miR-888* | GACUGACACCUCUUUGGGUGAA | 911 | GGTGTCAGT | 1848 | GTGTCAGT | 2785 | TGTCAGT | 3722 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-889 | UUAAUAUCGGACAACCAUUGU | 912 | CCGATATTA | 1849 | CGATATTA | 2786 | GATATTA | 3723 |
| hsa-miR-890 | UACUUGGAAAGGCAUCAGUUG | 913 | TTTCCAAGT | 1850 | TTCCAAGT | 2787 | TCCAAGT | 3724 |
| hsa-miR-891a | UGCAACGAACCUGAGCCACUGA | 914 | GTTCGTTGC | 1851 | TTCGTTGC | 2788 | TCGTTGC | 3725 |
| hsa-miR-891b | UGCAACUUACCUGAGUCAUUGA | 915 | GTAAGTTGC | 1852 | TAAGTTGC | 2789 | AAGTTGC | 3726 |
| hsa-miR-892a | CACUGUGUCCUUUCUGCGUAG | 916 | GGACACAGT | 1853 | GACACAGT | 2790 | ACACAGT | 3727 |
| hsa-miR-892b | CACUGGCUCCUUUCUGGGUAGA | 917 | GGAGCCAGT | 1854 | GAGCCAGT | 2791 | AGCCAGT | 3728 |
| hsa-miR-9 | UCUUUGGUUAUCUAGCUGUAUGA | 918 | TAACCAAAG | 1855 | AACCAAAG | 2792 | ACCAAAG | 3729 |
| hsa-miR-9* | AUAAAGCUAGAUAACCGAAAGU | 919 | CTAGCTTTA | 1856 | TAGCTTTA | 2793 | AGCTTTA | 3730 |
| hsa-miR-920 | GGGGAGCUGUGGAAGCAGUA | 920 | ACAGCTCCC | 1857 | CAGCTCCC | 2794 | AGCTCCC | 3731 |
| hsa-miR-921 | CUAGUGAGGGACAGAACCAGGAUUC | 921 | CCCTCACTA | 1858 | CCTCACTA | 2795 | CTCACTA | 3732 |
| hsa-miR-922 | GCAGCAGAGAAUAGGACUACGUC | 922 | TCTCTGCTG | 1859 | CTCTGCTG | 2796 | TCTGCTG | 3733 |
| hsa-miR-923 | GUCAGCGGAGGAAAAGAAACU | 923 | CTCCGCTGA | 1860 | TCCGCTGA | 2797 | CCGCTGA | 3734 |
| hsa-miR-924 | AGAGUCUUGUGAUGUCUUGC | 924 | ACAAGACTC | 1861 | CAAGACTC | 2798 | AAGACTC | 3735 |
| hsa-miR-92a | UAUUGCACUUGUCCCGGCCUGU | 925 | AAGTGCAAT | 1862 | AGTGCAAT | 2799 | GTGCAAT | 3736 |
| hsa-miR-92a-1* | AGGUUGGGAUCGGUUGCAAUGCU | 926 | ATCCCAACC | 1863 | TCCCAACC | 2800 | CCCAACC | 3737 |
| hsa-miR-92a-2* | GGGUGGGGAUUUGUUGCAUUAC | 927 | ATCCCCACC | 1864 | TCCCCACC | 2801 | CCCCACC | 3738 |
| hsa-miR-92b | UAUUGCACUCGUCCCGGCCUCC | 928 | GAGTGCAAT | 1865 | AGTGCAAT | 2802 | GTGCAAT | 3739 |
| hsa-miR-92b* | AGGGACGGGACGCGGUGCAGUG | 929 | TCCCGTCCC | 1866 | CCCGTCCC | 2803 | CCGTCCC | 3740 |
| hsa-miR-93 | CAAAGUGCUGUUCGUGCAGGUAG | 930 | CAGCACTTT | 1867 | AGCACTTT | 2804 | GCACTTT | 3741 |
| hsa-miR-93* | ACUGCUGAGCUAGCACUUCCCG | 931 | GCTCAGCAG | 1868 | CTCAGCAG | 2805 | TCAGCAG | 3742 |
| hsa-miR-933 | UGUGCGCAGGGAGACCUCUCCC | 932 | CCTGCGCAC | 1869 | CTGCGCAC | 2806 | TGCGCAC | 3743 |
| hsa-miR-934 | UGUCUACUACUGGAGACACUGG | 933 | GTAGTAGAC | 1870 | TAGTAGAC | 2807 | AGTAGAC | 3744 |
| hsa-miR-935 | CCAGUUACCGCUUCCGCUACCGC | 934 | CGGTAACTG | 1871 | GGTAACTG | 2808 | GTAACTG | 3745 |
| hsa-miR-936 | ACAGUAGAGGGAGGAAUCGCAG | 935 | CCTCTACTG | 1872 | CTCTACTG | 2809 | TCTACTG | 3746 |
| hsa-miR-937 | AUCCGCGCUCUGACUCUCUGCC | 936 | GAGCGCGGA | 1873 | AGCGCGGA | 2810 | GCGCGGA | 3747 |
| hsa-miR-938 | UGCCCUUAAAGGUGAACCCAGU | 937 | TTTAAGGGC | 1874 | TTAAGGGC | 2811 | TAAGGGC | 3748 |
| hsa-miR-939 | UGGGGAGCUGAGGCUCUGGGGGUG | 938 | CAGCTCCCC | 1875 | AGCTCCCC | 2812 | GCTCCCC | 3749 |
| hsa-miR-940 | AAGGCAGGGCCCCCGCUCCCC | 939 | GCCCTGCCT | 1976 | CCCTGCCT | 2813 | CCTGCCT | 3750 |
| hsa-miR-941 | CACCCGGCUGUGUGCACAUGUGC | 940 | CAGCCGGGT | 1877 | AGCCGGGT | 2814 | GCCGGGT | 3751 |
| hsa-miR-942 | UCUUCUCUGUUUUGGCCAUGUG | 941 | ACAGAGAAG | 1878 | CAGAGAAG | 2815 | AGAGAAG | 3752 |
| hsa-miR-943 | CUGACUGUUGCCGUCCUCCAG | 942 | CAACAGTCA | 1879 | AACAGTCA | 2816 | ACAGTCA | 3753 |
| hsa-miR-944 | AAAUUAUUGUACAUCGGAUGAG | 943 | ACAATAATT | 1880 | CAATAATT | 2817 | AATAATT | 3754 |
| hsa-miR-95 | UUCAACGGGUAUUUAUUGAGCA | 944 | ACCCGTTGA | 1881 | CCCGTTGA | 2818 | CCGTTGA | 3755 |
| hsa-miR-96 | UUUGGCACUAGCACAUUUUUGCU | 945 | TAGTGCCAA | 1882 | AGTGCCAA | 2819 | GTGCCAA | 3756 |
| hsa-miR-96* | AAUCAUGUGCAGUGCCAAUAUG | 946 | GCACATGAT | 1883 | CACATGAT | 2820 | ACATGAT | 3757 |
| hsa-miR-98 | UGAGGUAGUAAGUUGUAUUGUU | 947 | TACTACCTC | 1884 | ACTACCTC | 2821 | CTACCTC | 3758 |
| hsa-miR-99a | AACCCGUAGAUCCGAUCUUGUG | 948 | TCTACGGGT | 1885 | CTACGGGT | 2822 | TACGGGT | 3759 |

TABLE 2-continued miR ID No 40-976 correspond to SEQ ID NOs 29-965

| microRNA | MicroRNA target Sequence | miR ID NO | 9-mer | Comp ID NO | 8-mer | C ID NO | 7-mer | C ID NO |
|---|---|---|---|---|---|---|---|---|
| hsa-miR-99a* | CAAGCUCGCUUCUAUGGGUCUG | 949 | AGCGAGCTT | 1886 | GCGAGCTT | 2823 | CGAGCTT | 3760 |
| hsa-miR-99b | CACCCGUAGAACCGACCUUGCG | 950 | TCTACGGGT | 1887 | CTACGGGT | 2824 | TACGGGT | 3761 |
| hsa-miR-99b* | CAAGCUCGUGUCUGUGGGUCCG | 951 | CACGAGCTT | 1888 | ACGAGCTT | 2825 | CGAGCTT | 3762 |
| hsv1-miR-H1 | UGGAAGGACGGGAAGUGGAAG | 952 | CGTCCTTTC | 1889 | GTCCTTCC | 2826 | TCCTTCC | 3763 |
| hsv1-miR-H2-3p | CCUGAGCCAGGGACGAGUGCGACU | 953 | CTGGCTCAG | 1890 | TGGCTCAG | 2827 | GGCTCAG | 3764 |
| hsv1-miR-H2-5p | UCGCACGCGCCCGGCACAGACU | 954 | GCGCGTGCG | 1891 | CGCGTGCG | 2828 | GCGTGCG | 3765 |
| hsv1-miR-H3 | CUGGGACUGUGCGGUUGGGA | 955 | ACAGTCCCA | 1892 | CAGTCCCA | 2829 | AGTCCCA | 3766 |
| hsv1-miR-H4-3p | CUUGCCUGUCUAACUCGCUAGU | 956 | GACAGGCAA | 1893 | ACAGGCAA | 2830 | CAGGCAA | 3767 |
| hsv1-miR-H4-5p | GGUAGAGUUUGACAGGCAAGCA | 957 | AAACTCTAC | 1894 | AACTCTAC | 2831 | ACTCTAC | 3768 |
| hsv1-miR-H5 | GUCAGAGAUCCAAACCCUCCGG | 958 | GATCTCTGA | 1895 | ATCTCTGA | 2832 | TCTCTGA | 3769 |
| hsv1-miR-H6 | CACUUCCCGUCCUUCCAUCCC | 959 | ACGGGAAGT | 1896 | CGGGAAGT | 2833 | GGGAAGT | 3770 |
| kshv-miR-K12-1 | AUUACAGGAAACUGGGUGUAAGC | 960 | TTCCTGTAA | 1897 | TCCTGTAA | 2834 | CCTGTAA | 3771 |
| kshv-miR-K12-10a | UAGUGUUGUCCCCCCGAGUGGC | 961 | GACAACACT | 1898 | ACAACACT | 2835 | CAACACT | 3772 |
| kshv-miR-K12-10b | UGGUGUUGUCCCCCCGAGUGGC | 962 | GACAACACC | 1899 | ACAACACC | 2836 | CAACACC | 3773 |
| kshv-miR-K12-11 | UUAAUGCUUAGCCUGUGUCCGA | 963 | TAAGCATTA | 1900 | AAGCATTA | 2837 | AGCATTA | 3774 |
| kshv-miR-K12-12 | ACCAGGCCACCAUUCCUCUCCG | 964 | GTGGCCTGG | 1901 | TGGCCTGG | 2838 | GGCCTGG | 3775 |
| kshv-miR-K12-2 | AACUGUAGUCCGGGUCGAUCUG | 965 | GACTACAGT | 1902 | ACTACAGT | 2839 | CTACAGT | 3776 |
| kshv-miR-K12-3 | UCACAUUCUGAGGACGGCAGCGA | 966 | CAGAATGTG | 1903 | AGAATGTG | 2840 | GAATGTG | 3777 |
| kshv-miR-K12-3* | UCGCGGUCACAGAAUGUGACA | 967 | GTGACCGCG | 1904 | TGACCGCG | 2841 | GACCGCG | 3778 |
| kshv-miR-K12-4-3p | UAGAAUACUGAGGCCUAGCUGA | 968 | CAGTATTCT | 1905 | AGTATTCT | 2842 | GTATTCT | 3779 |
| kshv-miR-K12-4-5p | AGCUAAACCGCAGUACUCUAGG | 969 | CGGTTTAGC | 1906 | GGTTTAGC | 2843 | GTTTAGC | 3780 |
| kshv-miR-K12-5 | UAGGAUGCCUGGAACUUGCCGG | 970 | AGGCATCCT | 1907 | GGCATCCT | 2844 | GCATCCT | 3781 |
| kshv-miR-K12-6-3p | UGAUGGUUUUCGGGCUGUUGAG | 971 | AAAACCATC | 1908 | AAACCATC | 2845 | AACCATC | 3782 |
| kshv-miR-K12-6-5p | CCAGCAGCACCUAAUCCAUCGG | 972 | GTGCTGCTG | 1909 | TGCTGCTG | 2846 | GCTGCTG | 3783 |
| kshv-miR-K12-7 | UGAUCCCAUGUUGCUGGCGCU | 973 | CATGGGATC | 1910 | ATGGGATC | 2847 | TGGGATC | 3784 |
| kshv-miR-K12-8 | UAGGCGCGACUGAGAGAGCACG | 974 | GTCGCGCCT | 1911 | TCGCGCCT | 2848 | CGCGCCT | 3785 |
| kshv-miR-K12-9 | CUGGGUAUACGCAGCUGCGUAA | 975 | GTATACCCA | 1912 | TATACCCA | 2849 | ATACCCA | 3786 |
| kshv-miR-K12-9* | ACCCAGCUGCGUAAACCCCGCU | 976 | GCAGCTGGG | 1913 | CAGCTGGG | 2850 | AGCTGGG | 3787 |

The above 7-9mer compounds (or oligomer regions) may be fully LNA modified, fully phosphorothioate, and LNA cytosine may be 5-methyl cytosine. The LNA may in some embodiments be beta-D-oxy LNA or for example, (S)cET.

In an independent embodiment, the invention provides for an oligomer comprising 7-12, such as 7-10, such as 7, 8 or 9 consecutive LNA nucleosides (see Table 2 for examples), conjugated to a GalNAc conjugate, such as a trivalent GalNAc conjugate, such as a GalNAc conjugate selected from the group consisting of any one of Conj1, 2, 3, 4, 1a, 2a, 3a, 4a, such as conj2a. Such oligomers may, in some embodiments be one of the oligomer regions as described herein. The above Table 2 or 7-12mer compounds (or oligomer regions) may be fully LNA modified, fully phosphorothioate, and LNA cytosine may be 5-methyl cytosine. The LNA may in some embodiments be beta-D-oxy LNA or for example, (S)cET. Beta-D-oxy LNA is a preferred nucleoside. The 7-12 mer compounds may, for example, be capable of inhibiting a microRNA in a cell expressing said microRNA.

In an independent embodiment, the invention provides for an oligomer comprising one (or more, such as to or three) of the compounds or table 2, and a GalNAc conjugate, such as a trivalent GalNAc conjugate such as a GalNAc conjugate selected from the group consisting of any one of Conj1, 2, 3, 4, 1a, 2a, 3a, 4a, such as conj2a.

EMBODIMENTS

The following aspects of the invention may be combined with other aspects herein described.
1. An oligomeric compound comprising i) a first region of a contiguous sequence of 7-26 phosphorothioate linked nucleosides; ii) a second region of a contiguous sequence of 7-26 phosphorothioate linked nucleosides; wherein the first and the second regions are covalently linked via iii) a region of 1-5 physiologically labile nucleotides, such as 1-5 phosphodiester linked nucleotides, such as DNA or RNA nucleosides.
2. The oligomeric compound according to embodiment 1, wherein the first region (i) and second region (ii) are positioned 5' and 3' respectively to the region of physiologically labile nucleotides (iii).
3. The oligomeric compound according to embodiment 1 or 2, wherein the first region or second region are covalently linked to a functional group (iv), such as a conjugate moiety.
4. The oligomeric compound according to embodiment 2 or 3, wherein the functional group is covalently linked to the first or the second region via a bio-cleavable linker (v).
5. The oligomeric compound according to embodiment 4, wherein the bio cleavable linker (v) comprises a region of 1-5 physiologically labile nucleotides, such as 1-5 phosphodiester linked nucleotides, such as DNA [or RNA] nucleosides.
6. The oligomeric compound according to any one of embodiments 3-5, wherein the conjugate moiety comprises a sterol, for example cholesterol, or a carbohydrate, such as GalNac/GalNac cluster.
7. The oligomeric compound complex according to any one of embodiments 3-5, wherein the conjugate moiety comprises a lipophilic group (e.g. a lipid, a fatty acid, a sterol), a protein, a peptide, an antibody or fragment thereof, a polymer, a reporter group, a dye, a receptor ligand, a small molecule drug, a prodrug, or a vitamin.
8. The oligomeric compound according to any one of embodiments 1-7 wherein the contiguous sequence of nucleobases of the first and the second region are identical.
9. The oligomeric compound according to any one of embodiments 1-7 wherein the contiguous sequence of nucleobases of the first and the second region are different.
10. The oligomeric compound according to any one of embodiments 1-9 wherein the first and the second regions are targeted to the same nucleic acid target.
11. The oligomeric compound according to any one of embodiments 1-10 wherein the first and the second regions each comprise at least 1 LNA nucleoside.
12. The oligomeric compound according to any one of embodiments 1-11 wherein the first and/or second regions are gapmer oligomers, such as LNA gapmers.
13. The oligomeric compound according to any one of embodiments 1-12 wherein the first and/or second region target mRNA targets.
14. The oligomeric compound according to any one of embodiments 1-13 wherein the first and/or second regions target microRNA targets.
15. The oligomeric compound according to any one of embodiments 1-14 wherein the first and/or second regions are mixmer or totalmer oligomers.
16. The oligomeric compound according to any one of embodiments 1-15 wherein the first and second regions are 10-16 nucleotides in length.
17. The oligomeric compound according to any one of embodiments 1-15 wherein the first and second regions are 8-10 nucleotides in length.
18. The oligomeric compound according to any one of embodiments 1-16 wherein the first region is complementary to a [human] ApoB-100 mRNA nucleotide sequence and/or wherein the second region is complementary to a [human] mtGPAT mRNA nucleotide sequence.
19. The oligomeric compound according to any one of embodiments 1-18, wherein the first sequence is positioned 5' of the second sequence.
20. The oligomeric compound according to any one of embodiments 1-18, wherein the first sequence is positioned 3' of the second sequence.
21. A pharmaceutical composition comprising the oligomeric compound of any one of the preceding embodiments, and a pharmaceutically acceptable diluent, carrier, salt or adjuvant.
22. The oligomeric compound according to any one of the preceding embodiments for use in the inhibition of a nucleic acid target in a cell.
23. The oligomeric compound according to any one of the preceding embodiments for use in medicine.
24. The oligomeric compound according to any one of the preceding embodiments for use in the treatment of a medical disease or disorder.
25. The use of the oligomeric compound according to any one of the preceding embodiments for the preparation of a medicament for the treatment of a disease or disorder, such as a metabolic disease or disorder.
26. A method of treatment of a disease or disorder in a subject in need of treatment, said method comprising the steps of administering a pharmaceutical composition comprising the oligomeric compound of any one of the preceding embodiments to said subject in a therapeutically effective amount.
27. A method of inhibiting the expression of a target gene in a cell, said method comprising administering the oligomeric compound according to any one of the preceding embodiments to a cell which is expressing said target gene, suitably in an amount effective to reduce the expression of the target gene in said cell.

EXAMPLES

Oligonucleotide List

In the following list, Capital letters represent LNA nucleosides, such as beta-D-oxy LNA, lower case letters represent DNA nucleosides. Capital L is a LNA, such as beta-D-oxy, and lower case d is a DNA nucleoside. LNA cytosines are optionally 5'methyl cytosine. The internucleosides within region A are phosphorothioate, and within region B are phosphodiester (as shown). The internucleoside linkage between region A and B is phosphodiester, but where region B is >1 DNA nucleotide, may optionally be other than phosphodiester (e.g. may be phosphorothioate). There is, optionally a further linker (Y), between region B and region C, such as a C6 linker. # refers to SEQ ID No.

| ApoB Targeting Compounds with FAM label conjugates | | | | |
|---|---|---|---|---|
| #C | Seq (5'-3') | Cleavable linker (B) | Conjugate (C) | SEQ ID NO |
| 16 | GCattggtatTCA 3PO-DNA (5'tca3') | | FAM | 21 |
| 17 | GCattggtatTCA 2PO-DNA (5'ca3') | | FAM | 22 |
| 18 | GCattggtatTCA 1PO-DNA (5'a3') | | FAM | 23 |
| 19 | GCattggtatTCA 3PO-DNA (5'gac3') | | FAM | 24 |
| 20 | GCattggtatTCA no | | FAM | 25 |

Examples 1-5 and 7-11—see PCT/EP2013/07358 Examples 1-11.

Example 6. In Vitro Cleavage of Different DNA/PO-Linkers

Figure 6:
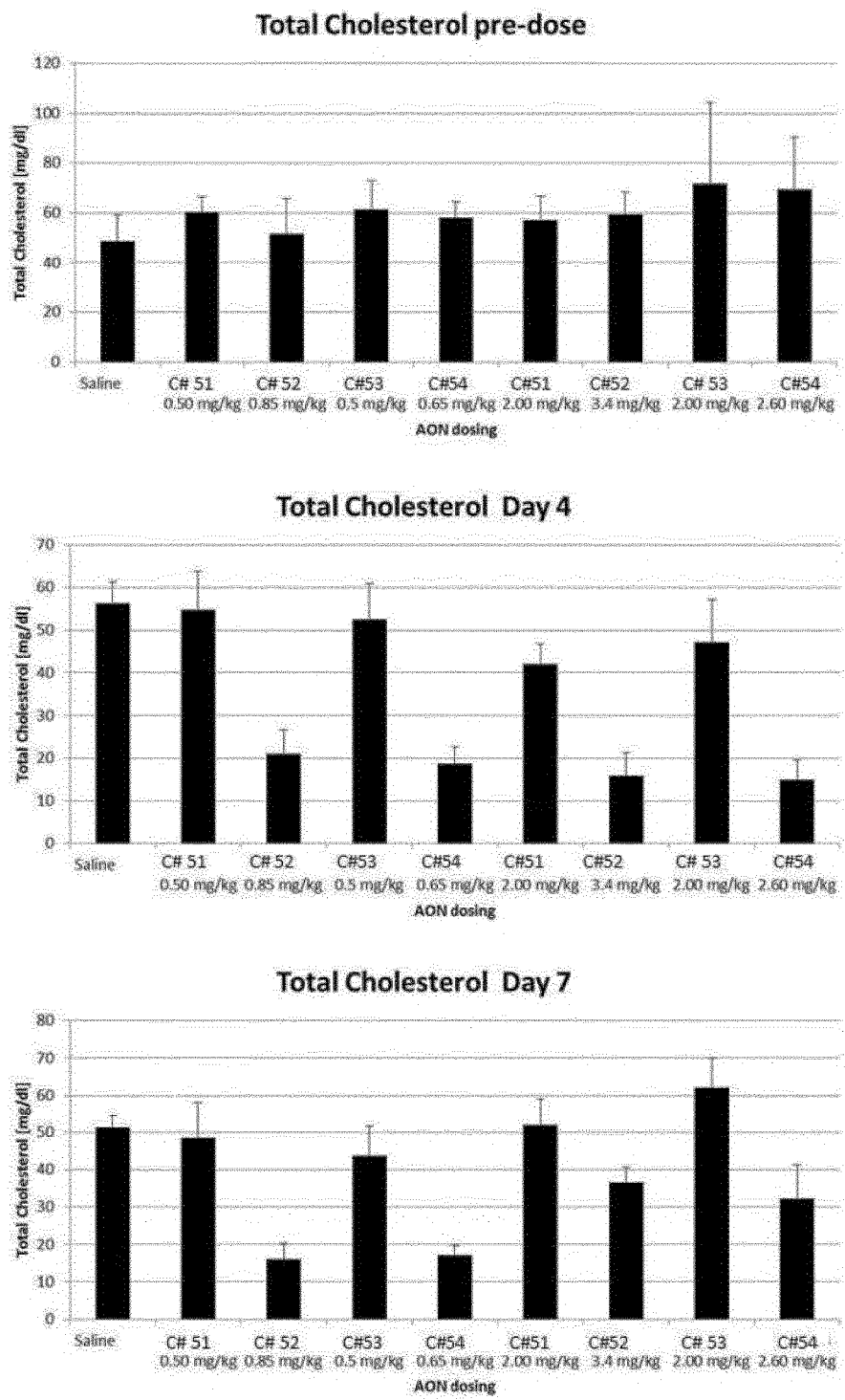
FIG. 6: Total Cholesterol analysis at pre-dose, day 4 and day 7. Cholesterol is upregulated due to decreased miR122.
Figure 7:
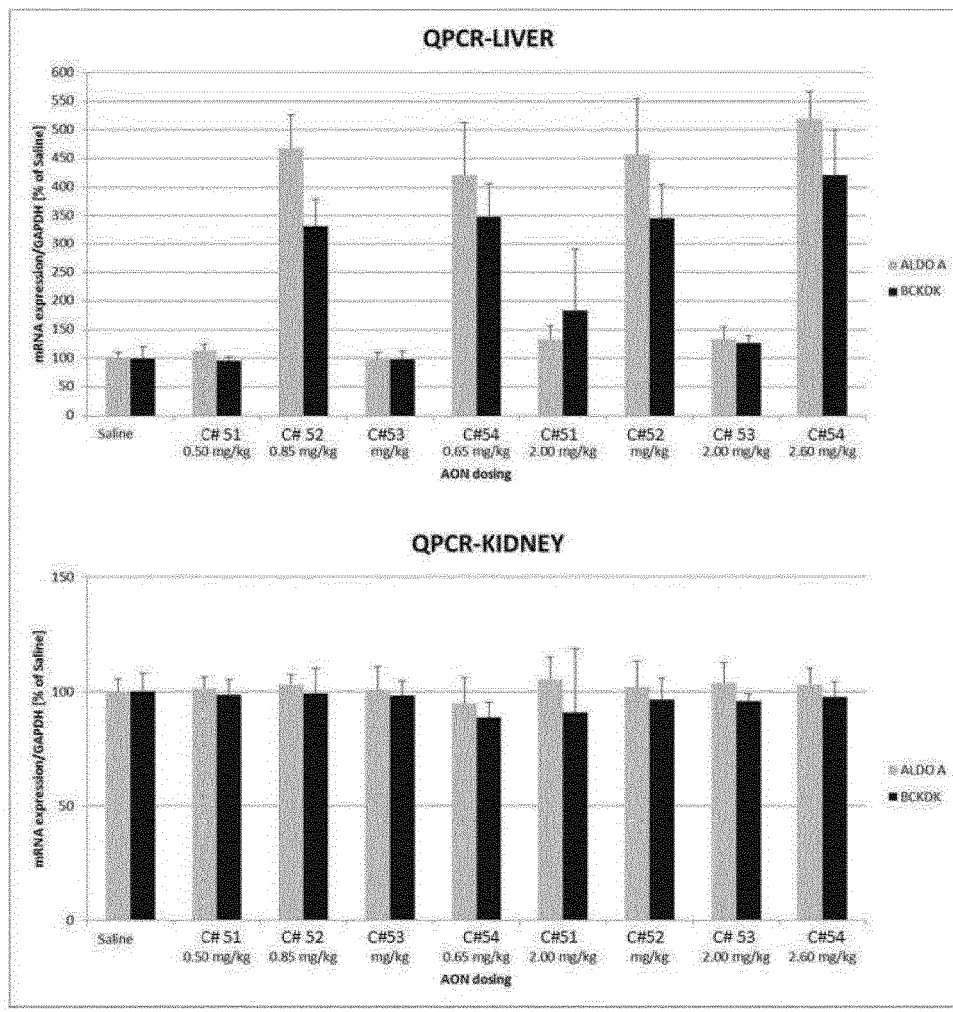
FIG. 7: Expression of Aldo A and Bckdk was measured by standard TaqMan Q-PCR assays. The mRNA levels of these genes are upregulated due to decreased miR122.
Figure 8:
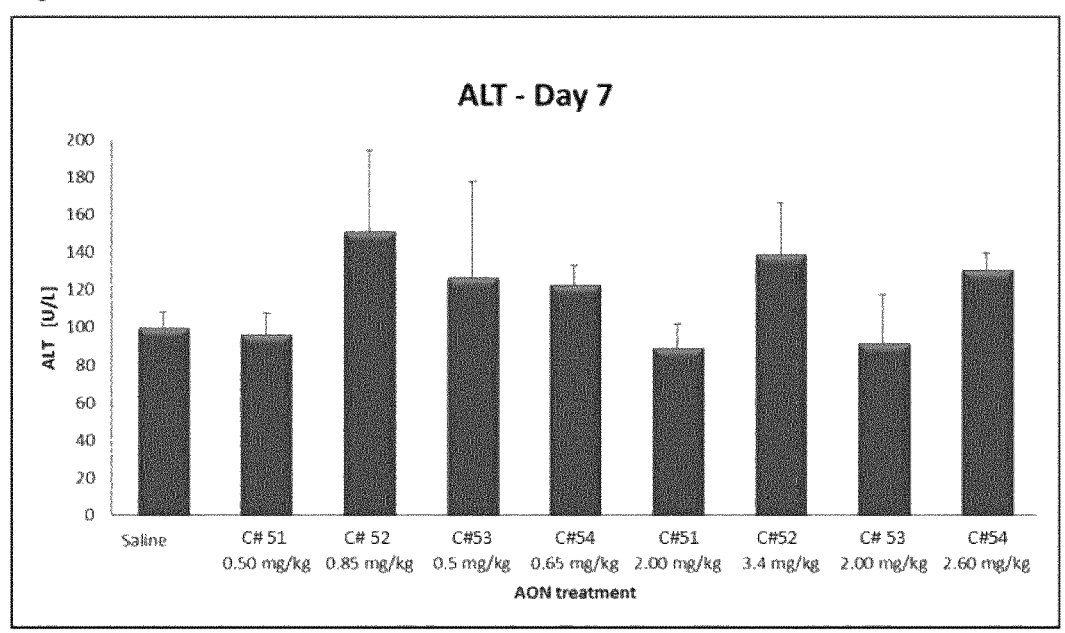
FIG. 8: ALT was measured from final serum (day 7) to assess tolerability of the compounds.
Figure 9:
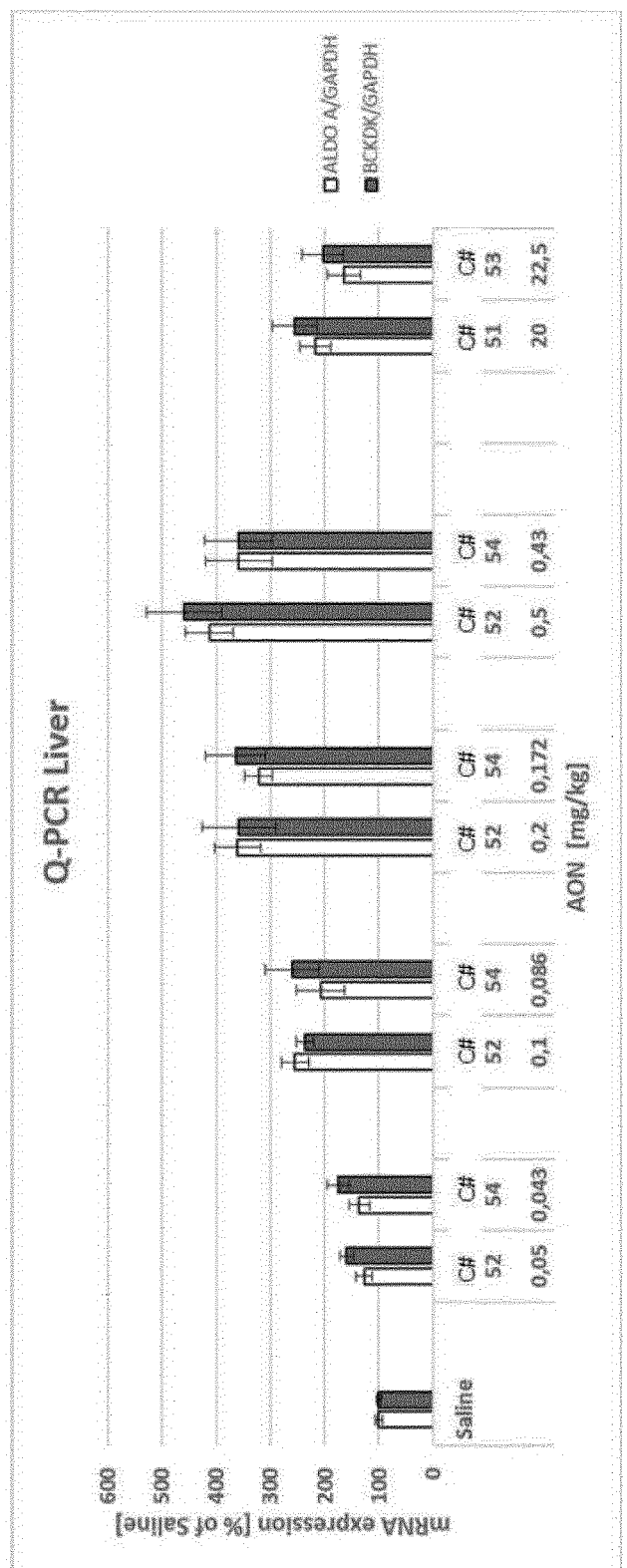
FIG. 9: Expression of Aldo A and Bckdk was measured by standard TaqMan Q-PCR assays. The mRNA levels of these genes are upregulated due to decreased miR122.

FAM-labeled ASOs with different DNA/PO-linkers (PO linkers) were subjected to in vitro cleavage either in S1 nuclease extract (FIG. 6A), Liver or kidney homogenates or Serum FAM-labeled ASOs 100 μM with different DNA/PO-linkers were subjected to in vitro cleavage by S1 nuclease in nuclease buffer (60 U pr. 100 μL) for 20 and 120 minutes (A). The enzymatic activity was stopped by adding EDTA to the buffer solution. The solutions were then subjected to AIE HPLC analyses on a Dionex Ultimate 3000 using an Dionex DNApac p-100 column and a gradient ranging from 10 mM-1 M sodium perchlorate at pH 7.5. The content of cleaved and non cleaved oligonucleotide were determined against a standard using both a fluorescence detector at 615 nm and a uv detector at 260 nm.

| #C | Linker sequence | % cleaved after 20 min S1 | % cleaved after 120 min S1 |
|---|---|---|---|
| 20 | — | 2 | 5 |
| 18 | a | 29.1 | 100 |
| 17 | ca | 40.8 | 100 |
| 16 | tca | 74.2 | 100 |
| 19 | gac | 22.9 | n.d |

Conclusion:

The PO linkers (or region B as referred to herein) results in the conjugate (or group C) being cleaved off, and both the length and/or the sequence composition of the linker can be used to modulate susceptibility to nucleolytic cleavage of region B. The Sequence of DNA/PO-linkers can modulate the cleavage rate as seen after 20 min in Nuclease S1 extract Sequence selection for region B (e.g. for the DNA/PO-linker) can therefore also be used to modulate the level of cleavage in serum and in cells of target tissues.

Liver, kidney and Serum (B) were spiked with oligonucleotide NO 16 to concentrations of 200 μg/g tissue. Liver and kidney samples collected from NMRI mice were homogenized in a homogenisation buffer (0.5% Igepal CA-630, 25 mM Tris pH 8.0, 100 mM NaCl, pH 8.0 (adjusted with 1 N NaOH). The homogenates were incubated for 24 hours at 37° and thereafter the homogenates were extracted with phenol-chloroform. The content of cleaved and non cleaved oligonucleotide in the extract from liver and kidney and from the serum were determined against a standard using the above HPLC method.

| Seq ID | Linker Sequence | % cleaved after 24 hrs liver homogenate | % cleaved after 24 hrs kidney homogenate | % cleaved after 24 hours in serum |
|---|---|---|---|---|
| 16 | tca | 83 | 95 | 0 |

Conclusion:

The PO linkers (or region B as referred to herein) results in cleavage of the conjugate (or group C) from the oligonucleotide, in liver or kidney homogenate, but not in serum.

Note: cleavage in the above assays refers to the cleavage of the cleavable linker, the oligomer or region A should remain functionally intact. The susceptibility to cleavage in the above assays can be used to determine whether a linker is biocleavable or physiologically labile.

Example 12: LNA AntimiRs GalNac Poly-Oligo Conjugates

Compounds

Capital letters are LNA, such as beta-D-oxy LNA. Lower case letters are DNA. Subscript s is a phosphorothioate linkage. Other internucleoside linkages are phosphodiester (phosphate) linkages. Superscript m before a C represents LNA 5-methyl cytosine. In some embodiments, the compounds may also be made with LNA cytosine. In some embodiments, the Conj1a group may be another GalNAc conjugate group, such as those disclosed herein, for example Conj2a.

miR-21 (Tiny)
5'-$^mC_sA_s^mC_sA_s^mC_sT_s^mC_s^mC$-3' (Comp NO 51)

GalNAc-tiny
5'-Conj1a $^mC_sA_s^mC_sA_s^mC_sT_s^mC_s^mC$-3' (Comp NO 52)

tiny-linker-tiny
SEQ ID No 26
5'-$^mC_sA_s^mC_sA_s^mC_sT_s^mC_s^mCca^mC_sA_s^mC_sA_s^mC_sT_s^mC_s^mC$-3'
(Comp NO 53)

GalNac-tiny-linker-tiny
SEQ ID NO 27
5'-Conj1a
$^mC_sA_s^mC_sA_s^mC_sT_s^mC_s^mCca^mC_sA_s^mC_sA_s^mC_sT_s^mC_s^mC$-3'
(Comp NO 54)

An in vivo mouse study was performed using a total of 9 groups of mice (n=5). Each mouse was dosed i.v. on days 0, 2 and 4 with either 0.5 mg/kg or 2 mg/kg or equimolar doses of the GalNAc conjugated LNA's compared to parent LNA compound and equimolar active compound after cleavage of the double 8mer compared to the single 8mer compound. A saline control group was included (see study set up below). Serum samples were taken 4 days pre administration, interim at day 4 and at endpoint day 7. Liver and kidney samples were stored in RNA later. Validation of miR122 knock down of miR122 was done as described in Obad Nat Genet. 2011 Mar. 20; 43(4):371-8 (FIG. 17). The cholesterol level in serum were analyzed as described in Elmen J, et al. LNA-mediated microRNA silencing in non-human primates. Nature. 2008; 452:896-899. (FIG. 18) and mRNA levels of two miR122 down regulated genes (Aldo A and Bckdk) were analyzed using standard QPCR assay techniques (FIG. 19). ALT was measured to assess tolerability of the compounds (FIG. 20).

| Study Set-up | | | | |
|---|---|---|---|---|
| group | compound | termination time point post dose | group size | dose (d0, d2, d4) mg/kg |
| | Saline | D7 | 5 | none |
| | Comp ID 51 | D7 | 5 | 3 × 0.5 |
| | Comp ID 52 | D7 | 5 | 3 × 0.85 |
| | Comp ID 53 | D7 | 5 | 3 × 0.5 |
| | Comp ID 54 | D7 | 5 | 3 × 0.65 |
| | Comp ID 51 | D7 | 5 | 3 × 2 |
| | Comp ID 52 | D7 | 5 | 3 × 3.4 |
| | Comp ID 53 | D7 | 5 | 3 × 2 |
| | Comp ID 54 | D7 | 5 | 3 × 2.6 |

Figure 3:
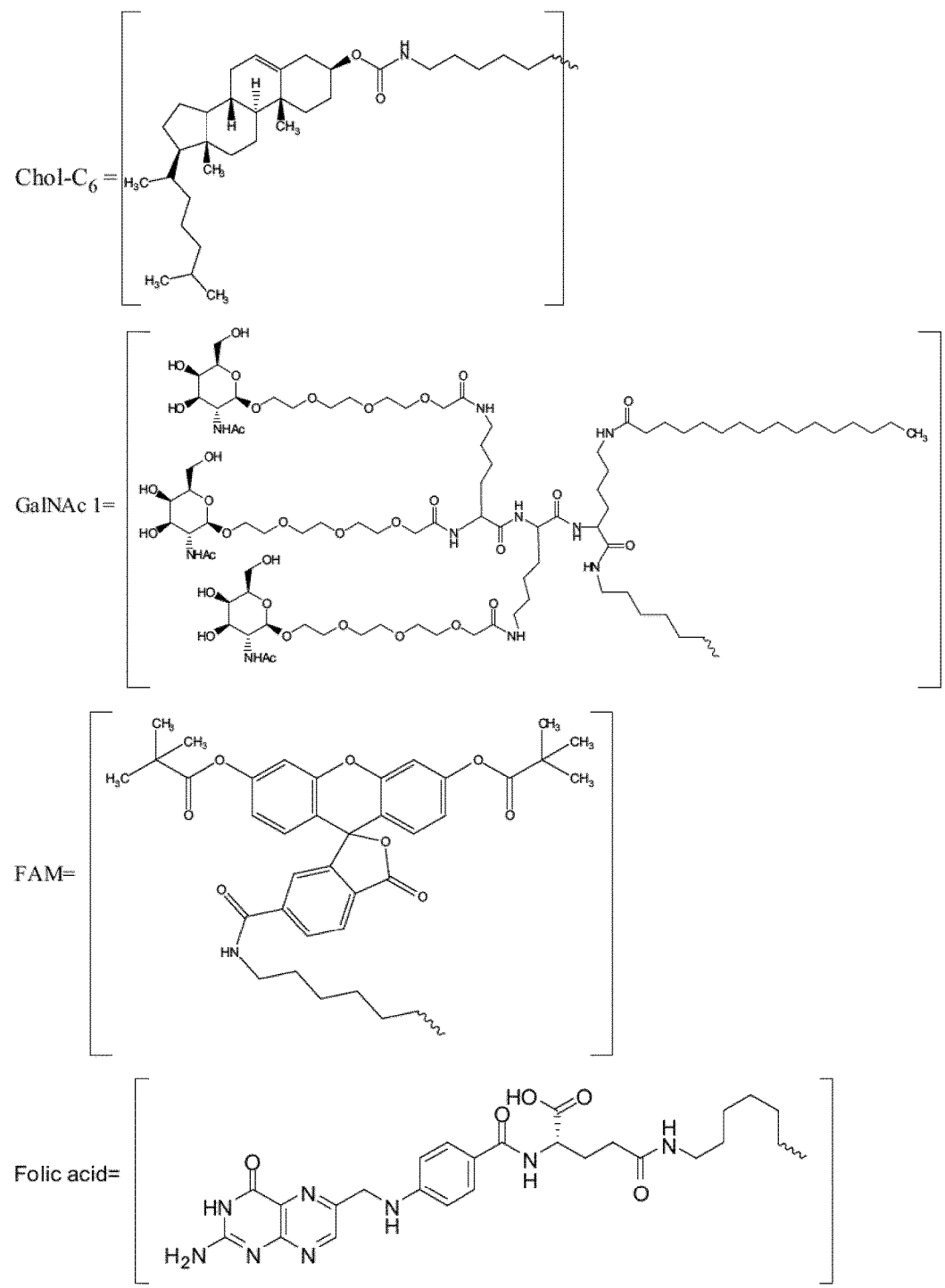
FIG. 3: Examples of cholesterol, trivalent GalNac, FAM, folic acid, monovalent GalNac and tocopherol conjugates.
Figure 3:
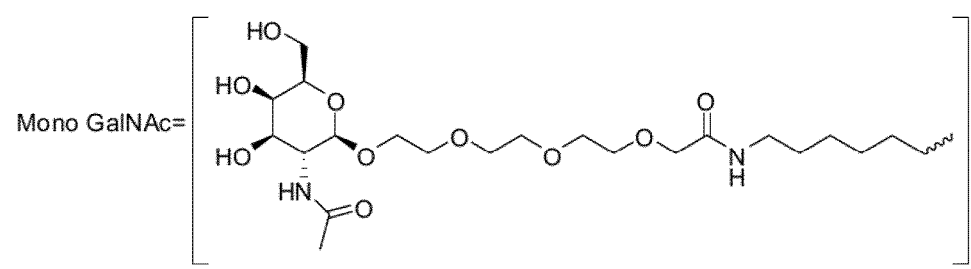
Figure 3:
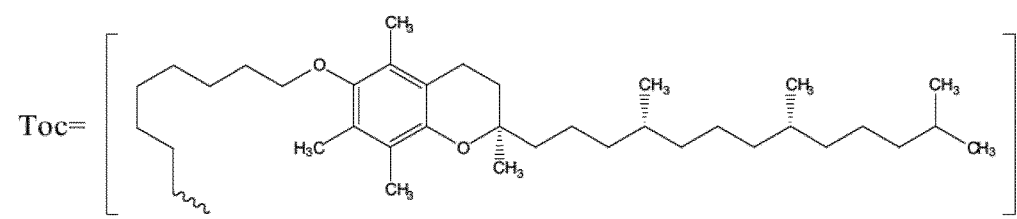
Figure 4:
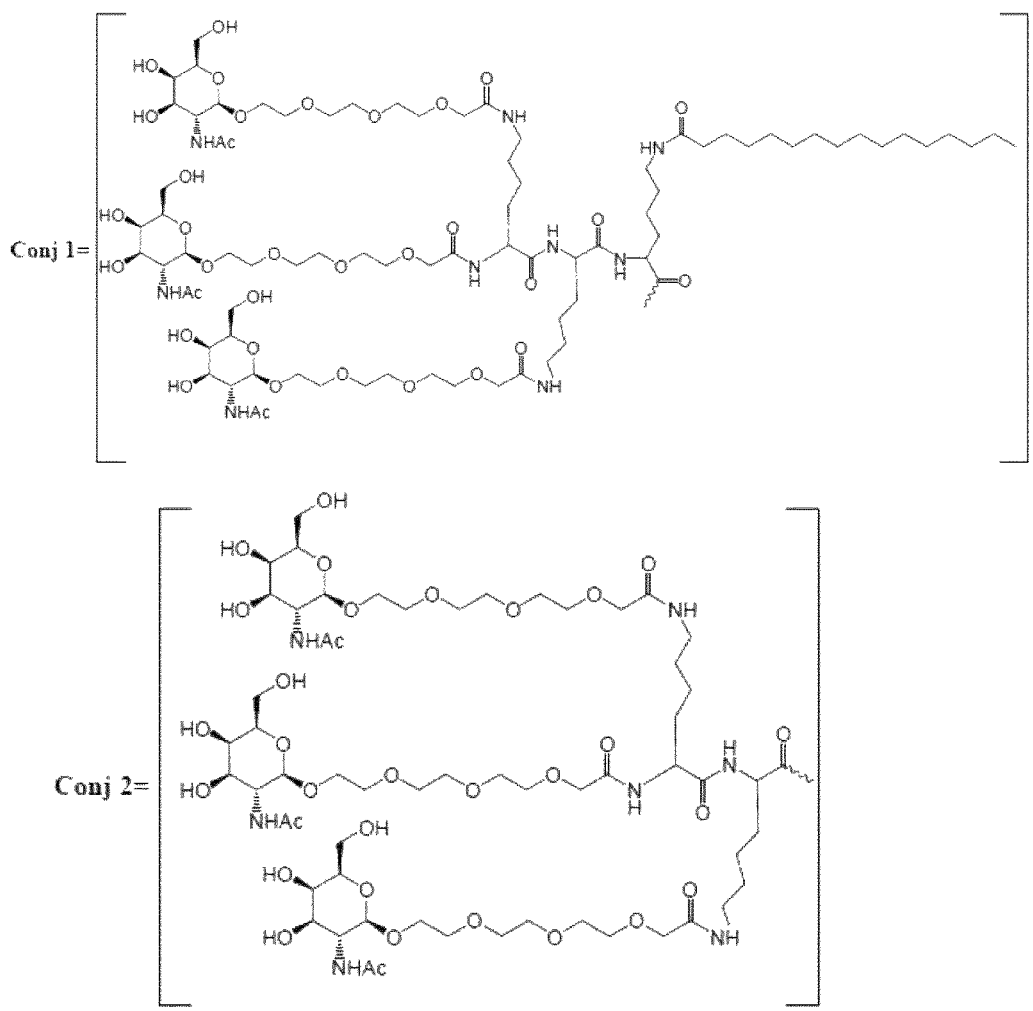
FIG. 4: Examples of tri-GalNac conjugates which may be used. Conjugates 1-4 illustrate 4 suitable GalNac conjugate moieties, and conjugates 1a-4a refer to the same conjugates with an additional linker moiety (Y) which is used to link the conjugate to the oligomer (region A or to a biocleavable linker, such as region B). The wavy line represents the covalent link to the oligomer. Also shown are examples of cholesterol and tocopherol conjugate moieties (5a and 6a). The wavy line represents the covalent link to the oligomer.
Figure 4:
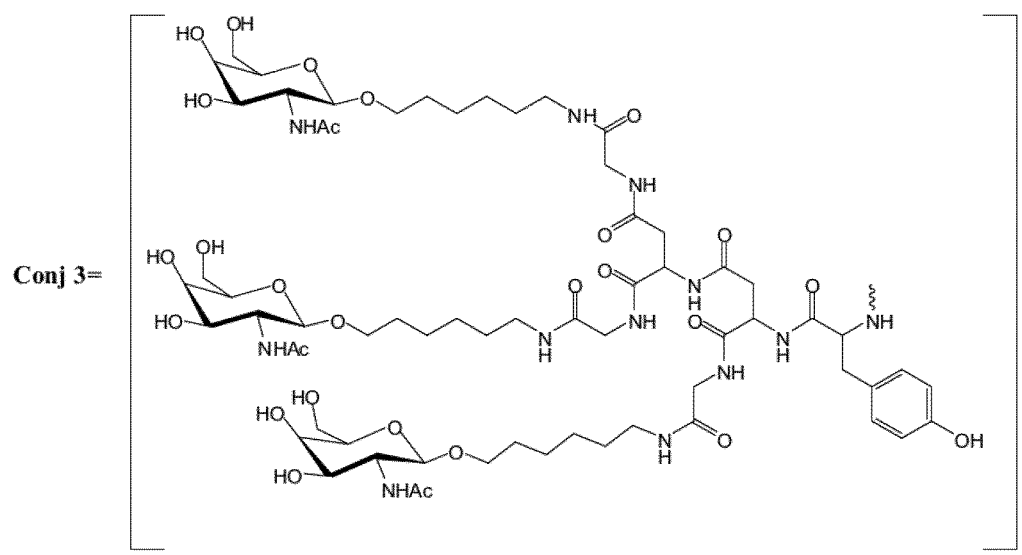
Figure 4:
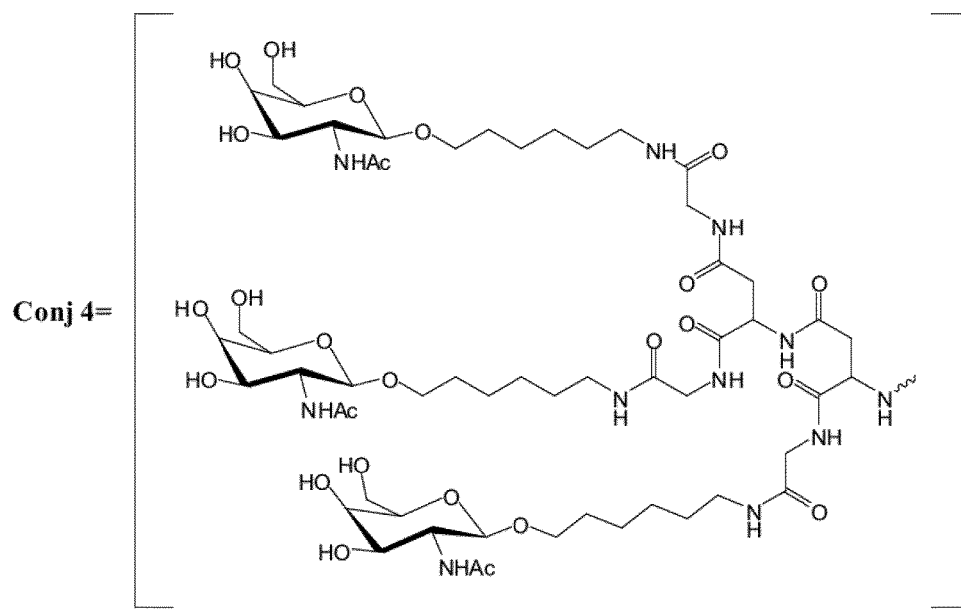
Figure 4:
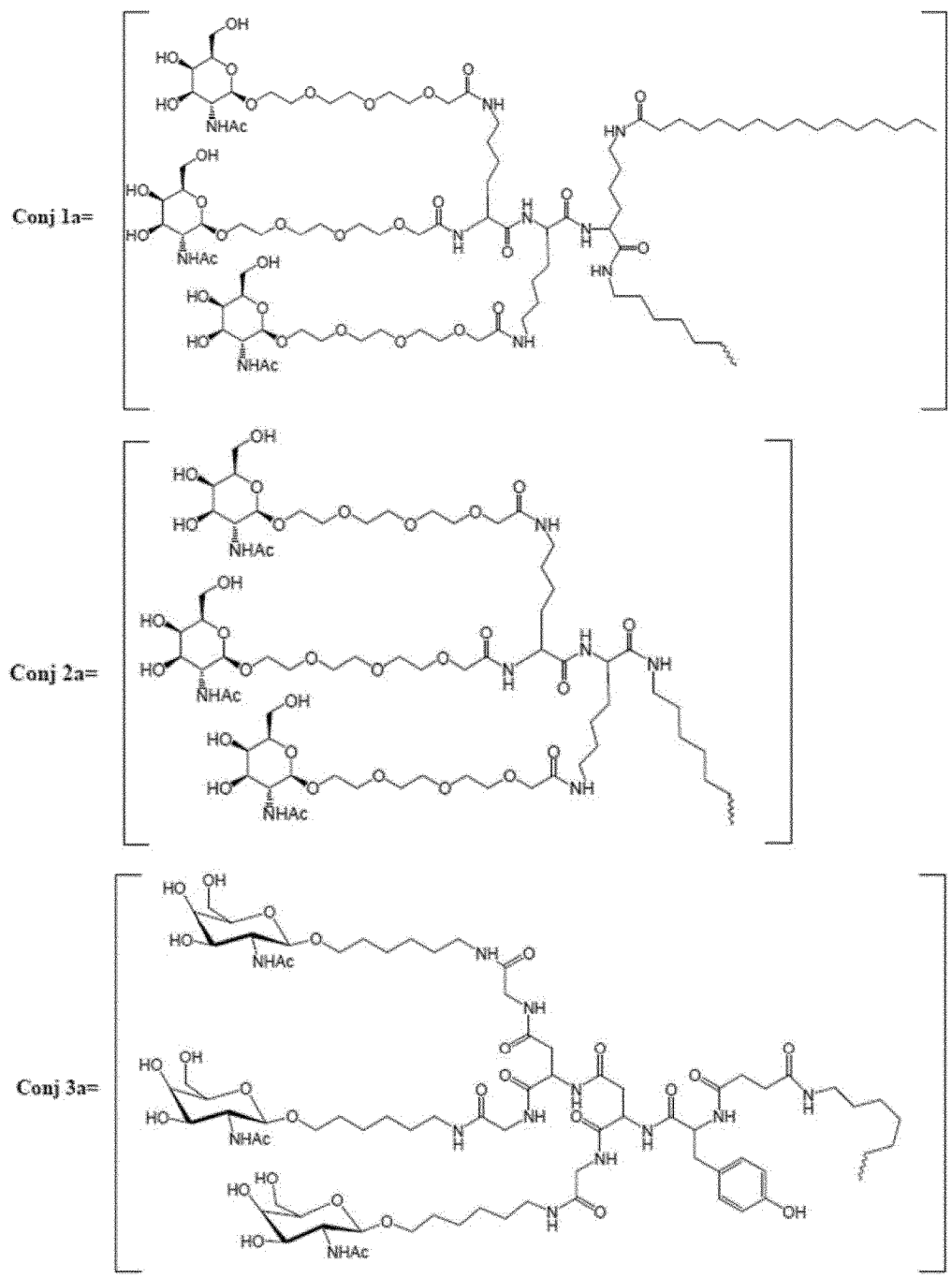
Figure 4:
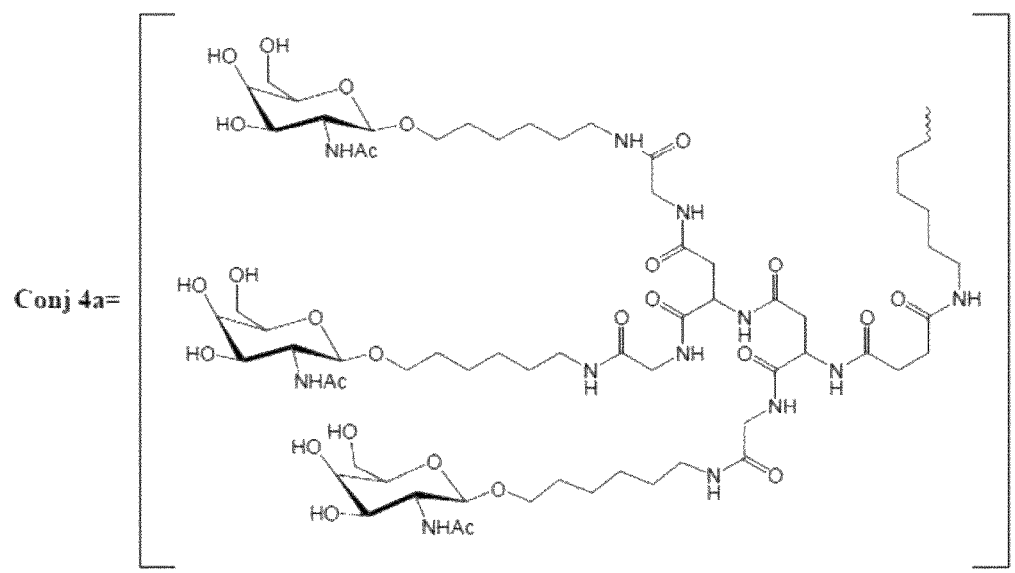
Figure 5:
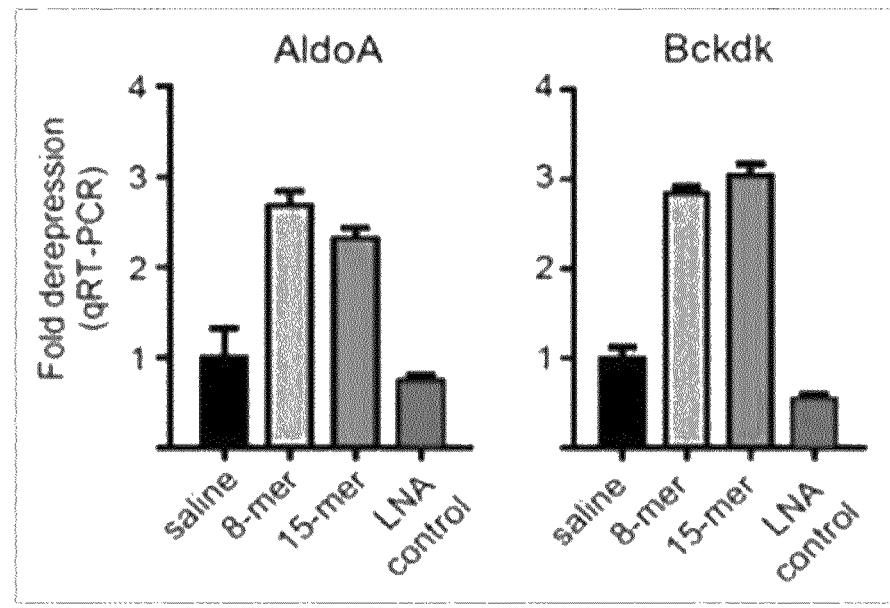
FIG. 5: Silencing of miR-122 in the mouse liver by seed-targeting tiny LNA. (a) RNA blot analysis of liver RNAs from mice after treatment with three intravenous doses of 20 mg/kg tiny antimiR-122, 15-mer antimiR-122 or LNA scramble control or with saline.

Conclusions: Conjugation of GalNAc to anti-miR122 (Comp ID 52 and 54) showed a remarkable improvement of miR122 knock down in the liver indicated by decreased total cholesterol levels (FIG. 2) and up regulation of Aldo A and Bckdk mRNA already in the low dose group (FIG. 3, 3×0.5 mg/kg). No effect of the anti-miR122 oligonucleotide was seen in the kidney. A very slight increase in ALT was measured for Comp ID 52 which showed a tendency to improve by conjugation of 2 oligonucleotides to one GalNAc (Comp ID 54). No major difference could be observed in activity of the GalNAc conjugated single Tiny LNA compound compared to the poly-oligo compound comp ID 52 compared to 54, FIGS. 18 and 19) which might be due to overdosing. The unconjugated Tiny LNA and poly-oligo compound showed no activity due to the low dose range. To allow better comparison of the single and poly-oligo concept a dose range finding study was conducted (Example 13).

Example 13: LNA AntimiRs GalNac Poly-Oligo Conjugates-Dose Range Finding

Compounds: as in Example 12.

An in vivo mouse study was performed using a total of 11 groups of mice (n=5). Each mouse was dosed i.v. on day 0 with either 0.05 mg/kg, 0.1 mg/kg, 0.2 mg/kg or 0.5 mg/kg of the GalNAc conjugated Tiny LNA (comp ID 52) or equimolar active compound after cleavage of the poly-oligo compound (comp ID 54). For comparison two groups were dosed with 20 mg/kg of the unconjugated parent Tiny LNA (comp ID 51) and equimolar active compound after cleavage of the poly-oligo compound (comp ID 53). A saline control group was included (see study set up).

Samples were taken and analyzed as described in Example 12. mRNA levels of two miR122 down regulated genes (Aldo A and Bckdk) were analyzed using standard QPCR assay techniques (FIG. 21). ALT measurement showed no significant rise in ALT compared over compounds.

| Study Set-up | | | | |
|---|---|---|---|---|
| group | compound | termination time point post dose | group size | dose (d0) mg/kg |
| 1 | Saline | D7 | 5 | none |
| 2 | Comp ID 52 | D7 | 5 | 0.05 |
| 3 | Comp ID 54 | D7 | 5 | 0.043 |
| 4 | Comp ID 52 | D7 | 5 | 0.1 |
| 5 | Comp ID 54 | D7 | 5 | 0.086 |
| 6 | Comp ID 52 | D7 | 5 | 0.2 |
| 7 | Comp ID 54 | D7 | 5 | 0.17 |
| 8 | Comp ID 52 | D7 | 5 | 0.5 |

-continued

| Study Set-up | | | | |
|---|---|---|---|---|
| group | compound | termination time point post dose | group size | dose (d0) mg/kg |
| 9 | Comp ID 54 | D7 | 5 | 0.43 |
| 10 | Comp ID 51 | D7 | 5 | 20 |
| 11 | Comp ID 53 | D7 | 5 | 22.5 |

Conclusions: Activity of the GalNAc conjugated compounds, measured as increase of the 2 marker genes ALDO A and BCKDK, showed dose dependency and comparable activity for the Tiny LNA and the poly-oligonucleotide compound. The unconjugated parent compounds (single Tiny and poly-oligonucleotide) also showed comparable activity dosed at 20 mg/kg (FIG. 21). The poly-oligonucleotide concept therefore offers improved cost of goods at same activity. It is likely that a poly-oligonucleotide approach could be beneficial when using a conjugate binding to a receptor class with limited expression or slower turnover than the Asialoglycoprotein-Receptor or when using a conjugate or receptor with impact on tolerability.

Example 14: GalNAc Conjugated LNA Antisense Oligonucleotides

Figure 10:
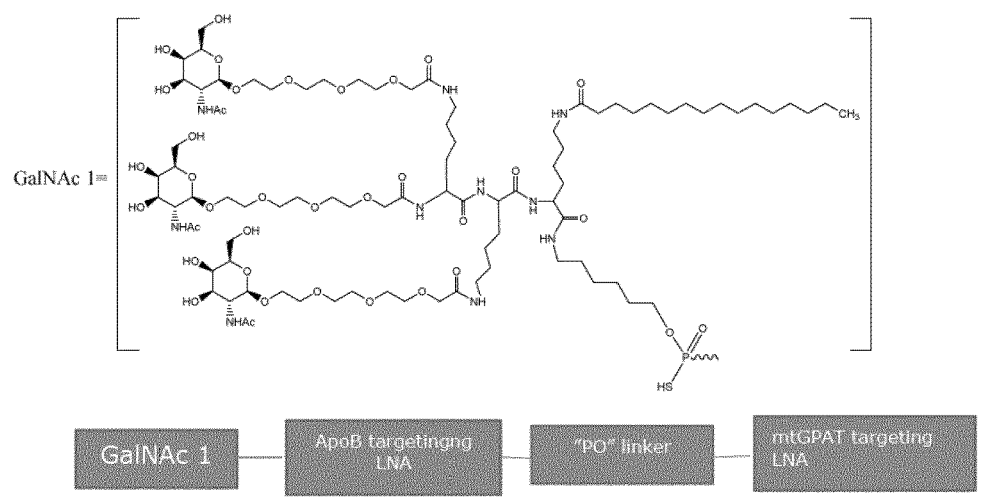
FIG. 10: The ApoB/mtGPAT targeting compound SEQ ID NO 55. Other conjugate moieties may be used, and alternative cleavable linker may be used, e.g. between the conjugate moiety and 5' of region 1, e.g. a PO linker which may comprise a region of 1, 2, 3, 4 or 5 phosphodiester linked DNA nucleosides. Note GalNAc 1 comprises the biocleavable dilysine linker.

Comp ID NO 55 is shown in FIG. 10, and has the structure: Trivalent GalNAc-5'-$G^L_sT^L_sT_sG_sA_sC_sA_sC_sT_sG_sT^L_s{}^{Me}C^L_sC_oA_oA^L_sT^L_sT^L_sC_sC_sC_sT_sG_sC_sC_sT_sG^L_sT^L_sG^L$-3' (SEQ ID NO 28). In this example GalNAc1 conjugate was used, but other conjugates as described herein may be used. Note a capital L superscript after a capital A, T, C or G represents a LNA nucleoside, otherwise nucleosides are DNA, subscript s is a phosphorothioate linkage, and a subscript O is a phosphodiester linkage.

Figure 11:
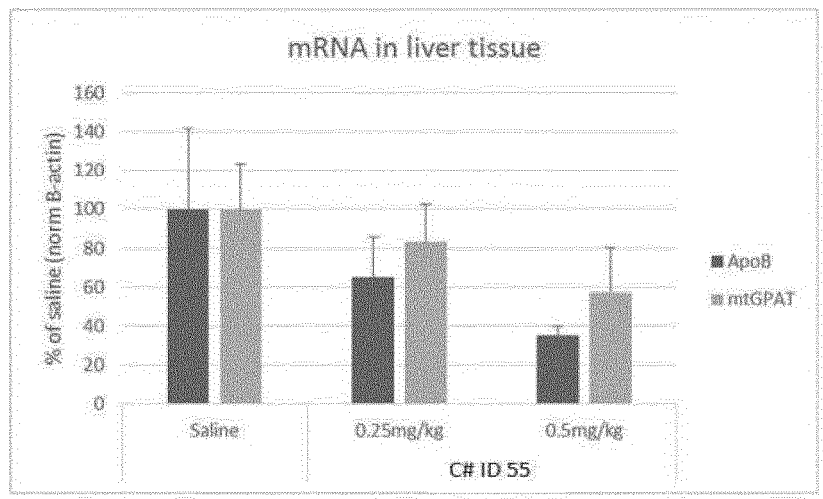
FIG. 11: Results obtained using a polyoligo GalNAc conjugate targeting both ApoB and mtGPAT in the liver of mice in vivo.

An in vivo mouse study was performed using a total of 3 groups of mice (n5, C57/bl). Each mouse was dosed i.v. on day 0 with either 0.25 mg/kg, or 0.5 mg/kg of the GalNAc conjugated poly LNA (Seq ID 55). A saline control group was included (see study set up in Table below). Liver and kidney samples were stored in RNA later. mRNA levels of the two targeted genes (ApoB and mtGPAT) were analyzed using standard QPCR assay techniques (FIG. 11).

| Study Set-up: | | | | |
|---|---|---|---|---|
| group | compound | termination time point post dose | group size | dose (d0) mg/kg |
| 1 | Saline | D4 | 5 | none |
| 2 | Comp ID 55 | D4 | 5 | 0.25 |
| 3 | Comp ID 55 | D4 | 5 | 0.5 |

Conclusions: GalNAc-poly LNA compound induced a down regulation of both targeted mRNA (ApoB and mtG-PAT). Moreover, a dose dependency was found. The poly-oligonucleotide concept therefore offers the possibility to attach multiple LNA's to one conjugate linked together via a cleavable linker and have activity on intended targets from all the LNA parent compounds linked together in the original construct. It is likely that a poly-oligonucleotide approach could be beneficial when using a conjugate binding to a receptor class with limited expression or slower turnover than the Asialoglycoprotein-Receptor or when using a conjugate or receptor with impact on tolerability.

The invention claimed is:

1. An oligomeric compound comprising
   a. a first region of a contiguous sequence of 7-26 phosphorothioate linked nucleosides (A);
   b. a second region of a contiguous sequence of 7-26 phosphorothioate linked nucleosides (A');
   c. 1-5 phosphodiester linked DNA nucleotides (B) which covalently links region A and A'; and
   d. a conjugate moiety (C) covalently linked to region A or A' by 1 5 phosphodiester linked DNA nucleotides;
   wherein the conjugate moiety comprises a trivalent GalNAc cluster.

2. The oligomeric compound according to claim 1, wherein the first region (A) and second region (A') are positioned 5' and 3' respectively to (B).

3. The oligomeric compound according to claim 1 wherein the contiguous sequence of nucleobases of A and A' the first and the second region are identical.

4. The oligomeric compound according to claim 1 wherein the contiguous sequence of nucleobases of A and A' are different.

5. The oligomeric compound according to claim 1 wherein the first and the second regions are targeted to the same nucleic acid target.

6. The oligomeric compound according to claim 1 wherein A and A' are targeted to different independent nucleic acid targets.

7. The oligomeric compound according to claim 1 wherein A and A' each comprise at least one LNA nucleoside.

8. The oligomeric compound according to claim 1 wherein A and A' are LNA gapmers.

9. The oligomeric compound according to claim 1 wherein the first and/or second region target mRNA targets.

10. The oligomeric compound according to claim 1 wherein A and/or A' target microRNA targets.

11. The oligomeric compound according to claim 1 wherein A and/or A' are mixmer or totalmer oligomers.

12. The oligomeric compound according to claim 1 wherein A and A' are 10-16 nucleotides in length.

13. The oligomeric compound according to claim 1 wherein A and A' are 8-10 nucleotides in length.

14. The oligomeric compound according to claim 1, wherein at least one or both of A and A' target a microRNA selected from the group consisting of microRNA ID NO 40-976.

15. The oligomeric compound according to claim 1 wherein A is complementary to human ApoB-100 mRNA nucleotide sequence and/or wherein A' is complementary to human mtGPAT mRNA nucleotide sequence.

16. The oligomeric compound according to claim 1, the second region (A') and first region (A) are positioned 5' and 3' respectively to (B).

17. The oligomeric compound according to claim 1, wherein A is positioned 3' of A'.

18. A pharmaceutical composition comprising the oligomeric compound according to claim 1, and a pharmaceutically acceptable diluent, carrier, salt or adjuvant.

* * * * *

SEQUENCE LISTING

<160> NUMBER OF SEQ ID NOS: 965

<210> SEQ ID NO 1
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(15)
<223> OTHER INFORMATION: LNA nucleosides at positions 1, 3, 6, 7, 10, 12, 14 & 15 LNA C are 5-methyl C

<400> SEQUENCE: 1
ccattgtcac actcc                                                   15

<210> SEQ ID NO 2
<211> LENGTH: 23
<212> TYPE: RNA
<213> ORGANISM: homo sapiens

<400> SEQUENCE: 2
uggaguguga caauguguu ugu                                           23

<210> SEQ ID NO 3
<211> LENGTH: 21
<212> TYPE: RNA
<213> ORGANISM: homo sapiens

<400> SEQUENCE: 3
gugcauugua guugcauugc a                                            21

<210> SEQ ID NO 4
<211> LENGTH: 20
<212> TYPE: RNA
<213> ORGANISM: homo sapiens

<400> SEQUENCE: 4
gugcauugcu guugcauugc                                              20

<210> SEQ ID NO 5
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(15)
<223> OTHER INFORMATION: LNA nucleosides at positions 1, 3, 4, 6, 7, 8, 10, 12, 14 & 15 LNA C are 5-methyl C

<400> SEQUENCE: 5
tcagtctgat aagct                                                   15

<210> SEQ ID NO 6
<211> LENGTH: 22
<212> TYPE: RNA
<213> ORGANISM: homo sapiens

-continued

<400> SEQUENCE: 6
uagcuuauca gacugauguu ga                                                22

<210> SEQ ID NO 7
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(15)
<223> OTHER INFORMATION: LNA nucleosides at positions 1, 3, 6, 7, 10,
      12, 14 & 15 LNA C are 5-methyl C

<400> SEQUENCE: 7
tcacgattag catta                                                        15

<210> SEQ ID NO 8
<211> LENGTH: 22
<212> TYPE: RNA
<213> ORGANISM: homo sapiens

<400> SEQUENCE: 8
gcuacauugu cugcugdgguu uc                                               22

<210> SEQ ID NO 9
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(13)
<223> OTHER INFORMATION: LNA nucleosides at positions 1, 2, 11 & 12 LNA
      C are 5-methyl C

<400> SEQUENCE: 9
gcattggtat tca                                                          13

<210> SEQ ID NO 10
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphorothioate lnternucleoside linkages
<220> FEATURE:
<221> NAME/KEY: misc_feature
<222> LOCATION: (1)..(12)
<223> OTHER INFORMATION: LNA nucleosides at positions 1, 2, 11 & 12 LNA
      C are 5-methyl C

<400> SEQUENCE: 10
gttgacactg tc                                                           12

```
<210> SEQ ID NO 11
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(14)
<223> OTHER INFORMATION: LNA nucleosides at positions 1, 2, 3, 12, 13 &
      14 LNA C are 5-methyl C

<400> SEQUENCE: 11
tgctacaaaa ccca                                                          14

<210> SEQ ID NO 12
<211> LENGTH: 85
<212> TYPE: RNA
<213> ORGANISM: homo sapiens

<400> SEQUENCE: 12
ccuuagcaga gcuguggagu gugacaaugg uguuuguguc uaaacuauca aacgccauua        60
ucacacuaaa uagcuacugc uaggc                                              85

<210> SEQ ID NO 13
<211> LENGTH: 22
<212> TYPE: RNA
<213> ORGANISM: homo sapiens

<400> SEQUENCE: 13
uggaguguga caauguguu ug                                                  22

<210> SEQ ID NO 14
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(14)
<223> OTHER INFORMATION: LNA nucleosides at positions 1, 2, 3, 12, 13 &
      14 LNA C are 5-methyl C

<400> SEQUENCE: 14
attccctgcc tgtg                                                          14

<210> SEQ ID NO 15
<211> LENGTH: 27
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(27)
<223> OTHER INFORMATION: phosphorothioate lnternucleoside linkages
<220> FEATURE:
<221> NAME/KEY: misc_feature
<222> LOCATION: (1)..(27)
<223> OTHER INFORMATION: LNA nucleosides at positions 1, 2, 11, 12, 15,
      16, 25, 26 & 27 LNA C are 5-methyl C
```

```
<220> FEATURE:
<221> NAME/KEY: misc_feature
<222> LOCATION: (1)..(1)
<223> OTHER INFORMATION: 5' trivalent PO linked GalNAc conjugate

<400> SEQUENCE: 15
gttgacactg tccagcattg gtattca                                              27

<210> SEQ ID NO 16
<211> LENGTH: 28
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(28)
<223> OTHER INFORMATION: phosphorothioate lnternucleoside linkages
<220> FEATURE:
<221> NAME/KEY: misc_feature
<222> LOCATION: (1)..(28)
<223> OTHER INFORMATION: LNA nucleosides at positions 1, 2, 11, 12, 13,
      16, 17, 26,  27 & 28 LNA C are 5-methyl C
<220> FEATURE:
<221> NAME/KEY: misc_feature
<222> LOCATION: (1)..(1)
<223> OTHER INFORMATION: 5' trivalent PO linked GalNAc conjugate

<400> SEQUENCE: 16
gcattggtat tcacagcatt ggtattca                                             28

<210> SEQ ID NO 17
<211> LENGTH: 26
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(26)
<223> OTHER INFORMATION: phosphorothioate lnternucleoside linkages
<220> FEATURE:
<221> NAME/KEY: misc_feature
<222> LOCATION: (1)..(26)
<223> OTHER INFORMATION: LNA nucleosides at positions 1, 2, 11, 12, 15,
      16, 17, 25 & 26 LNA C are 5-methyl C
<220> FEATURE:
<221> NAME/KEY: misc_feature
<222> LOCATION: (1)..(1)
<223> OTHER INFORMATION: 5' trivalent PO linked GalNAc conjugate

<400> SEQUENCE: 17
gttgacactg tccagttgac actgtc                                               26

<210> SEQ ID NO 18
<211> LENGTH: 27
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(27)
<223> OTHER INFORMATION: phosphorothioate lnternucleoside linkages
<220> FEATURE:
<221> NAME/KEY: misc_feature
<222> LOCATION: (1)..(27)
<223> OTHER INFORMATION: LNA nucleosides at positions 1, 2, 11, 12, 13,
      16, 17, 26 & 27 LNA C are 5-methyl C
<220> FEATURE:
<221> NAME/KEY: misc_feature
<222> LOCATION: (1)..(1)
<223> OTHER INFORMATION: 5' trivalent PO linked GalNAc conjugate
```

<400> SEQUENCE: 18
gcattggtat tcacagttga cactgtc                                27

<210> SEQ ID NO 19
<211> LENGTH: 28
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(28)
<223> OTHER INFORMATION: phosphorothioate lnternucleoside linkages
<220> FEATURE:
<221> NAME/KEY: misc_feature
<222> LOCATION: (1)..(28)
<223> OTHER INFORMATION: LNA nucleosides at positions 1, 2, 11, 12, 15,
      16, 17, 26, 27 & 28 LNA C are 5-methyl C
<220> FEATURE:
<221> NAME/KEY: misc_feature
<222> LOCATION: (1)..(1)
<223> OTHER INFORMATION: 5' trivalent PO linked GalNAc conjugate

<400> SEQUENCE: 19
gttgacactg tccaattccc tgcctgtg                               28

<210> SEQ ID NO 20
<211> LENGTH: 29
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(29)
<223> OTHER INFORMATION: phosphorothioate lnternucleoside linkages
<220> FEATURE:
<221> NAME/KEY: misc_feature
<222> LOCATION: (1)..(29)
<223> OTHER INFORMATION: LNA nucleosides at positions 1, 2, 11, 12, 13,
      16, 17, 18, 27, 28 & 29 LNA C are 5-methyl C
<220> FEATURE:
<221> NAME/KEY: misc_feature
<222> LOCATION: (1)..(1)
<223> OTHER INFORMATION: 5' trivalent PO linked GalNAc conjugate

<400> SEQUENCE: 20
gcattggtat tcacaattcc ctgcctgtg                              29

<210> SEQ ID NO 21
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(16)
<223> OTHER INFORMATION: LNA nucleosides at positions 4, 5, 14, 15 & 16
      LNA C are 5-methyl C
<220> FEATURE:
<221> NAME/KEY: misc_feature
<222> LOCATION: (1)..(1)
<223> OTHER INFORMATION: 5 FAM conjugate

<400> SEQUENCE: 21
tcagcattgg tattca                                            16

```
<210> SEQ ID NO 22
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(15)
<223> OTHER INFORMATION: LNA nucleosides at positions 3, 4, 13, 14 & 15
      LNA C are 5-methyl C
<220> FEATURE:
<221> NAME/KEY: misc_feature
<222> LOCATION: (1)..(1)
<223> OTHER INFORMATION: 5 FAM conjugate

<400> SEQUENCE: 22
cagcattggt attca                                                     15

<210> SEQ ID NO 23
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(14)
<223> OTHER INFORMATION: LNA nucleosides at positions 2, 3, 12, 13 & 14
      LNA C are 5-methyl C
<220> FEATURE:
<221> NAME/KEY: misc_feature
<222> LOCATION: (1)..(1)
<223> OTHER INFORMATION: 5 FAM conjugate

<400> SEQUENCE: 23
agcattggta ttca                                                      14

<210> SEQ ID NO 24
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(16)
<223> OTHER INFORMATION: LNA nucleosides at positions 4, 5, 14, 15 & 16
      LNA C are 5-methyl C
<220> FEATURE:
<221> NAME/KEY: misc_feature
<222> LOCATION: (1)..(1)
<223> OTHER INFORMATION: 5 FAM conjugate

<400> SEQUENCE: 24
gacgcattgg tattca                                                    16

<210> SEQ ID NO 25
<211> LENGTH: 13
```

```
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(13)
<223> OTHER INFORMATION: LNA nucleosides at positions 1, 2, 11, 12 & 13
      LNA C are 5-methyl C
<220> FEATURE:
<221> NAME/KEY: misc_feature
<222> LOCATION: (1)..(1)
<223> OTHER INFORMATION: 5 FAM conjugate

<400> SEQUENCE: 25
gcattggtat tca                                                        13

<210> SEQ ID NO 26
<211> LENGTH: 18
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(18)
<223> OTHER INFORMATION: phosphorothioate lnternucleoside linkages
<220> FEATURE:
<221> NAME/KEY: misc_feature
<222> LOCATION: (1)..(18)
<223> OTHER INFORMATION: LNA nucleosides at positions 1 -8, 11  18, LNA
      C are 5-methyl C
<400> SEQUENCE: 26
cacactccca cacactcc                                                   18

<210> SEQ ID NO 27
<211> LENGTH: 18
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(18)
<223> OTHER INFORMATION: phosphorothioate lnternucleoside linkages
<220> FEATURE:
<221> NAME/KEY: misc_feature
<222> LOCATION: (1)..(18)
<223> OTHER INFORMATION: LNA nucleosides at positions 1 -8, 11  18, LNA
      C are 5-methyl C
<220> FEATURE:
<221> NAME/KEY: misc_feature
<222> LOCATION: (1)..(1)
<223> OTHER INFORMATION: 5' trivalent PO linked GalNAc conjugate

<400> SEQUENCE: 27
cacactccca cacactcc                                                   18

<210> SEQ ID NO 28
<211> LENGTH: 28
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(28)
<223> OTHER INFORMATION: phosphorothioate lnternucleoside linkages
<220> FEATURE:
```

```
<221> NAME/KEY: misc_feature
<222> LOCATION: (1)..(28)
<223> OTHER INFORMATION: LNA nucleosides at positions 1, 2, 11, 12, 15,
      16, 17, 26, 27 & 28 LNA C are 5-methyl C
<220> FEATURE:
<221> NAME/KEY: misc_feature
<222> LOCATION: (1)..(1)
<223> OTHER INFORMATION: 5 trivalent PO linked GalNAc conjugate

<400> SEQUENCE: 28
gttgacactg tccaattccc tgcctgtg                                      28

<210> SEQ ID NO 29
<211> LENGTH: 22
<212> TYPE: RNA
<213> ORGANISM: homo sapiens

<400> SEQUENCE: 29
uagcaccgcu auccacuaug uc                                            22

<210> SEQ ID NO 30
<211> LENGTH: 24
<212> TYPE: RNA
<213> ORGANISM: homo sapiens

<400> SEQUENCE: 30
ucuuagugga agugacgugc ugug                                          24

<210> SEQ ID NO 31
<211> LENGTH: 23
<212> TYPE: RNA
<213> ORGANISM: homo sapiens

<400> SEQUENCE: 31
uacauaacca uggaguuggc ugu                                           23

<210> SEQ ID NO 32
<211> LENGTH: 22
<212> TYPE: RNA
<213> ORGANISM: homo sapiens

<400> SEQUENCE: 32
gccaccucuu ugguucugua ca                                            22

<210> SEQ ID NO 33
<211> LENGTH: 21
<212> TYPE: RNA
<213> ORGANISM: homo sapiens

<400> SEQUENCE: 33
acgcacacca ggcugacugc c                                             21

<210> SEQ ID NO 34
<211> LENGTH: 24
<212> TYPE: RNA
<213> ORGANISM: homo sapiens

<400> SEQUENCE: 34
ucagacaguu uggugcgcua guug                                          24

<210> SEQ ID NO 35
<211> LENGTH: 22
<212> TYPE: RNA
<213> ORGANISM: homo sapiens
```

-continued

```
<400> SEQUENCE: 35
uccuguggug uuuggugugg uu                                              22

<210> SEQ ID NO 36
<211> LENGTH: 23
<212> TYPE: RNA
<213> ORGANISM: homo sapiens

<400> SEQUENCE: 36
uguaacuugc cagggacggc uga                                             23

<210> SEQ ID NO 37
<211> LENGTH: 22
<212> TYPE: RNA
<213> ORGANISM: homo sapiens

<400> SEQUENCE: 37
aaccggcucg uggcucguac ag                                              22

<210> SEQ ID NO 38
<211> LENGTH: 22
<212> TYPE: RNA
<213> ORGANISM: homo sapiens

<400> SEQUENCE: 38
uaaaugcugc aguaguaggg au                                              22

<210> SEQ ID NO 39
<211> LENGTH: 22
<212> TYPE: RNA
<213> ORGANISM: homo sapiens

<400> SEQUENCE: 39
uacccuacgc ugccgauuua ca                                              22

<210> SEQ ID NO 40
<211> LENGTH: 22
<212> TYPE: RNA
<213> ORGANISM: homo sapiens

<400> SEQUENCE: 40
gucagugguu uguuuccuu ga                                               22

<210> SEQ ID NO 41
<211> LENGTH: 24
<212> TYPE: RNA
<213> ORGANISM: homo sapiens

<400> SEQUENCE: 41
uuagauagag ugggugugug cucu                                            24

<210> SEQ ID NO 42
<211> LENGTH: 23
<212> TYPE: RNA
<213> ORGANISM: homo sapiens

<400> SEQUENCE: 42
uguaugccug gugucccuu agu                                              23

<210> SEQ ID NO 43
<211> LENGTH: 22
<212> TYPE: RNA
<213> ORGANISM: homo sapiens
```

```
<400> SEQUENCE: 43
uaagaggacg caggcauaca ag                                          22

<210> SEQ ID NO 44
<211> LENGTH: 22
<212> TYPE: RNA
<213> ORGANISM: homo sapiens

<400> SEQUENCE: 44
uaucggaagu uugggcuucg uc                                          22

<210> SEQ ID NO 45
<211> LENGTH: 22
<212> TYPE: RNA
<213> ORGANISM: homo sapiens

<400> SEQUENCE: 45
ucaaguucgc acuuccuaua ca                                          22

<210> SEQ ID NO 46
<211> LENGTH: 21
<212> TYPE: RNA
<213> ORGANISM: homo sapiens

<400> SEQUENCE: 46
uuuuguuugc uugggaaugc u                                           21

<210> SEQ ID NO 47
<211> LENGTH: 23
<212> TYPE: RNA
<213> ORGANISM: homo sapiens

<400> SEQUENCE: 47 acauucccg caaacaugac aug                                          23

<210> SEQ ID NO 48
<211> LENGTH: 24
<212> TYPE: RNA
<213> ORGANISM: homo sapiens

<400> SEQUENCE: 48
aaggagcgau uuggagaaaa uaaa                                        24

<210> SEQ ID NO 49
<211> LENGTH: 22
<212> TYPE: RNA
<213> ORGANISM: homo sapiens

<400> SEQUENCE: 49
uauuuucugc auucgcccuu gc                                          22

<210> SEQ ID NO 50
<211> LENGTH: 22
<212> TYPE: RNA
<213> ORGANISM: homo sapiens

<400> SEQUENCE: 50
caugaaggca cagccuguua cc                                          22

<210> SEQ ID NO 51
<211> LENGTH: 21
<212> TYPE: RNA
```

<213> ORGANISM: homo sapiens

<400> SEQUENCE: 51
uagcaggcau gucuucauuc c                                              21

<210> SEQ ID NO 52
<211> LENGTH: 22
<212> TYPE: RNA
<213> ORGANISM: homo sapiens

<400> SEQUENCE: 52
cgcaccacua gucaccaggu gu                                             22

<210> SEQ ID NO 53
<211> LENGTH: 21
<212> TYPE: RNA
<213> ORGANISM: homo sapiens

<400> SEQUENCE: 53
accuaguguu aguuugugc u                                               21

<210> SEQ ID NO 54
<211> LENGTH: 22
<212> TYPE: RNA
<213> ORGANISM: homo sapiens

<400> SEQUENCE: 54
gaccugaugc ugcuggugug cu                                             22

<210> SEQ ID NO 55
<211> LENGTH: 24
<212> TYPE: RNA
<213> ORGANISM: homo sapiens

<400> SEQUENCE: 55
caaggugaau auagcugccc aucg                                           24

<210> SEQ ID NO 56
<211> LENGTH: 22
<212> TYPE: RNA
<213> ORGANISM: homo sapiens

<400> SEQUENCE: 56
cggggaucgg acuagccuua ga                                             22

<210> SEQ ID NO 57
<211> LENGTH: 22
<212> TYPE: RNA
<213> ORGANISM: homo sapiens

<400> SEQUENCE: 57
uaagguuggu ccaauccaua gg                                             22

<210> SEQ ID NO 58
<211> LENGTH: 22
<212> TYPE: RNA
<213> ORGANISM: homo sapiens

<400> SEQUENCE: 58
caucauaguc caguguccag gg                                             22

<210> SEQ ID NO 59
<211> LENGTH: 22

```
<212> TYPE: RNA
<213> ORGANISM: homo sapiens

<400> SEQUENCE: 59
ccuggaccuu gacuaugaaa ca                                          22

<210> SEQ ID NO 60
<211> LENGTH: 22
<212> TYPE: RNA
<213> ORGANISM: homo sapiens

<400> SEQUENCE: 60
uacgguuucc uagauuguac ag                                          22

<210> SEQ ID NO 61
<211> LENGTH: 23
<212> TYPE: RNA
<213> ORGANISM: homo sapiens

<400> SEQUENCE: 61
gucacaaucu augggucgu aga                                          23

<210> SEQ ID NO 62
<211> LENGTH: 23
<212> TYPE: RNA
<213> ORGANISM: homo sapiens

<400> SEQUENCE: 62
uaacacuuca uggucccgu agu                                          23

<210> SEQ ID NO 63
<211> LENGTH: 22
<212> TYPE: RNA
<213> ORGANISM: homo sapiens

<400> SEQUENCE: 63
uacuggaccc ugaauuggaa ac                                          22

<210> SEQ ID NO 64
<211> LENGTH: 22
<212> TYPE: RNA
<213> ORGANISM: homo sapiens

<400> SEQUENCE: 64
uaaccugauc agccccggag uu                                          22

<210> SEQ ID NO 65
<211> LENGTH: 22
<212> TYPE: RNA
<213> ORGANISM: homo sapiens

<400> SEQUENCE: 65
uaucuuuugc ggcagaaauu ga                                          22

<210> SEQ ID NO 66
<211> LENGTH: 22
<212> TYPE: RNA
<213> ORGANISM: homo sapiens

<400> SEQUENCE: 66
aaauucuguu gcagcagaua gc                                          22

<210> SEQ ID NO 67
```

```
<211> LENGTH: 22
<212> TYPE: RNA
<213> ORGANISM: homo sapiens

<400> SEQUENCE: 67
uaacgggaag uguguaagca ca                                              22

<210> SEQ ID NO 68
<211> LENGTH: 22
<212> TYPE: RNA
<213> ORGANISM: homo sapiens

<400> SEQUENCE: 68
aagugacggu gagauccagg cu                                              22

<210> SEQ ID NO 69
<211> LENGTH: 21
<212> TYPE: RNA
<213> ORGANISM: homo sapiens

<400> SEQUENCE: 69
ucguccuccc cuucuucacc g                                               21

<210> SEQ ID NO 70
<211> LENGTH: 20
<212> TYPE: RNA
<213> ORGANISM: homo sapiens

<400> SEQUENCE: 70
uaacuagccu ucccgugaga                                                 20

<210> SEQ ID NO 71
<211> LENGTH: 22
<212> TYPE: RNA
<213> ORGANISM: homo sapiens

<400> SEQUENCE: 71
ucaccagaau gcuaguuugu ag                                              22

<210> SEQ ID NO 72
<211> LENGTH: 22
<212> TYPE: RNA
<213> ORGANISM: homo sapiens

<400> SEQUENCE: 72
ucguugaaga caccuggaaa ga                                              22

<210> SEQ ID NO 73
<211> LENGTH: 22
<212> TYPE: RNA
<213> ORGANISM: homo sapiens

<400> SEQUENCE: 73
uuuccaggug uuuucaacgu gc                                              22

<210> SEQ ID NO 74
<211> LENGTH: 20
<212> TYPE: RNA
<213> ORGANISM: homo sapiens

<400> SEQUENCE: 74
ggggaugggc uggcgcgcgg                                                 20
```

```
<210> SEQ ID NO 75
<211> LENGTH: 21
<212> TYPE: RNA
<213> ORGANISM: homo sapiens

<400> SEQUENCE: 75
ugcgucucgg ccucguccag a                                              21

<210> SEQ ID NO 76
<211> LENGTH: 21
<212> TYPE: RNA
<213> ORGANISM: homo sapiens

<400> SEQUENCE: 76
aaccgcucag uggcucggac c                                              21

<210> SEQ ID NO 77
<211> LENGTH: 22
<212> TYPE: RNA
<213> ORGANISM: homo sapiens

<400> SEQUENCE: 77
uccgaacgcu aggucgguuc uc                                             22

<210> SEQ ID NO 78
<211> LENGTH: 23
<212> TYPE: RNA
<213> ORGANISM: homo sapiens

<400> SEQUENCE: 78
auccacuugg agagcucccg cgg                                            23

<210> SEQ ID NO 79
<211> LENGTH: 22
<212> TYPE: RNA
<213> ORGANISM: homo sapiens

<400> SEQUENCE: 79
agcggucugu ucagguggau ga                                             22

<210> SEQ ID NO 80
<211> LENGTH: 20
<212> TYPE: RNA
<213> ORGANISM: homo sapiens

<400> SEQUENCE: 80
ucacggaccg agcacaucca                                                20

<210> SEQ ID NO 81
<211> LENGTH: 22
<212> TYPE: RNA
<213> ORGANISM: homo sapiens

<400> SEQUENCE: 81
gauugugccc ggaccgugggg cg                                            22

<210> SEQ ID NO 82
<211> LENGTH: 22
<212> TYPE: RNA
<213> ORGANISM: homo sapiens

<400> SEQUENCE: 82
cgacauggac gugcaggggg au                                             22
```

```
<210> SEQ ID NO 83
<211> LENGTH: 21
<212> TYPE: RNA
<213> ORGANISM: homo sapiens

<400> SEQUENCE: 83
ugacaagccu gacgagagcg u                                          21

<210> SEQ ID NO 84
<211> LENGTH: 22
<212> TYPE: RNA
<213> ORGANISM: homo sapiens

<400> SEQUENCE: 84
uuaugauagg ugugacgaug uc                                         22

<210> SEQ ID NO 85
<211> LENGTH: 22
<212> TYPE: RNA
<213> ORGANISM: homo sapiens

<400> SEQUENCE: 85
ugagguagua gguuguauag uu                                         22

<210> SEQ ID NO 86
<211> LENGTH: 21
<212> TYPE: RNA
<213> ORGANISM: homo sapiens

<400> SEQUENCE: 86
cuauacaauc uacugucuuu c                                          21

<210> SEQ ID NO 87
<211> LENGTH: 22
<212> TYPE: RNA
<213> ORGANISM: homo sapiens

<400> SEQUENCE: 87
ugagguagua gguugugugg uu                                         22

<210> SEQ ID NO 88
<211> LENGTH: 22
<212> TYPE: RNA
<213> ORGANISM: homo sapiens

<400> SEQUENCE: 88
cuauacaacc uacugccuuc cc                                         22

<210> SEQ ID NO 89
<211> LENGTH: 22
<212> TYPE: RNA
<213> ORGANISM: homo sapiens

<400> SEQUENCE: 89
ugagguagua gguuguaugg uu                                         22

<210> SEQ ID NO 90
<211> LENGTH: 22
<212> TYPE: RNA
<213> ORGANISM: homo sapiens

<400> SEQUENCE: 90
uagaguuaca cccugggagu ua                                         22
```

```
<210> SEQ ID NO 91
<211> LENGTH: 22
<212> TYPE: RNA
<213> ORGANISM: homo sapiens

<400> SEQUENCE: 91
agagguagua gguugcauag uu                                              22

<210> SEQ ID NO 92
<211> LENGTH: 22
<212> TYPE: RNA
<213> ORGANISM: homo sapiens

<400> SEQUENCE: 92
cuauacgacc ugcugccuuu cu                                              22

<210> SEQ ID NO 93
<211> LENGTH: 22
<212> TYPE: RNA
<213> ORGANISM: homo sapiens

<400> SEQUENCE: 93
ugagguagga gguuguauag uu                                              22

<210> SEQ ID NO 94
<211> LENGTH: 22
<212> TYPE: RNA
<213> ORGANISM: homo sapiens

<400> SEQUENCE: 94
cuauacggcc uccuagcuuu cc                                              22

<210> SEQ ID NO 95
<211> LENGTH: 22
<212> TYPE: RNA
<213> ORGANISM: homo sapiens

<400> SEQUENCE: 95
ugagguagua gauuguauag uu                                              22

<210> SEQ ID NO 96
<211> LENGTH: 22
<212> TYPE: RNA
<213> ORGANISM: homo sapiens

<400> SEQUENCE: 96
cuauacaauc uauugccuuc cc                                              22

<210> SEQ ID NO 97
<211> LENGTH: 22
<212> TYPE: RNA
<213> ORGANISM: homo sapiens

<400> SEQUENCE: 97
cuauacaguc uacugucuuu cc                                              22

<210> SEQ ID NO 98
<211> LENGTH: 22
<212> TYPE: RNA
<213> ORGANISM: homo sapiens

<400> SEQUENCE: 98
```
ugagguagua guuuguacag uu                    22

<210> SEQ ID NO 99
<211> LENGTH: 21
<212> TYPE: RNA
<213> ORGANISM: homo sapiens

<400> SEQUENCE: 99 cguacaggc cacugccuug c                     21

<210> SEQ ID NO 100
<211> LENGTH: 22
<212> TYPE: RNA
<213> ORGANISM: homo sapiens

<400> SEQUENCE: 100
ugagguagua guuugugcug uu                    22

<210> SEQ ID NO 101
<211> LENGTH: 22
<212> TYPE: RNA
<213> ORGANISM: homo sapiens

<400> SEQUENCE: 101
cugcgcaagc uacugccuug cu                    22

<210> SEQ ID NO 102
<211> LENGTH: 22
<212> TYPE: RNA
<213> ORGANISM: homo sapiens

<400> SEQUENCE: 102
uggaauguaa agaaguaugu au                    22

<210> SEQ ID NO 103
<211> LENGTH: 22
<212> TYPE: RNA
<213> ORGANISM: homo sapiens

<400> SEQUENCE: 103
aacccguaga uccgaacuug ug                    22

<210> SEQ ID NO 104
<211> LENGTH: 22
<212> TYPE: RNA
<213> ORGANISM: homo sapiens

<400> SEQUENCE: 104
caagcuugua ucuauaggua ug                    22

<210> SEQ ID NO 105
<211> LENGTH: 21
<212> TYPE: RNA
<213> ORGANISM: homo sapiens

<400> SEQUENCE: 105
uacaguacug ugauaacuga a                     21

<210> SEQ ID NO 106
<211> LENGTH: 22
<212> TYPE: RNA
<213> ORGANISM: homo sapiens

<400> SEQUENCE: 106

```
caguuaucac agugcugaug cu                                              22

<210> SEQ ID NO 107
<211> LENGTH: 23
<212> TYPE: RNA
<213> ORGANISM: homo sapiens

<400> SEQUENCE: 107
agcagcauug uacagggcua uga                                             23

<210> SEQ ID NO 108
<211> LENGTH: 23
<212> TYPE: RNA
<213> ORGANISM: homo sapiens

<400> SEQUENCE: 108
ucauagcccu guacaaugcu gcu                                             23

<210> SEQ ID NO 109
<211> LENGTH: 23
<212> TYPE: RNA
<213> ORGANISM: homo sapiens

<400> SEQUENCE: 109
ucaaaugcuc agacuccugu ggu                                             23

<210> SEQ ID NO 110
<211> LENGTH: 22
<212> TYPE: RNA
<213> ORGANISM: homo sapiens

<400> SEQUENCE: 110
acggauguuu gagcaugugc ua                                              22

<210> SEQ ID NO 111
<211> LENGTH: 23
<212> TYPE: RNA
<213> ORGANISM: homo sapiens

<400> SEQUENCE: 111
aaaagugcuu acagugcagg uag                                             23

<210> SEQ ID NO 112
<211> LENGTH: 22
<212> TYPE: RNA
<213> ORGANISM: homo sapiens

<400> SEQUENCE: 112
cugcaaugua agcacuucuu ac                                              22

<210> SEQ ID NO 113
<211> LENGTH: 21
<212> TYPE: RNA
<213> ORGANISM: homo sapiens

<400> SEQUENCE: 113
uaaagugcug acagugcaga u                                               21

<210> SEQ ID NO 114
<211> LENGTH: 22
<212> TYPE: RNA
<213> ORGANISM: homo sapiens
```

```
<400> SEQUENCE: 114
ccgcacugug gguacuugcu gc                                              22

<210> SEQ ID NO 115
<211> LENGTH: 23
<212> TYPE: RNA
<213> ORGANISM: homo sapiens

<400> SEQUENCE: 115
agcagcauug uacagggcua uca                                             23

<210> SEQ ID NO 116
<211> LENGTH: 23
<212> TYPE: RNA
<213> ORGANISM: homo sapiens

<400> SEQUENCE: 116
uacccuguag auccgaauuu gug                                             23

<210> SEQ ID NO 117
<211> LENGTH: 22
<212> TYPE: RNA
<213> ORGANISM: homo sapiens

<400> SEQUENCE: 117
caaauucgua ucuagggaa ua                                               22

<210> SEQ ID NO 118
<211> LENGTH: 23
<212> TYPE: RNA
<213> ORGANISM: homo sapiens

<400> SEQUENCE: 118
uacccuguag aaccgaauuu gug                                             23

<210> SEQ ID NO 119
<211> LENGTH: 22
<212> TYPE: RNA
<213> ORGANISM: homo sapiens

<400> SEQUENCE: 119
acagauucga uucuagggga au                                              22

<210> SEQ ID NO 120
<211> LENGTH: 21
<212> TYPE: RNA
<213> ORGANISM: homo sapiens

<400> SEQUENCE: 120
uugcucacug uucuucccua g                                               21

<210> SEQ ID NO 121
<211> LENGTH: 21
<212> TYPE: RNA
<213> ORGANISM: homo sapiens

<400> SEQUENCE: 121
aagcauucuu ucauugguug g                                               21

<210> SEQ ID NO 122
<211> LENGTH: 22
<212> TYPE: RNA
<213> ORGANISM: homo sapiens
```

-continued

```
<400> SEQUENCE: 122
uuuccggcuc gcguggugu gu                                    22

<210> SEQ ID NO 123
<211> LENGTH: 21
<212> TYPE: RNA
<213> ORGANISM: homo sapiens

<400> SEQUENCE: 123
ccgucgccgc cacccgagcc g                                    21

<210> SEQ ID NO 124
<211> LENGTH: 23
<212> TYPE: RNA
<213> ORGANISM: homo sapiens

<400> SEQUENCE: 124
gagggucuug ggagggaugu gac                                  23

<210> SEQ ID NO 125
<211> LENGTH: 27
<212> TYPE: RNA
<213> ORGANISM: homo sapiens

<400> SEQUENCE: 125
cacuguaggu gauggugaga gugggca                              27

<210> SEQ ID NO 126
<211> LENGTH: 23
<212> TYPE: RNA
<213> ORGANISM: homo sapiens

<400> SEQUENCE: 126
ccugcagcga cuugauggcu ucc                                  23

<210> SEQ ID NO 127
<211> LENGTH: 21
<212> TYPE: RNA
<213> ORGANISM: homo sapiens

<400> SEQUENCE: 127
agaggauacc cuuuguaugu u                                    21

<210> SEQ ID NO 128
<211> LENGTH: 21
<212> TYPE: RNA
<213> ORGANISM: homo sapiens

<400> SEQUENCE: 128
uaggacacau ggucuacuuc u                                    21

<210> SEQ ID NO 129
<211> LENGTH: 22
<212> TYPE: RNA
<213> ORGANISM: homo sapiens

<400> SEQUENCE: 129
cuccugagcc auucugagcc uc                                   22

<210> SEQ ID NO 130
<211> LENGTH: 24
<212> TYPE: RNA
```

```
<213> ORGANISM: homo sapiens

<400> SEQUENCE: 130
agccugauua aacacaugcu cuga                                  24

<210> SEQ ID NO 131
<211> LENGTH: 21
<212> TYPE: RNA
<213> ORGANISM: homo sapiens

<400> SEQUENCE: 131
gugccagcug caguggggga g                                     21

<210> SEQ ID NO 132
<211> LENGTH: 21
<212> TYPE: RNA
<213> ORGANISM: homo sapiens

<400> SEQUENCE: 132
cccggagcca ggaugcagcu c                                     21

<210> SEQ ID NO 133
<211> LENGTH: 21
<212> TYPE: RNA
<213> ORGANISM: homo sapiens

<400> SEQUENCE: 133
ucguggccug gucuccauua u                                     21

<210> SEQ ID NO 134
<211> LENGTH: 20
<212> TYPE: RNA
<213> ORGANISM: homo sapiens

<400> SEQUENCE: 134
ucugcagggu uugcuuugag                                       20

<210> SEQ ID NO 135
<211> LENGTH: 21
<212> TYPE: RNA
<213> ORGANISM: homo sapiens

<400> SEQUENCE: 135
uguucaugua gauguuuaag c                                     21

<210> SEQ ID NO 136
<211> LENGTH: 18
<212> TYPE: RNA
<213> ORGANISM: homo sapiens

<400> SEQUENCE: 136
ucagcuggcc cucauuuc                                         18

<210> SEQ ID NO 137
<211> LENGTH: 21
<212> TYPE: RNA
<213> ORGANISM: homo sapiens

<400> SEQUENCE: 137
uggcagggag gcugggaggg g                                     21

<210> SEQ ID NO 138
<211> LENGTH: 20
```

```
<212> TYPE: RNA
<213> ORGANISM: homo sapiens

<400> SEQUENCE: 138
ucacuguuca gacaggcgga                                               20

<210> SEQ ID NO 139
<211> LENGTH: 22
<212> TYPE: RNA
<213> ORGANISM: homo sapiens

<400> SEQUENCE: 139
uggaguguga caauguguu ug                                             22

<210> SEQ ID NO 140
<211> LENGTH: 22
<212> TYPE: RNA
<213> ORGANISM: homo sapiens

<400> SEQUENCE: 140
aacgccauua ucacacuaaa ua                                            22

<210> SEQ ID NO 141
<211> LENGTH: 21
<212> TYPE: RNA
<213> ORGANISM: homo sapiens

<400> SEQUENCE: 141
ccccaccucc ucucuccuca g                                             21

<210> SEQ ID NO 142
<211> LENGTH: 19
<212> TYPE: RNA
<213> ORGANISM: homo sapiens

<400> SEQUENCE: 142
gugaggacuc gggaggugg                                                19

<210> SEQ ID NO 143
<211> LENGTH: 22
<212> TYPE: RNA
<213> ORGANISM: homo sapiens

<400> SEQUENCE: 143
ugagccccug ugccgccccc ag                                            22

<210> SEQ ID NO 144
<211> LENGTH: 22
<212> TYPE: RNA
<213> ORGANISM: homo sapiens

<400> SEQUENCE: 144
guggguacgg cccagugggg gg                                            22

<210> SEQ ID NO 145
<211> LENGTH: 22
<212> TYPE: RNA
<213> ORGANISM: homo sapiens

<400> SEQUENCE: 145
ucaccagccc uguguucccu ag                                            22

<210> SEQ ID NO 146
```

```
<211> LENGTH: 26
<212> TYPE: RNA
<213> ORGANISM: homo sapiens

<400> SEQUENCE: 146
gugagggcau gcaggccugg augggg                                        26

<210> SEQ ID NO 147
<211> LENGTH: 20
<212> TYPE: RNA
<213> ORGANISM: homo sapiens

<400> SEQUENCE: 147
cgugccaccc uuuucccag                                                20

<210> SEQ ID NO 148
<211> LENGTH: 20
<212> TYPE: RNA
<213> ORGANISM: homo sapiens

<400> SEQUENCE: 148
ucacaccugc cucgccccccc                                              20

<210> SEQ ID NO 149
<211> LENGTH: 21
<212> TYPE: RNA
<213> ORGANISM: homo sapiens

<400> SEQUENCE: 149
gugggcgggg gcaggugugu g                                             21

<210> SEQ ID NO 150
<211> LENGTH: 23
<212> TYPE: RNA
<213> ORGANISM: homo sapiens

<400> SEQUENCE: 150
cucucaccac ugcccuccca cag                                           23

<210> SEQ ID NO 151
<211> LENGTH: 20
<212> TYPE: RNA
<213> ORGANISM: homo sapiens

<400> SEQUENCE: 151
gugucugggc ggacagcugc                                               20

<210> SEQ ID NO 152
<211> LENGTH: 20
<212> TYPE: RNA
<213> ORGANISM: homo sapiens

<400> SEQUENCE: 152
ugagcccugu ccucccgcag                                               20

<210> SEQ ID NO 153
<211> LENGTH: 22
<212> TYPE: RNA
<213> ORGANISM: homo sapiens

<400> SEQUENCE: 153
ucggccugac cacccacccc ac                                            22
```

```
<210> SEQ ID NO 154
<211> LENGTH: 22
<212> TYPE: RNA
<213> ORGANISM: homo sapiens

<400> SEQUENCE: 154
ccucuucccc uugucucucc ag                                              22

<210> SEQ ID NO 155
<211> LENGTH: 21
<212> TYPE: RNA
<213> ORGANISM: homo sapiens

<400> SEQUENCE: 155
uccuucugcu ccguccccca g                                               21

<210> SEQ ID NO 156
<211> LENGTH: 20
<212> TYPE: RNA
<213> ORGANISM: homo sapiens

<400> SEQUENCE: 156
cuuccucguc ugucugcccc                                                 20

<210> SEQ ID NO 157
<211> LENGTH: 20
<212> TYPE: RNA
<213> ORGANISM: homo sapiens

<400> SEQUENCE: 157
uaaggcacgc ggugaaugcc                                                 20

<210> SEQ ID NO 158
<211> LENGTH: 22
<212> TYPE: RNA
<213> ORGANISM: homo sapiens

<400> SEQUENCE: 158
cguguucaca gcggaccuug au                                              22

<210> SEQ ID NO 159
<211> LENGTH: 22
<212> TYPE: RNA
<213> ORGANISM: homo sapiens

<400> SEQUENCE: 159
aacuggauca auuauaggag ug                                              22

<210> SEQ ID NO 160
<211> LENGTH: 26
<212> TYPE: RNA
<213> ORGANISM: homo sapiens

<400> SEQUENCE: 160
aaguaguugg uuuguaugag augguu                                          26

<210> SEQ ID NO 161
<211> LENGTH: 21
<212> TYPE: RNA
<213> ORGANISM: homo sapiens

<400> SEQUENCE: 161
aagugaucua aaggccuaca u                                               21
```

```
<210> SEQ ID NO 162
<211> LENGTH: 19
<212> TYPE: RNA
<213> ORGANISM: homo sapiens

<400> SEQUENCE: 162
aauggauuuu uggagcagg                                            19

<210> SEQ ID NO 163
<211> LENGTH: 22
<212> TYPE: RNA
<213> ORGANISM: homo sapiens

<400> SEQUENCE: 163
acccgucccg uucguccccg ga                                        22

<210> SEQ ID NO 164
<211> LENGTH: 27
<212> TYPE: RNA
<213> ORGANISM: homo sapiens

<400> SEQUENCE: 164
accuucuugu auaagcacug ugcuaaa                                   27

<210> SEQ ID NO 165
<211> LENGTH: 22
<212> TYPE: RNA
<213> ORGANISM: homo sapiens

<400> SEQUENCE: 165
acgcccuucc cccccuucuu ca                                        22

<210> SEQ ID NO 166
<211> LENGTH: 21
<212> TYPE: RNA
<213> ORGANISM: homo sapiens

<400> SEQUENCE: 166
acggugcugg auguggccuu u                                         21

<210> SEQ ID NO 167
<211> LENGTH: 21
<212> TYPE: RNA
<213> ORGANISM: homo sapiens

<400> SEQUENCE: 167
acucuagcug ccaaaggcgc u                                         21

<210> SEQ ID NO 168
<211> LENGTH: 22
<212> TYPE: RNA
<213> ORGANISM: homo sapiens

<400> SEQUENCE: 168
agaaggaaau ugaauucauu ua                                        22

<210> SEQ ID NO 169
<211> LENGTH: 21
<212> TYPE: RNA
<213> ORGANISM: homo sapiens

<400> SEQUENCE: 169
agagaagaag aucagccugc a                                         21
```

```
<210> SEQ ID NO 170
<211> LENGTH: 24
<212> TYPE: RNA
<213> ORGANISM: homo sapiens

<400> SEQUENCE: 170
agccuggaag cuggagccug cagu                                          24

<210> SEQ ID NO 171
<211> LENGTH: 23
<212> TYPE: RNA
<213> ORGANISM: homo sapiens

<400> SEQUENCE: 171
aggaugagca aagaaaguag auu                                           23

<210> SEQ ID NO 172
<211> LENGTH: 22
<212> TYPE: RNA
<213> ORGANISM: homo sapiens

<400> SEQUENCE: 172
cggaugagca aagaaagugg uu                                            22

<210> SEQ ID NO 173
<211> LENGTH: 22
<212> TYPE: RNA
<213> ORGANISM: homo sapiens

<400> SEQUENCE: 173
aggcauugac uucucacuag cu                                            22

<210> SEQ ID NO 174
<211> LENGTH: 21
<212> TYPE: RNA
<213> ORGANISM: homo sapiens

<400> SEQUENCE: 174
agugaaugau ggguucugac c                                             21

<210> SEQ ID NO 175
<211> LENGTH: 21
<212> TYPE: RNA
<213> ORGANISM: homo sapiens

<400> SEQUENCE: 175
aguuaggauu aggucgugga a                                             21

<210> SEQ ID NO 176
<211> LENGTH: 21
<212> TYPE: RNA
<213> ORGANISM: homo sapiens

<400> SEQUENCE: 176
auauaugaug acuuagcuuu u                                             21

<210> SEQ ID NO 177
<211> LENGTH: 22
<212> TYPE: RNA
<213> ORGANISM: homo sapiens

<400> SEQUENCE: 177
```
acaggugagg uucuugggag cc                                              22

<210> SEQ ID NO 178
<211> LENGTH: 24
<212> TYPE: RNA
<213> ORGANISM: homo sapiens

<400> SEQUENCE: 178
ucccugagac ccuuuaaccu guga                                            24

<210> SEQ ID NO 179
<211> LENGTH: 22
<212> TYPE: RNA
<213> ORGANISM: homo sapiens

<400> SEQUENCE: 179
ucccugagac ccuaacuugu ga                                              22

<210> SEQ ID NO 180
<211> LENGTH: 22
<212> TYPE: RNA
<213> ORGANISM: homo sapiens

<400> SEQUENCE: 180
acggguuagg cucuugggag cu                                              22

<210> SEQ ID NO 181
<211> LENGTH: 22
<212> TYPE: RNA
<213> ORGANISM: homo sapiens

<400> SEQUENCE: 181
ucacaaguca ggcucuuggg ac                                              22

<210> SEQ ID NO 182
<211> LENGTH: 22
<212> TYPE: RNA
<213> ORGANISM: homo sapiens

<400> SEQUENCE: 182
ucguaccgug aguaauaaug cg                                              22

<210> SEQ ID NO 183
<211> LENGTH: 21
<212> TYPE: RNA
<213> ORGANISM: homo sapiens

<400> SEQUENCE: 183
cauuauuacu uuugguacgc g                                               21

<210> SEQ ID NO 184
<211> LENGTH: 18
<212> TYPE: RNA
<213> ORGANISM: homo sapiens

<400> SEQUENCE: 184
aucccaccuc ugccacca                                                   18

<210> SEQ ID NO 185
<211> LENGTH: 19
<212> TYPE: RNA
<213> ORGANISM: homo sapiens

<400> SEQUENCE: 185

-continued auggauaagg cuuuggcuu    19

<210> SEQ ID NO 186
<211> LENGTH: 22
<212> TYPE: RNA
<213> ORGANISM: homo sapiens

<400> SEQUENCE: 186
augggugaau uuguagaagg au    22

<210> SEQ ID NO 187
<211> LENGTH: 22
<212> TYPE: RNA
<213> ORGANISM: homo sapiens

<400> SEQUENCE: 187
augguacccu ggcauacuga gu    22

<210> SEQ ID NO 188
<211> LENGTH: 23
<212> TYPE: RNA
<213> ORGANISM: homo sapiens

<400> SEQUENCE: 188
caagucuuau uugagcaccu guu    23

<210> SEQ ID NO 189
<211> LENGTH: 22
<212> TYPE: RNA
<213> ORGANISM: homo sapiens

<400> SEQUENCE: 189
caggaugugg ucaaguguug uu    22

<210> SEQ ID NO 190
<211> LENGTH: 23
<212> TYPE: RNA
<213> ORGANISM: homo sapiens

<400> SEQUENCE: 190
ccucagggcu guagaacagg gcu    23

<210> SEQ ID NO 191
<211> LENGTH: 21
<212> TYPE: RNA
<213> ORGANISM: homo sapiens

<400> SEQUENCE: 191
ccuguugaag uguaaucccc a    21

<210> SEQ ID NO 192
<211> LENGTH: 18
<212> TYPE: RNA
<213> ORGANISM: homo sapiens

<400> SEQUENCE: 192
cgggcguggu ggugggg    18

<210> SEQ ID NO 193
<211> LENGTH: 22
<212> TYPE: RNA
<213> ORGANISM: homo sapiens

```
<400> SEQUENCE: 193
cuggacugag ccgugcuacu gg                                              22

<210> SEQ ID NO 194
<211> LENGTH: 22
<212> TYPE: RNA
<213> ORGANISM: homo sapiens

<400> SEQUENCE: 194
ucggauccgu cugagcuugg cu                                              22

<210> SEQ ID NO 195
<211> LENGTH: 22
<212> TYPE: RNA
<213> ORGANISM: homo sapiens

<400> SEQUENCE: 195
cugaagcuca gagggcucug au                                              22

<210> SEQ ID NO 196
<211> LENGTH: 23
<212> TYPE: RNA
<213> ORGANISM: homo sapiens

<400> SEQUENCE: 196
cuggagauau ggaagagcug ugu                                             23

<210> SEQ ID NO 197
<211> LENGTH: 22
<212> TYPE: RNA
<213> ORGANISM: homo sapiens

<400> SEQUENCE: 197
cuuggcaccu agcaagcacu ca                                              22

<210> SEQ ID NO 198
<211> LENGTH: 26
<212> TYPE: RNA
<213> ORGANISM: homo sapiens

<400> SEQUENCE: 198
gaugaugaug gcagcaaauu cugaaa                                          26

<210> SEQ ID NO 199
<211> LENGTH: 25
<212> TYPE: RNA
<213> ORGANISM: homo sapiens

<400> SEQUENCE: 199
gggcgacaaa gcaagacucu uucuu                                           25

<210> SEQ ID NO 200
<211> LENGTH: 18
<212> TYPE: RNA
<213> ORGANISM: homo sapiens

<400> SEQUENCE: 200
gucccuguuc aggcgcca                                                   18

<210> SEQ ID NO 201
<211> LENGTH: 17
<212> TYPE: RNA
<213> ORGANISM: homo sapiens
```

```
<400> SEQUENCE: 201
ucccuguucg ggcgcca                                              17

<210> SEQ ID NO 202
<211> LENGTH: 17
<212> TYPE: RNA
<213> ORGANISM: homo sapiens

<400> SEQUENCE: 202 guggggaga ggcuguc                                               17

<210> SEQ ID NO 203
<211> LENGTH: 20
<212> TYPE: RNA
<213> ORGANISM: homo sapiens

<400> SEQUENCE: 203
uaaagagccc uguggagaca                                           20

<210> SEQ ID NO 204
<211> LENGTH: 22
<212> TYPE: RNA
<213> ORGANISM: homo sapiens

<400> SEQUENCE: 204
uacguagaua uauauguauu uu                                        22

<210> SEQ ID NO 205
<211> LENGTH: 22
<212> TYPE: RNA
<213> ORGANISM: homo sapiens

<400> SEQUENCE: 205
uaguacugug cauaucaucu au                                        22

<210> SEQ ID NO 206
<211> LENGTH: 17
<212> TYPE: RNA
<213> ORGANISM: homo sapiens

<400> SEQUENCE: 206
ucauauugcu ucuuucu                                              17

<210> SEQ ID NO 207
<211> LENGTH: 21
<212> TYPE: RNA
<213> ORGANISM: homo sapiens

<400> SEQUENCE: 207
ucacagugaa ccggucucuu u                                         21

<210> SEQ ID NO 208
<211> LENGTH: 17
<212> TYPE: RNA
<213> ORGANISM: homo sapiens

<400> SEQUENCE: 208
ucccaccgcu gccaccc                                              17

<210> SEQ ID NO 209
<211> LENGTH: 17
<212> TYPE: RNA
```

<213> ORGANISM: homo sapiens

<400> SEQUENCE: 209
ucgccuccuc cucuccc                                                        17

<210> SEQ ID NO 210
<211> LENGTH: 20
<212> TYPE: RNA
<213> ORGANISM: homo sapiens

<400> SEQUENCE: 210
ucguuugccu uuucugcuu                                                      20

<210> SEQ ID NO 211
<211> LENGTH: 22
<212> TYPE: RNA
<213> ORGANISM: homo sapiens

<400> SEQUENCE: 211
ucuacaaagg aaagcgcuuu cu                                                  22

<210> SEQ ID NO 212
<211> LENGTH: 22
<212> TYPE: RNA
<213> ORGANISM: homo sapiens

<400> SEQUENCE: 212
ucuauacaga cccuggcuuu uc                                                  22

<210> SEQ ID NO 213
<211> LENGTH: 22
<212> TYPE: RNA
<213> ORGANISM: homo sapiens

<400> SEQUENCE: 213
ucugggcaac aaagugagac cu                                                  22

<210> SEQ ID NO 214
<211> LENGTH: 21
<212> TYPE: RNA
<213> ORGANISM: homo sapiens

<400> SEQUENCE: 214
ugcaggacca agaugagccc u                                                   21

<210> SEQ ID NO 215
<211> LENGTH: 22
<212> TYPE: RNA
<213> ORGANISM: homo sapiens

<400> SEQUENCE: 215
ugcuggauca gugguucgag uc                                                  22

<210> SEQ ID NO 216
<211> LENGTH: 21
<212> TYPE: RNA
<213> ORGANISM: homo sapiens

<400> SEQUENCE: 216
uggacugccc ugaucuggag a                                                   21

<210> SEQ ID NO 217
<211> LENGTH: 23

```
<212> TYPE: RNA
<213> ORGANISM: homo sapiens

<400> SEQUENCE: 217 uggagccag gaaucugcau uuu                                     23

<210> SEQ ID NO 218
<211> LENGTH: 22
<212> TYPE: RNA
<213> ORGANISM: homo sapiens

<400> SEQUENCE: 218
aagcccuuac cccaaaaagu au                                     22

<210> SEQ ID NO 219
<211> LENGTH: 22
<212> TYPE: RNA
<213> ORGANISM: homo sapiens

<400> SEQUENCE: 219
aagcccuuac cccaaaaagc au                                     22

<210> SEQ ID NO 220
<211> LENGTH: 21
<212> TYPE: RNA
<213> ORGANISM: homo sapiens

<400> SEQUENCE: 220
cuuuuugcgg ucugggcuug c                                      21

<210> SEQ ID NO 221
<211> LENGTH: 19
<212> TYPE: RNA
<213> ORGANISM: homo sapiens

<400> SEQUENCE: 221
uggauuuuug gaucaggga                                         19

<210> SEQ ID NO 222
<211> LENGTH: 24
<212> TYPE: RNA
<213> ORGANISM: homo sapiens

<400> SEQUENCE: 222
uggcccugac ugaagaccag cagu                                   24

<210> SEQ ID NO 223
<211> LENGTH: 25
<212> TYPE: RNA
<213> ORGANISM: homo sapiens

<400> SEQUENCE: 223
ugggaacggg uuccggcaga cgcug                                  25

<210> SEQ ID NO 224
<211> LENGTH: 22
<212> TYPE: RNA
<213> ORGANISM: homo sapiens

<400> SEQUENCE: 224 ugggugguu ggagauuugu gc                                      22

<210> SEQ ID NO 225
```

```
<211> LENGTH: 22
<212> TYPE: RNA
<213> ORGANISM: homo sapiens

<400> SEQUENCE: 225
ugugagguug gcauuguugu cu                                              22

<210> SEQ ID NO 226
<211> LENGTH: 21
<212> TYPE: RNA
<213> ORGANISM: homo sapiens

<400> SEQUENCE: 226
uuaggccgca gaucugggug a                                               21

<210> SEQ ID NO 227
<211> LENGTH: 22
<212> TYPE: RNA
<213> ORGANISM: homo sapiens

<400> SEQUENCE: 227
uuagggcccu ggcuccaucu cc                                              22

<210> SEQ ID NO 228
<211> LENGTH: 17
<212> TYPE: RNA
<213> ORGANISM: homo sapiens

<400> SEQUENCE: 228
uucaaguaau ucaggug                                                    17

<210> SEQ ID NO 229
<211> LENGTH: 22
<212> TYPE: RNA
<213> ORGANISM: homo sapiens

<400> SEQUENCE: 229
uucauucggc uguccagaug ua                                              22

<210> SEQ ID NO 230
<211> LENGTH: 22
<212> TYPE: RNA
<213> ORGANISM: homo sapiens

<400> SEQUENCE: 230
uucuggaauu cugugugagg ga                                              22

<210> SEQ ID NO 231
<211> LENGTH: 18
<212> TYPE: RNA
<213> ORGANISM: homo sapiens

<400> SEQUENCE: 231
uugagaagga ggcugcug                                                   18

<210> SEQ ID NO 232
<211> LENGTH: 24
<212> TYPE: RNA
<213> ORGANISM: homo sapiens

<400> SEQUENCE: 232
uugcagcugc cugggaguga cuuc                                            24
```

```
<210> SEQ ID NO 233
<211> LENGTH: 21
<212> TYPE: RNA
<213> ORGANISM: homo sapiens

<400> SEQUENCE: 233
uugggacaua cuuaugcuaa a                                              21

<210> SEQ ID NO 234
<211> LENGTH: 22
<212> TYPE: RNA
<213> ORGANISM: homo sapiens

<400> SEQUENCE: 234
uuuagagacg gggucuugcu cu                                             22

<210> SEQ ID NO 235
<211> LENGTH: 22
<212> TYPE: RNA
<213> ORGANISM: homo sapiens

<400> SEQUENCE: 235
uuugaggcua cagugagaug ug                                             22

<210> SEQ ID NO 236
<211> LENGTH: 22
<212> TYPE: RNA
<213> ORGANISM: homo sapiens

<400> SEQUENCE: 236
uuuucaacuc uaaugggaga ga                                             22

<210> SEQ ID NO 237
<211> LENGTH: 18
<212> TYPE: RNA
<213> ORGANISM: homo sapiens

<400> SEQUENCE: 237
acguuggcuc uggugguG                                                  18

<210> SEQ ID NO 238
<211> LENGTH: 22
<212> TYPE: RNA
<213> ORGANISM: homo sapiens

<400> SEQUENCE: 238
acucggcgug gcgucggucg ug                                             22

<210> SEQ ID NO 239
<211> LENGTH: 18
<212> TYPE: RNA
<213> ORGANISM: homo sapiens

<400> SEQUENCE: 239
gcaugggugg uucagugg                                                  18

<210> SEQ ID NO 240
<211> LENGTH: 22
<212> TYPE: RNA
<213> ORGANISM: homo sapiens

<400> SEQUENCE: 240
cagugcaaug uuaaaagggc au                                             22
```

```
<210> SEQ ID NO 241
<211> LENGTH: 22
<212> TYPE: RNA
<213> ORGANISM: homo sapiens

<400> SEQUENCE: 241
uucacauugu gcuacugucu gc                                              22

<210> SEQ ID NO 242
<211> LENGTH: 22
<212> TYPE: RNA
<213> ORGANISM: homo sapiens

<400> SEQUENCE: 242
cagugcaaug augaaagggc au                                              22

<210> SEQ ID NO 243
<211> LENGTH: 21
<212> TYPE: RNA
<213> ORGANISM: homo sapiens

<400> SEQUENCE: 243
acucuuuccc uguugcacua c                                               21

<210> SEQ ID NO 244
<211> LENGTH: 22
<212> TYPE: RNA
<213> ORGANISM: homo sapiens

<400> SEQUENCE: 244
uaacagucua cagccauggu cg                                              22

<210> SEQ ID NO 245
<211> LENGTH: 22
<212> TYPE: RNA
<213> ORGANISM: homo sapiens

<400> SEQUENCE: 245
accguggcuu ucgauuguua cu                                              22

<210> SEQ ID NO 246
<211> LENGTH: 18
<212> TYPE: RNA
<213> ORGANISM: homo sapiens

<400> SEQUENCE: 246
cagggaggug aaugugau                                                   18

<210> SEQ ID NO 247
<211> LENGTH: 19
<212> TYPE: RNA
<213> ORGANISM: homo sapiens

<400> SEQUENCE: 247
gaugaugcug cugaugcug                                                  19

<210> SEQ ID NO 248
<211> LENGTH: 22
<212> TYPE: RNA
<213> ORGANISM: homo sapiens

<400> SEQUENCE: 248
ucaaaacuga ggggcauuuu cu                                              22
```

<210> SEQ ID NO 249
<211> LENGTH: 24
<212> TYPE: RNA
<213> ORGANISM: homo sapiens

<400> SEQUENCE: 249
ccagacagaa uucuaugcac uuuc                                          24

<210> SEQ ID NO 250
<211> LENGTH: 22
<212> TYPE: RNA
<213> ORGANISM: homo sapiens

<400> SEQUENCE: 250
uuuggucccc uucaaccagc ug                                            22

<210> SEQ ID NO 251
<211> LENGTH: 22
<212> TYPE: RNA
<213> ORGANISM: homo sapiens

<400> SEQUENCE: 251
uuuggucccc uucaaccagc ua                                            22

<210> SEQ ID NO 252
<211> LENGTH: 22
<212> TYPE: RNA
<213> ORGANISM: homo sapiens

<400> SEQUENCE: 252
ugugacuggu ugaccagagg gg                                            22

<210> SEQ ID NO 253
<211> LENGTH: 23
<212> TYPE: RNA
<213> ORGANISM: homo sapiens

<400> SEQUENCE: 253
uauggcuuuu uauuccuaug uga                                           23

<210> SEQ ID NO 254
<211> LENGTH: 22
<212> TYPE: RNA
<213> ORGANISM: homo sapiens

<400> SEQUENCE: 254
uauagggauu ggagccgugg cg                                            22

<210> SEQ ID NO 255
<211> LENGTH: 23
<212> TYPE: RNA
<213> ORGANISM: homo sapiens

<400> SEQUENCE: 255
uauggcuuuu cauuccuaug uga                                           23

<210> SEQ ID NO 256
<211> LENGTH: 22
<212> TYPE: RNA
<213> ORGANISM: homo sapiens

<400> SEQUENCE: 256
auguagggcu aaaagccaug gg                                    22

<210> SEQ ID NO 257
<211> LENGTH: 23
<212> TYPE: RNA
<213> ORGANISM: homo sapiens

<400> SEQUENCE: 257
acuccauuug uuuugaugau gga                                   23

<210> SEQ ID NO 258
<211> LENGTH: 22
<212> TYPE: RNA
<213> ORGANISM: homo sapiens

<400> SEQUENCE: 258
caucaucguc ucaaugagu cu                                     22

<210> SEQ ID NO 259
<211> LENGTH: 23
<212> TYPE: RNA
<213> ORGANISM: homo sapiens

<400> SEQUENCE: 259
uuauugcuua agaauacgcg uag                                   23

<210> SEQ ID NO 260
<211> LENGTH: 23
<212> TYPE: RNA
<213> ORGANISM: homo sapiens

<400> SEQUENCE: 260
agcugguguu gugaaucagg ccg                                   23

<210> SEQ ID NO 261
<211> LENGTH: 22
<212> TYPE: RNA
<213> ORGANISM: homo sapiens

<400> SEQUENCE: 261
gcuacuucac aacaccaggg cc                                    22

<210> SEQ ID NO 262
<211> LENGTH: 22
<212> TYPE: RNA
<213> ORGANISM: homo sapiens

<400> SEQUENCE: 262
gcuauuucac gacaccaggg uu                                    22

<210> SEQ ID NO 263
<211> LENGTH: 22
<212> TYPE: RNA
<213> ORGANISM: homo sapiens

<400> SEQUENCE: 263
ggagacgcgg cccuguugga gu                                    22

<210> SEQ ID NO 264
<211> LENGTH: 22
<212> TYPE: RNA
<213> ORGANISM: homo sapiens

<400> SEQUENCE: 264
ucuacagugc acgugucucc ag         22

<210> SEQ ID NO 265
<211> LENGTH: 21
<212> TYPE: RNA
<213> ORGANISM: homo sapiens

<400> SEQUENCE: 265
uaccacaggg uagaaccacg g          21

<210> SEQ ID NO 266
<211> LENGTH: 22
<212> TYPE: RNA
<213> ORGANISM: homo sapiens

<400> SEQUENCE: 266
cagugguuuu acccuauggu ag         22

<210> SEQ ID NO 267
<211> LENGTH: 22
<212> TYPE: RNA
<213> ORGANISM: homo sapiens

<400> SEQUENCE: 267
uaacacuguc ugguaaagau gg         22

<210> SEQ ID NO 268
<211> LENGTH: 22
<212> TYPE: RNA
<213> ORGANISM: homo sapiens

<400> SEQUENCE: 268
caucuuccag uacaguguug ga         22

<210> SEQ ID NO 269
<211> LENGTH: 23
<212> TYPE: RNA
<213> ORGANISM: homo sapiens

<400> SEQUENCE: 269
uguaguguuu ccuacuuuau gga        23

<210> SEQ ID NO 270
<211> LENGTH: 21
<212> TYPE: RNA
<213> ORGANISM: homo sapiens

<400> SEQUENCE: 270
cauaaaguag aaagcacuac u          21

<210> SEQ ID NO 271
<211> LENGTH: 21
<212> TYPE: RNA
<213> ORGANISM: homo sapiens

<400> SEQUENCE: 271
ugagaugaag cacuguagcu c          21

<210> SEQ ID NO 272
<211> LENGTH: 22
<212> TYPE: RNA
<213> ORGANISM: homo sapiens

<400> SEQUENCE: 272
ggugcagugc ugcaucucug gu                                    22

<210> SEQ ID NO 273
<211> LENGTH: 20
<212> TYPE: RNA
<213> ORGANISM: homo sapiens

<400> SEQUENCE: 273
uacaguauag augauguacu                                       20

<210> SEQ ID NO 274
<211> LENGTH: 22
<212> TYPE: RNA
<213> ORGANISM: homo sapiens

<400> SEQUENCE: 274
ggauaucauc auauacugua ag                                    22

<210> SEQ ID NO 275
<211> LENGTH: 23
<212> TYPE: RNA
<213> ORGANISM: homo sapiens

<400> SEQUENCE: 275
guccaguuuu cccaggaauc ccu                                   23

<210> SEQ ID NO 276
<211> LENGTH: 22
<212> TYPE: RNA
<213> ORGANISM: homo sapiens

<400> SEQUENCE: 276
ggauuccugg aaauacuguu cu                                    22

<210> SEQ ID NO 277
<211> LENGTH: 21
<212> TYPE: RNA
<213> ORGANISM: homo sapiens

<400> SEQUENCE: 277
cuccguuugc cuguuucgcu g                                     21

<210> SEQ ID NO 278
<211> LENGTH: 22
<212> TYPE: RNA
<213> ORGANISM: homo sapiens

<400> SEQUENCE: 278
cucggcgcgg ggcgcgggcu cc                                    22

<210> SEQ ID NO 279
<211> LENGTH: 22
<212> TYPE: RNA
<213> ORGANISM: homo sapiens

<400> SEQUENCE: 279
ugagaacuga auuccauggg uu                                    22

<210> SEQ ID NO 280
<211> LENGTH: 22
<212> TYPE: RNA
<213> ORGANISM: homo sapiens -continued

```
<400> SEQUENCE: 280
ccucugaaau ucaguucuuc ag                                              22

<210> SEQ ID NO 281
<211> LENGTH: 22
<212> TYPE: RNA
<213> ORGANISM: homo sapiens

<400> SEQUENCE: 281
ugcccugugg acucaguucu gg                                              22

<210> SEQ ID NO 282
<211> LENGTH: 22
<212> TYPE: RNA
<213> ORGANISM: homo sapiens

<400> SEQUENCE: 282
ugagaacuga auuccauagg cu                                              22

<210> SEQ ID NO 283
<211> LENGTH: 20
<212> TYPE: RNA
<213> ORGANISM: homo sapiens

<400> SEQUENCE: 283
guguguggaa augcuucugc                                                 20

<210> SEQ ID NO 284
<211> LENGTH: 21
<212> TYPE: RNA
<213> ORGANISM: homo sapiens

<400> SEQUENCE: 284
gcccuccgcc cgugcacccc g                                               21

<210> SEQ ID NO 285
<211> LENGTH: 22
<212> TYPE: RNA
<213> ORGANISM: homo sapiens

<400> SEQUENCE: 285
gcccgcgugu ggagccaggu gu                                              22

<210> SEQ ID NO 286
<211> LENGTH: 22
<212> TYPE: RNA
<213> ORGANISM: homo sapiens

<400> SEQUENCE: 286
gugugcggaa augcuucugc ua                                              22

<210> SEQ ID NO 287
<211> LENGTH: 22
<212> TYPE: RNA
<213> ORGANISM: homo sapiens

<400> SEQUENCE: 287
ucagugcacu acagaacuuu gu                                              22

<210> SEQ ID NO 288
<211> LENGTH: 22
<212> TYPE: RNA
```

<213> ORGANISM: homo sapiens

<400> SEQUENCE: 288
aaaguucuga gacacuccga cu                    22

<210> SEQ ID NO 289
<211> LENGTH: 22
<212> TYPE: RNA
<213> ORGANISM: homo sapiens

<400> SEQUENCE: 289
ucagugcauc acagaacuuu gu                    22

<210> SEQ ID NO 290
<211> LENGTH: 22
<212> TYPE: RNA
<213> ORGANISM: homo sapiens

<400> SEQUENCE: 290
aaguucuguu auacacucag gc                    22

<210> SEQ ID NO 291
<211> LENGTH: 23
<212> TYPE: RNA
<213> ORGANISM: homo sapiens

<400> SEQUENCE: 291
ucuggcuccg ugucuucacu ccc                   23

<210> SEQ ID NO 292
<211> LENGTH: 21
<212> TYPE: RNA
<213> ORGANISM: homo sapiens

<400> SEQUENCE: 292
agggagggac gggggcugug c                     21

<210> SEQ ID NO 293
<211> LENGTH: 22
<212> TYPE: RNA
<213> ORGANISM: homo sapiens

<400> SEQUENCE: 293
ucucccaacc cuuguaccag ug                    22

<210> SEQ ID NO 294
<211> LENGTH: 22
<212> TYPE: RNA
<213> ORGANISM: homo sapiens

<400> SEQUENCE: 294
cugguacagg ccuggggggac ag                   22

<210> SEQ ID NO 295
<211> LENGTH: 21
<212> TYPE: RNA
<213> ORGANISM: homo sapiens

<400> SEQUENCE: 295
cuagacugaa gcuccuugag g                     21

<210> SEQ ID NO 296
<211> LENGTH: 21

```
<212> TYPE: RNA
<213> ORGANISM: homo sapiens

<400> SEQUENCE: 296
ucgaggagcu cacagucuag u                                              21

<210> SEQ ID NO 297
<211> LENGTH: 21
<212> TYPE: RNA
<213> ORGANISM: homo sapiens

<400> SEQUENCE: 297
ucagugcaug acagaacuug g                                              21

<210> SEQ ID NO 298
<211> LENGTH: 22
<212> TYPE: RNA
<213> ORGANISM: homo sapiens

<400> SEQUENCE: 298
uugcauaguc acaaaaguga uc                                             22

<210> SEQ ID NO 299
<211> LENGTH: 22
<212> TYPE: RNA
<213> ORGANISM: homo sapiens

<400> SEQUENCE: 299
aaaaccgucu aguuacaguu gu                                             22

<210> SEQ ID NO 300
<211> LENGTH: 23
<212> TYPE: RNA
<213> ORGANISM: homo sapiens

<400> SEQUENCE: 300
cggcccgggc ugcugcuguu ccu                                            23

<210> SEQ ID NO 301
<211> LENGTH: 21
<212> TYPE: RNA
<213> ORGANISM: homo sapiens

<400> SEQUENCE: 301
uccugcgcgu cccagaugcc c                                              21

<210> SEQ ID NO 302
<211> LENGTH: 22
<212> TYPE: RNA
<213> ORGANISM: homo sapiens

<400> SEQUENCE: 302
uagguuaucc guguugccuu cg                                             22

<210> SEQ ID NO 303
<211> LENGTH: 22
<212> TYPE: RNA
<213> ORGANISM: homo sapiens

<400> SEQUENCE: 303
aaucauacac gguugaccua uu                                             22

<210> SEQ ID NO 304
```

```
<211> LENGTH: 23
<212> TYPE: RNA
<213> ORGANISM: homo sapiens

<400> SEQUENCE: 304
uuaaugcuaa ucgugauagg ggu                                              23

<210> SEQ ID NO 305
<211> LENGTH: 22
<212> TYPE: RNA
<213> ORGANISM: homo sapiens

<400> SEQUENCE: 305
cuccuacaua uuagcauuaa ca                                               22

<210> SEQ ID NO 306
<211> LENGTH: 22
<212> TYPE: RNA
<213> ORGANISM: homo sapiens

<400> SEQUENCE: 306
uagcagcaca uaaugguuug ug                                               22

<210> SEQ ID NO 307
<211> LENGTH: 22
<212> TYPE: RNA
<213> ORGANISM: homo sapiens

<400> SEQUENCE: 307
caggccauau ugugcugccu ca                                               22

<210> SEQ ID NO 308
<211> LENGTH: 22
<212> TYPE: RNA
<213> ORGANISM: homo sapiens

<400> SEQUENCE: 308
uagcagcaca ucaugguuua ca                                               22

<210> SEQ ID NO 309
<211> LENGTH: 22
<212> TYPE: RNA
<213> ORGANISM: homo sapiens

<400> SEQUENCE: 309
cgaaucauua uuugcugcuc ua                                               22

<210> SEQ ID NO 310
<211> LENGTH: 22
<212> TYPE: RNA
<213> ORGANISM: homo sapiens

<400> SEQUENCE: 310
uagcagcacg uaaauauugg cg                                               22

<210> SEQ ID NO 311
<211> LENGTH: 22
<212> TYPE: RNA
<213> ORGANISM: homo sapiens

<400> SEQUENCE: 311
ccaguauuaa cugugcugcu ga                                               22
```

-continued

```
<210> SEQ ID NO 312
<211> LENGTH: 22
<212> TYPE: RNA
<213> ORGANISM: homo sapiens

<400> SEQUENCE: 312
ccaauauuac ugugcugcuu ua                                              22

<210> SEQ ID NO 313
<211> LENGTH: 23
<212> TYPE: RNA
<213> ORGANISM: homo sapiens

<400> SEQUENCE: 313
caaagugcuu acagugcagg uag                                             23

<210> SEQ ID NO 314
<211> LENGTH: 22
<212> TYPE: RNA
<213> ORGANISM: homo sapiens

<400> SEQUENCE: 314
acugcaguga aggcacuugu ag                                              22

<210> SEQ ID NO 315
<211> LENGTH: 23
<212> TYPE: RNA
<213> ORGANISM: homo sapiens

<400> SEQUENCE: 315
aacauucaac gcugucggug agu                                             23

<210> SEQ ID NO 316
<211> LENGTH: 22
<212> TYPE: RNA
<213> ORGANISM: homo sapiens

<400> SEQUENCE: 316
accaucgacc guugauugua cc                                              22

<210> SEQ ID NO 317
<211> LENGTH: 22
<212> TYPE: RNA
<213> ORGANISM: homo sapiens

<400> SEQUENCE: 317
accacugacc guugacugua cc                                              22

<210> SEQ ID NO 318
<211> LENGTH: 23
<212> TYPE: RNA
<213> ORGANISM: homo sapiens

<400> SEQUENCE: 318
aacauucauu gcugucggug ggu                                             23

<210> SEQ ID NO 319
<211> LENGTH: 22
<212> TYPE: RNA
<213> ORGANISM: homo sapiens

<400> SEQUENCE: 319
aacauucaac cugucgguga gu                                              22
```

```
<210> SEQ ID NO 320
<211> LENGTH: 22
<212> TYPE: RNA
<213> ORGANISM: homo sapiens

<400> SEQUENCE: 320
aaccaucgac cguugagugg ac                                              22

<210> SEQ ID NO 321
<211> LENGTH: 23
<212> TYPE: RNA
<213> ORGANISM: homo sapiens

<400> SEQUENCE: 321
aacauucauu guugucggug ggu                                             23

<210> SEQ ID NO 322
<211> LENGTH: 24
<212> TYPE: RNA
<213> ORGANISM: homo sapiens

<400> SEQUENCE: 322
uuuggcaaug guagaacuca cacu                                            24

<210> SEQ ID NO 323
<211> LENGTH: 21
<212> TYPE: RNA
<213> ORGANISM: homo sapiens

<400> SEQUENCE: 323
ugguucuaga cuugccaacu a                                               21

<210> SEQ ID NO 324
<211> LENGTH: 18
<212> TYPE: RNA
<213> ORGANISM: homo sapiens

<400> SEQUENCE: 324
uccagugccc uccucucc                                                   18

<210> SEQ ID NO 325
<211> LENGTH: 27
<212> TYPE: RNA
<213> ORGANISM: homo sapiens

<400> SEQUENCE: 325
auugaucauc gacacuucga acgcaau                                         27

<210> SEQ ID NO 326
<211> LENGTH: 18
<212> TYPE: RNA
<213> ORGANISM: homo sapiens

<400> SEQUENCE: 326
ugaggcagua gauugaau                                                   18

<210> SEQ ID NO 327
<211> LENGTH: 22
<212> TYPE: RNA
<213> ORGANISM: homo sapiens

<400> SEQUENCE: 327
uauggcacug guagaauuca cu                                              22
```

```
<210> SEQ ID NO 328
<211> LENGTH: 22
<212> TYPE: RNA
<213> ORGANISM: homo sapiens

<400> SEQUENCE: 328
gugaauuacc gaagggccau aa                                              22

<210> SEQ ID NO 329
<211> LENGTH: 22
<212> TYPE: RNA
<213> ORGANISM: homo sapiens

<400> SEQUENCE: 329
uggacggaga acugauaagg gu                                              22

<210> SEQ ID NO 330
<211> LENGTH: 22
<212> TYPE: RNA
<213> ORGANISM: homo sapiens

<400> SEQUENCE: 330
uggagagaaa ggcaguuccu ga                                              22

<210> SEQ ID NO 331
<211> LENGTH: 22
<212> TYPE: RNA
<213> ORGANISM: homo sapiens

<400> SEQUENCE: 331
aggggcuggc uuccucugg uc                                               22

<210> SEQ ID NO 332
<211> LENGTH: 22
<212> TYPE: RNA
<213> ORGANISM: homo sapiens

<400> SEQUENCE: 332
caaagaauuc uccuuuuggg cu                                              22

<210> SEQ ID NO 333
<211> LENGTH: 22
<212> TYPE: RNA
<213> ORGANISM: homo sapiens

<400> SEQUENCE: 333
gcccaaaggu gaauuuuug gg                                               22

<210> SEQ ID NO 334
<211> LENGTH: 22
<212> TYPE: RNA
<213> ORGANISM: homo sapiens

<400> SEQUENCE: 334
ucgugucuug uguugcagcc gg                                              22

<210> SEQ ID NO 335
<211> LENGTH: 22
<212> TYPE: RNA
<213> ORGANISM: homo sapiens

<400> SEQUENCE: 335
```

```
ggcuacaaca caggacccgg gc                                              22

<210> SEQ ID NO 336
<211> LENGTH: 21
<212> TYPE: RNA
<213> ORGANISM: homo sapiens

<400> SEQUENCE: 336
cucccacaug caggguuugc a                                               21

<210> SEQ ID NO 337
<211> LENGTH: 21
<212> TYPE: RNA
<213> ORGANISM: homo sapiens

<400> SEQUENCE: 337
caucccuugc augguggagg g                                               21

<210> SEQ ID NO 338
<211> LENGTH: 23
<212> TYPE: RNA
<213> ORGANISM: homo sapiens

<400> SEQUENCE: 338
uaaggugcau cuagugcaga uag                                             23

<210> SEQ ID NO 339
<211> LENGTH: 23
<212> TYPE: RNA
<213> ORGANISM: homo sapiens

<400> SEQUENCE: 339
acugcccuaa gugcuccuuc ugg                                             23

<210> SEQ ID NO 340
<211> LENGTH: 23
<212> TYPE: RNA
<213> ORGANISM: homo sapiens

<400> SEQUENCE: 340
uaaggugcau cuagugcagu uag                                             23

<210> SEQ ID NO 341
<211> LENGTH: 22
<212> TYPE: RNA
<213> ORGANISM: homo sapiens

<400> SEQUENCE: 341
ugcccuaaau gccccuucug gc                                              22

<210> SEQ ID NO 342
<211> LENGTH: 22
<212> TYPE: RNA
<213> ORGANISM: homo sapiens

<400> SEQUENCE: 342
ugauauguuu gauauauuag gu                                              22

<210> SEQ ID NO 343
<211> LENGTH: 21
<212> TYPE: RNA
<213> ORGANISM: homo sapiens

<400> SEQUENCE: 343
```

```
cggcggggac ggcgauuggu c                                           21

<210> SEQ ID NO 344
<211> LENGTH: 22
<212> TYPE: RNA
<213> ORGANISM: homo sapiens

<400> SEQUENCE: 344
cgcaggggcc gggugcucac cg                                          22

<210> SEQ ID NO 345
<211> LENGTH: 21
<212> TYPE: RNA
<213> ORGANISM: homo sapiens

<400> SEQUENCE: 345
ugagugccgg ugccugcccu g                                           21

<210> SEQ ID NO 346
<211> LENGTH: 21
<212> TYPE: RNA
<213> ORGANISM: homo sapiens

<400> SEQUENCE: 346
ugauauguuu gauauugggu u                                           21

<210> SEQ ID NO 347
<211> LENGTH: 23
<212> TYPE: RNA
<213> ORGANISM: homo sapiens

<400> SEQUENCE: 347
caacggaauc ccaaaagcag cug                                         23

<210> SEQ ID NO 348
<211> LENGTH: 22
<212> TYPE: RNA
<213> ORGANISM: homo sapiens

<400> SEQUENCE: 348
gcugcgcuug gauuucgucc cc                                          22

<210> SEQ ID NO 349
<211> LENGTH: 21
<212> TYPE: RNA
<213> ORGANISM: homo sapiens

<400> SEQUENCE: 349
ccaguccugu gccugccgcc u                                           21

<210> SEQ ID NO 350
<211> LENGTH: 23
<212> TYPE: RNA
<213> ORGANISM: homo sapiens

<400> SEQUENCE: 350
ugaguaccgc caugucuguu ggg                                         23

<210> SEQ ID NO 351
<211> LENGTH: 20
<212> TYPE: RNA
<213> ORGANISM: homo sapiens
```

```
<400> SEQUENCE: 351
caccaggcau uguggucucc                                               20

<210> SEQ ID NO 352
<211> LENGTH: 22
<212> TYPE: RNA
<213> ORGANISM: homo sapiens

<400> SEQUENCE: 352
uacccagagc augcagugug aa                                            22

<210> SEQ ID NO 353
<211> LENGTH: 22
<212> TYPE: RNA
<213> ORGANISM: homo sapiens

<400> SEQUENCE: 353 ucugccccu ccgcugcugc ca                                             22

<210> SEQ ID NO 354
<211> LENGTH: 22
<212> TYPE: RNA
<213> ORGANISM: homo sapiens

<400> SEQUENCE: 354
cccugugccc ggcccacuuc ug                                            22

<210> SEQ ID NO 355
<211> LENGTH: 22
<212> TYPE: RNA
<213> ORGANISM: homo sapiens

<400> SEQUENCE: 355
ggaggggucc cgcacuggga gg                                            22

<210> SEQ ID NO 356
<211> LENGTH: 20
<212> TYPE: RNA
<213> ORGANISM: homo sapiens

<400> SEQUENCE: 356
ccccagggcg acgcggcggg                                               20

<210> SEQ ID NO 357
<211> LENGTH: 22
<212> TYPE: RNA
<213> ORGANISM: homo sapiens

<400> SEQUENCE: 357
accuugccuu gcugcccggg cc                                            22

<210> SEQ ID NO 358
<211> LENGTH: 21
<212> TYPE: RNA
<213> ORGANISM: homo sapiens

<400> SEQUENCE: 358
cugaccuaug aauugacagc c                                             21

<210> SEQ ID NO 359
<211> LENGTH: 22
<212> TYPE: RNA
<213> ORGANISM: homo sapiens
```

<400> SEQUENCE: 359
cugccaauuc cauaggucac ag                                              22

<210> SEQ ID NO 360
<211> LENGTH: 22
<212> TYPE: RNA
<213> ORGANISM: homo sapiens

<400> SEQUENCE: 360
aacuggccua caaagcccca gu                                              22

<210> SEQ ID NO 361
<211> LENGTH: 22
<212> TYPE: RNA
<213> ORGANISM: homo sapiens

<400> SEQUENCE: 361
ugggucuuug cgggcgagau ga                                              22

<210> SEQ ID NO 362
<211> LENGTH: 22
<212> TYPE: RNA
<213> ORGANISM: homo sapiens

<400> SEQUENCE: 362
aacuggcccu caaagucccg cu                                              22

<210> SEQ ID NO 363
<211> LENGTH: 22
<212> TYPE: RNA
<213> ORGANISM: homo sapiens

<400> SEQUENCE: 363
cgggguuuug agggcgagau ga                                              22

<210> SEQ ID NO 364
<211> LENGTH: 22
<212> TYPE: RNA
<213> ORGANISM: homo sapiens

<400> SEQUENCE: 364
uguaacagca acuccaugug ga                                              22

<210> SEQ ID NO 365
<211> LENGTH: 22
<212> TYPE: RNA
<213> ORGANISM: homo sapiens

<400> SEQUENCE: 365 ccagugggggc ugcuguuauc ug                                             22

<210> SEQ ID NO 366
<211> LENGTH: 21
<212> TYPE: RNA
<213> ORGANISM: homo sapiens

<400> SEQUENCE: 366
uagcagcaca gaaauauugg c                                               21

<210> SEQ ID NO 367
<211> LENGTH: 22
<212> TYPE: RNA

```
<213> ORGANISM: homo sapiens

<400> SEQUENCE: 367
ccaauauugg cugugcugcu cc                                              22

<210> SEQ ID NO 368
<211> LENGTH: 22
<212> TYPE: RNA
<213> ORGANISM: homo sapiens

<400> SEQUENCE: 368
uagguaguuu cauguuguug gg                                              22

<210> SEQ ID NO 369
<211> LENGTH: 22
<212> TYPE: RNA
<213> ORGANISM: homo sapiens

<400> SEQUENCE: 369
cggcaacaag aaacugccug ag                                              22

<210> SEQ ID NO 370
<211> LENGTH: 22
<212> TYPE: RNA
<213> ORGANISM: homo sapiens

<400> SEQUENCE: 370
uagguaguuu ccuguuguug gg                                              22

<210> SEQ ID NO 371
<211> LENGTH: 22
<212> TYPE: RNA
<213> ORGANISM: homo sapiens

<400> SEQUENCE: 371
uucaccaccu ucuccaccca gc                                              22

<210> SEQ ID NO 372
<211> LENGTH: 22
<212> TYPE: RNA
<213> ORGANISM: homo sapiens

<400> SEQUENCE: 372
gguccagagg ggagauaggu uc                                              22

<210> SEQ ID NO 373
<211> LENGTH: 23
<212> TYPE: RNA
<213> ORGANISM: homo sapiens

<400> SEQUENCE: 373
cccaguguuc agacuaccug uuc                                             23

<210> SEQ ID NO 374
<211> LENGTH: 22
<212> TYPE: RNA
<213> ORGANISM: homo sapiens

<400> SEQUENCE: 374
acaguagucu gcacauuggu ua                                              22

<210> SEQ ID NO 375
<211> LENGTH: 23
```

```
<212> TYPE: RNA
<213> ORGANISM: homo sapiens

<400> SEQUENCE: 375
cccaguguuu agacuaucug uuc                                              23

<210> SEQ ID NO 376
<211> LENGTH: 23
<212> TYPE: RNA
<213> ORGANISM: homo sapiens

<400> SEQUENCE: 376
ugugcaaauc uaugcaaaac uga                                              23

<210> SEQ ID NO 377
<211> LENGTH: 22
<212> TYPE: RNA
<213> ORGANISM: homo sapiens

<400> SEQUENCE: 377
aguuuugcau aguugcacua ca                                               22

<210> SEQ ID NO 378
<211> LENGTH: 23
<212> TYPE: RNA
<213> ORGANISM: homo sapiens

<400> SEQUENCE: 378
ugugcaaauc caugcaaaac uga                                              23

<210> SEQ ID NO 379
<211> LENGTH: 23
<212> TYPE: RNA
<213> ORGANISM: homo sapiens

<400> SEQUENCE: 379
aguuuugcag guuugcaucc agc                                              23

<210> SEQ ID NO 380
<211> LENGTH: 22
<212> TYPE: RNA
<213> ORGANISM: homo sapiens

<400> SEQUENCE: 380
aguuuugcag guuugcauuu ca                                               22

<210> SEQ ID NO 381
<211> LENGTH: 22
<212> TYPE: RNA
<213> ORGANISM: homo sapiens

<400> SEQUENCE: 381
uaacacuguc ugguaacgau gu                                               22

<210> SEQ ID NO 382
<211> LENGTH: 22
<212> TYPE: RNA
<213> ORGANISM: homo sapiens

<400> SEQUENCE: 382
caucuuaccg gacagugcug ga                                               22

<210> SEQ ID NO 383
```

```
<211> LENGTH: 22
<212> TYPE: RNA
<213> ORGANISM: homo sapiens

<400> SEQUENCE: 383
uaauacugcc ugguaaugau ga                                              22

<210> SEQ ID NO 384
<211> LENGTH: 22
<212> TYPE: RNA
<213> ORGANISM: homo sapiens

<400> SEQUENCE: 384
caucuuacug ggcagcauug ga                                              22

<210> SEQ ID NO 385
<211> LENGTH: 23
<212> TYPE: RNA
<213> ORGANISM: homo sapiens

<400> SEQUENCE: 385
uaauacugcc ggguaaugau gga                                             23

<210> SEQ ID NO 386
<211> LENGTH: 22
<212> TYPE: RNA
<213> ORGANISM: homo sapiens

<400> SEQUENCE: 386
cgucuuaccc agcaguguuu gg                                              22

<210> SEQ ID NO 387
<211> LENGTH: 20
<212> TYPE: RNA
<213> ORGANISM: homo sapiens

<400> SEQUENCE: 387
agagguauag ggcaugggaa                                                 20

<210> SEQ ID NO 388
<211> LENGTH: 22
<212> TYPE: RNA
<213> ORGANISM: homo sapiens

<400> SEQUENCE: 388
uuccuaugca uauacuucuu ug                                              22

<210> SEQ ID NO 389
<211> LENGTH: 22
<212> TYPE: RNA
<213> ORGANISM: homo sapiens

<400> SEQUENCE: 389
gugaaauguu uaggaccacu ag                                              22

<210> SEQ ID NO 390
<211> LENGTH: 22
<212> TYPE: RNA
<213> ORGANISM: homo sapiens

<400> SEQUENCE: 390
uucccuuugu cauccuaugc cu                                              22
```

```
<210> SEQ ID NO 391
<211> LENGTH: 22
<212> TYPE: RNA
<213> ORGANISM: homo sapiens

<400> SEQUENCE: 391
uccuucauuc caccggaguc ug                                                  22

<210> SEQ ID NO 392
<211> LENGTH: 22
<212> TYPE: RNA
<213> ORGANISM: homo sapiens

<400> SEQUENCE: 392
uggaauguaa ggaagugugu gg                                                  22

<210> SEQ ID NO 393
<211> LENGTH: 22
<212> TYPE: RNA
<213> ORGANISM: homo sapiens

<400> SEQUENCE: 393
auaagacgag caaaaagcuu gu                                                  22

<210> SEQ ID NO 394
<211> LENGTH: 22
<212> TYPE: RNA
<213> ORGANISM: homo sapiens

<400> SEQUENCE: 394
auaagacgaa caaaagguuu gu                                                  22

<210> SEQ ID NO 395
<211> LENGTH: 23
<212> TYPE: RNA
<213> ORGANISM: homo sapiens

<400> SEQUENCE: 395
uaaagugcuu auagugcagg uag                                                 23

<210> SEQ ID NO 396
<211> LENGTH: 22
<212> TYPE: RNA
<213> ORGANISM: homo sapiens

<400> SEQUENCE: 396
acugcauuau gagcacuuaa ag                                                  22

<210> SEQ ID NO 397
<211> LENGTH: 23
<212> TYPE: RNA
<213> ORGANISM: homo sapiens

<400> SEQUENCE: 397
caaagugcuc auagugcagg uag                                                 23

<210> SEQ ID NO 398
<211> LENGTH: 22
<212> TYPE: RNA
<213> ORGANISM: homo sapiens

<400> SEQUENCE: 398
acuguaguau gggcacuucc ag                                                  22
```

```
<210> SEQ ID NO 399
<211> LENGTH: 22
<212> TYPE: RNA
<213> ORGANISM: homo sapiens

<400> SEQUENCE: 399
uagcuuauca gacugauguu ga                                            22

<210> SEQ ID NO 400
<211> LENGTH: 21
<212> TYPE: RNA
<213> ORGANISM: homo sapiens

<400> SEQUENCE: 400
caacaccagu cgaugggcug u                                             21

<210> SEQ ID NO 401
<211> LENGTH: 22
<212> TYPE: RNA
<213> ORGANISM: homo sapiens

<400> SEQUENCE: 401
cugugcgugu gacagcggcu ga                                            22

<210> SEQ ID NO 402
<211> LENGTH: 22
<212> TYPE: RNA
<213> ORGANISM: homo sapiens

<400> SEQUENCE: 402
uucccuuugu cauccuucgc cu                                            22

<210> SEQ ID NO 403
<211> LENGTH: 21
<212> TYPE: RNA
<213> ORGANISM: homo sapiens

<400> SEQUENCE: 403
uaacagucuc cagucacggc c                                             21

<210> SEQ ID NO 404
<211> LENGTH: 22
<212> TYPE: RNA
<213> ORGANISM: homo sapiens

<400> SEQUENCE: 404
acagcaggca cagacaggca gu                                            22

<210> SEQ ID NO 405
<211> LENGTH: 22
<212> TYPE: RNA
<213> ORGANISM: homo sapiens

<400> SEQUENCE: 405
ugccugucua cacuugcugu gc                                            22

<210> SEQ ID NO 406
<211> LENGTH: 21
<212> TYPE: RNA
<213> ORGANISM: homo sapiens

<400> SEQUENCE: 406
augaccuaug aauugacaga c                                             21
```

```
<210> SEQ ID NO 407
<211> LENGTH: 22
<212> TYPE: RNA
<213> ORGANISM: homo sapiens

<400> SEQUENCE: 407
uaaucucagc uggcaacugu ga                                              22

<210> SEQ ID NO 408
<211> LENGTH: 22
<212> TYPE: RNA
<213> ORGANISM: homo sapiens

<400> SEQUENCE: 408
aaaucucugc aggcaaaugu ga                                              22

<210> SEQ ID NO 409
<211> LENGTH: 23
<212> TYPE: RNA
<213> ORGANISM: homo sapiens

<400> SEQUENCE: 409
uacugcauca ggaacugauu gga                                             23

<210> SEQ ID NO 410
<211> LENGTH: 21
<212> TYPE: RNA
<213> ORGANISM: homo sapiens

<400> SEQUENCE: 410
uugugcuuga ucuaaccaug u                                               21

<210> SEQ ID NO 411
<211> LENGTH: 22
<212> TYPE: RNA
<213> ORGANISM: homo sapiens

<400> SEQUENCE: 411
augguuccgu caagcaccau gg                                              22

<210> SEQ ID NO 412
<211> LENGTH: 22
<212> TYPE: RNA
<213> ORGANISM: homo sapiens

<400> SEQUENCE: 412 cagguucug ucaagcaccg cg                                               22

<210> SEQ ID NO 413
<211> LENGTH: 22
<212> TYPE: RNA
<213> ORGANISM: homo sapiens

<400> SEQUENCE: 413
agaguugagu cuggacgucc cg                                              22

<210> SEQ ID NO 414
<211> LENGTH: 22
<212> TYPE: RNA
<213> ORGANISM: homo sapiens

<400> SEQUENCE: 414
```
agaauugugg cuggacaucu gu                                              22

<210> SEQ ID NO 415
<211> LENGTH: 21
<212> TYPE: RNA
<213> ORGANISM: homo sapiens

<400> SEQUENCE: 415
ugauugucca aacgcaauuc u                                               21

<210> SEQ ID NO 416
<211> LENGTH: 22
<212> TYPE: RNA
<213> ORGANISM: homo sapiens

<400> SEQUENCE: 416
aagcugccag uugaagaacu gu                                              22

<210> SEQ ID NO 417
<211> LENGTH: 22
<212> TYPE: RNA
<213> ORGANISM: homo sapiens

<400> SEQUENCE: 417
aguucuucag uggcaagcuu ua                                              22

<210> SEQ ID NO 418
<211> LENGTH: 21
<212> TYPE: RNA
<213> ORGANISM: homo sapiens

<400> SEQUENCE: 418
ccacaccgua ucugacacuu u                                               21

<210> SEQ ID NO 419
<211> LENGTH: 21
<212> TYPE: RNA
<213> ORGANISM: homo sapiens

<400> SEQUENCE: 419
ccaccaccgu gucugacacu u                                               21

<210> SEQ ID NO 420
<211> LENGTH: 22
<212> TYPE: RNA
<213> ORGANISM: homo sapiens

<400> SEQUENCE: 420
acacagggcu guugugaaga cu                                              22

<210> SEQ ID NO 421
<211> LENGTH: 23
<212> TYPE: RNA
<213> ORGANISM: homo sapiens

<400> SEQUENCE: 421
agcuacauug ucugcugggu uuc                                             23

<210> SEQ ID NO 422
<211> LENGTH: 22
<212> TYPE: RNA
<213> ORGANISM: homo sapiens

<400> SEQUENCE: 422
accuggcaua caauguagau uu                                               22

<210> SEQ ID NO 423
<211> LENGTH: 21
<212> TYPE: RNA
<213> ORGANISM: homo sapiens

<400> SEQUENCE: 423
agcuacaucu ggcuacuggg u                                                21

<210> SEQ ID NO 424
<211> LENGTH: 22
<212> TYPE: RNA
<213> ORGANISM: homo sapiens

<400> SEQUENCE: 424
cucaguagcc aguguagauc cu                                               22

<210> SEQ ID NO 425
<211> LENGTH: 22
<212> TYPE: RNA
<213> ORGANISM: homo sapiens

<400> SEQUENCE: 425
ugucaguuug ucaaauaccc ca                                               22

<210> SEQ ID NO 426
<211> LENGTH: 22
<212> TYPE: RNA
<213> ORGANISM: homo sapiens

<400> SEQUENCE: 426
cguguauuug acaagcugag uu                                               22

<210> SEQ ID NO 427
<211> LENGTH: 21
<212> TYPE: RNA
<213> ORGANISM: homo sapiens

<400> SEQUENCE: 427
caagucacua gugguuccgu u                                                21

<210> SEQ ID NO 428
<211> LENGTH: 21
<212> TYPE: RNA
<213> ORGANISM: homo sapiens

<400> SEQUENCE: 428
aucacauugc cagggauuuc c                                                21

<210> SEQ ID NO 429
<211> LENGTH: 22
<212> TYPE: RNA
<213> ORGANISM: homo sapiens

<400> SEQUENCE: 429
gggguuccug gggaugggau uu                                               22

<210> SEQ ID NO 430
<211> LENGTH: 21
<212> TYPE: RNA
<213> ORGANISM: homo sapiens

```
-continued

<400> SEQUENCE: 430
aucacauugc cagggauuac c                                      21

<210> SEQ ID NO 431
<211> LENGTH: 22
<212> TYPE: RNA
<213> ORGANISM: homo sapiens

<400> SEQUENCE: 431
uggguuccug gcaugcugau uu                                     22

<210> SEQ ID NO 432
<211> LENGTH: 22
<212> TYPE: RNA
<213> ORGANISM: homo sapiens

<400> SEQUENCE: 432
uggcucaguu cagcaggaac ag                                     22

<210> SEQ ID NO 433
<211> LENGTH: 22
<212> TYPE: RNA
<213> ORGANISM: homo sapiens

<400> SEQUENCE: 433
ugccuacuga gcugauauca gu                                     22

<210> SEQ ID NO 434
<211> LENGTH: 22
<212> TYPE: RNA
<213> ORGANISM: homo sapiens

<400> SEQUENCE: 434
ugccuacuga gcugaaacac ag                                     22

<210> SEQ ID NO 435
<211> LENGTH: 22
<212> TYPE: RNA
<213> ORGANISM: homo sapiens

<400> SEQUENCE: 435
cauugcacuu gucucggucu ga                                     22

<210> SEQ ID NO 436
<211> LENGTH: 21
<212> TYPE: RNA
<213> ORGANISM: homo sapiens

<400> SEQUENCE: 436
aggcggagac uugggcaauu g                                      21

<210> SEQ ID NO 437
<211> LENGTH: 22
<212> TYPE: RNA
<213> ORGANISM: homo sapiens

<400> SEQUENCE: 437
uucaaguaau ccaggauagg cu                                     22

<210> SEQ ID NO 438
<211> LENGTH: 22
<212> TYPE: RNA
<213> ORGANISM: homo sapiens
```

```
<400> SEQUENCE: 438
ccuauucuug guuacuugca cg                                    22

<210> SEQ ID NO 439
<211> LENGTH: 22
<212> TYPE: RNA
<213> ORGANISM: homo sapiens

<400> SEQUENCE: 439
ccuauucuug auuacuuguu uc                                    22

<210> SEQ ID NO 440
<211> LENGTH: 21
<212> TYPE: RNA
<213> ORGANISM: homo sapiens

<400> SEQUENCE: 440
uucaaguaau ucaggauagg u                                     21

<210> SEQ ID NO 441
<211> LENGTH: 22
<212> TYPE: RNA
<213> ORGANISM: homo sapiens

<400> SEQUENCE: 441
ccuguucucc auuacuuggc uc                                    22

<210> SEQ ID NO 442
<211> LENGTH: 21
<212> TYPE: RNA
<213> ORGANISM: homo sapiens

<400> SEQUENCE: 442
uucacagugg cuaaguuccg c                                     21

<210> SEQ ID NO 443
<211> LENGTH: 22
<212> TYPE: RNA
<213> ORGANISM: homo sapiens

<400> SEQUENCE: 443
agggcuuagc ugcuugugag ca                                    22

<210> SEQ ID NO 444
<211> LENGTH: 21
<212> TYPE: RNA
<213> ORGANISM: homo sapiens

<400> SEQUENCE: 444
uucacagugg cuaaguucug c                                     21

<210> SEQ ID NO 445
<211> LENGTH: 22
<212> TYPE: RNA
<213> ORGANISM: homo sapiens

<400> SEQUENCE: 445
agagcuuagc ugauugguga ac                                    22

<210> SEQ ID NO 446
<211> LENGTH: 22
<212> TYPE: RNA
```

<213> ORGANISM: homo sapiens

<400> SEQUENCE: 446
cacuagauug ugagcccug ga					22

<210> SEQ ID NO 447
<211> LENGTH: 22
<212> TYPE: RNA
<213> ORGANISM: homo sapiens

<400> SEQUENCE: 447
aaggagcuca cagucuauug ag					22

<210> SEQ ID NO 448
<211> LENGTH: 22
<212> TYPE: RNA
<213> ORGANISM: homo sapiens

<400> SEQUENCE: 448
gaggguuggg uggaggcucu cc					22

<210> SEQ ID NO 449
<211> LENGTH: 21
<212> TYPE: RNA
<213> ORGANISM: homo sapiens

<400> SEQUENCE: 449 agggccccc cucaauccug u					21

<210> SEQ ID NO 450
<211> LENGTH: 21
<212> TYPE: RNA
<213> ORGANISM: homo sapiens

<400> SEQUENCE: 450
auguaugugu gcaugugcau g					21

<210> SEQ ID NO 451
<211> LENGTH: 24
<212> TYPE: RNA
<213> ORGANISM: homo sapiens

<400> SEQUENCE: 451
agcagaagca gggagguucu ccca					24

<210> SEQ ID NO 452
<211> LENGTH: 22
<212> TYPE: RNA
<213> ORGANISM: homo sapiens

<400> SEQUENCE: 452
uaugugggau gguaaaccgc uu					22

<210> SEQ ID NO 453
<211> LENGTH: 22
<212> TYPE: RNA
<213> ORGANISM: homo sapiens

<400> SEQUENCE: 453
ugguuuaccg ucccacauac au					22

<210> SEQ ID NO 454
<211> LENGTH: 22

```
<212> TYPE: RNA
<213> ORGANISM: homo sapiens

<400> SEQUENCE: 454
uagcaccauc ugaaaucggu ua                                          22

<210> SEQ ID NO 455
<211> LENGTH: 22
<212> TYPE: RNA
<213> ORGANISM: homo sapiens

<400> SEQUENCE: 455
acugauuucu uuggguguuc ag                                          22

<210> SEQ ID NO 456
<211> LENGTH: 23
<212> TYPE: RNA
<213> ORGANISM: homo sapiens

<400> SEQUENCE: 456
uagcaccauu ugaaaucagu guu                                         23

<210> SEQ ID NO 457
<211> LENGTH: 24
<212> TYPE: RNA
<213> ORGANISM: homo sapiens

<400> SEQUENCE: 457
gcugguuuca uauggugguu uaga                                        24

<210> SEQ ID NO 458
<211> LENGTH: 22
<212> TYPE: RNA
<213> ORGANISM: homo sapiens

<400> SEQUENCE: 458
cugguuucac augguggcuu ag                                          22

<210> SEQ ID NO 459
<211> LENGTH: 22
<212> TYPE: RNA
<213> ORGANISM: homo sapiens

<400> SEQUENCE: 459
uagcaccauu ugaaaucggu ua                                          22

<210> SEQ ID NO 460
<211> LENGTH: 22
<212> TYPE: RNA
<213> ORGANISM: homo sapiens

<400> SEQUENCE: 460
ugaccgauuu cuccuggugu uc                                          22

<210> SEQ ID NO 461
<211> LENGTH: 22
<212> TYPE: RNA
<213> ORGANISM: homo sapiens

<400> SEQUENCE: 461
uauacaaggg cagacucucu cu                                          22

<210> SEQ ID NO 462
```

```
<211> LENGTH: 23
<212> TYPE: RNA
<213> ORGANISM: homo sapiens

<400> SEQUENCE: 462
cagugcaaua guauugucaa agc                                              23

<210> SEQ ID NO 463
<211> LENGTH: 23
<212> TYPE: RNA
<213> ORGANISM: homo sapiens

<400> SEQUENCE: 463
cagugcaaug auauugucaa agc                                              23

<210> SEQ ID NO 464
<211> LENGTH: 23
<212> TYPE: RNA
<213> ORGANISM: homo sapiens

<400> SEQUENCE: 464
uaagugcuuc cauguuuugg uga                                              23

<210> SEQ ID NO 465
<211> LENGTH: 23
<212> TYPE: RNA
<213> ORGANISM: homo sapiens

<400> SEQUENCE: 465
acuuaaacgu ggauguacuu gcu                                              23

<210> SEQ ID NO 466
<211> LENGTH: 23
<212> TYPE: RNA
<213> ORGANISM: homo sapiens

<400> SEQUENCE: 466
uaagugcuuc cauguuuag uag                                               23

<210> SEQ ID NO 467
<211> LENGTH: 22
<212> TYPE: RNA
<213> ORGANISM: homo sapiens

<400> SEQUENCE: 467
acuuuaacau ggaagugcuu uc                                               22

<210> SEQ ID NO 468
<211> LENGTH: 23
<212> TYPE: RNA
<213> ORGANISM: homo sapiens

<400> SEQUENCE: 468
uaagugcuuc cauguuucag ugg                                              23

<210> SEQ ID NO 469
<211> LENGTH: 22
<212> TYPE: RNA
<213> ORGANISM: homo sapiens

<400> SEQUENCE: 469
uuuaacaugg ggguaccugc ug                                               22
```

```
<210> SEQ ID NO 470
<211> LENGTH: 23
<212> TYPE: RNA
<213> ORGANISM: homo sapiens

<400> SEQUENCE: 470
uaagugcuuc cauguuugag ugu                                           23

<210> SEQ ID NO 471
<211> LENGTH: 22
<212> TYPE: RNA
<213> ORGANISM: homo sapiens

<400> SEQUENCE: 471
acuuuaacau ggaggcacuu gc                                            22

<210> SEQ ID NO 472
<211> LENGTH: 17
<212> TYPE: RNA
<213> ORGANISM: homo sapiens

<400> SEQUENCE: 472
uaagugcuuc caugcuu                                                  17

<210> SEQ ID NO 473
<211> LENGTH: 17
<212> TYPE: RNA
<213> ORGANISM: homo sapiens

<400> SEQUENCE: 473
uaauugcuuc cauguuu                                                  17

<210> SEQ ID NO 474
<211> LENGTH: 22
<212> TYPE: RNA
<213> ORGANISM: homo sapiens

<400> SEQUENCE: 474
uguaaacauc cucgacugga ag                                            22

<210> SEQ ID NO 475
<211> LENGTH: 22
<212> TYPE: RNA
<213> ORGANISM: homo sapiens

<400> SEQUENCE: 475
cuuucagucg gauguuugca gc                                            22

<210> SEQ ID NO 476
<211> LENGTH: 22
<212> TYPE: RNA
<213> ORGANISM: homo sapiens

<400> SEQUENCE: 476
uguaaacauc cuacacucag cu                                            22

<210> SEQ ID NO 477
<211> LENGTH: 22
<212> TYPE: RNA
<213> ORGANISM: homo sapiens

<400> SEQUENCE: 477
cugggaggug gauguuuacu uc                                            22
```

```
<210> SEQ ID NO 478
<211> LENGTH: 23
<212> TYPE: RNA
<213> ORGANISM: homo sapiens

<400> SEQUENCE: 478
uguaaacauc cuacacucuc agc                                           23

<210> SEQ ID NO 479
<211> LENGTH: 22
<212> TYPE: RNA
<213> ORGANISM: homo sapiens

<400> SEQUENCE: 479
cugggagagg guuguuuacu cc                                            22

<210> SEQ ID NO 480
<211> LENGTH: 22
<212> TYPE: RNA
<213> ORGANISM: homo sapiens

<400> SEQUENCE: 480
cugggagaag gcuguuuacu cu                                            22

<210> SEQ ID NO 481
<211> LENGTH: 22
<212> TYPE: RNA
<213> ORGANISM: homo sapiens

<400> SEQUENCE: 481
uguaaacauc cccgacugga ag                                            22

<210> SEQ ID NO 482
<211> LENGTH: 22
<212> TYPE: RNA
<213> ORGANISM: homo sapiens

<400> SEQUENCE: 482
cuuucaguca gauguuugcu gc                                            22

<210> SEQ ID NO 483
<211> LENGTH: 22
<212> TYPE: RNA
<213> ORGANISM: homo sapiens

<400> SEQUENCE: 483
uguaaacauc cuugacugga ag                                            22

<210> SEQ ID NO 484
<211> LENGTH: 22
<212> TYPE: RNA
<213> ORGANISM: homo sapiens

<400> SEQUENCE: 484
cuuucagucg gauguuuaca gc                                            22

<210> SEQ ID NO 485
<211> LENGTH: 21
<212> TYPE: RNA
<213> ORGANISM: homo sapiens

<400> SEQUENCE: 485
aggcaagaug cuggcauagc u                                             21
```

```
<210> SEQ ID NO 486
<211> LENGTH: 22
<212> TYPE: RNA
<213> ORGANISM: homo sapiens

<400> SEQUENCE: 486
ugcuaugcca acauauugcc au                                              22

<210> SEQ ID NO 487
<211> LENGTH: 22
<212> TYPE: RNA
<213> ORGANISM: homo sapiens

<400> SEQUENCE: 487
uauugcacau uacuaaguug ca                                              22

<210> SEQ ID NO 488
<211> LENGTH: 22
<212> TYPE: RNA
<213> ORGANISM: homo sapiens

<400> SEQUENCE: 488
caauuuagug ugugugauau uu                                              22

<210> SEQ ID NO 489
<211> LENGTH: 22
<212> TYPE: RNA
<213> ORGANISM: homo sapiens

<400> SEQUENCE: 489
aaaagcuggg uugagagggc ga                                              22

<210> SEQ ID NO 490
<211> LENGTH: 22
<212> TYPE: RNA
<213> ORGANISM: homo sapiens

<400> SEQUENCE: 490
aaaagcuggg uugagagggc aa                                              22

<210> SEQ ID NO 491
<211> LENGTH: 20
<212> TYPE: RNA
<213> ORGANISM: homo sapiens

<400> SEQUENCE: 491
aaaagcuggg uugagagggu                                                 20

<210> SEQ ID NO 492
<211> LENGTH: 19
<212> TYPE: RNA
<213> ORGANISM: homo sapiens

<400> SEQUENCE: 492
aaaagcuggg uugagagga                                                  19

<210> SEQ ID NO 493
<211> LENGTH: 21
<212> TYPE: RNA
<213> ORGANISM: homo sapiens

<400> SEQUENCE: 493
```
cacauuacac ggucgaccuc u               21

<210> SEQ ID NO 494
<211> LENGTH: 22
<212> TYPE: RNA
<213> ORGANISM: homo sapiens

<400> SEQUENCE: 494
aggugguccg uggcgcguuc gc              22

<210> SEQ ID NO 495
<211> LENGTH: 20
<212> TYPE: RNA
<213> ORGANISM: homo sapiens

<400> SEQUENCE: 495
acugccccag gugcugcugg                 20

<210> SEQ ID NO 496
<211> LENGTH: 23
<212> TYPE: RNA
<213> ORGANISM: homo sapiens

<400> SEQUENCE: 496
cgcauccccu agggcauugg ugu             23

<210> SEQ ID NO 497
<211> LENGTH: 23
<212> TYPE: RNA
<213> ORGANISM: homo sapiens

<400> SEQUENCE: 497
ccuaguaggu guccaguaag ugu             23

<210> SEQ ID NO 498
<211> LENGTH: 20
<212> TYPE: RNA
<213> ORGANISM: homo sapiens

<400> SEQUENCE: 498
ccucugggcc cuuccuccag                 20

<210> SEQ ID NO 499
<211> LENGTH: 22
<212> TYPE: RNA
<213> ORGANISM: homo sapiens

<400> SEQUENCE: 499
cuggcccucu cugcccuucc gu              22

<210> SEQ ID NO 500
<211> LENGTH: 22
<212> TYPE: RNA
<213> ORGANISM: homo sapiens

<400> SEQUENCE: 500
aacacaccug guuaaccucu uu              22

<210> SEQ ID NO 501
<211> LENGTH: 23
<212> TYPE: RNA
<213> ORGANISM: homo sapiens

<400> SEQUENCE: 501
gcaaagcaca cggccugcag aga                                         23

<210> SEQ ID NO 502
<211> LENGTH: 22
<212> TYPE: RNA
<213> ORGANISM: homo sapiens

<400> SEQUENCE: 502 ucucuggcc ugugucuuag gc                                           22

<210> SEQ ID NO 503
<211> LENGTH: 21
<212> TYPE: RNA
<213> ORGANISM: homo sapiens

<400> SEQUENCE: 503
gccccugggc cuauccuaga a                                           21

<210> SEQ ID NO 504
<211> LENGTH: 22
<212> TYPE: RNA
<213> ORGANISM: homo sapiens

<400> SEQUENCE: 504
cuagguaugg ucccagggau cc                                          22

<210> SEQ ID NO 505
<211> LENGTH: 23
<212> TYPE: RNA
<213> ORGANISM: homo sapiens

<400> SEQUENCE: 505
ucaagagcaa uaacgaaaaa ugu                                         23

<210> SEQ ID NO 506
<211> LENGTH: 22
<212> TYPE: RNA
<213> ORGANISM: homo sapiens

<400> SEQUENCE: 506
uuuuucauua uugcuccuga cc                                          22

<210> SEQ ID NO 507
<211> LENGTH: 22
<212> TYPE: RNA
<213> ORGANISM: homo sapiens

<400> SEQUENCE: 507
cuccuauaug augccuuucu uc                                          22

<210> SEQ ID NO 508
<211> LENGTH: 21
<212> TYPE: RNA
<213> ORGANISM: homo sapiens

<400> SEQUENCE: 508
gaacggcuuc auacaggagu u                                           21

<210> SEQ ID NO 509
<211> LENGTH: 22
<212> TYPE: RNA
<213> ORGANISM: homo sapiens

```
<400> SEQUENCE: 509
uccagcauca gugauuugu ug                                        22

<210> SEQ ID NO 510
<211> LENGTH: 22
<212> TYPE: RNA
<213> ORGANISM: homo sapiens

<400> SEQUENCE: 510
aacaauaucc uggugcugag ug                                       22

<210> SEQ ID NO 511
<211> LENGTH: 23
<212> TYPE: RNA
<213> ORGANISM: homo sapiens

<400> SEQUENCE: 511
ugagcgccuc gacgacagag ccg                                      23

<210> SEQ ID NO 512
<211> LENGTH: 23
<212> TYPE: RNA
<213> ORGANISM: homo sapiens

<400> SEQUENCE: 512
ucccuguccu ccaggagcuc acg                                      23

<210> SEQ ID NO 513
<211> LENGTH: 21
<212> TYPE: RNA
<213> ORGANISM: homo sapiens

<400> SEQUENCE: 513
gugcauugua guugcauugc a                                        21

<210> SEQ ID NO 514
<211> LENGTH: 22
<212> TYPE: RNA
<213> ORGANISM: homo sapiens

<400> SEQUENCE: 514
caauguuucc acagugcauc ac                                       22

<210> SEQ ID NO 515
<211> LENGTH: 20
<212> TYPE: RNA
<213> ORGANISM: homo sapiens

<400> SEQUENCE: 515
gugcauugcu guugcauugc                                          20

<210> SEQ ID NO 516
<211> LENGTH: 22
<212> TYPE: RNA
<213> ORGANISM: homo sapiens

<400> SEQUENCE: 516
cagugccucg gcagugcagc cc                                       22

<210> SEQ ID NO 517
<211> LENGTH: 22
<212> TYPE: RNA
<213> ORGANISM: homo sapiens
```

```
<400> SEQUENCE: 517
uuauaaagca augagacuga uu                                              22

<210> SEQ ID NO 518
<211> LENGTH: 22
<212> TYPE: RNA
<213> ORGANISM: homo sapiens

<400> SEQUENCE: 518
uccgucucag uuacuuuaua gc                                              22

<210> SEQ ID NO 519
<211> LENGTH: 23
<212> TYPE: RNA
<213> ORGANISM: homo sapiens

<400> SEQUENCE: 519
ucucacacag aaaucgcacc cgu                                             23

<210> SEQ ID NO 520
<211> LENGTH: 21
<212> TYPE: RNA
<213> ORGANISM: homo sapiens

<400> SEQUENCE: 520 agggguugcua ucugugauug a                                              21

<210> SEQ ID NO 521
<211> LENGTH: 22
<212> TYPE: RNA
<213> ORGANISM: homo sapiens

<400> SEQUENCE: 521
gcugacuccu aguccagggc uc                                              22

<210> SEQ ID NO 522
<211> LENGTH: 23
<212> TYPE: RNA
<213> ORGANISM: homo sapiens

<400> SEQUENCE: 522
ugucugcccg caugccugcc ucu                                             23

<210> SEQ ID NO 523
<211> LENGTH: 22
<212> TYPE: RNA
<213> ORGANISM: homo sapiens

<400> SEQUENCE: 523
uggcaguguc uuagcugguu gu                                              22

<210> SEQ ID NO 524
<211> LENGTH: 22
<212> TYPE: RNA
<213> ORGANISM: homo sapiens

<400> SEQUENCE: 524
caaucagcaa guauacugcc cu                                              22

<210> SEQ ID NO 525
<211> LENGTH: 22
<212> TYPE: RNA
```

<213> ORGANISM: homo sapiens

<400> SEQUENCE: 525
caaucacuaa cuccacugcc au                                        22

<210> SEQ ID NO 526
<211> LENGTH: 23
<212> TYPE: RNA
<213> ORGANISM: homo sapiens

<400> SEQUENCE: 526
uaggcagugu cauuagcuga uug                                       23

<210> SEQ ID NO 527
<211> LENGTH: 22
<212> TYPE: RNA
<213> ORGANISM: homo sapiens

<400> SEQUENCE: 527
aaucacuaac cacacggcca gg                                        22

<210> SEQ ID NO 528
<211> LENGTH: 23
<212> TYPE: RNA
<213> ORGANISM: homo sapiens

<400> SEQUENCE: 528
aggcagugua guuagcugau ugc                                       23

<210> SEQ ID NO 529
<211> LENGTH: 23
<212> TYPE: RNA
<213> ORGANISM: homo sapiens

<400> SEQUENCE: 529 uccccaggu gugauucuga uuu                                        23

<210> SEQ ID NO 530
<211> LENGTH: 22
<212> TYPE: RNA
<213> ORGANISM: homo sapiens

<400> SEQUENCE: 530
uuaucagaau cuccagggu ac                                         22

<210> SEQ ID NO 531
<211> LENGTH: 22
<212> TYPE: RNA
<213> ORGANISM: homo sapiens

<400> SEQUENCE: 531
aacacaccua uucaaggauu ca                                        22

<210> SEQ ID NO 532
<211> LENGTH: 24
<212> TYPE: RNA
<213> ORGANISM: homo sapiens

<400> SEQUENCE: 532
aauccuugga accuaggugu gagu                                      24

<210> SEQ ID NO 533
<211> LENGTH: 22

```
<212> TYPE: RNA
<213> ORGANISM: homo sapiens

<400> SEQUENCE: 533
aauugcacgg uauccaucug ua                                          22

<210> SEQ ID NO 534
<211> LENGTH: 22
<212> TYPE: RNA
<213> ORGANISM: homo sapiens

<400> SEQUENCE: 534
cggguggauc acgaugcaau uu                                          22

<210> SEQ ID NO 535
<211> LENGTH: 22
<212> TYPE: RNA
<213> ORGANISM: homo sapiens

<400> SEQUENCE: 535
uaaugccccu aaaaauccuu au                                          22

<210> SEQ ID NO 536
<211> LENGTH: 22
<212> TYPE: RNA
<213> ORGANISM: homo sapiens

<400> SEQUENCE: 536
aauugcacuu uagcaauggu ga                                          22

<210> SEQ ID NO 537
<211> LENGTH: 22
<212> TYPE: RNA
<213> ORGANISM: homo sapiens

<400> SEQUENCE: 537
acuguugcua auaugcaacu cu                                          22

<210> SEQ ID NO 538
<211> LENGTH: 21
<212> TYPE: RNA
<213> ORGANISM: homo sapiens

<400> SEQUENCE: 538
aauaauacau gguugaucuu u                                           21

<210> SEQ ID NO 539
<211> LENGTH: 22
<212> TYPE: RNA
<213> ORGANISM: homo sapiens

<400> SEQUENCE: 539
agaucgaccg uguuauauuc gc                                          22

<210> SEQ ID NO 540
<211> LENGTH: 22
<212> TYPE: RNA
<213> ORGANISM: homo sapiens

<400> SEQUENCE: 540
gccugcuggg guggaaccug gu                                          22

<210> SEQ ID NO 541
```

```
<211> LENGTH: 23
<212> TYPE: RNA
<213> ORGANISM: homo sapiens

<400> SEQUENCE: 541
aagugccgcc aucuuugag ugu                                              23

<210> SEQ ID NO 542
<211> LENGTH: 20
<212> TYPE: RNA
<213> ORGANISM: homo sapiens

<400> SEQUENCE: 542
acucaaacug uggggggcacu                                                20

<210> SEQ ID NO 543
<211> LENGTH: 23
<212> TYPE: RNA
<213> ORGANISM: homo sapiens

<400> SEQUENCE: 543
aaagugcugc gacauuugag cgu                                             23

<210> SEQ ID NO 544
<211> LENGTH: 23
<212> TYPE: RNA
<213> ORGANISM: homo sapiens

<400> SEQUENCE: 544
gaagugcuuc gauuuugggg ugu                                             23

<210> SEQ ID NO 545
<211> LENGTH: 22
<212> TYPE: RNA
<213> ORGANISM: homo sapiens

<400> SEQUENCE: 545
acucaaaaug ggggcgcuuu cc                                              22

<210> SEQ ID NO 546
<211> LENGTH: 22
<212> TYPE: RNA
<213> ORGANISM: homo sapiens

<400> SEQUENCE: 546
uuauaauaca accugauaag ug                                              22

<210> SEQ ID NO 547
<211> LENGTH: 22
<212> TYPE: RNA
<213> ORGANISM: homo sapiens

<400> SEQUENCE: 547
cuuaucagau uguauuguaa uu                                              22

<210> SEQ ID NO 548
<211> LENGTH: 22
<212> TYPE: RNA
<213> ORGANISM: homo sapiens

<400> SEQUENCE: 548
auauaauaca accugcuaag ug                                              22
```

-continued

```
<210> SEQ ID NO 549
<211> LENGTH: 22
<212> TYPE: RNA
<213> ORGANISM: homo sapiens

<400> SEQUENCE: 549
cuuagcaggu uguauuauca uu                                                  22

<210> SEQ ID NO 550
<211> LENGTH: 22
<212> TYPE: RNA
<213> ORGANISM: homo sapiens

<400> SEQUENCE: 550
uuuguucguu cggcucgcgu ga                                                  22

<210> SEQ ID NO 551
<211> LENGTH: 21
<212> TYPE: RNA
<213> ORGANISM: homo sapiens

<400> SEQUENCE: 551
aucauagagg aaaauccacg u                                                   21

<210> SEQ ID NO 552
<211> LENGTH: 22
<212> TYPE: RNA
<213> ORGANISM: homo sapiens

<400> SEQUENCE: 552
guagauucuc cuucuaugag ua                                                  22

<210> SEQ ID NO 553
<211> LENGTH: 22
<212> TYPE: RNA
<213> ORGANISM: homo sapiens

<400> SEQUENCE: 553
aucauagagg aaaauccaug uu                                                  22

<210> SEQ ID NO 554
<211> LENGTH: 21
<212> TYPE: RNA
<213> ORGANISM: homo sapiens

<400> SEQUENCE: 554
aacauagagg aaauuccacg u                                                   21

<210> SEQ ID NO 555
<211> LENGTH: 22
<212> TYPE: RNA
<213> ORGANISM: homo sapiens

<400> SEQUENCE: 555
aucacacaaa ggcaacuuuu gu                                                  22

<210> SEQ ID NO 556
<211> LENGTH: 22
<212> TYPE: RNA
<213> ORGANISM: homo sapiens

<400> SEQUENCE: 556
agagguugcc cuuggugaau uc                                                  22
```

```
<210> SEQ ID NO 557
<211> LENGTH: 21
<212> TYPE: RNA
<213> ORGANISM: homo sapiens

<400> SEQUENCE: 557
acuggacuug gagucagaag g                                             21

<210> SEQ ID NO 558
<211> LENGTH: 22
<212> TYPE: RNA
<213> ORGANISM: homo sapiens

<400> SEQUENCE: 558
cuccugacuc cagguccugu gu                                            22

<210> SEQ ID NO 559
<211> LENGTH: 21
<212> TYPE: RNA
<213> ORGANISM: homo sapiens

<400> SEQUENCE: 559
ugguagacua uggaacguag g                                             21

<210> SEQ ID NO 560
<211> LENGTH: 22
<212> TYPE: RNA
<213> ORGANISM: homo sapiens

<400> SEQUENCE: 560
uauguaacau gguccacuaa cu                                            22

<210> SEQ ID NO 561
<211> LENGTH: 22
<212> TYPE: RNA
<213> ORGANISM: homo sapiens

<400> SEQUENCE: 561
uauguaauau gguccacauc uu                                            22

<210> SEQ ID NO 562
<211> LENGTH: 22
<212> TYPE: RNA
<213> ORGANISM: homo sapiens

<400> SEQUENCE: 562
ugguugacca uagaacaugc gc                                            22

<210> SEQ ID NO 563
<211> LENGTH: 22
<212> TYPE: RNA
<213> ORGANISM: homo sapiens

<400> SEQUENCE: 563
uauacaaggg caagcucucu gu                                            22

<210> SEQ ID NO 564
<211> LENGTH: 22
<212> TYPE: RNA
<213> ORGANISM: homo sapiens

<400> SEQUENCE: 564
gaaguuguuc gugguggauu cg                                            22
```

<210> SEQ ID NO 565
<211> LENGTH: 22
<212> TYPE: RNA
<213> ORGANISM: homo sapiens

<400> SEQUENCE: 565
agaucagaag gugauugugg cu                                            22

<210> SEQ ID NO 566
<211> LENGTH: 20
<212> TYPE: RNA
<213> ORGANISM: homo sapiens

<400> SEQUENCE: 566 auccuagaa auuguucaua                                                20

<210> SEQ ID NO 567
<211> LENGTH: 22
<212> TYPE: RNA
<213> ORGANISM: homo sapiens

<400> SEQUENCE: 567
gaauguugcu cggugaaccc cu                                            22

<210> SEQ ID NO 568
<211> LENGTH: 23
<212> TYPE: RNA
<213> ORGANISM: homo sapiens

<400> SEQUENCE: 568
agguuacccg agcaacuuug cau                                           23

<210> SEQ ID NO 569
<211> LENGTH: 21
<212> TYPE: RNA
<213> ORGANISM: homo sapiens

<400> SEQUENCE: 569
aauauaacac agauggccug u                                             21

<210> SEQ ID NO 570
<211> LENGTH: 21
<212> TYPE: RNA
<213> ORGANISM: homo sapiens

<400> SEQUENCE: 570
uaguagaccg uauagcguac g                                             21

<210> SEQ ID NO 571
<211> LENGTH: 22
<212> TYPE: RNA
<213> ORGANISM: homo sapiens

<400> SEQUENCE: 571
uauguaacac gguccacuaa cc                                            22

<210> SEQ ID NO 572
<211> LENGTH: 23
<212> TYPE: RNA
<213> ORGANISM: homo sapiens

<400> SEQUENCE: 572

-continued acuucaccug guccacuagc cgu                                          23

<210> SEQ ID NO 573
<211> LENGTH: 23
<212> TYPE: RNA
<213> ORGANISM: homo sapiens

<400> SEQUENCE: 573
aucaacagac auuaauuggg cgc                                          23

<210> SEQ ID NO 574
<211> LENGTH: 22
<212> TYPE: RNA
<213> ORGANISM: homo sapiens

<400> SEQUENCE: 574
acuggacuua gggucagaag gc                                           22

<210> SEQ ID NO 575
<211> LENGTH: 23
<212> TYPE: RNA
<213> ORGANISM: homo sapiens

<400> SEQUENCE: 575
agcucggucu gaggccccuc agu                                          23

<210> SEQ ID NO 576
<211> LENGTH: 23
<212> TYPE: RNA
<213> ORGANISM: homo sapiens

<400> SEQUENCE: 576
ugaggggcag agagcgagac uuu                                          23

<210> SEQ ID NO 577
<211> LENGTH: 22
<212> TYPE: RNA
<213> ORGANISM: homo sapiens

<400> SEQUENCE: 577
cagcagcaau ucauguuuug aa                                           22

<210> SEQ ID NO 578
<211> LENGTH: 21
<212> TYPE: RNA
<213> ORGANISM: homo sapiens

<400> SEQUENCE: 578
caaaacguga ggcgcugcua u                                            21

<210> SEQ ID NO 579
<211> LENGTH: 23
<212> TYPE: RNA
<213> ORGANISM: homo sapiens

<400> SEQUENCE: 579
aaugacacga ucacucccgu uga                                          23

<210> SEQ ID NO 580
<211> LENGTH: 22
<212> TYPE: RNA
<213> ORGANISM: homo sapiens

<400> SEQUENCE: 580
aucgggaaug ucguguccgc cc                                    22

<210> SEQ ID NO 581
<211> LENGTH: 22
<212> TYPE: RNA
<213> ORGANISM: homo sapiens

<400> SEQUENCE: 581
uaauacuguc ugguaaaacc gu                                    22

<210> SEQ ID NO 582
<211> LENGTH: 21
<212> TYPE: RNA
<213> ORGANISM: homo sapiens

<400> SEQUENCE: 582
ugucuugcag gccgucaugc a                                     21

<210> SEQ ID NO 583
<211> LENGTH: 22
<212> TYPE: RNA
<213> ORGANISM: homo sapiens

<400> SEQUENCE: 583
caggucgucu ugcagggcuu cu                                    22

<210> SEQ ID NO 584
<211> LENGTH: 23
<212> TYPE: RNA
<213> ORGANISM: homo sapiens

<400> SEQUENCE: 584
ucuuggagua ggucauuggg ugg                                   23

<210> SEQ ID NO 585
<211> LENGTH: 21
<212> TYPE: RNA
<213> ORGANISM: homo sapiens

<400> SEQUENCE: 585
cuggauggcu ccuccauguc u                                     21

<210> SEQ ID NO 586
<211> LENGTH: 22
<212> TYPE: RNA
<213> ORGANISM: homo sapiens

<400> SEQUENCE: 586
aucaugaugg gcuccucggu gu                                    22

<210> SEQ ID NO 587
<211> LENGTH: 22
<212> TYPE: RNA
<213> ORGANISM: homo sapiens

<400> SEQUENCE: 587
uugcauaugu aggauguccc au                                    22

<210> SEQ ID NO 588
<211> LENGTH: 22
<212> TYPE: RNA
<213> ORGANISM: homo sapiens

```
<400> SEQUENCE: 588
uggcagugua uuguuagcug gu                                          22

<210> SEQ ID NO 589
<211> LENGTH: 22
<212> TYPE: RNA
<213> ORGANISM: homo sapiens

<400> SEQUENCE: 589
aggcagugua uuguuagcug gc                                          22

<210> SEQ ID NO 590
<211> LENGTH: 22
<212> TYPE: RNA
<213> ORGANISM: homo sapiens

<400> SEQUENCE: 590
uuuugcgaug uguuccuaau au                                          22

<210> SEQ ID NO 591
<211> LENGTH: 22
<212> TYPE: RNA
<213> ORGANISM: homo sapiens

<400> SEQUENCE: 591
uugggaucau uuugcaucca ua                                          22

<210> SEQ ID NO 592
<211> LENGTH: 22
<212> TYPE: RNA
<213> ORGANISM: homo sapiens

<400> SEQUENCE: 592
uuuugcaaua uguuccugaa ua                                          22

<210> SEQ ID NO 593
<211> LENGTH: 22
<212> TYPE: RNA
<213> ORGANISM: homo sapiens

<400> SEQUENCE: 593
aaaccguuac cauuacugag uu                                          22

<210> SEQ ID NO 594
<211> LENGTH: 22
<212> TYPE: RNA
<213> ORGANISM: homo sapiens

<400> SEQUENCE: 594
aacuguuugc agaggaaacu ga                                          22

<210> SEQ ID NO 595
<211> LENGTH: 22
<212> TYPE: RNA
<213> ORGANISM: homo sapiens

<400> SEQUENCE: 595
cucaucugca aagaaguaag ug                                          22

<210> SEQ ID NO 596
<211> LENGTH: 23
<212> TYPE: RNA
<213> ORGANISM: homo sapiens
```

```
<400> SEQUENCE: 596
agguuguccg uggugaguuc gca                                              23

<210> SEQ ID NO 597
<211> LENGTH: 23
<212> TYPE: RNA
<213> ORGANISM: homo sapiens

<400> SEQUENCE: 597
uagugcaaua uugcuuauag ggu                                              23

<210> SEQ ID NO 598
<211> LENGTH: 22
<212> TYPE: RNA
<213> ORGANISM: homo sapiens

<400> SEQUENCE: 598
acccuaucaa uauugucucu gc                                               22

<210> SEQ ID NO 599
<211> LENGTH: 21
<212> TYPE: RNA
<213> ORGANISM: homo sapiens

<400> SEQUENCE: 599
gcaguccaug ggcauauaca c                                                21

<210> SEQ ID NO 600
<211> LENGTH: 22
<212> TYPE: RNA
<213> ORGANISM: homo sapiens

<400> SEQUENCE: 600
uaugugccuu uggacuacau cg                                               22

<210> SEQ ID NO 601
<211> LENGTH: 21
<212> TYPE: RNA
<213> ORGANISM: homo sapiens

<400> SEQUENCE: 601
ucacuccucu ccucccgucu u                                                21

<210> SEQ ID NO 602
<211> LENGTH: 22
<212> TYPE: RNA
<213> ORGANISM: homo sapiens

<400> SEQUENCE: 602
aagacgggag gaaagaaggg ag                                               22

<210> SEQ ID NO 603
<211> LENGTH: 22
<212> TYPE: RNA
<213> ORGANISM: homo sapiens

<400> SEQUENCE: 603
ucaggcucag uccccucccg au                                               22

<210> SEQ ID NO 604
<211> LENGTH: 22
<212> TYPE: RNA
```

<213> ORGANISM: homo sapiens

<400> SEQUENCE: 604
gucauacacg gcucuccucu cu                                          22

<210> SEQ ID NO 605
<211> LENGTH: 22
<212> TYPE: RNA
<213> ORGANISM: homo sapiens

<400> SEQUENCE: 605
agaggcuggc cgugaugaau uc                                          22

<210> SEQ ID NO 606
<211> LENGTH: 21
<212> TYPE: RNA
<213> ORGANISM: homo sapiens

<400> SEQUENCE: 606
cggggcagcu caguacagga u                                           21

<210> SEQ ID NO 607
<211> LENGTH: 22
<212> TYPE: RNA
<213> ORGANISM: homo sapiens

<400> SEQUENCE: 607
uccuguacug agcugccccg ag                                          22

<210> SEQ ID NO 608
<211> LENGTH: 22
<212> TYPE: RNA
<213> ORGANISM: homo sapiens

<400> SEQUENCE: 608
aaucauacag ggacauccag uu                                          22

<210> SEQ ID NO 609
<211> LENGTH: 22
<212> TYPE: RNA
<213> ORGANISM: homo sapiens

<400> SEQUENCE: 609
aaucguacag ggucauccac uu                                          22

<210> SEQ ID NO 610
<211> LENGTH: 21
<212> TYPE: RNA
<213> ORGANISM: homo sapiens

<400> SEQUENCE: 610
uugaaaggcu auuucuuggu c                                           21

<210> SEQ ID NO 611
<211> LENGTH: 21
<212> TYPE: RNA
<213> ORGANISM: homo sapiens

<400> SEQUENCE: 611
cccagauaau ggcacucuca a                                           21

<210> SEQ ID NO 612
<211> LENGTH: 22

<210> SEQ ID NO 612
<211> LENGTH: 22
<212> TYPE: RNA
<213> ORGANISM: homo sapiens

<400> SEQUENCE: 612
gugacaucac auauacggca gc                                          22

<210> SEQ ID NO 613
<211> LENGTH: 22
<212> TYPE: RNA
<213> ORGANISM: homo sapiens

<400> SEQUENCE: 613
caaccuggag gacuccaugc ug                                          22

<210> SEQ ID NO 614
<211> LENGTH: 20
<212> TYPE: RNA
<213> ORGANISM: homo sapiens

<400> SEQUENCE: 614
ccauggaucu ccaggugggu                                             20

<210> SEQ ID NO 615
<211> LENGTH: 22
<212> TYPE: RNA
<213> ORGANISM: homo sapiens

<400> SEQUENCE: 615
cuuaugcaag auucccuucu ac                                          22

<210> SEQ ID NO 616
<211> LENGTH: 22
<212> TYPE: RNA
<213> ORGANISM: homo sapiens

<400> SEQUENCE: 616
aguggggaac ccuuccauga gg                                          22

<210> SEQ ID NO 617
<211> LENGTH: 23
<212> TYPE: RNA
<213> ORGANISM: homo sapiens

<400> SEQUENCE: 617
aggaccugcg ggacaagauu cuu                                         23

<210> SEQ ID NO 618
<211> LENGTH: 22
<212> TYPE: RNA
<213> ORGANISM: homo sapiens

<400> SEQUENCE: 618
ugaaggucua cugugugcca gg                                          22

<210> SEQ ID NO 619
<211> LENGTH: 22
<212> TYPE: RNA
<213> ORGANISM: homo sapiens

<400> SEQUENCE: 619
uuguacaugg uaggcuuuca uu                                          22

<210> SEQ ID NO 620

```
<211> LENGTH: 22
<212> TYPE: RNA
<213> ORGANISM: homo sapiens

<400> SEQUENCE: 620
ugaaacauac acgggaaacc uc                                    22

<210> SEQ ID NO 621
<211> LENGTH: 22
<212> TYPE: RNA
<213> ORGANISM: homo sapiens

<400> SEQUENCE: 621
aaacaaacau ggugcacuuc uu                                    22

<210> SEQ ID NO 622
<211> LENGTH: 22
<212> TYPE: RNA
<213> ORGANISM: homo sapiens

<400> SEQUENCE: 622
ugaguauuac auggccaauc uc                                    22

<210> SEQ ID NO 623
<211> LENGTH: 21
<212> TYPE: RNA
<213> ORGANISM: homo sapiens

<400> SEQUENCE: 623
cagcagcaca cugugguuug u                                     21

<210> SEQ ID NO 624
<211> LENGTH: 22
<212> TYPE: RNA
<213> ORGANISM: homo sapiens

<400> SEQUENCE: 624
caaaccacac uguggguuua ga                                    22

<210> SEQ ID NO 625
<211> LENGTH: 23
<212> TYPE: RNA
<213> ORGANISM: homo sapiens

<400> SEQUENCE: 625
uuucaagcca gggggcguuu uuc                                   23

<210> SEQ ID NO 626
<211> LENGTH: 22
<212> TYPE: RNA
<213> ORGANISM: homo sapiens

<400> SEQUENCE: 626
aacaucacag caagucugug cu                                    22

<210> SEQ ID NO 627
<211> LENGTH: 21
<212> TYPE: RNA
<213> ORGANISM: homo sapiens

<400> SEQUENCE: 627
uuaagacuug cagugauguu u                                     21
```

```
<210> SEQ ID NO 628
<211> LENGTH: 23
<212> TYPE: RNA
<213> ORGANISM: homo sapiens

<400> SEQUENCE: 628
uaauccuugc uaccugggug aga                                              23

<210> SEQ ID NO 629
<211> LENGTH: 22
<212> TYPE: RNA
<213> ORGANISM: homo sapiens

<400> SEQUENCE: 629
augcaccugg gcaaggauuc ug                                               22

<210> SEQ ID NO 630
<211> LENGTH: 22
<212> TYPE: RNA
<213> ORGANISM: homo sapiens

<400> SEQUENCE: 630
aaugcacccg ggcaaggauu cu                                               22

<210> SEQ ID NO 631
<211> LENGTH: 22
<212> TYPE: RNA
<213> ORGANISM: homo sapiens

<400> SEQUENCE: 631
aauccuuugu cccuggguga ga                                               22

<210> SEQ ID NO 632
<211> LENGTH: 22
<212> TYPE: RNA
<213> ORGANISM: homo sapiens

<400> SEQUENCE: 632
aaugcaccug ggcaaggauu ca                                               22

<210> SEQ ID NO 633
<211> LENGTH: 21
<212> TYPE: RNA
<213> ORGANISM: homo sapiens

<400> SEQUENCE: 633
auccuugcua ucuggguugcu a                                               21

<210> SEQ ID NO 634
<211> LENGTH: 23
<212> TYPE: RNA
<213> ORGANISM: homo sapiens

<400> SEQUENCE: 634
uagcagcggg aacaguucug cag                                              23

<210> SEQ ID NO 635
<211> LENGTH: 22
<212> TYPE: RNA
<213> ORGANISM: homo sapiens

<400> SEQUENCE: 635
agacccuggu cugcacucua uc                                               22
```

```
<210> SEQ ID NO 636
<211> LENGTH: 22
<212> TYPE: RNA
<213> ORGANISM: homo sapiens

<400> SEQUENCE: 636
cgucaacacu ugcugguuuc cu                                          22

<210> SEQ ID NO 637
<211> LENGTH: 22
<212> TYPE: RNA
<213> ORGANISM: homo sapiens

<400> SEQUENCE: 637
gggagccagg aaguauugau gu                                          22

<210> SEQ ID NO 638
<211> LENGTH: 21
<212> TYPE: RNA
<213> ORGANISM: homo sapiens

<400> SEQUENCE: 638
uaaggcaccc uucugaguag a                                           21

<210> SEQ ID NO 639
<211> LENGTH: 21
<212> TYPE: RNA
<213> ORGANISM: homo sapiens

<400> SEQUENCE: 639
uuuugcaccu uuuggaguga a                                           21

<210> SEQ ID NO 640
<211> LENGTH: 23
<212> TYPE: RNA
<213> ORGANISM: homo sapiens

<400> SEQUENCE: 640
ugauuguagc cuuuuggagu aga                                         23

<210> SEQ ID NO 641
<211> LENGTH: 23
<212> TYPE: RNA
<213> ORGANISM: homo sapiens

<400> SEQUENCE: 641
uacuccagag ggcgucacuc aug                                         23

<210> SEQ ID NO 642
<211> LENGTH: 22
<212> TYPE: RNA
<213> ORGANISM: homo sapiens

<400> SEQUENCE: 642
uacugcagac guggcaauca ug                                          22

<210> SEQ ID NO 643
<211> LENGTH: 22
<212> TYPE: RNA
<213> ORGANISM: homo sapiens

<400> SEQUENCE: 643 ugauuggguac gucugugggu ag                                         22
```

<210> SEQ ID NO 644
<211> LENGTH: 21
<212> TYPE: RNA
<213> ORGANISM: homo sapiens

<400> SEQUENCE: 644
uacugcagac aguggcaauc a                                             21

<210> SEQ ID NO 645
<211> LENGTH: 22
<212> TYPE: RNA
<213> ORGANISM: homo sapiens

<400> SEQUENCE: 645
uacucaggag aguggcaauc ac                                            22

<210> SEQ ID NO 646
<211> LENGTH: 21
<212> TYPE: RNA
<213> ORGANISM: homo sapiens

<400> SEQUENCE: 646
gugucuuuug cucugcaguc a                                             21

<210> SEQ ID NO 647
<211> LENGTH: 22
<212> TYPE: RNA
<213> ORGANISM: homo sapiens

<400> SEQUENCE: 647
aagugcuguc auagcugagg uc                                            22

<210> SEQ ID NO 648
<211> LENGTH: 23
<212> TYPE: RNA
<213> ORGANISM: homo sapiens

<400> SEQUENCE: 648
cacucagccu ugagggcacu uuc                                           23

<210> SEQ ID NO 649
<211> LENGTH: 23
<212> TYPE: RNA
<213> ORGANISM: homo sapiens

<400> SEQUENCE: 649
uaaauuucac cuuucugaga agg                                           23

<210> SEQ ID NO 650
<211> LENGTH: 18
<212> TYPE: RNA
<213> ORGANISM: homo sapiens

<400> SEQUENCE: 650
uucacaggga ggugucau                                                 18

<210> SEQ ID NO 651
<211> LENGTH: 22
<212> TYPE: RNA
<213> ORGANISM: homo sapiens

<400> SEQUENCE: 651
uucacaagga ggugucauuu au                                22

<210> SEQ ID NO 652
<211> LENGTH: 22
<212> TYPE: RNA
<213> ORGANISM: homo sapiens

<400> SEQUENCE: 652
uucucaagga ggugucguuu au                                22

<210> SEQ ID NO 653
<211> LENGTH: 21
<212> TYPE: RNA
<213> ORGANISM: homo sapiens

<400> SEQUENCE: 653
auugacacuu cugugaguag a                                 21

<210> SEQ ID NO 654
<211> LENGTH: 22
<212> TYPE: RNA
<213> ORGANISM: homo sapiens

<400> SEQUENCE: 654
gagugccuuc uuuuggagcg uu                                22

<210> SEQ ID NO 655
<211> LENGTH: 24
<212> TYPE: RNA
<213> ORGANISM: homo sapiens

<400> SEQUENCE: 655
uucuccaaaa gaaagcacuu ucug                              24

<210> SEQ ID NO 656
<211> LENGTH: 18
<212> TYPE: RNA
<213> ORGANISM: homo sapiens

<400> SEQUENCE: 656
ugcuuccuuu cagagggu                                     18

<210> SEQ ID NO 657
<211> LENGTH: 23
<212> TYPE: RNA
<213> ORGANISM: homo sapiens

<400> SEQUENCE: 657
uucucgagga aagaagcacu uuc                               23

<210> SEQ ID NO 658
<211> LENGTH: 22
<212> TYPE: RNA
<213> ORGANISM: homo sapiens

<400> SEQUENCE: 658
aucuggaggu aagaagcacu uu                                22

<210> SEQ ID NO 659
<211> LENGTH: 22
<212> TYPE: RNA
<213> ORGANISM: homo sapiens

<400> SEQUENCE: 659
ccucuagaug gaagcacugu cu 22

<210> SEQ ID NO 660
<211> LENGTH: 22
<212> TYPE: RNA
<213> ORGANISM: homo sapiens

<400> SEQUENCE: 660
aucgugcauc ccuuuagagu gu 22

<210> SEQ ID NO 661
<211> LENGTH: 22
<212> TYPE: RNA
<213> ORGANISM: homo sapiens

<400> SEQUENCE: 661
ucgugcaucc cuuuagagug uu 22

<210> SEQ ID NO 662
<211> LENGTH: 22
<212> TYPE: RNA
<213> ORGANISM: homo sapiens

<400> SEQUENCE: 662
aucgugcauc cuuuuagagu gu 22

<210> SEQ ID NO 663
<211> LENGTH: 22
<212> TYPE: RNA
<213> ORGANISM: homo sapiens

<400> SEQUENCE: 663
gaaagcgcuu cccuuugcug ga 22

<210> SEQ ID NO 664
<211> LENGTH: 22
<212> TYPE: RNA
<213> ORGANISM: homo sapiens

<400> SEQUENCE: 664
caaagcgcuc cccuuuagag gu 22

<210> SEQ ID NO 665
<211> LENGTH: 23
<212> TYPE: RNA
<213> ORGANISM: homo sapiens

<400> SEQUENCE: 665
caaagcgcuu cucuuuagag ugu 23

<210> SEQ ID NO 666
<211> LENGTH: 23
<212> TYPE: RNA
<213> ORGANISM: homo sapiens

<400> SEQUENCE: 666
ucucuggagg gaagcacuuu cug 23

<210> SEQ ID NO 667
<211> LENGTH: 21
<212> TYPE: RNA
<213> ORGANISM: homo sapiens

```
<400> SEQUENCE: 667
caaagcgcuu cccuuuggag c                                            21

<210> SEQ ID NO 668
<211> LENGTH: 22
<212> TYPE: RNA
<213> ORGANISM: homo sapiens

<400> SEQUENCE: 668
cucuagaggg aagcacuuuc ug                                           22

<210> SEQ ID NO 669
<211> LENGTH: 21
<212> TYPE: RNA
<213> ORGANISM: homo sapiens

<400> SEQUENCE: 669
aaagcgcuuc ccuucagagu g                                            21

<210> SEQ ID NO 670
<211> LENGTH: 21
<212> TYPE: RNA
<213> ORGANISM: homo sapiens

<400> SEQUENCE: 670
gaaagcgcuu cucuuuagag g                                            21

<210> SEQ ID NO 671
<211> LENGTH: 22
<212> TYPE: RNA
<213> ORGANISM: homo sapiens

<400> SEQUENCE: 671
cucuagaggg aagcacuuuc uc                                           22

<210> SEQ ID NO 672
<211> LENGTH: 22
<212> TYPE: RNA
<213> ORGANISM: homo sapiens

<400> SEQUENCE: 672
aaagugcauc cuuuuagagu gu                                           22

<210> SEQ ID NO 673
<211> LENGTH: 22
<212> TYPE: RNA
<213> ORGANISM: homo sapiens

<400> SEQUENCE: 673
cucuagaggg aagcgcuuuc ug                                           22

<210> SEQ ID NO 674
<211> LENGTH: 22
<212> TYPE: RNA
<213> ORGANISM: homo sapiens

<400> SEQUENCE: 674
aaagugcauc cuuuuagagg uu                                           22

<210> SEQ ID NO 675
<211> LENGTH: 22
<212> TYPE: RNA
<213> ORGANISM: homo sapiens
```

-continued

```
<400> SEQUENCE: 675
aaagugcauc uuuuuagagg au                                              22

<210> SEQ ID NO 676
<211> LENGTH: 22
<212> TYPE: RNA
<213> ORGANISM: homo sapiens

<400> SEQUENCE: 676
caaagugccu cccuuuagag ug                                              22

<210> SEQ ID NO 677
<211> LENGTH: 22
<212> TYPE: RNA
<213> ORGANISM: homo sapiens

<400> SEQUENCE: 677
aagugccucc uuuuagagug uu                                              22

<210> SEQ ID NO 678
<211> LENGTH: 22
<212> TYPE: RNA
<213> ORGANISM: homo sapiens

<400> SEQUENCE: 678
uucuccaaaa gggagcacuu uc                                              22

<210> SEQ ID NO 679
<211> LENGTH: 22
<212> TYPE: RNA
<213> ORGANISM: homo sapiens

<400> SEQUENCE: 679
aaagugcuuc ccuuuggacu gu                                              22

<210> SEQ ID NO 680
<211> LENGTH: 21
<212> TYPE: RNA
<213> ORGANISM: homo sapiens

<400> SEQUENCE: 680
cuccagaggg aaguacuuuc u                                               21

<210> SEQ ID NO 681
<211> LENGTH: 21
<212> TYPE: RNA
<213> ORGANISM: homo sapiens

<400> SEQUENCE: 681
aaagugcuuc cuuuuagagg g                                               21

<210> SEQ ID NO 682
<211> LENGTH: 22
<212> TYPE: RNA
<213> ORGANISM: homo sapiens

<400> SEQUENCE: 682
aaagugcuuc cuuuuagagg gu                                              22

<210> SEQ ID NO 683
<211> LENGTH: 22
<212> TYPE: RNA
```

```
<213> ORGANISM: homo sapiens

<400> SEQUENCE: 683
aaagugcuuc ucuuuggugg gu                                    22

<210> SEQ ID NO 684
<211> LENGTH: 20
<212> TYPE: RNA
<213> ORGANISM: homo sapiens

<400> SEQUENCE: 684
cuacaaaggg aagcccuuuc                                       20

<210> SEQ ID NO 685
<211> LENGTH: 21
<212> TYPE: RNA
<213> ORGANISM: homo sapiens

<400> SEQUENCE: 685
aaagugcuuc cuuuuugagg g                                     21

<210> SEQ ID NO 686
<211> LENGTH: 22
<212> TYPE: RNA
<213> ORGANISM: homo sapiens

<400> SEQUENCE: 686
aagugcuucc uuuuagaggg uu                                    22

<210> SEQ ID NO 687
<211> LENGTH: 24
<212> TYPE: RNA
<213> ORGANISM: homo sapiens

<400> SEQUENCE: 687
acaaagugcu ucccuuuaga gugu                                  24

<210> SEQ ID NO 688
<211> LENGTH: 22
<212> TYPE: RNA
<213> ORGANISM: homo sapiens

<400> SEQUENCE: 688
acaaagugcu ucccuuuaga gu                                    22

<210> SEQ ID NO 689
<211> LENGTH: 22
<212> TYPE: RNA
<213> ORGANISM: homo sapiens

<400> SEQUENCE: 689
aacgcacuuc ccuuuagagu gu                                    22

<210> SEQ ID NO 690
<211> LENGTH: 22
<212> TYPE: RNA
<213> ORGANISM: homo sapiens

<400> SEQUENCE: 690
aaaaugguuc ccuuuagagu gu                                    22

<210> SEQ ID NO 691
<211> LENGTH: 23
```

```
<212> TYPE: RNA
<213> ORGANISM: homo sapiens

<400> SEQUENCE: 691
gaacgcgcuu cccauauagag ggu                                       23

<210> SEQ ID NO 692
<211> LENGTH: 21
<212> TYPE: RNA
<213> ORGANISM: homo sapiens

<400> SEQUENCE: 692
gaaggcgcuu cccuuuggag u                                          21

<210> SEQ ID NO 693
<211> LENGTH: 22
<212> TYPE: RNA
<213> ORGANISM: homo sapiens

<400> SEQUENCE: 693
cuacaaaggg aagcacuuuc uc                                         22

<210> SEQ ID NO 694
<211> LENGTH: 22
<212> TYPE: RNA
<213> ORGANISM: homo sapiens

<400> SEQUENCE: 694
gaaggcgcuu cccuuuagag cg                                         22

<210> SEQ ID NO 695
<211> LENGTH: 21
<212> TYPE: RNA
<213> ORGANISM: homo sapiens

<400> SEQUENCE: 695
cuccagaggg augcacuuuc u                                          21

<210> SEQ ID NO 696
<211> LENGTH: 23
<212> TYPE: RNA
<213> ORGANISM: homo sapiens

<400> SEQUENCE: 696
cucuugaggg aagcacuuuc ugu                                        23

<210> SEQ ID NO 697
<211> LENGTH: 22
<212> TYPE: RNA
<213> ORGANISM: homo sapiens

<400> SEQUENCE: 697
gaaagugcuu ccuuuuagag gc                                         22

<210> SEQ ID NO 698
<211> LENGTH: 20
<212> TYPE: RNA
<213> ORGANISM: homo sapiens

<400> SEQUENCE: 698
cugcaaaggg aagcccuuuc                                            20

<210> SEQ ID NO 699
```

-continued

<211> LENGTH: 22
<212> TYPE: RNA
<213> ORGANISM: homo sapiens

<400> SEQUENCE: 699
ccucccacac ccaaggcuug ca                                              22

<210> SEQ ID NO 700
<211> LENGTH: 22
<212> TYPE: RNA
<213> ORGANISM: homo sapiens

<400> SEQUENCE: 700
caugccuuga guguaggacc gu                                              22

<210> SEQ ID NO 701
<211> LENGTH: 22
<212> TYPE: RNA
<213> ORGANISM: homo sapiens

<400> SEQUENCE: 701
ggagaaauua uccuuggugu gu                                              22

<210> SEQ ID NO 702
<211> LENGTH: 22
<212> TYPE: RNA
<213> ORGANISM: homo sapiens

<400> SEQUENCE: 702 ugguggggcac agaaucugga cu                                             22

<210> SEQ ID NO 703
<211> LENGTH: 25
<212> TYPE: RNA
<213> ORGANISM: homo sapiens

<400> SEQUENCE: 703
aaaggauucu gcugucgguc ccacu                                           25

<210> SEQ ID NO 704
<211> LENGTH: 22
<212> TYPE: RNA
<213> ORGANISM: homo sapiens

<400> SEQUENCE: 704
ugugacagau ugauaacuga aa                                              22

<210> SEQ ID NO 705
<211> LENGTH: 23
<212> TYPE: RNA
<213> ORGANISM: homo sapiens

<400> SEQUENCE: 705
ucggggauca ucaugucacg aga                                             23

<210> SEQ ID NO 706
<211> LENGTH: 22
<212> TYPE: RNA
<213> ORGANISM: homo sapiens

<400> SEQUENCE: 706
aaacauucgc ggugcacuuc uu                                              22

-continued

```
<210> SEQ ID NO 707
<211> LENGTH: 22
<212> TYPE: RNA
<213> ORGANISM: homo sapiens

<400> SEQUENCE: 707
auucugcauu uuuagcaagu uc                                              22

<210> SEQ ID NO 708
<211> LENGTH: 22
<212> TYPE: RNA
<213> ORGANISM: homo sapiens

<400> SEQUENCE: 708
ucagcaaaca uuuauugugu gc                                              22

<210> SEQ ID NO 709
<211> LENGTH: 22
<212> TYPE: RNA
<213> ORGANISM: homo sapiens

<400> SEQUENCE: 709
ucaguaaaug uuuauuagau ga                                              22

<210> SEQ ID NO 710
<211> LENGTH: 22
<212> TYPE: RNA
<213> ORGANISM: homo sapiens

<400> SEQUENCE: 710
caaaacuggc aauuacuuuu gc                                              22

<210> SEQ ID NO 711
<211> LENGTH: 22
<212> TYPE: RNA
<213> ORGANISM: homo sapiens

<400> SEQUENCE: 711
aaaaguaauu gcgaguuuua cc                                              22

<210> SEQ ID NO 712
<211> LENGTH: 22
<212> TYPE: RNA
<213> ORGANISM: homo sapiens

<400> SEQUENCE: 712
caagaaccuc aguugcuuuu gu                                              22

<210> SEQ ID NO 713
<211> LENGTH: 22
<212> TYPE: RNA
<213> ORGANISM: homo sapiens

<400> SEQUENCE: 713
aaaaguaauu gugguuuugg cc                                              22

<210> SEQ ID NO 714
<211> LENGTH: 22
<212> TYPE: RNA
<213> ORGANISM: homo sapiens

<400> SEQUENCE: 714 caaaaucuc aauuacuuuu gc                                               22
```

<210> SEQ ID NO 715
<211> LENGTH: 22
<212> TYPE: RNA
<213> ORGANISM: homo sapiens

<400> SEQUENCE: 715
aaaaguaauu gcgguuuuug cc                                              22

<210> SEQ ID NO 716
<211> LENGTH: 22
<212> TYPE: RNA
<213> ORGANISM: homo sapiens

<400> SEQUENCE: 716
caaaaaccac aguuucuuuu gc                                              22

<210> SEQ ID NO 717
<211> LENGTH: 22
<212> TYPE: RNA
<213> ORGANISM: homo sapiens

<400> SEQUENCE: 717
aaaaguaauu gugguuuuug cc                                              22

<210> SEQ ID NO 718
<211> LENGTH: 22
<212> TYPE: RNA
<213> ORGANISM: homo sapiens

<400> SEQUENCE: 718
aaaaacugag acuacuuuug ca                                              22

<210> SEQ ID NO 719
<211> LENGTH: 19
<212> TYPE: RNA
<213> ORGANISM: homo sapiens

<400> SEQUENCE: 719
aaaaacugua auuacuuuu                                                  19

<210> SEQ ID NO 720
<211> LENGTH: 22
<212> TYPE: RNA
<213> ORGANISM: homo sapiens

<400> SEQUENCE: 720
aaaacuguaa uuacuuuugu ac                                              22

<210> SEQ ID NO 721
<211> LENGTH: 22
<212> TYPE: RNA
<213> ORGANISM: homo sapiens

<400> SEQUENCE: 721
aaaaguaauc gcgguuuuug uc                                              22

<210> SEQ ID NO 722
<211> LENGTH: 22
<212> TYPE: RNA
<213> ORGANISM: homo sapiens

<400> SEQUENCE: 722
aaaaguaauu gcggauuuug cc                                              22

```
<210> SEQ ID NO 723
<211> LENGTH: 22
<212> TYPE: RNA
<213> ORGANISM: homo sapiens

<400> SEQUENCE: 723
aaaaguaauu gcggucuuug gu                                              22

<210> SEQ ID NO 724
<211> LENGTH: 22
<212> TYPE: RNA
<213> ORGANISM: homo sapiens

<400> SEQUENCE: 724
aaaaguacuu gcggauuuug cu                                              22

<210> SEQ ID NO 725
<211> LENGTH: 22
<212> TYPE: RNA
<213> ORGANISM: homo sapiens

<400> SEQUENCE: 725
aaaaguauuu gcggguuuug uc                                              22

<210> SEQ ID NO 726
<211> LENGTH: 21
<212> TYPE: RNA
<213> ORGANISM: homo sapiens

<400> SEQUENCE: 726
caaagguauu uguggutuuu g                                               21

<210> SEQ ID NO 727
<211> LENGTH: 22
<212> TYPE: RNA
<213> ORGANISM: homo sapiens

<400> SEQUENCE: 727
caaaaguaau uguggauuuu gu                                              22

<210> SEQ ID NO 728
<211> LENGTH: 22
<212> TYPE: RNA
<213> ORGANISM: homo sapiens

<400> SEQUENCE: 728
ccaaaacugc aguuacuuuu gc                                              22

<210> SEQ ID NO 729
<211> LENGTH: 22
<212> TYPE: RNA
<213> ORGANISM: homo sapiens

<400> SEQUENCE: 729
uagcaaaaac ugcaguuacu uu                                              22

<210> SEQ ID NO 730
<211> LENGTH: 21
<212> TYPE: RNA
<213> ORGANISM: homo sapiens

<400> SEQUENCE: 730
```

-continued ugacaacuau ggaugagcuc u                                              21

<210> SEQ ID NO 731
<211> LENGTH: 23
<212> TYPE: RNA
<213> ORGANISM: homo sapiens

<400> SEQUENCE: 731
agugccugag ggaguaagag ccc                                            23

<210> SEQ ID NO 732
<211> LENGTH: 22
<212> TYPE: RNA
<213> ORGANISM: homo sapiens

<400> SEQUENCE: 732
ugucuuacuc ccucaggcac au                                             22

<210> SEQ ID NO 733
<211> LENGTH: 21
<212> TYPE: RNA
<213> ORGANISM: homo sapiens

<400> SEQUENCE: 733
gcgacccacu cuugguuucc a                                              21

<210> SEQ ID NO 734
<211> LENGTH: 21
<212> TYPE: RNA
<213> ORGANISM: homo sapiens

<400> SEQUENCE: 734
gcgacccaua cuugguuuca g                                              21

<210> SEQ ID NO 735
<211> LENGTH: 22
<212> TYPE: RNA
<213> ORGANISM: homo sapiens

<400> SEQUENCE: 735
gaaaucaagc gugggugaga cc                                             22

<210> SEQ ID NO 736
<211> LENGTH: 21
<212> TYPE: RNA
<213> ORGANISM: homo sapiens

<400> SEQUENCE: 736
aacaggugac ugguuagaca a                                              21

<210> SEQ ID NO 737
<211> LENGTH: 21
<212> TYPE: RNA
<213> ORGANISM: homo sapiens

<400> SEQUENCE: 737
aaaacgguga gauuuuguuu u                                              21

<210> SEQ ID NO 738
<211> LENGTH: 21
<212> TYPE: RNA
<213> ORGANISM: homo sapiens

<400> SEQUENCE: 738
gcuaguccug acucagccag u    21

<210> SEQ ID NO 739
<211> LENGTH: 21
<212> TYPE: RNA
<213> ORGANISM: homo sapiens

<400> SEQUENCE: 739
aggguaagcu gaaccucuga u    21

<210> SEQ ID NO 740
<211> LENGTH: 22
<212> TYPE: RNA
<213> ORGANISM: homo sapiens

<400> SEQUENCE: 740
auauuaccau uagcucaucu uu    22

<210> SEQ ID NO 741
<211> LENGTH: 22
<212> TYPE: RNA
<213> ORGANISM: homo sapiens

<400> SEQUENCE: 741
gaugagcuca uuguaauaug ag    22

<210> SEQ ID NO 742
<211> LENGTH: 23
<212> TYPE: RNA
<213> ORGANISM: homo sapiens

<400> SEQUENCE: 742
guuugcacgg gugggccuug ucu    23

<210> SEQ ID NO 743
<211> LENGTH: 19
<212> TYPE: RNA
<213> ORGANISM: homo sapiens

<400> SEQUENCE: 743
ugagcugcug uaccaaaau    19

<210> SEQ ID NO 744
<211> LENGTH: 21
<212> TYPE: RNA
<213> ORGANISM: homo sapiens

<400> SEQUENCE: 744
uaaaguaaau augcaccaaa a    21

<210> SEQ ID NO 745
<211> LENGTH: 22
<212> TYPE: RNA
<213> ORGANISM: homo sapiens

<400> SEQUENCE: 745
caaaguuuaa gauccuugaa gu    22

<210> SEQ ID NO 746
<211> LENGTH: 20
<212> TYPE: RNA
<213> ORGANISM: homo sapiens

```
<400> SEQUENCE: 746
aaaguagcug uaccauuugc                                           20

<210> SEQ ID NO 747
<211> LENGTH: 19
<212> TYPE: RNA
<213> ORGANISM: homo sapiens

<400> SEQUENCE: 747
agguugacau acguuuccc                                            19

<210> SEQ ID NO 748
<211> LENGTH: 19
<212> TYPE: RNA
<213> ORGANISM: homo sapiens

<400> SEQUENCE: 748
aggcacggug ucagcaggc                                            19

<210> SEQ ID NO 749
<211> LENGTH: 19
<212> TYPE: RNA
<213> ORGANISM: homo sapiens

<400> SEQUENCE: 749
gggcgccugu gaucccaac                                            19

<210> SEQ ID NO 750
<211> LENGTH: 23
<212> TYPE: RNA
<213> ORGANISM: homo sapiens

<400> SEQUENCE: 750
aguauguucu uccaggacag aac                                       23

<210> SEQ ID NO 751
<211> LENGTH: 20
<212> TYPE: RNA
<213> ORGANISM: homo sapiens

<400> SEQUENCE: 751
auguauaaau guauacacac                                           20

<210> SEQ ID NO 752
<211> LENGTH: 21
<212> TYPE: RNA
<213> ORGANISM: homo sapiens

<400> SEQUENCE: 752
aguuaaugaa uccuggaaag u                                         21

<210> SEQ ID NO 753
<211> LENGTH: 22
<212> TYPE: RNA
<213> ORGANISM: homo sapiens

<400> SEQUENCE: 753
cgaaaacagc aauuaccuuu gc                                        22

<210> SEQ ID NO 754
<211> LENGTH: 21
<212> TYPE: RNA
<213> ORGANISM: homo sapiens
```

```
<400> SEQUENCE: 754
ugaguuggcc aucugaguga g                                          21

<210> SEQ ID NO 755
<211> LENGTH: 20
<212> TYPE: RNA
<213> ORGANISM: homo sapiens

<400> SEQUENCE: 755
guccgcucgg cgguggccca                                            20

<210> SEQ ID NO 756
<211> LENGTH: 24
<212> TYPE: RNA
<213> ORGANISM: homo sapiens

<400> SEQUENCE: 756
cugaagugau guguaacuga ucag                                       24

<210> SEQ ID NO 757
<211> LENGTH: 22
<212> TYPE: RNA
<213> ORGANISM: homo sapiens

<400> SEQUENCE: 757
cacgcucaug cacacaccca ca                                         22

<210> SEQ ID NO 758
<211> LENGTH: 23
<212> TYPE: RNA
<213> ORGANISM: homo sapiens

<400> SEQUENCE: 758
ugagugugug ugugugagug ugu                                        23

<210> SEQ ID NO 759
<211> LENGTH: 19
<212> TYPE: RNA
<213> ORGANISM: homo sapiens

<400> SEQUENCE: 759
gagccaguug gacaggagc                                             19

<210> SEQ ID NO 760
<211> LENGTH: 22
<212> TYPE: RNA
<213> ORGANISM: homo sapiens

<400> SEQUENCE: 760
aagaugugga aaaauuggaa uc                                         22

<210> SEQ ID NO 761
<211> LENGTH: 22
<212> TYPE: RNA
<213> ORGANISM: homo sapiens

<400> SEQUENCE: 761
auucuaauuu cuccacgucu uu                                         22

<210> SEQ ID NO 762
<211> LENGTH: 21
<212> TYPE: RNA
```

<213> ORGANISM: homo sapiens

<400> SEQUENCE: 762
uagauaaaau auugguaccu g                                              21

<210> SEQ ID NO 763
<211> LENGTH: 21
<212> TYPE: RNA
<213> ORGANISM: homo sapiens

<400> SEQUENCE: 763
cuucuugugc ucuaggauug u                                              21

<210> SEQ ID NO 764
<211> LENGTH: 23
<212> TYPE: RNA
<213> ORGANISM: homo sapiens

<400> SEQUENCE: 764
uucauuuggu auaaaccgcg auu                                            23

<210> SEQ ID NO 765
<211> LENGTH: 22
<212> TYPE: RNA
<213> ORGANISM: homo sapiens

<400> SEQUENCE: 765
uugagaauga ugaaucauua gg                                             22

<210> SEQ ID NO 766
<211> LENGTH: 21
<212> TYPE: RNA
<213> ORGANISM: homo sapiens

<400> SEQUENCE: 766
ucuuguguuc ucuagaucag u                                              21

<210> SEQ ID NO 767
<211> LENGTH: 22
<212> TYPE: RNA
<213> ORGANISM: homo sapiens

<400> SEQUENCE: 767
uaacugguug aacaacugaa cc                                             22

<210> SEQ ID NO 768
<211> LENGTH: 23
<212> TYPE: RNA
<213> ORGANISM: homo sapiens

<400> SEQUENCE: 768
uuacaguugu ucaaccaguu acu                                            23

<210> SEQ ID NO 769
<211> LENGTH: 21
<212> TYPE: RNA
<213> ORGANISM: homo sapiens

<400> SEQUENCE: 769
caaagaggaa ggucccauua c                                              21

<210> SEQ ID NO 770
<211> LENGTH: 22

```
<212> TYPE: RNA
<213> ORGANISM: homo sapiens

<400> SEQUENCE: 770
uuaugguuug ccugggacug ag                                          22

<210> SEQ ID NO 771
<211> LENGTH: 19
<212> TYPE: RNA
<213> ORGANISM: homo sapiens

<400> SEQUENCE: 771
ugggcguauc uguaugcua                                              19

<210> SEQ ID NO 772
<211> LENGTH: 22
<212> TYPE: RNA
<213> ORGANISM: homo sapiens

<400> SEQUENCE: 772
uaugcauugu auuuuaggu cc                                           22

<210> SEQ ID NO 773
<211> LENGTH: 21
<212> TYPE: RNA
<213> ORGANISM: homo sapiens

<400> SEQUENCE: 773
uuuccauagg ugaugaguca c                                           21

<210> SEQ ID NO 774
<211> LENGTH: 21
<212> TYPE: RNA
<213> ORGANISM: homo sapiens

<400> SEQUENCE: 774
uuggccacaa uggguuagaa c                                           21

<210> SEQ ID NO 775
<211> LENGTH: 22
<212> TYPE: RNA
<213> ORGANISM: homo sapiens

<400> SEQUENCE: 775
ugagaaccac gucugcucug ag                                          22

<210> SEQ ID NO 776
<211> LENGTH: 24
<212> TYPE: RNA
<213> ORGANISM: homo sapiens

<400> SEQUENCE: 776
ucagaacaaa ugccgguucc caga                                        24

<210> SEQ ID NO 777
<211> LENGTH: 21
<212> TYPE: RNA
<213> ORGANISM: homo sapiens

<400> SEQUENCE: 777
uaauuuuaug uauaagcuag u                                           21

<210> SEQ ID NO 778
```

<211> LENGTH: 22
<212> TYPE: RNA
<213> ORGANISM: homo sapiens

<400> SEQUENCE: 778
gagcuuauuc auaaaagugc ag                                          22

<210> SEQ ID NO 779
<211> LENGTH: 20
<212> TYPE: RNA
<213> ORGANISM: homo sapiens

<400> SEQUENCE: 779
agaccauggg uucucauugu                                             20

<210> SEQ ID NO 780
<211> LENGTH: 22
<212> TYPE: RNA
<213> ORGANISM: homo sapiens

<400> SEQUENCE: 780
uugugucaau augcgaugau gu                                          22

<210> SEQ ID NO 781
<211> LENGTH: 19
<212> TYPE: RNA
<213> ORGANISM: homo sapiens

<400> SEQUENCE: 781
ugucucugcu gggguuucu                                              19

<210> SEQ ID NO 782
<211> LENGTH: 25
<212> TYPE: RNA
<213> ORGANISM: homo sapiens

<400> SEQUENCE: 782
aggcaccagc caggcauugc ucagc                                       25

<210> SEQ ID NO 783
<211> LENGTH: 21
<212> TYPE: RNA
<213> ORGANISM: homo sapiens

<400> SEQUENCE: 783
gaagugugcc guggugguguc u                                          21

<210> SEQ ID NO 784
<211> LENGTH: 21
<212> TYPE: RNA
<213> ORGANISM: homo sapiens

<400> SEQUENCE: 784
aagccugccc ggcuccucgg g                                           21

<210> SEQ ID NO 785
<211> LENGTH: 22
<212> TYPE: RNA
<213> ORGANISM: homo sapiens

<400> SEQUENCE: 785
ugugucacuc gaugaccacu gu                                          22

<210> SEQ ID NO 786
<211> LENGTH: 22
<212> TYPE: RNA
<213> ORGANISM: homo sapiens

<400> SEQUENCE: 786
uacgucaucg uugucaucgu ca                                              22

<210> SEQ ID NO 787
<211> LENGTH: 20
<212> TYPE: RNA
<213> ORGANISM: homo sapiens

<400> SEQUENCE: 787
guugugucag uuuaucaaac                                                 20

<210> SEQ ID NO 788
<211> LENGTH: 23
<212> TYPE: RNA
<213> ORGANISM: homo sapiens

<400> SEQUENCE: 788
acuuacagac aagagccuug cuc                                             23

<210> SEQ ID NO 789
<211> LENGTH: 22
<212> TYPE: RNA
<213> ORGANISM: homo sapiens

<400> SEQUENCE: 789
uggucuagga uuguuggagg ag                                              22

<210> SEQ ID NO 790
<211> LENGTH: 23
<212> TYPE: RNA
<213> ORGANISM: homo sapiens

<400> SEQUENCE: 790
gacacgggcg acagcugcgg ccc                                             23

<210> SEQ ID NO 791
<211> LENGTH: 22
<212> TYPE: RNA
<213> ORGANISM: homo sapiens

<400> SEQUENCE: 791
cacacacugc aauuacuuuu gc                                              22

<210> SEQ ID NO 792
<211> LENGTH: 19
<212> TYPE: RNA
<213> ORGANISM: homo sapiens

<400> SEQUENCE: 792
aggcugcgga auucaggac                                                  19

<210> SEQ ID NO 793
<211> LENGTH: 23
<212> TYPE: RNA
<213> ORGANISM: homo sapiens

<400> SEQUENCE: 793
uaaaucccau ggugccuucu ccu                                             23

<210> SEQ ID NO 794
<211> LENGTH: 21
<212> TYPE: RNA
<213> ORGANISM: homo sapiens

<400> SEQUENCE: 794
aaacuacuga aaaucaaaga u                                              21

<210> SEQ ID NO 795
<211> LENGTH: 21
<212> TYPE: RNA
<213> ORGANISM: homo sapiens

<400> SEQUENCE: 795
guucaaaucc agaucuauaa c                                              21

<210> SEQ ID NO 796
<211> LENGTH: 25
<212> TYPE: RNA
<213> ORGANISM: homo sapiens

<400> SEQUENCE: 796
agggguggug uugggacagc uccgu                                          25

<210> SEQ ID NO 797
<211> LENGTH: 20
<212> TYPE: RNA
<213> ORGANISM: homo sapiens

<400> SEQUENCE: 797
aggguguuuc ucucaucucu                                                20

<210> SEQ ID NO 798
<211> LENGTH: 21
<212> TYPE: RNA
<213> ORGANISM: homo sapiens

<400> SEQUENCE: 798
ugagcuaaau gugugcuggg a                                              21

<210> SEQ ID NO 799
<211> LENGTH: 23
<212> TYPE: RNA
<213> ORGANISM: homo sapiens

<400> SEQUENCE: 799
gcgaggaccc cucgggucu gac                                             23

<210> SEQ ID NO 800
<211> LENGTH: 25
<212> TYPE: RNA
<213> ORGANISM: homo sapiens

<400> SEQUENCE: 800
gcugggcagg gcuucugagc uccuu                                          25

<210> SEQ ID NO 801
<211> LENGTH: 20
<212> TYPE: RNA
<213> ORGANISM: homo sapiens

<400> SEQUENCE: 801
aggaauguuc cuucuuugcc                                                20

<210> SEQ ID NO 802
<211> LENGTH: 23
<212> TYPE: RNA
<213> ORGANISM: homo sapiens

<400> SEQUENCE: 802
gaacgccugu ucuugccagg ugg                                    23

<210> SEQ ID NO 803
<211> LENGTH: 22
<212> TYPE: RNA
<213> ORGANISM: homo sapiens

<400> SEQUENCE: 803
uccgagccug ggucucccuc uu                                     22

<210> SEQ ID NO 804
<211> LENGTH: 22
<212> TYPE: RNA
<213> ORGANISM: homo sapiens

<400> SEQUENCE: 804
gggggucccc ggugcucgga uc                                     22

<210> SEQ ID NO 805
<211> LENGTH: 22
<212> TYPE: RNA
<213> ORGANISM: homo sapiens

<400> SEQUENCE: 805
agucauugga ggguuugagc ag                                     22

<210> SEQ ID NO 806
<211> LENGTH: 22
<212> TYPE: RNA
<213> ORGANISM: homo sapiens

<400> SEQUENCE: 806
acucaaaacc cuucagugac uu                                     22

<210> SEQ ID NO 807
<211> LENGTH: 22
<212> TYPE: RNA
<213> ORGANISM: homo sapiens

<400> SEQUENCE: 807
agacuuccca uuugaaggug gc                                     22

<210> SEQ ID NO 808
<211> LENGTH: 23
<212> TYPE: RNA
<213> ORGANISM: homo sapiens

<400> SEQUENCE: 808
aaacucuacu uguccuucug agu                                    23

<210> SEQ ID NO 809
<211> LENGTH: 24
<212> TYPE: RNA
<213> ORGANISM: homo sapiens

<400> SEQUENCE: 809
gaccuggaca uguuugugcc cagu                24

<210> SEQ ID NO 810
<211> LENGTH: 20
<212> TYPE: RNA
<213> ORGANISM: homo sapiens

<400> SEQUENCE: 810
auggagauag auauagaaau                     20

<210> SEQ ID NO 811
<211> LENGTH: 21
<212> TYPE: RNA
<213> ORGANISM: homo sapiens

<400> SEQUENCE: 811
ggcuagcaac agcgcuuacc u                   21

<210> SEQ ID NO 812
<211> LENGTH: 21
<212> TYPE: RNA
<213> ORGANISM: homo sapiens

<400> SEQUENCE: 812
acagucugcu gagguuggag c                   21

<210> SEQ ID NO 813
<211> LENGTH: 23
<212> TYPE: RNA
<213> ORGANISM: homo sapiens

<400> SEQUENCE: 813
aucccuugca ggggcuguug ggu                 23

<210> SEQ ID NO 814
<211> LENGTH: 21
<212> TYPE: RNA
<213> ORGANISM: homo sapiens

<400> SEQUENCE: 814
cacaagguau ugguauuacc u                   21

<210> SEQ ID NO 815
<211> LENGTH: 22
<212> TYPE: RNA
<213> ORGANISM: homo sapiens

<400> SEQUENCE: 815
uaguaccagu accuuguguu ca                  22

<210> SEQ ID NO 816
<211> LENGTH: 21
<212> TYPE: RNA
<213> ORGANISM: homo sapiens

<400> SEQUENCE: 816 aggggggaaag uucuauaguc c                  21

<210> SEQ ID NO 817
<211> LENGTH: 22
<212> TYPE: RNA
<213> ORGANISM: homo sapiens

<400> SEQUENCE: 817

-continued

| gacuauagaa cuuuccccu ca | 22 |

<210> SEQ ID NO 818
<211> LENGTH: 19
<212> TYPE: RNA
<213> ORGANISM: homo sapiens

<400> SEQUENCE: 818

| agcugucuga aaaugucuu | 19 |

<210> SEQ ID NO 819
<211> LENGTH: 22
<212> TYPE: RNA
<213> ORGANISM: homo sapiens

<400> SEQUENCE: 819

| gugagucucu aagaaaagag ga | 22 |

<210> SEQ ID NO 820
<211> LENGTH: 21
<212> TYPE: RNA
<213> ORGANISM: homo sapiens

<400> SEQUENCE: 820

| ucuaguaaga guggcagucg a | 21 |

<210> SEQ ID NO 821
<211> LENGTH: 22
<212> TYPE: RNA
<213> ORGANISM: homo sapiens

<400> SEQUENCE: 821

| augcugacau auuuacuaga gg | 22 |

<210> SEQ ID NO 822
<211> LENGTH: 21
<212> TYPE: RNA
<213> ORGANISM: homo sapiens

<400> SEQUENCE: 822

| uggguuuacg uugggagaac u | 21 |

<210> SEQ ID NO 823
<211> LENGTH: 22
<212> TYPE: RNA
<213> ORGANISM: homo sapiens

<400> SEQUENCE: 823

| guucucccaa cguaagccca gc | 22 |

<210> SEQ ID NO 824
<211> LENGTH: 22
<212> TYPE: RNA
<213> ORGANISM: homo sapiens

<400> SEQUENCE: 824

| aguauucugu accagggaag gu | 22 |

<210> SEQ ID NO 825
<211> LENGTH: 21
<212> TYPE: RNA
<213> ORGANISM: homo sapiens

<400> SEQUENCE: 825
agaccuggcc cagaccucag c                                              21

<210> SEQ ID NO 826
<211> LENGTH: 19
<212> TYPE: RNA
<213> ORGANISM: homo sapiens

<400> SEQUENCE: 826
gugucugcuu ccuguggga                                                 19

<210> SEQ ID NO 827
<211> LENGTH: 23
<212> TYPE: RNA
<213> ORGANISM: homo sapiens

<400> SEQUENCE: 827
cuaauaguau cuaccacaau aaa                                            23

<210> SEQ ID NO 828
<211> LENGTH: 22
<212> TYPE: RNA
<213> ORGANISM: homo sapiens

<400> SEQUENCE: 828
aaccagcacc ccaacuuugg ac                                             22

<210> SEQ ID NO 829
<211> LENGTH: 23
<212> TYPE: RNA
<213> ORGANISM: homo sapiens

<400> SEQUENCE: 829
acuugggcac ugaaacaaug ucc                                            23

<210> SEQ ID NO 830
<211> LENGTH: 23
<212> TYPE: RNA
<213> ORGANISM: homo sapiens

<400> SEQUENCE: 830
ugugcuugcu cgucccgccc gca                                            23

<210> SEQ ID NO 831
<211> LENGTH: 24
<212> TYPE: RNA
<213> ORGANISM: homo sapiens

<400> SEQUENCE: 831 acuggggcu uucgggcucu gcgu                                            24

<210> SEQ ID NO 832
<211> LENGTH: 25
<212> TYPE: RNA
<213> ORGANISM: homo sapiens

<400> SEQUENCE: 832
agggaucgcg ggcggguggc ggccu                                          25

<210> SEQ ID NO 833
<211> LENGTH: 23
<212> TYPE: RNA
<213> ORGANISM: homo sapiens

```
<400> SEQUENCE: 833
aucgcugcgg uugcgagcgc ugu                                    23

<210> SEQ ID NO 834
<211> LENGTH: 21
<212> TYPE: RNA
<213> ORGANISM: homo sapiens

<400> SEQUENCE: 834
augauccagg aaccugccuc u                                      21

<210> SEQ ID NO 835
<211> LENGTH: 24
<212> TYPE: RNA
<213> ORGANISM: homo sapiens

<400> SEQUENCE: 835
aaagacauag gauagaguca ccuc                                   24

<210> SEQ ID NO 836
<211> LENGTH: 22
<212> TYPE: RNA
<213> ORGANISM: homo sapiens

<400> SEQUENCE: 836
gucccucucc aaaugugucu ug                                     22

<210> SEQ ID NO 837
<211> LENGTH: 22
<212> TYPE: RNA
<213> ORGANISM: homo sapiens

<400> SEQUENCE: 837
acuuguaugc uagcucaggu ag                                     22

<210> SEQ ID NO 838
<211> LENGTH: 19
<212> TYPE: RNA
<213> ORGANISM: homo sapiens

<400> SEQUENCE: 838
aguguggcuu ucuuagagc                                         19

<210> SEQ ID NO 839
<211> LENGTH: 19
<212> TYPE: RNA
<213> ORGANISM: homo sapiens

<400> SEQUENCE: 839
ucuaggcugg uacugcuga                                         19

<210> SEQ ID NO 840
<211> LENGTH: 19
<212> TYPE: RNA
<213> ORGANISM: homo sapiens

<400> SEQUENCE: 840
aagcagcugc cucugaggc                                         19

<210> SEQ ID NO 841
<211> LENGTH: 21
<212> TYPE: RNA
```

<213> ORGANISM: homo sapiens

<400> SEQUENCE: 841
guggcugcac ucacuuccuu c                                    21

<210> SEQ ID NO 842
<211> LENGTH: 19
<212> TYPE: RNA
<213> ORGANISM: homo sapiens

<400> SEQUENCE: 842
aagugugcag ggcacuggu                                       19

<210> SEQ ID NO 843
<211> LENGTH: 22
<212> TYPE: RNA
<213> ORGANISM: homo sapiens

<400> SEQUENCE: 843
aaaccugugu uguucaagag uc                                   22

<210> SEQ ID NO 844
<211> LENGTH: 21
<212> TYPE: RNA
<213> ORGANISM: homo sapiens

<400> SEQUENCE: 844
aggaggcagc gcucucagga c                                    21

<210> SEQ ID NO 845
<211> LENGTH: 22
<212> TYPE: RNA
<213> ORGANISM: homo sapiens

<400> SEQUENCE: 845
uuuaggauaa gcuugacuuu ug                                   22

<210> SEQ ID NO 846
<211> LENGTH: 21
<212> TYPE: RNA
<213> ORGANISM: homo sapiens

<400> SEQUENCE: 846
aauggcgcca cuaggguugu g                                    21

<210> SEQ ID NO 847
<211> LENGTH: 21
<212> TYPE: RNA
<213> ORGANISM: homo sapiens

<400> SEQUENCE: 847
guguugaaac aaucucuacu g                                    21

<210> SEQ ID NO 848
<211> LENGTH: 22
<212> TYPE: RNA
<213> ORGANISM: homo sapiens

<400> SEQUENCE: 848
uaugucugcu gaccaucacc uu                                   22

<210> SEQ ID NO 849
<211> LENGTH: 22

```
<212> TYPE: RNA
<213> ORGANISM: homo sapiens

<400> SEQUENCE: 849 ugugggccg cagaacaugu gc                                          22

<210> SEQ ID NO 850
<211> LENGTH: 22
<212> TYPE: RNA
<213> ORGANISM: homo sapiens

<400> SEQUENCE: 850 auaaucaug guuaaccucu uu                                          22

<210> SEQ ID NO 851
<211> LENGTH: 21
<212> TYPE: RNA
<213> ORGANISM: homo sapiens

<400> SEQUENCE: 851
aauauuauac agucaaccuc u                                          21

<210> SEQ ID NO 852
<211> LENGTH: 23
<212> TYPE: RNA
<213> ORGANISM: homo sapiens

<400> SEQUENCE: 852
ggcagguucu cacccucucu agg                                        23

<210> SEQ ID NO 853
<211> LENGTH: 25
<212> TYPE: RNA
<213> ORGANISM: homo sapiens

<400> SEQUENCE: 853
ggcggaggga aguagguccg uuggu                                      25

<210> SEQ ID NO 854
<211> LENGTH: 22
<212> TYPE: RNA
<213> ORGANISM: homo sapiens

<400> SEQUENCE: 854
cuugguucag ggaggguccc ca                                         22

<210> SEQ ID NO 855
<211> LENGTH: 22
<212> TYPE: RNA
<213> ORGANISM: homo sapiens

<400> SEQUENCE: 855
uacccauugc auaucggagu ug                                         22

<210> SEQ ID NO 856
<211> LENGTH: 24
<212> TYPE: RNA
<213> ORGANISM: homo sapiens

<400> SEQUENCE: 856
ugccuggguc ucuggccugc gcgu                                       24

<210> SEQ ID NO 857
```

```
<211> LENGTH: 21
<212> TYPE: RNA
<213> ORGANISM: homo sapiens

<400> SEQUENCE: 857
ucccacguug uggcccagca g                                              21

<210> SEQ ID NO 858
<211> LENGTH: 22
<212> TYPE: RNA
<213> ORGANISM: homo sapiens

<400> SEQUENCE: 858
aggcggggcg ccgcgggacc gc                                             22

<210> SEQ ID NO 859
<211> LENGTH: 22
<212> TYPE: RNA
<213> ORGANISM: homo sapiens

<400> SEQUENCE: 859
gguggcccgg ccgugccuga gg                                             22

<210> SEQ ID NO 860
<211> LENGTH: 23
<212> TYPE: RNA
<213> ORGANISM: homo sapiens

<400> SEQUENCE: 860
uauucauuua ucccagccu aca                                             23

<210> SEQ ID NO 861
<211> LENGTH: 24
<212> TYPE: RNA
<213> ORGANISM: homo sapiens

<400> SEQUENCE: 861
acuggcuagg gaaaaugauu ggau                                           24

<210> SEQ ID NO 862
<211> LENGTH: 20
<212> TYPE: RNA
<213> ORGANISM: homo sapiens

<400> SEQUENCE: 862
accaggaggc ugaggcccu                                                 20

<210> SEQ ID NO 863
<211> LENGTH: 23
<212> TYPE: RNA
<213> ORGANISM: homo sapiens

<400> SEQUENCE: 863
ugucacucgg cucggcccac uac                                            23

<210> SEQ ID NO 864
<211> LENGTH: 21
<212> TYPE: RNA
<213> ORGANISM: homo sapiens

<400> SEQUENCE: 864
uccgguucuc agggcuccac c                                              21
```

```
<210> SEQ ID NO 865
<211> LENGTH: 23
<212> TYPE: RNA
<213> ORGANISM: homo sapiens

<400> SEQUENCE: 865
aggaagcccu ggaggggcug gag                                           23

<210> SEQ ID NO 866
<211> LENGTH: 23
<212> TYPE: RNA
<213> ORGANISM: homo sapiens

<400> SEQUENCE: 866
uggugcggag agggcccaca gug                                           23

<210> SEQ ID NO 867
<211> LENGTH: 20
<212> TYPE: RNA
<213> ORGANISM: homo sapiens

<400> SEQUENCE: 867
cuguaugccc ucaccgcuca                                               20

<210> SEQ ID NO 868
<211> LENGTH: 23
<212> TYPE: RNA
<213> ORGANISM: homo sapiens

<400> SEQUENCE: 868
uggaagacua gugauuuugu ugu                                           23

<210> SEQ ID NO 869
<211> LENGTH: 22
<212> TYPE: RNA
<213> ORGANISM: homo sapiens

<400> SEQUENCE: 869
caacaaauca cagucugcca ua                                            22

<210> SEQ ID NO 870
<211> LENGTH: 22
<212> TYPE: RNA
<213> ORGANISM: homo sapiens

<400> SEQUENCE: 870
caacaaaucc cagucuaccu aa                                            22

<210> SEQ ID NO 871
<211> LENGTH: 23
<212> TYPE: RNA
<213> ORGANISM: homo sapiens

<400> SEQUENCE: 871
aaggagcuua caaucuagcu ggg                                           23

<210> SEQ ID NO 872
<211> LENGTH: 22
<212> TYPE: RNA
<213> ORGANISM: homo sapiens

<400> SEQUENCE: 872
caacuagacu gugagcuucu ag                                            22
```

```
<210> SEQ ID NO 873
<211> LENGTH: 17
<212> TYPE: RNA
<213> ORGANISM: homo sapiens

<400> SEQUENCE: 873
ucucgcuggg gccucca                                                    17

<210> SEQ ID NO 874
<211> LENGTH: 22
<212> TYPE: RNA
<213> ORGANISM: homo sapiens

<400> SEQUENCE: 874
ugcggggcua gggcuaacag ca                                              22

<210> SEQ ID NO 875
<211> LENGTH: 22
<212> TYPE: RNA
<213> ORGANISM: homo sapiens

<400> SEQUENCE: 875 cguugccac uaaccucaac cu                                               22

<210> SEQ ID NO 876
<211> LENGTH: 22
<212> TYPE: RNA
<213> ORGANISM: homo sapiens

<400> SEQUENCE: 876
uuugugaccu gguccacuaa cc                                              22

<210> SEQ ID NO 877
<211> LENGTH: 20
<212> TYPE: RNA
<213> ORGANISM: homo sapiens

<400> SEQUENCE: 877
cggcucuggg ucuguggga                                                  20

<210> SEQ ID NO 878
<211> LENGTH: 21
<212> TYPE: RNA
<213> ORGANISM: homo sapiens

<400> SEQUENCE: 878
uggaggagaa ggaaggugau g                                               21

<210> SEQ ID NO 879
<211> LENGTH: 22
<212> TYPE: RNA
<213> ORGANISM: homo sapiens

<400> SEQUENCE: 879
acuccagccc cacagccuca gc                                              22

<210> SEQ ID NO 880
<211> LENGTH: 23
<212> TYPE: RNA
<213> ORGANISM: homo sapiens

<400> SEQUENCE: 880
ucugcucaua ccccaugguu ucu                                             23
```

```
<210> SEQ ID NO 881
<211> LENGTH: 23
<212> TYPE: RNA
<213> ORGANISM: homo sapiens

<400> SEQUENCE: 881
ugcaccaugg uugucugagc aug                                              23

<210> SEQ ID NO 882
<211> LENGTH: 23
<212> TYPE: RNA
<213> ORGANISM: homo sapiens

<400> SEQUENCE: 882
cugggaucuc cgggucuug guu                                               23

<210> SEQ ID NO 883
<211> LENGTH: 22
<212> TYPE: RNA
<213> ORGANISM: homo sapiens

<400> SEQUENCE: 883
ugagaccucu ggguucugag cu                                               22

<210> SEQ ID NO 884
<211> LENGTH: 23
<212> TYPE: RNA
<213> ORGANISM: homo sapiens

<400> SEQUENCE: 884
uccaguacca cgugucaggg cca                                              23

<210> SEQ ID NO 885
<211> LENGTH: 23
<212> TYPE: RNA
<213> ORGANISM: homo sapiens

<400> SEQUENCE: 885
caguaacaaa gauucauccu ugu                                              23

<210> SEQ ID NO 886
<211> LENGTH: 21
<212> TYPE: RNA
<213> ORGANISM: homo sapiens

<400> SEQUENCE: 886
gcaggaacuu gugagucucc u                                                21

<210> SEQ ID NO 887
<211> LENGTH: 22
<212> TYPE: RNA
<213> ORGANISM: homo sapiens

<400> SEQUENCE: 887
cugcccuggc ccgagggacc ga                                               22

<210> SEQ ID NO 888
<211> LENGTH: 21
<212> TYPE: RNA
<213> ORGANISM: homo sapiens

<400> SEQUENCE: 888
```
ccuggaaaca cugagguugu g                              21

<210> SEQ ID NO 889
<211> LENGTH: 22
<212> TYPE: RNA
<213> ORGANISM: homo sapiens

<400> SEQUENCE: 889
uauaccucag uuuuaucagg ug                             22

<210> SEQ ID NO 890
<211> LENGTH: 22
<212> TYPE: RNA
<213> ORGANISM: homo sapiens

<400> SEQUENCE: 890
uggugguuua caaaguaauu ca                             22

<210> SEQ ID NO 891
<211> LENGTH: 22
<212> TYPE: RNA
<213> ORGANISM: homo sapiens

<400> SEQUENCE: 891
uggauuucuu ugugaaucac ca                             22

<210> SEQ ID NO 892
<211> LENGTH: 20
<212> TYPE: RNA
<213> ORGANISM: homo sapiens

<400> SEQUENCE: 892
guagaggaga uggcgcaggg                                20

<210> SEQ ID NO 893
<211> LENGTH: 21
<212> TYPE: RNA
<213> ORGANISM: homo sapiens

<400> SEQUENCE: 893
uccucuucuc ccuccuccca g                              21

<210> SEQ ID NO 894
<211> LENGTH: 22
<212> TYPE: RNA
<213> ORGANISM: homo sapiens

<400> SEQUENCE: 894
aggcagcggg guguagugga ua                             22

<210> SEQ ID NO 895
<211> LENGTH: 22
<212> TYPE: RNA
<213> ORGANISM: homo sapiens

<400> SEQUENCE: 895
uccauuacac uacccugccu cu                             22

<210> SEQ ID NO 896
<211> LENGTH: 21
<212> TYPE: RNA
<213> ORGANISM: homo sapiens

<400> SEQUENCE: 896
cgcgggugcu uacugacccu u                          21

<210> SEQ ID NO 897
<211> LENGTH: 23
<212> TYPE: RNA
<213> ORGANISM: homo sapiens

<400> SEQUENCE: 897
cgggucggag uuagcucaag cgg                        23

<210> SEQ ID NO 898
<211> LENGTH: 22
<212> TYPE: RNA
<213> ORGANISM: homo sapiens

<400> SEQUENCE: 898
gugaacgggc gccaucccga gg                         22

<210> SEQ ID NO 899
<211> LENGTH: 21
<212> TYPE: RNA
<213> ORGANISM: homo sapiens

<400> SEQUENCE: 899
uacucaaaaa gcugucaguc a                          21

<210> SEQ ID NO 900
<211> LENGTH: 22
<212> TYPE: RNA
<213> ORGANISM: homo sapiens

<400> SEQUENCE: 900
gacugacacc ucuuugggug aa                         22

<210> SEQ ID NO 901
<211> LENGTH: 21
<212> TYPE: RNA
<213> ORGANISM: homo sapiens

<400> SEQUENCE: 901
uuaauaucgg acaaccauug u                          21

<210> SEQ ID NO 902
<211> LENGTH: 21
<212> TYPE: RNA
<213> ORGANISM: homo sapiens

<400> SEQUENCE: 902
uacuuggaaa ggcaucaguu g                          21

<210> SEQ ID NO 903
<211> LENGTH: 22
<212> TYPE: RNA
<213> ORGANISM: homo sapiens

<400> SEQUENCE: 903
ugcaacgaac cugagccacu ga                         22

<210> SEQ ID NO 904
<211> LENGTH: 22
<212> TYPE: RNA
<213> ORGANISM: homo sapiens

```
<400> SEQUENCE: 904
ugcaacuuac cugagucauu ga                                          22

<210> SEQ ID NO 905
<211> LENGTH: 21
<212> TYPE: RNA
<213> ORGANISM: homo sapiens

<400> SEQUENCE: 905
cacugugucc uuucugcgua g                                           21

<210> SEQ ID NO 906
<211> LENGTH: 22
<212> TYPE: RNA
<213> ORGANISM: homo sapiens

<400> SEQUENCE: 906
cacuggcucc uuucugggua ga                                          22

<210> SEQ ID NO 907
<211> LENGTH: 23
<212> TYPE: RNA
<213> ORGANISM: homo sapiens

<400> SEQUENCE: 907
ucuuugguua ucuagcugua uga                                         23

<210> SEQ ID NO 908
<211> LENGTH: 22
<212> TYPE: RNA
<213> ORGANISM: homo sapiens

<400> SEQUENCE: 908
auaaagcuag auaaccgaaa gu                                          22

<210> SEQ ID NO 909
<211> LENGTH: 20
<212> TYPE: RNA
<213> ORGANISM: homo sapiens

<400> SEQUENCE: 909
ggggagcugu ggaagcagua                                             20

<210> SEQ ID NO 910
<211> LENGTH: 25
<212> TYPE: RNA
<213> ORGANISM: homo sapiens

<400> SEQUENCE: 910
cuagugaggg acagaaccag gauuc                                       25

<210> SEQ ID NO 911
<211> LENGTH: 23
<212> TYPE: RNA
<213> ORGANISM: homo sapiens

<400> SEQUENCE: 911
gcagcagaga auaggacuac guc                                         23

<210> SEQ ID NO 912
<211> LENGTH: 21
<212> TYPE: RNA
<213> ORGANISM: homo sapiens
```

-continued

<400> SEQUENCE: 912
gucagcggag gaaaagaaac u                                              21

<210> SEQ ID NO 913
<211> LENGTH: 20
<212> TYPE: RNA
<213> ORGANISM: homo sapiens

<400> SEQUENCE: 913
agagucuugu gaugucuugc                                                20

<210> SEQ ID NO 914
<211> LENGTH: 22
<212> TYPE: RNA
<213> ORGANISM: homo sapiens

<400> SEQUENCE: 914
uauugcacuu gucccggccu gu                                             22

<210> SEQ ID NO 915
<211> LENGTH: 23
<212> TYPE: RNA
<213> ORGANISM: homo sapiens

<400> SEQUENCE: 915
agguugggau cgguugcaau gcu                                            23

<210> SEQ ID NO 916
<211> LENGTH: 22
<212> TYPE: RNA
<213> ORGANISM: homo sapiens

<400> SEQUENCE: 916 gggugggggau uuguugcauu ac                                            22

<210> SEQ ID NO 917
<211> LENGTH: 22
<212> TYPE: RNA
<213> ORGANISM: homo sapiens

<400> SEQUENCE: 917
uauugcacuc gucccggccu cc                                             22

<210> SEQ ID NO 918
<211> LENGTH: 22
<212> TYPE: RNA
<213> ORGANISM: homo sapiens

<400> SEQUENCE: 918
agggacggga cgcggugcag ug                                             22

<210> SEQ ID NO 919
<211> LENGTH: 23
<212> TYPE: RNA
<213> ORGANISM: homo sapiens

<400> SEQUENCE: 919
caaagugcug uucgugcagg uag                                            23

<210> SEQ ID NO 920
<211> LENGTH: 22
<212> TYPE: RNA
<213> ORGANISM: homo sapiens

```
<400> SEQUENCE: 920
acugcugagc uagcacuucc cg                                          22

<210> SEQ ID NO 921
<211> LENGTH: 22
<212> TYPE: RNA
<213> ORGANISM: homo sapiens

<400> SEQUENCE: 921
ugugcgcagg gagaccucuc cc                                          22

<210> SEQ ID NO 922
<211> LENGTH: 22
<212> TYPE: RNA
<213> ORGANISM: homo sapiens

<400> SEQUENCE: 922
ugucuacuac uggagacacu gg                                          22

<210> SEQ ID NO 923
<211> LENGTH: 23
<212> TYPE: RNA
<213> ORGANISM: homo sapiens

<400> SEQUENCE: 923
ccaguuaccg cuuccgcuac cgc                                         23

<210> SEQ ID NO 924
<211> LENGTH: 22
<212> TYPE: RNA
<213> ORGANISM: homo sapiens

<400> SEQUENCE: 924
acaguagagg gaggaaucgc ag                                          22

<210> SEQ ID NO 925
<211> LENGTH: 22
<212> TYPE: RNA
<213> ORGANISM: homo sapiens

<400> SEQUENCE: 925
auccgcgcuc ugacucucug cc                                          22

<210> SEQ ID NO 926
<211> LENGTH: 22
<212> TYPE: RNA
<213> ORGANISM: homo sapiens

<400> SEQUENCE: 926
ugcccuuaaa ggugaaccca gu                                          22

<210> SEQ ID NO 927
<211> LENGTH: 24
<212> TYPE: RNA
<213> ORGANISM: homo sapiens

<400> SEQUENCE: 927
uggggagcug aggcucuggg ggug                                        24

<210> SEQ ID NO 928
<211> LENGTH: 21
<212> TYPE: RNA
<213> ORGANISM: homo sapiens
```

```
<400> SEQUENCE: 928
aaggcagggc ccccgcuccc c                                             21

<210> SEQ ID NO 929
<211> LENGTH: 23
<212> TYPE: RNA
<213> ORGANISM: homo sapiens

<400> SEQUENCE: 929
cacccggcug ugugcacaug ugc                                           23

<210> SEQ ID NO 930
<211> LENGTH: 22
<212> TYPE: RNA
<213> ORGANISM: homo sapiens

<400> SEQUENCE: 930
ucuucucugu uuuggccaug ug                                            22

<210> SEQ ID NO 931
<211> LENGTH: 21
<212> TYPE: RNA
<213> ORGANISM: homo sapiens

<400> SEQUENCE: 931
cugacuguug ccguccucca g                                             21

<210> SEQ ID NO 932
<211> LENGTH: 22
<212> TYPE: RNA
<213> ORGANISM: homo sapiens

<400> SEQUENCE: 932
aaauuauugu acaucggaug ag                                            22

<210> SEQ ID NO 933
<211> LENGTH: 22
<212> TYPE: RNA
<213> ORGANISM: homo sapiens

<400> SEQUENCE: 933
uucaacgggu auuuauugag ca                                            22

<210> SEQ ID NO 934
<211> LENGTH: 23
<212> TYPE: RNA
<213> ORGANISM: homo sapiens

<400> SEQUENCE: 934
uuuggcacua gcacauuuuu gcu                                           23

<210> SEQ ID NO 935
<211> LENGTH: 22
<212> TYPE: RNA
<213> ORGANISM: homo sapiens

<400> SEQUENCE: 935
aaucaugugc agugccaaua ug                                            22

<210> SEQ ID NO 936
<211> LENGTH: 22
<212> TYPE: RNA
<213> ORGANISM: homo sapiens
```

```
<400> SEQUENCE: 936
ugagguagua aguuguauug uu                                    22

<210> SEQ ID NO 937
<211> LENGTH: 22
<212> TYPE: RNA
<213> ORGANISM: homo sapiens

<400> SEQUENCE: 937
aacccguaga uccgaucuug ug                                    22

<210> SEQ ID NO 938
<211> LENGTH: 22
<212> TYPE: RNA
<213> ORGANISM: homo sapiens

<400> SEQUENCE: 938
caagcucgcu ucuaugdguc ug                                    22

<210> SEQ ID NO 939
<211> LENGTH: 22
<212> TYPE: RNA
<213> ORGANISM: homo sapiens

<400> SEQUENCE: 939
cacccguaga accgaccuug cg                                    22

<210> SEQ ID NO 940
<211> LENGTH: 22
<212> TYPE: RNA
<213> ORGANISM: homo sapiens

<400> SEQUENCE: 940
caagcucgug ucugugdguc cg                                    22

<210> SEQ ID NO 941
<211> LENGTH: 21
<212> TYPE: RNA
<213> ORGANISM: homo sapiens

<400> SEQUENCE: 941
uggaaggacg ggaaguggaa g                                     21

<210> SEQ ID NO 942
<211> LENGTH: 24
<212> TYPE: RNA
<213> ORGANISM: homo sapiens

<400> SEQUENCE: 942
ccugagccag ggacgagugc gacu                                  24

<210> SEQ ID NO 943
<211> LENGTH: 22
<212> TYPE: RNA
<213> ORGANISM: homo sapiens

<400> SEQUENCE: 943
ucgcacgcgc ccggcacaga cu                                    22

<210> SEQ ID NO 944
<211> LENGTH: 20
<212> TYPE: RNA
<213> ORGANISM: homo sapiens
```

```
<400> SEQUENCE: 944
cugggacugu gcgguuggga                                              20

<210> SEQ ID NO 945
<211> LENGTH: 22
<212> TYPE: RNA
<213> ORGANISM: homo sapiens

<400> SEQUENCE: 945
cuugccuguc uaacucgcua gu                                           22

<210> SEQ ID NO 946
<211> LENGTH: 22
<212> TYPE: RNA
<213> ORGANISM: homo sapiens

<400> SEQUENCE: 946
gguagaguuu gacaggcaag ca                                           22

<210> SEQ ID NO 947
<211> LENGTH: 22
<212> TYPE: RNA
<213> ORGANISM: homo sapiens

<400> SEQUENCE: 947
gucagagauc caaacccucc gg                                           22

<210> SEQ ID NO 948
<211> LENGTH: 21
<212> TYPE: RNA
<213> ORGANISM: homo sapiens

<400> SEQUENCE: 948
cacuucccgu ccuuccaucc c                                            21

<210> SEQ ID NO 949
<211> LENGTH: 23
<212> TYPE: RNA
<213> ORGANISM: homo sapiens

<400> SEQUENCE: 949
auuacaggaa acugggugua agc                                          23

<210> SEQ ID NO 950
<211> LENGTH: 22
<212> TYPE: RNA
<213> ORGANISM: homo sapiens

<400> SEQUENCE: 950
uaguguuguc cccccgagug gc                                           22

<210> SEQ ID NO 951
<211> LENGTH: 22
<212> TYPE: RNA
<213> ORGANISM: homo sapiens

<400> SEQUENCE: 951
ugguguuguc cccccgagug gc                                           22

<210> SEQ ID NO 952
<211> LENGTH: 22
<212> TYPE: RNA
<213> ORGANISM: homo sapiens
```

```
<400> SEQUENCE: 952
uuaaugcuua gccugugucc ga                                              22

<210> SEQ ID NO 953
<211> LENGTH: 22
<212> TYPE: RNA
<213> ORGANISM: homo sapiens

<400> SEQUENCE: 953
accaggccac cauccucuc cg                                               22

<210> SEQ ID NO 954
<211> LENGTH: 22
<212> TYPE: RNA
<213> ORGANISM: homo sapiens

<400> SEQUENCE: 954
aacuguaguc cgggucgauc ug                                              22

<210> SEQ ID NO 955
<211> LENGTH: 23
<212> TYPE: RNA
<213> ORGANISM: homo sapiens

<400> SEQUENCE: 955
ucacauucug aggacggcag cga                                             23

<210> SEQ ID NO 956
<211> LENGTH: 21
<212> TYPE: RNA
<213> ORGANISM: homo sapiens

<400> SEQUENCE: 956
ucgcggucac agaaugugac a                                               21

<210> SEQ ID NO 957
<211> LENGTH: 22
<212> TYPE: RNA
<213> ORGANISM: homo sapiens

<400> SEQUENCE: 957
uagaauacug aggccuagcu ga                                              22

<210> SEQ ID NO 958
<211> LENGTH: 22
<212> TYPE: RNA
<213> ORGANISM: homo sapiens

<400> SEQUENCE: 958
agcuaaaccg caguacucua gg                                              22

<210> SEQ ID NO 959
<211> LENGTH: 22
<212> TYPE: RNA
<213> ORGANISM: homo sapiens

<400> SEQUENCE: 959
uaggaugccu ggaacuugcc gg                                              22

<210> SEQ ID NO 960
<211> LENGTH: 22
<212> TYPE: RNA
<213> ORGANISM: homo sapiens
```

```
<400> SEQUENCE: 960
ugaugguuuu cgggcuguug ag                                              22

<210> SEQ ID NO 961
<211> LENGTH: 22
<212> TYPE: RNA
<213> ORGANISM: homo sapiens

<400> SEQUENCE: 961
ccagcagcac cuaauccauc gg                                              22

<210> SEQ ID NO 962
<211> LENGTH: 21
<212> TYPE: RNA
<213> ORGANISM: homo sapiens

<400> SEQUENCE: 962
ugaucccaug uugcuggcgc u                                               21

<210> SEQ ID NO 963
<211> LENGTH: 22
<212> TYPE: RNA
<213> ORGANISM: homo sapiens

<400> SEQUENCE: 963
uaggcgcgac ugagagagca cg                                              22

<210> SEQ ID NO 964
<211> LENGTH: 22
<212> TYPE: RNA
<213> ORGANISM: homo sapiens

<400> SEQUENCE: 964
cuggguauac gcagcugcgu aa                                              22

<210> SEQ ID NO 965
<211> LENGTH: 22
<212> TYPE: RNA
<213> ORGANISM: homo sapiens

<400> SEQUENCE: 965
acccagcugc guaaaccccg cu                                              22
```